United States Patent
Wong et al.

(10) Patent No.: US 10,086,054 B2
(45) Date of Patent: Oct. 2, 2018

(54) RM2 ANTIGENS AND USE THEREOF

(71) Applicant: ACADEMIA SINICA, Taipei (TW)

(72) Inventors: Chi-Huey Wong, Rancho Santa Fe, CA (US); Chung-Yi Wu, New Taipei (TW); Hong-Yang Chuang, Tainan (TW); Chien-Tai Ren, Taipei (TW)

(73) Assignee: ACADEMIA SINICA, Taipei (TW)

( * ) Notice: Subject to any disclaimer, the term of this patent is extended or adjusted under 35 U.S.C. 154(b) by 1 day.

(21) Appl. No.: 14/392,341

(22) PCT Filed: Jun. 26, 2014

(86) PCT No.: PCT/US2014/044465
§ 371 (c)(1),
(2) Date: Dec. 23, 2015

(87) PCT Pub. No.: WO2014/210397
PCT Pub. Date: Dec. 31, 2014

(65) Prior Publication Data
US 2016/0193310 A1 Jul. 7, 2016

Related U.S. Application Data

(60) Provisional application No. 61/839,648, filed on Jun. 26, 2013.

(51) Int. Cl.
| | |
|---|---|
| C07H 15/04 | (2006.01) |
| A61K 39/00 | (2006.01) |
| A61K 39/385 | (2006.01) |
| A61K 31/7028 | (2006.01) |
| C07K 14/47 | (2006.01) |
| A61K 49/00 | (2006.01) |
| C07H 15/10 | (2006.01) |
| C07H 15/14 | (2006.01) |

(52) U.S. Cl.
CPC ...... *A61K 39/0011* (2013.01); *A61K 31/7028* (2013.01); *A61K 39/385* (2013.01); *A61K 49/00* (2013.01); *C07H 15/04* (2013.01); *C07H 15/10* (2013.01); *C07H 15/14* (2013.01); *C07K 14/4748* (2013.01); *A61K 2039/575* (2013.01); *A61K 2039/585* (2013.01); *A61K 2039/6037* (2013.01); *A61K 2039/627* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,270,537 A | 6/1981 | Romaine | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Abrahmsén et al, "Analysis of signals for secretion in the staphylococcal protein A gene," *Embo J.*, Dec. 30, 1985, 4(13B):3901-3906.

(Continued)

*Primary Examiner* — Eric Olson
(74) *Attorney, Agent, or Firm* — Duane Morris LLP

(57) ABSTRACT

Described herein are synthetic glycan conjugates, immunogenic compositions thereof, vaccines thereof, and kits thereof. The present invention further provides methods of using the synthetic glycan conjugates, immunogenic compositions, or vaccines thereof to treat and/or prevent and/or diagnose proliferative diseases such as cancer. The provided glycan conjugate comprises a carrier and a glycan moiety of Formula (I-i) or Formula (I-ii): (structurally represented).

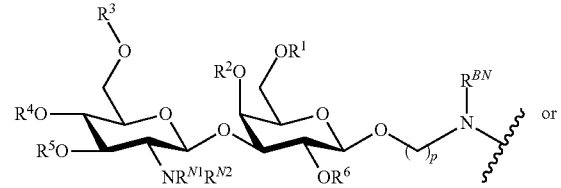

(I-i)

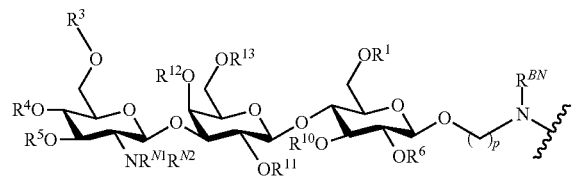

(I-ii)

147 Claims, 37 Drawing Sheets

(56) References Cited

U.S. PATENT DOCUMENTS

| | | |
|---|---|---|
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Daffier |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 * | 6/2002 | Duthaler .......... A61K 47/48315 424/194.1 |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |

(56) References Cited

U.S. PATENT DOCUMENTS

| | | |
|---|---|---|
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,803,177 B2 | 10/2017 | Rossi et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1* | 3/2007 | Blixt ................ G01N 33/54386 435/7.1 |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |

(56) References Cited

FOREIGN PATENT DOCUMENTS

| | | |
|---|---|---|
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |

OTHER PUBLICATIONS

Altschul SF et al., "Basic local alignment search tool", *J Mol Biol.* Oct. 5, 1990;215(3):403-10.

Altschul SF, et al., "Gapped BLAST and PSI-BLAST: a new generation of protein database search programs", *Nucleic Acids Res.* Sep. 1, 1997;25(17):3389-402.

Anderson et al., "Stimulation of Natural Killer T Cells by Glycolipids", *Molecules*, May 2013, 18(12), 15662-15688.

Arié et al., "Chaperone function of FkpA, a heat shock prolyl isomerase, in the periplasm of *Escherichia coli*," Mol. Microbiol., Jan. 2001, 39(1):199-210.

Bachmann, *Cellular and Molecular Biology*, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.

Baldwin et al., "Monoclonal antibodies in cancer treatment," *Lancet*, Mar. 15, 1986, 327(8481):603-605.

Barbas et al., "Assembly of combinatorial antibody libraries on phage surfaces: the gene III site," *Proc. Natl. Acad. Sci. U.S.A.*, Sep. 15, 1991, 88(18):7978-7982.

Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.

Barbas et al., "Semisynthetic combinatorial antibody libraries: a chemical solution to the diversity problem," *Proc. Natl. Acad. Sci. U.S.A.*, May 15, 1992, 89(10):4457-4461.

Barnes et al., "Methods for growth of cultured cells in serum-free medium," *Anal. Biochem.*, Mar. 1, 1980, 102(2):255-270.

Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.

Bass et al., "Hormone phage: an enrichment method for variant proteins with altered binding properties," *Proteins*, 1990, 8(4):309-314.

Beck A., "Biosimilar, biobetter and next generation therapeutic antibodies" *MAbs*. Mar.-Apr. 2011;3(2):107-10. Epub Mar. 1, 2011.

Berra et al., "Correlation between ganglioside distribution and histological grading of human astrocytomas," *Int. J. Cancer*, Sep. 15, 1985, 36(3):363-366.

Birkléet al., "Role of tumor-associated gangliosides in cancer progression," *Biochimie*, Mar.-Apr. 2003, 85(3-4):455-463.

Bobo et al., "Convection-enhanced delivery of macromolecules in the brain," *Proc. Natl. Acad. Sci. U.S.A.*, Mar. 15, 1994, 91(6) 2076-2080.

Boerner et al., "Production of antigen-specific human monoclonal antibodies from in vitro-primed human splenocytes," *J. Immunol.*, Jul. 1, 1991, 147(1):86-95.

Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.

Brennan et al., "Preparation of bispecific antibodies by chemical recombination of monoclonal immunoglobulin $G_1$ fragments," *Science*, Jul. 5, 1985, 229(4708):81-83.

Brimble et al., "The cell surface glycosphingolipids SSEA-3 and SSEA-4 are not essential for human ESC pluripotency," *Stem Cells*, Jan. 2007, 25(1):54-62.

Brodeur et al., *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.

(56) References Cited

OTHER PUBLICATIONS

Brüggemann et al., "Designer mice: the production of human antibody repertoires in transgenic animals," Year in Immunol., 1993, 7:33-40.
Capel PJ et al., "Heterogeneity of human IgG Fc receptors" Immunomethods. Feb. 1994;4(1):25-34.
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Carter PJ. "Potent antibody therapeutics by design" Nat Rev Immunol. May 2006;6(5):343-357.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J Bio. Chem., Jul. 9. 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chothia et al., "Canonical structures for the hypervariable regions of immunoglobulins," J. Mol. Biol., Aug. 20, 1987, 196(4):901-917.
Clackson et al., "Making antibody fragments using phage display libraries," Nature, Aug. 15, 1991, 352(6336):624-628.
Clark EA et al., "Structure, function, and genetics of human B cell-associated surface molecules" Adv Cancer Res. 1989;52:81-149.
Clynes R, et al., "Fc receptors are required in passive and active immunity to melanoma" Proc Natl Acad Sci U S A. Jan. 20, 1998;95(2):652-6.
Cunningham et al., "High-resolution epitope mapping of hGH-receptor interactions by alanine-scanning mutagenesis," Science, Jun. 2, 1989, 244(4908):1081-1085.
Daëron, "Fc receptor biology," Annu. Rev. Immunol., 1997, 15:203-234.
De Haas et al., "Fcγ receptors of phagocytes," J. Lab. Clin. Med., Oct. 1995, 126(4):330-341.
Durrant et al., "Immunology in the clinic review series; focus on cancer: glycolipids as targets for tumour immunotherapy," Clin. Exp. Immunol., Feb. 2012, 167(2):206-215.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Fishwild et al., "High-avidity human IgGκ monoclonal antibodies from a novel strain of minilocus transgenic mice," Nature Biotechnol., Jul. 1996, 14(7):845-851.
Fredman et al., "Expression of gangliosides GD3 and 3'-isoLM1 in autopsy brains from patients with malignant tumors," J. Neurochem., Jan. 1993, 60(1):99-105.
Fredman et al., "Potential ganglioside antigens associated with human gliomas," Neurol. Res., Jun. 1986, 8(2):123-126.
Fredman et al., "Sialyllactotetraosylceramide, a ganglioside marker for human malignant gliomas," J. Neurochem., Mar. 1988, 50(3):912-919.
Fujita M et al., "A novel disaccharide substrate having 1,2-oxazoline moiety for detection of transglycosylating activity of endoglycosidases" Biochim Biophys Acta. Sep. 3, 2001;1528(1):9-14.

Galfrè et al., "Preparation of monoclonal antibodies: strategies and procedures," Methods Enzymol., 1981, 73(Pt B):3-46.
Gazzano-Santoro et al., "A non-radioactive complement-dependent cytotoxicity assay for anti-CD20 nonclonal antibody," J. Immunol. Methods, Mar. 28, 1997, 202(2): 163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2$^{nd}$ ed., Chapter 3: Production of Monoclonal Antibodies, 1986, pp. 59-103, Academic Press, London.
Goochee CF et al., "The oligosaccharides of glycoproteins: bioprocess factors affecting oligosaccharide structure and their effect on glycoprotein properties", Biotechnology (N Y). Dec. 1991;9(12):1347-55.
Gottschling et al., "Stage-specific embryonic antigen-4 is expressed in basaloid lung cancer and associated with poor prognosis," Eur. Respir. J., Mar. 2013, 41(3):656-663.
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Green, "Targeting targeted therapy," N. Engl. J. Med., May 20, 2004, 350(21):2191-2193.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in Escherichia coli," J. Immunol., Jun. 1, 1994, 152(11):5368-5374.
Guss et al., "Structure of the IgG-binding regions of streptococcal protein G," EMBO J., Jul. 1986, 5(7):1567-1575.
Guyer et al., "Immunoglobulin binding by mouse intestinal epithelial cell receptors," J. Immunol., Aug. 1976, 117(2):587-593.
Hakomori et al., "Glycosphingolipid antigens and cancer therapy," Chem. Biol., Feb. 1997, 4(2):97-104.
Hakomori, "Glycosylation defining cancer malignancy: new wine in an old bottle," Proc. Natl. Acad. Sci. U.S.A., Aug. 6, 2002, 99(16):10231-10233.
Hara et al., "Overproduction of penicillin-binding protein 7 suppresses thermosensitive growth defect at low osmolarity due to an spr mutation of Escherichia coli," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.
Hawkins et al., "Selection of phage antibodies by binding affinity. Mimicking affinity maturation," J. Mol. Biol., 1992, 226(3):889-896.
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hogrefe et al., "A bacteriophage lambda vector for the cloning and expression of immunoglobulin Fab fragments on the surface of filamentous phage," Gene, Jun. 15, 1993, 128(1):119-126.

(56) References Cited

OTHER PUBLICATIONS

Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of geiniline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of F(ab')$_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells,"*Embo J.*, 1983, 2(12):2355-2361.
Karlin S. et al., "Methods for assessing the statistical significance of molecular sequence features by using general scoring schemes", *Proc Natl Acad Sci U S A*. Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell*. Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood*. May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15,1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Louis et al., "The 2007 WHO classification of tumours of the central nervous system," *Acta. Neuropathol.*, Aug. 2007, 114(2):97-109.
MacFarlane GT, et al., "Formation of glycoprotein degrading enzymes by Bacteroides fragilis" *FEMS Microbiol Lett*. Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matsuda et al., "Structure and physical map of 64 variable segments in the 3' 0.8-megabase region of the human immunoglobulin heavy-chain locus," *Nature Genet.*, Jan. 1993, 3(1):88-94.

(56) References Cited

OTHER PUBLICATIONS

McCafferty et al., "Phage antibodies: Filamentous phage displaying antibody variable domains," *Nature*, Dec. 6, 1990, 348:552-554.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.
Meyer, "Malignant gliomas in adults," *N. Engl. J. Med.*, Oct. 23, 2008, 359(17):1850.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Morelle, W. et al., "The Mass Spectrometric Analysis of Glycoproteins and their Glycan Sturctures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Nicolaou et al., "Calicheamicin$\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Noto et al., "CD44 and SSEA-4 positive cells in an oral cancer cell line HSC-4 possess cancer stem-like cell characteristics," *Oral Oncol.*, Aug. 2013, 49(8):787-795.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5$^-$) herpes simplex virus HSV1716 following intratumoural injection into human malignant glioma: a proof of principle study," *Gene Therapy*, Mar. 2002, 9(6):398-406.
Pearlman et al., *Peptide and Protein Drug Delivery*, Chapter 6: Analysis of Protein Drugs, Lee, ed., 1991, pp. 247-301, Marcel Dekker Publishing, New York.
Peipp et al., "Antibody fucosylation differentially impacts cytotoxicity mediated by NK and PMN effector cells," *Blood*, 2008, 112(6):2390-2399.
Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology*, vol. 113: The Pharacology of Monoclonal Antibodies, Chapter 11: Antibodies from *Escherichia coli*, Rosenberg et.al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigbò P, Guzmán E, Romeu A, Garcia-Vallvé S. OPTIMIZER: a web server for optimizing the codon usage of DNA sequences. Nucleic Acids Res. Jul. 2007;35(Web Server issue):W126-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol. Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups*, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-

(56) References Cited

OTHER PUBLICATIONS type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol*. Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tutt et al., "Trispecific F(ab')$_3$ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
Van Beek et al., "Increased sialic acid density in surface glycoprotein of transformed and malignant cells—a general phenomenon?" *Cancer Res.*, Nov. 1973, 33(11):2913-2922.

Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 2004, 4(2):89-99.
Yansura et al., "Nucleotide sequence selection for increased expression of heterologous genes in *Escherichia coli*," *Methods: A Companion to Methods in Enzymol.*, Aug. 1992, 4(2):151-158.
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "Selection of tumor antigens as targets for immune attack using immunohistochemistry: I. Focus on gangliosides," *Int. J. Cancer*, Sep. 26, 1997, 73(1):42-49.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
U.S. Appl. No. 15/005,930, filed Jan. 25, 2016, Wong et al.

(56) References Cited

OTHER PUBLICATIONS

U.S. Appl. No. 15/011,543, filed Jan 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related $\alpha$-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$CD4$^+$CD8$^-$thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R. "In vivo imaging of membraneassociated glycans in developing zebrafish." Science 2008, 320, 664-667.

Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by The Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," Nature, Jul. 5, 2007, 448(7149):44-49.
Bosmann et al., "Enzyme activity in invasive tumors of human breast and colon," Proc. Natl. Acad. Sci. USA, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell in Situ Using 16S rRNA-Targeted Probes, Biotechniques, 13, 928-931 (1992).
Bricard et al., "Enrichment of human CD4$^+$V$\alpha$24/V$\beta$11 invariant NKT cells in intrahepatic malignant tumors," J. Immunol., Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" MMWR, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).

(56) References Cited

OTHER PUBLICATIONS

Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.

Chang, S. H. et al. Glycan array on aluminum oxide-coated glass slides through phosphonate chemistry. J. Am. Chem. Soc. 132, 13371-13380, (2010).

Chang et al., "Potent immune-modulating and anticancer effects of NKT cell stimulatory glycolipids," *Proc. Natl. Acad. Sci. USA*, Jun. 19, 2007, 104(25):10299-10304.

Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.

Chari, Ravi et al., Immunoconjuates Containing Novel Maytansinoids: Promising Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Cheng, Peter et al., Oseltamivir- and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza a (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Domain association in immunoglobulin molecules. The packing of variable domains," J. Mol. Biol., Dec. 5, 1985, 186(3):651-663.

Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Codelli, J. A. et al., Second-Generation Difluorinated Cyclooctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2.6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis by Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDS vaccine development learned from studies of equine infectious, anemia virus infection and immunity. Viruses 5, 2963-76, (2013).

Crispin et al., "Carbohydrate and domain architecture of an immature antibody glycoform exhibiting enhanced effector functions," J. Mol. Biol., Apr. 17, 2009, 387(5):1061-1066.

Cyranoski, Threat of Pandemic Brings Flu Drug Back to Life, Nat. Med. Sep. 2005, 11(9): 909.

Davies, JW et al., Streamlining Lead Discovery by Aligning in Silico and High-Throughput Screening, Curr Opin Chem Biol. Aug. 2006; 10(4):343-51.

Davodeau et al., "Close phenotypic and functional similarities between human and murine αβ T cells expressing invariant TCR alpha-chains," *J. Immunol.*, Jun. 15, 1997, 158(12):5603-5611.

De Almeida et al., "Thiacycloalkynes for copper-free click chemistry," *Angew. Chem. Int. Ed. Engl.*, Mar. 5, 2012, 51(10):2443-2447.

Debets, M. F. et al., Bioconjugation with Strained Alkenes and Alkynes, Acc. Chem. Res. 2011, 44, 805-815.

Dejong et al., Fatal outcome of human influenza A (H5N1) is associated with high viral load and hypercytokinemia. Nat Med Oct. 2006;12(10):1203-7. Epub Sep. 10, 2006.

Delente, Jacqubs, Glycosylation Revisited, Trends in Biotechnology 3, letters to editor, No. 9 (1985).

Dellabona et al., "An invariant Vα24-JαQ/Vβ311 T cell receptor is expressed in all individuals by clonally expanded CD4⁻8⁻ T cells," *J. Exp. Med.*, Sep. 1, 1994, 180(3):1171-1176.

Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.

Dennis, Carina, Cancer: Off by a whisker, Nature 442: 739-741 (2006).

De Paz, J. L., Horlacher, T. & Seeberger, P.H. Oligosaccharide microarrays to map interactions of carbohydrates in biological systems. Methods Enzymol. 415, 269-292, (2006).

Dhodapkar et al., "α-Galactosyl ceramide-loaded dendritic cells for expansion of natural killer T cells" CAPLUS 145:354715 (2006).

Dhodapkar et al., "A reversible defect in natural killer T cell function characterizes the progression of premalignant to malignant multiple myeloma," *J. Exp. Med.*, Jun. 16, 2003, 197(12):1667-1676.

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.

Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.

Dommerholt, Jan, Readily Accessible Bicyclononynes for Bioorthogonal Labeling and Three-Dimensional Imaging of Living Cells, Angew. Chem. Int. Ed. 2010, 49, 9422-9425.

Doores KJ, et al. A nonself sugar mimic of the HIV glycan shield shows enhanced antigenicity. Proc. Natl. Acad Sci. US.A. 107(40), 17107-17112, (2010).

Doores, K. J. & Burton, D.R. Variable Loop Glycan Dependency of the Broad and Potent HIV-I-Neutralizing Antibodies PG9 and PG16. J. Virol. 84, 10510-10521.

Doores, K. J. et al. Envelope glycans of immunodeficiency virions are almost entirely oligomannose antigens. Proc. Natl. Acad. Sci. U. S. A 107, 13800-13805, (2010).

Doronina, Svetlana et al., Development of Potent Monoclonal Antibody Auristatin Conjugates for Cancer Therapy, Nat Biotechnol 21(7): 778-784 (2003).

Dougan, Michael et al., Immune Therapy for Cancer, Annual Review of Immunology, 2009, 27, pp. 83-117.

Drugs of the future 25(7): 686 (2000).

Dubertret. Benoit et al., In Vivo Imaging of Quantum Dots Encapsulated in Phospholipid Micelles, Science 298:759-1762, 2002.

Duncan, AR; Winter, G, The binding Site for C1q on IgG, Nature 322:738-40 (1988).

(56) References Cited

OTHER PUBLICATIONS

Dunn et al., Zanamivir: A Review of Its Use in Influenza, Drugs, Oct. 1999, 58(4):761-784.
Eberl et al., "Selective bystander proliferation of memory CD4+ and CD8+ T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
European Search Report issued in connection with corresponding European Patent Application No. 15181446.4, Dec. 7, 2015, 10 pages.
Evans, Michael et al., "Mechanism-based profiling of enzyme families," *Chem Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers Immunity 40, 657-68, 2014.
Fan, Shu-Quan et al., Remarkable Transglycosylation Activity of Glycosynthase Mutants of Endo-D, an Endo-β-N-acetylglucosaminidase from *Streptococcus pneumoniae*, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.

Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gpl40. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun 2005, 73, 4803.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Govorkova et al, Combination chemotherapy for influenza. Viruses. Aug. 2010;2(8):1510-29.
Gordon et al., "Reactivity of biarylazacyclooctynones in copper-free click chemistry," *J. Am. Chem. Soc.*, Jun. 6, 2012, 134(22): 9199-9208.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.
Greenbaum et al., "Chemical approaches for functionally probing the proteome," *Mol. Cell. Proteomics*, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.

(56) References Cited

OTHER PUBLICATIONS

Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.

Gulland, Fire Cases of Spread of Oseltamivir Resistant Swine Flu Between Patients are Reported in Wales, BMJ, Nov. 23, 2009:339:b4975.

Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.

Ha, Ya et al., X-Ray Structure of the Hemagglutinin of a Potential H3 Avian Progenitor of the 1968 Hong Kong Pandemic Influenza Virus, Virology, 309:209-218, 2003.

Hajishengallis, "Mucosal immunization with a bacterial protein antigen genetically coupled to cholera toxin A2/B subunits," *J. Immuol.*, May 1, 1995, 154(9):4322-4332.

Ham, Richard et al., Media and Growth Requirements, Meth. Enz 58, 44 (1979).

Hammerling et al., in: Monoclonal Antibodies and T-Cell Hybridomas 563-587, 1981.

Han, Junyan et al., 3- and 5-Functionalized BODIPYs via the Liebeskind-Srogl Reaction, Organic & Biomolecular Chemistry (2009), 7(1), 34-36.

Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).

Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).

Hasegawa, Akira, et al., Synthesis of Sialyl Lewis X Ganglioside Analogues Containing Modified L-Fucose Residues, Carbohydr. Res. 1995, 274, 165-181.

Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.

Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.

Henglein, A. et al., Absorption Spectrum and Some Chemical Reactions of Colloidal Platinum in Aqueous Solution, J. Phys. Chem., 99, 14129 (1995).

Herner, A et al., A new family of bioorthogonally applicable fluorogenic labelst, Org. Biomol. Chem. 2013, 11, 3297-3306.

Hey, Thomas et al., Artificial, non-antibody binding proteins for pharmaceutical and industrial application, Trends in Biotechnology 23(10) 514-522 (2005).

Hirabayashi, J. et al., Oligosaccharide Microarrays for Glycomics, Trends in Biotechnology 21 (4): 141-143, 2003.

Holmskov, Uffe et al., Collectins: Collagenous C-Type Lectins of the Innate Immune Defense System, 1994, Immunol. Today, 15: 67.

Honda et al., Synthesis and anti-influenza virus activity of 7-0-alkylated derivatives related to zanamivir. Bioorg Med Chem Lett. Aug. 5, 2002;12(15):1925-8.

Hotha, Srinivas et al., "Click Chemistry" Inspired Synthesis of Pseudo-Oligosaccharides and Amino Acid Glycoconjugates, J Org Chem 2006, 71, 364-367.

Horiya, S. et al., Recent strategies targeting HIV glycans in vaccine design. Nat. Chem. Biol. 10, 990-999, (2014).

Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.

Howard et al., "Biological properties of interleukin 10," *Immunol. Today*, Jun. 1992, 13(6):198-200.

Hsu et al., "Alkynyl sugar analogs for the labeling and visualization of glycoconjugates in cells," *Proc. Natl. Acad. Sci. USA*, Feb. 20, 2007, 104(8), 2614-2619.

Hsu, Nien-Yeen et al., Desorption Ionization of Biomolecules on Metals, Anal. Chem., 80, 5203-5210, 2008.

Huang, Lijun et al., Iterative One-Pot Syntheses of Chitotetroses, Carbohydr. Res. 2006, 341, 1669-1679.

Huang et al., Recombinant immunotherpaeutics: current state and perspectives regarding the feasibility and market, Appl Microbiol Biotechnol, 87: 401-410. 2010.

Immunogenicity, Wikipedia p. 1-3. Downloaded on Aug. 16, 2016 from https://en.wikipedia.org/wiki/Immunogenicity. (2016).

International Search Report and Written Opinion issued for International application No. PCT/US2015/011748, dated Aug. 21, 2015, 17 pages.

International Search Report dated Jan. 13, 2012, from corresponding International Patent Application No. PCT/US2011/035982, 17 pages.

International Search Report dated Nov. 13, 2014, from corresponding International Patent Application No. PCT/US2014/054617, 10 pages.

International Search Report issued for International application No. PCT/US15/22977, dated Jun. 22, 2015, 3 pages.

International Search Report issued for International application No. PCT/US15/40199, dated Mar. 2, 2016, 6 pages.

International Search Report issued for International application No. PCT/US2009/050754, dated Feb. 24, 2010, 10 pages.

International Search Report and Written Opinion in International Application No. PCT/US2017/021454, dated Jul. 31, 2017, 8 pages.

Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.

Ito, Akihiro et al., A Novel Ganglioside Isolated From Renal Cell Carcinoma, Biol Chem 2001, 276, 16695.

Jacobs et al., "Metabolic labeling of glycoproteins with chemical tags through unnatural sialic acid biosynthesis," *Methods Enzymol.*, 2000, 327:260-275.

Japanese Office Action dated Apr. 21, 2015, from Related Japanese Patent Application No. 2013-510261, 6 Pages.

Jayasena, Sumedha, Aptamers: An Emerging Class of Molecules That Rival Antibodies in Diagnostics, Clin. Chem. (1999), 45, 1628-1650.

Jewett, J.C.; Bertozzi, C.R., Cu-Free Click Cycloaddition Reactions in Chemical Biology, Chem. Soc. Rev. 2010, 39, 1272-1279.

Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.

Jewett et al., "Synthesis of a fluorogenic cyclooctyne activate by Cu-free click chemistry," *Org. Lett.*, Nov. 18, 2011, 13(22):5937-5939.

Jin, R. C. et al., Photoinduced Conversion of Silver Nanospheres to Nanoprisms, Science (2001), 294, 1901-1903.

Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.

John, F. & Hendrickson, T. L. Synthesis of Truncated Analogues for Studying the Process of Glycosyl Phosphatidylinositol Modification. Org. Lett. 12, 2080-2083, (2010).

Jonges, M. et al., Dynamics of Antiviral-Resistant Influenza Viruses in the Netherlands, 2005-2008, Antiviral Res., Sep. 2009, 83(3): 290-297.

Jorgensen, Trond et al., Up-Regulation of the Oligosaccharide Sialyl Lewisx: A New Prognostic Parameter in Metastatic Prostate Cancer, Cancer Res. 55, 1817-1819, 1995.

Jose, Jiney et al., Energy transfer dyads based on Nile Red, Tetrahedron Letters (2009), 50(47), 6442-6445.

Joshi, Shantaran et al., Cell Surface Properties Associated with Malignancy of Metastatic Large Cell Lymphoma Cells, (1987) Cancer Res. 47, 3551-3557.

Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A, 105, 15684-15689, (2008).

(56) References Cited

OTHER PUBLICATIONS

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," Chem. Commun., Jan. 28, 2010, 46(4):589-591.
Kamkaew, A. et al., "BODIPY dyes in photodynamic therapy." Chem. Soc. Rev. 2013, 42, 77-88.
Kawakami et al., "Critical role of V$\alpha$14$^+$ natural killer T cells in the innate phase of host protection against Streptococcus pneumoniae infection," Eur. J. Immunol., Dec. 2003, 33(12):3322-3330.
Kawano et al., "CD1d-restricted and TCR-mediated activation of v$\alpha$14 NKT cells by glycosylceramides," Science, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," Biol. Pharm. Bull., Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," Biochemistry, Apr. 3, 2001, 40(13):4005-4015.
Kiick, K.L. et al., Identification of an Expanded Set of Translationally Active Methionine Analogues in Escherichia Coli, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "$\alpha$-galactosylceramide induces early B-cell activation through IL-4 production by NKT cells," Cell. Immunol., Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," Angew. Chem. Int. Ed. Engl., Jun. 1, 2001, 40(11):2004-2021.
Kolb et al., "The growing impact of click chemistry on drug discovery," Drug Discov. Today, Dec. 15, 2003, 8(24):1128-1137.

Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," Immunol. Res., 1998,.17(3):303-312.
Koshihara et al., 1984, Biochmica et biophysica acta, 792(1), pp. 92-97.
Kotteas et al., Immunotherapy for pancreatic cancer, J cancer Res Clin Oncol, 142(8): 1795-1805, 2016.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor $\alpha$ chain is used by a unique subset of major histocompatibility complex class I-specific CD4$^+$ and CD4$^-$8$^-$ T cells in mice and humans," J. Exp. Med., Sep. 1, 1994, 180(3):1097-1106.
Lau, K. et al. Highly efficient chemoenzymatic synthesis of $\beta$1-4-linked galactosides with promiscuous bacterial $\beta$1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, Dev. Biol. Stand., 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected $\alpha$,$\omega$-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lemieux, R. U. et al., Halide ion catalyzed glycosidation reactions. Syntheses of a-linked disaccharides. J Am. Chem. Soc. 97(14), 4056-62, (1975).
Lew et al., Discovery and Development of GS 4104 (oseltamivir): an Orally Active Influenza Neuraminidase Inhibitor, Curr Med Chem, Jun. 2000, 7(6):663-672.
Li et al., $\beta$-endorphin omission analogs: Dissociation of Immunoreactivity from other biological activities, Proc Natl Avad Sci USA, 77:3211-3214 (1980).

(56) References Cited

OTHER PUBLICATIONS

Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," Proc. Natl. Acad. Sci. USA, Jul. 20, 2010, 107:13010-13015.
Li, J.; Hu, M.; Yao, S. Q. "Rapid synthesis, screening, and identification of xanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Liang et al., "Quantitative microarray analysis of intact glycolipid-CD1d interaction and correlation with cell-based cytokine production," J. Am. Chem. Soc., Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Lin et al., A common glycan structure on immunoglobulin G for enhancement of effector functions, PNAS, Aug. 25, 2015, vol. 112, No. 34, p. 10611-10616.
Liu et al., "Activity-based protein profiling: the serine hydrolases," Proc. Natl. Acad. Sci. USA, Dec. 21, 1999, 96(26):14694-14699.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu, Guokai et al., Reactivity-Based One-Pot Synthesis of Immunosuppressive Glycolipids From the Caribbean Sponge Plakortis Simplex, J. Chem. 2009, 27, 2217-2222.
Lu et al., "Single chain anti-c-Met antibody conjugated nanoparticles for in vivo tumor-targeted imaging and drug delivery," Biomaterials, Apr. 2011, 32(12):3265-3274.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR $\alpha$ chain in $NK1.1^+$ T cell populations, Int. Immunol., Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," Nat. Biotechnol., Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gpl20 V1/V2 domain with broadly neutralizing antibody PG9. Nature 480, 336-343, 2011.
Merck, MAB4304, Anti-Stage-Specific Embryonic Antigen-4 Antibody, Clone MV-813-70, 4 pages, 2017.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," Glycobiology, Jul. 2012, 22(7):880-896.
Miyagi et al., "Plasma membrane-associated sialidase as a crucial regulator of transmembrane signalling," J. Biochem., Sep. 2008, 144(3):279-285.
Miyagi et al., "Sialidase and malignancy: a minireview," Glycoconj. J., 2004, 20(3):189-198.
Miyagi, "Aberrant expression of sialidase and cancer progression," Proc. Jpn. Acad. Ser. B. Phys. Biol. Sci., 2008(10), 84:407-418.
Miyaji, E. N. et al., Induction of Neutralizing Antibodies Against Diphtheria Toxin By Priming with Recombinant Mycobacterium Bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H 2$ bias of natural killer T cells," Nature, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," Adv. Carbohydr. Chem. Biochem., 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," Immunol. Today, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).

(56) References Cited

OTHER PUBLICATIONS

Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).

Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).

Natarajan et al, Caffeic acid phenethyl ester is a potent and specific inhibitor of activation of nuclear transcription factor NF-kappa B. Proc Natl Acad Sci USA Aug. 20, 1996;93(17):9090-5.

Ni, Jing et al., Immunoassay Readout Method Using Extrinsic Raman Labels, Adsorbed on Immunogold Colloids, Anal. Chem., 1999, 71(21), pp. 4903-4908.

Nieuwenhuis et al., "CD1d-dependent macrophage-mediated clearance of *Pseudomonas aeruginosa* from lung," *Nat. Med.*, Jun. 2002, 8(6):588-593.

Nielsen, U. B. et al., Multiplexed Sandwich Assays in Microarray Format, Journal Immunol. Meth. (2004), 290, 107-120.

Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.

Nowak, MW et al., Nicotinic Receptor Binding Site Probed With Unnatural Amino Acid Incorporation in Intact Cells, Science 268:439, 1995.

Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.

Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.

Office Action dated Dec. 3, 2013, from corresponding Chinese Patent Application No. 201180034218.3, 15 total pages.

Office Action dated Oct. 22, 2014, from corresponding Chinese Patent Application No. 201180034218.3, 16 total pages.

O'Garra, "Cytokines induce the development of functionally heterogeneous T helper cell subsets," *Immunity*, Mar. 1998, 8(3):275-283.

Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.

Okamura et al., "Interleukin-18: a novel cytokine that augments both innate and acquired immunity," *Adv. Immunol.*, 1998, 70:281-312.

Olden, Kenneth et al., Carbohydrate Moieties of Glycoproteins: A Re-Evaluation of Their Function, Biochem et Biophys Acta 650:209-232 (1982).

Otsubo N, et al., An Efficient and Straightforward Synthesis of Sialyl Lex Glycolipid as a Potent Selectin Blocker[[1]], Carbohydr. Res. 1998, 306, 517-530.

Ottolini et al., Combination anti-inflammatory and antiviral therapy of influenza in a cotton rat model. Pediatr. Pulmonol. 2003:36;290-4.

Oyelaran, 0. & Gildersleeve, J. C. Glycan arrays: recent advances and future challenges. Curr. Opin. Chem. Biol. 13, 406-413, (2009).

Pabst, M. et al., Glycan profiles of the 27 Nglycosylation sites of the HIV envelope protein CN54gp140. Biol. Chem. 393, 719-730, (2012).

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.

Pan, Yanbin et al., Synthesis and Immunological Properties of N-Modified GM3 Antigens as Therapeutic Cancer Vaccines, J. Med. Chem., 48(3), 875-883, 2005.

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).

Pancera, M. et al. Structural basis for diverse N-glycan recognition by HIV-I-neutralizing V1-V2-directed antibody PG16. Nat. Struct. Mol. Biol. 20, 804-813, (2013).

Parker, C. A.; Rees, W. T., Correction of Fluorescence Spectra and Measurement of Fluorescence Quantum Efficiency, Analyst 1960, 85, 587-600.

Parrish, M. L. et al., A Microarray Platform Comparison for Neuroscience Applications, J. Neurosci. Methods, 2004, 132, 57-68.

Patricelli et al., "Functional interrogation of the kinome using nucleotide acyl phosphates," *Biochemistry*, Jan. 16, 2007, 46(2):350-358.

Paulson, J. C., Blixt, 0. & Collins, B. E. Sweet spots in functional glycomics. Nat. Chem. Biol. 2, 238-248, (2006).

Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.

Peiris et al., Re-emergence of fatal human influenza a subtype H5N1disease. Lancet. Feb. 21, 2004;363(9409):617-9.

Pejchal, R. et al. A potent and broad neutralizing antibody recognizes and penetrates the HIV glycan shield. Science 334, 1097-1103, (2011).

Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.

Perlmutter, R.M. et al., Subclass Restriction of Murine Anti-Carbohydrate Antibodies, Journal of Immunology 1978, 121, 566-572.

Pettit, George et al., Antineoplastic Agents. Part 189. The Absolute Configuration and Synthesis of Natural (−)-Dolastatin 10, J Am Chem Soc. 111:5463-5465 (1989).

Pettit, George et al., Dolastatins 23: Stereospecific Synthesis of Dolaisoleuine, J Chem Soc Perkin Trans. 15:853-858 (1996).

Pettit, George et al., Antineoplastic Agents 365. Dolastatin 10 SAR Probes, Anti-Cancer Drug Design 13:243-277 (1998).

Pettit, Robin et al., Specific Activities of Dolastatin 10 and Peptide Derivatives Against Cryptococcus Neoformans, Antimicrob Agents Chemother. 42:2961-2965.

Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.

Poloukhtine et al., "Selective labeling of living cells by a photo-triggered click reaction, " *J. Am. Chem. Soc.*, Nov. 4, 2009, 131(43):15769-15776.

Porcelli, S.A., "Preparation of α-galactosylceramide derivatives as modulators of immunity and autoimmunity," CAPLUS 147:440317 (2007).

Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.

Pratt, M. R. & Bertozzi, C. R. Chemoselective ligation applied to the synthesis of a biantennary N-linked glycoform of CD52. J Am. Chem. Soc. 125, 6149-6159, (2003).

Prescher, J. A.; Bertozzi, C.R. "Chemistry in living systems." Nat. Chem. Biol. 2005, 1, 13-21.

Pritchard, L. K. et al. Structural Constraints Determine the Glycosylation of HIV-I Envelope Trimers. Cell Rep. 11, 1604-13, (2015).

Pritchard, Laura et al., Cell- and Protein- Directed Glycosylation of Native Cleaved HIV-I Envelope. J. Virol. 89, 8932-44, (2015).

Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.

Qi, Jianjun et al., Developing visible fluorogenic 'clickon' dyes for cellular imaging, Bioconjugate Chem. 2011, 22, 1758-1762.

(56) References Cited

OTHER PUBLICATIONS

Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gpl20 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H1$ and $T_H2$ responses: a key role for the 'natural' immune response?" *Immunol. Today*, Oct. 1992, 13(10):379-381.
Rosenstein, N. E. et al, Meningococcal Disease, N. Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Bioterp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.

Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-Bodipy Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et al., "Proteomic profiling of metalloprotease activities with cocktails of active-site probes," *Nat. Chem. Biol.*, May 2006, 2(5):274-281.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.

(56) References Cited

OTHER PUBLICATIONS

Sletten et al., "Bioorthogonal Chemistry: Fishing for Selectivity in a Sea of Functionality," Angew. Che. Int. Ed. Engl., Aug. 27, 2009, 48(38):6974-6998.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced By 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Sutton, VR et al., Bcl-2 Prevents Apoptosis Induced by Perforin and Granzyme B, But Not That Mediated By Whole Cytotoxic Lymphocytes, J of Immunology 1997, 158(12), 5783.
Tahir et al., "Loss of IFN-γ production by invariant NK T cells in advanced cancer," J. Immunol., Oct. 1, 2001, 167(7):4046-4050.

Takakura, Yoshimitsu et al., Molecular cloning, expression and properties of an alpha/beta-Galactoside alpha 2,3-sialyltransferase from Vibrio sp. JT-FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai, Charng-sheng et al., Development of Trifunctional Probes for Glycoproteomic Analysis, Chem. Commun. 2010, 46, 5575-5577.
Tsai TI, et al., "Effective sugar nucleotide regeneration for the large-scale enzymatic synthesis of Globo H and SSEA4" J Am Chem Soc. Oct. 2, 2013;135(39):14831-9, Epub Sep. 17, 2013.
Tseng, Susan Y. et al., Glycan Arrays on Aluminum Coated Glass Slides. Chem. Asian. J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.

(56) References Cited

OTHER PUBLICATIONS

Van der Horst et al., "Photoaffinity labeling of a bacterial sialidase with an aryl azide derivative of sialic acid," J. Biol. Chem., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," Biochem. J., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," Angew. Chem. Int. Ed. Engl., Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases,"Methods Mol. Biol., 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J. Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew.Chem Int Ed (2013) vol. 52, pp. 9157-9161.
Wang, Michael et al., "Mechanism by which mutations at his274 alter sensitivity of influenza a virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "Trypanosoma cruzi trans-sialidase operates through a covalent sialyl-enzyme intermediate: tyrosine is the catalytic nucleophile," J. Am. Chem. Soc., Jun. 25, 2003, 125(25):7532-7533.
Weibel, Robert et al., Tumor-Associated Membrane Sialoglycoprotein on Human Small Cell Lung Carcinoma Identified by the 1gG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," Nat. Chem. Biol., Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," Proc. Natl. Acad. Sci. USA, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.

(56) References Cited

OTHER PUBLICATIONS

Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang et al., "New cerebrosides from Acanthopanax gracilistylus," CAPLUS 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogeneous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact 1gG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.
Greene, Theodora et al., Protective Groups in Organic Synthesis, pp. 42-51 and 96-100, 1991.
Unverzagt, Carlo et al., A Double Regio—and Stereoselective Glycosylation Strategy for the Synthesis of N-Glycans, Chem. Eur. J., 2008, 14, 1304-1311.

\* cited by examiner a. NaH, PMBCl, DMF, rt, 1 h;
b. BH₃, Bu₂BOTf, 0 °C, 2 h;
c. Ethylenediamine, ethanol, 80 °C, 16 h;
d. TrocCl, NaHCO₃, THF, rt, 16 h.

a. Ac$_2$O, pyridine, rt, 12 h;
b. NIS, cat. TfOH, benzyl 5-hydroxypentylcarbamate, CH$_2$Cl$_2$, -30 °C, 3 h;
c. NaOMe, MeOH, rt, 10 h;
d. BnBr, NaH, rt, 2 h;
e. DDQ, CH$_2$Cl$_2$/H$_2$O, rt, 2 h.

a. 7, 12, TMSOTf, MS 4Å, a. NIS, TfOH, dibutylphosphate, MS4Å, CH$_2$Cl$_2$, 0 °C, 10 h, 89%;
b. Et$_3$SiH, TfOH, MS4Å, CH$_2$Cl$_2$, -78 °C, 1 h, 85%;
c. TMSOTf, CH$_2$Cl$_2$, MS4Å, -78 °C, 2 h, 87%.

a. TMSOTf, MS4Å, CH$_2$Cl$_2$, -50°C, 2 h;
b. NIS, TfOH, MS4Å, CH$_2$Cl$_2$, 0 °C, 23 h.

a. 3, 4, TBDMSOTf, MS 4Å, CH$_2$Cl$_2$, -50 °C, 2 h;
b. 5, NIS, 0 °C, 22 h.

a. (i) LiOH · H₂O, Dioxane, H₂O, 90-95 °C, 36 h; (ii) Ac₂O, NaHCO₃, H₂O then LiOH, H₂O, rt, 12 h; (iii) Pd(OH)₂, H₂, CH₃OH, H₂O, rt, 12 h; b. (i) LiOH · H₂O, Dioxane, H₂O, 90-95 °C, 36 h; (ii) Ac₂O, pyridine, DMAP, 12 h; (iii) BF₃·OEt₂, CH₃CN, 0 °C→rt, 18 h; (iv) LiOH, H₂O, rt, 12 h (v) Pd(OH)₂, H₂, CH₃OH, H₂O, rt, 12 h.

27:

28:

29:

30:

31:

1:

C1, R = (CH₂)₂₄CH₃
C23, R = (CH2)₇PhF
C34, R = (CH₂)₁₀PhOPhF
7DW8-5, R = (CH₂)₁₀PhF

Binding curves for RM2 printed at different concentrations (100, 50, 25, 12.5, and 6.25 µM) are shown. The curves were obtained by using Cy3-labeled goat anti-mouse IgM secondary antibody.

Binding curve for RM2 antibody for 29 printed at different concentrations.

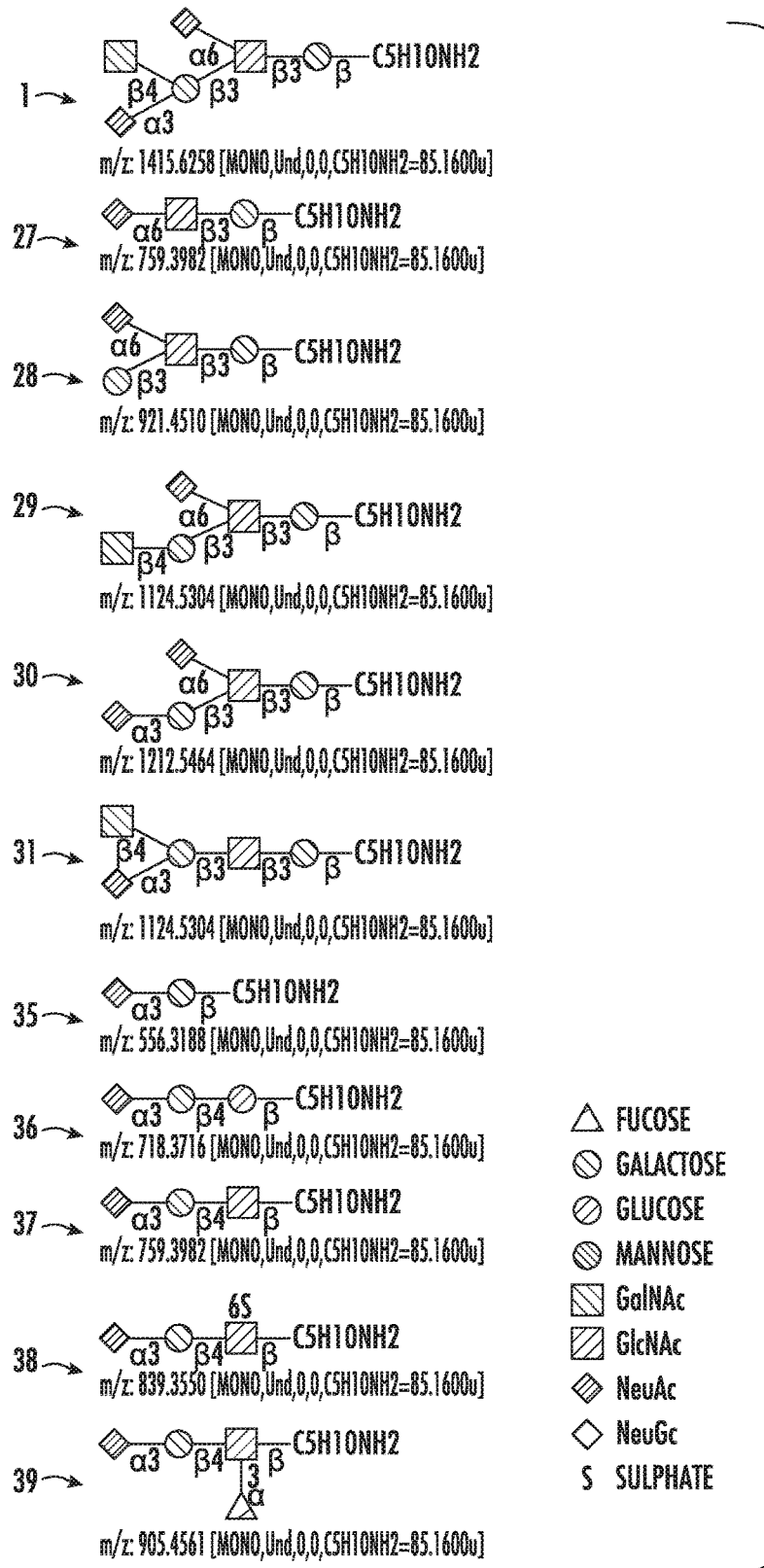

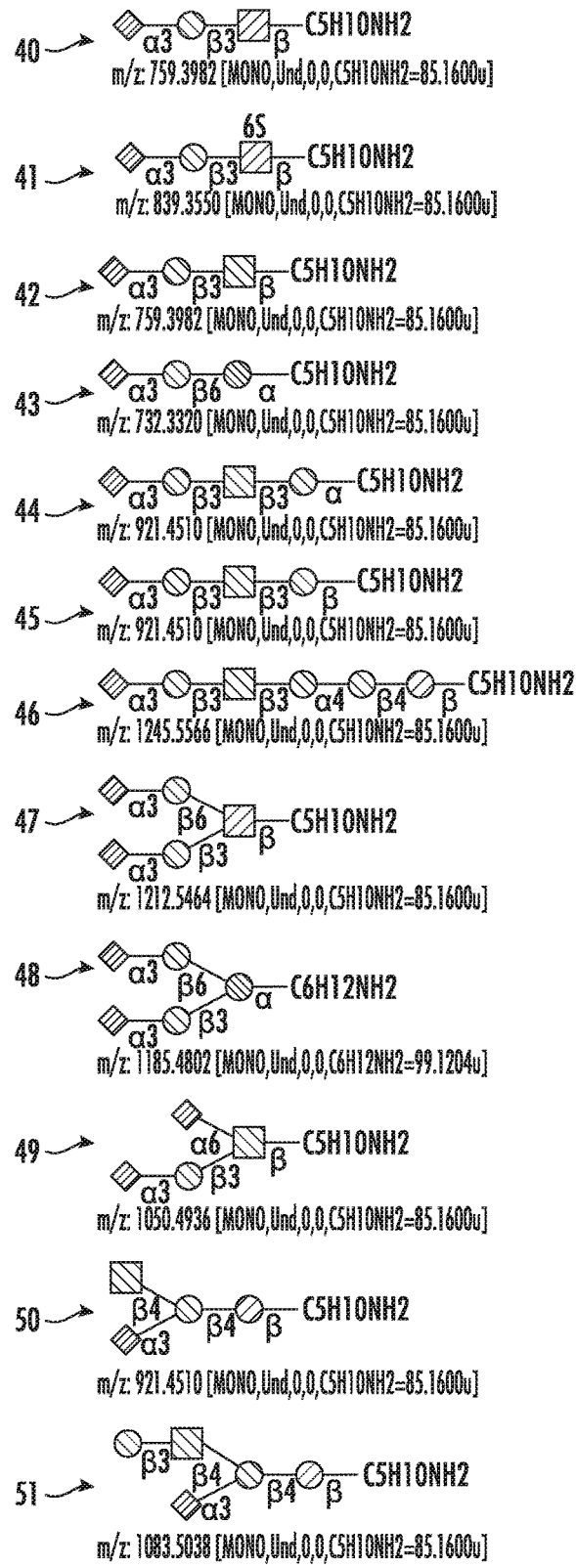

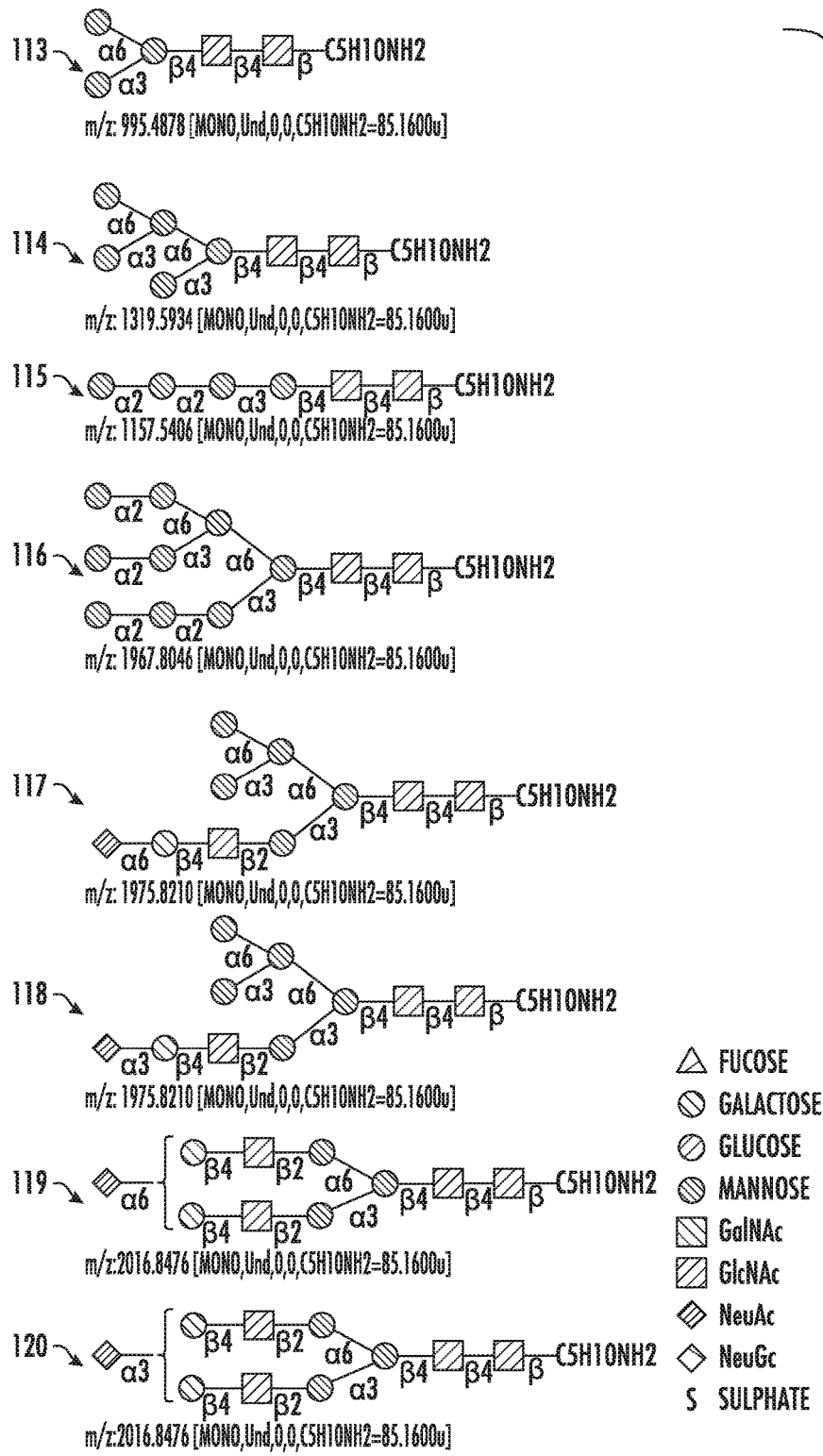

RM2 ANTIGENS AND USE THEREOF

CROSS-REFERENCE TO RELATED APPLICATION

This application is a § 371 national stage entry of International Application No. PCT/US2014/044465, filed Jun. 26, 2014, which claims the benefit of U.S. Provisional Patent Application Ser. No. 61/839,648, filed Jun. 26, 2013 and titled "RM2 CONJUGATES AND USE THEREOF," the contents of which are incorporated herein in the entirety by reference.

TECHNICAL FIELD OF INVENTION

This invention relates to cancer antigens such as RM2 and uses thereof for preparing cancer vaccines. In particular, the application relates to carbohydrate-based conjugates and their application in cancer therapy.

BACKGROUND OF THE INVENTION

Cancer immunotherapy has been an attractive target in the multidisciplinary treatment of cancer patients. Cancer immunotherapy can generally be classified as: (a) passive (or adaptive), consisting of administration of cells or antibodies ex vivo, and (b) active, represented by vaccines, which aims at eliciting a specific immune response against tumor-associate antigens (TAAs) (Dougan et al., *Annual Review of Immunology*, 2009, 27, pp 83-117). Tumor-associate carbohydrate antigens (TACAs) are not only most abundantly and sometimes aberrantly expressed on the surface of cancer cells but also absent or rarely expressed on normal cells, many of which have been characterized for specific types of cancer (Stevanovic, S., *Nat. Rev. Cancer*, 2002, 2, 514-520; Hakomori et al., *Chem. Biol.*, 1997, 4, 97-104). Thus, it is of great interest to identify TACAs for use in developing efficient cancer vaccines.

Recently, certain TACAs were identified by monoclonal antibodies and mass spectrometry (Shriver et al., *Nat. Rev. Drug Disc.*, 2004, 3, 863-873; Pacino et al. Br. J. Cancer, 1991, 63, 390-398). Many TACAs expressed on cancer cells in the form of glycolipids or glycoproteins have been characterized and correlated to certain types of cancers. (Bertozzi et al., Nat Rev Drug Discovery, 2005, 4, 477-488). The passively administered or vaccine-induced antibodies against these antigens have correlated with improved prognosis.

Monoclonal antibody (mAb) RM2 was established toward disialoganglioside and found to recognize the glycosyl epitope (b1.4-Gal-NAcDSLc4). Research correlates the grade of malignancy with the reactivity of mAb RM2 to prostate cancer cells (Saito et al., *Int. J. Cancer*, 2008, 123(3), 633-640). RM2 immunoreactivity was also detected in stroma, suggesting the glycoprotein recognized by RM2 may be shed from cancer cells into the surrounding stroma and then released into the bloodstream. Thus, the RM2 antigen may be a promising target for cancer immunotherapy.

SUMMARY OF THE INVENTION

The present invention is based on the RM2 antigen (β1,4-GalNAc-disialyl-Lc4) conjugated to a protein carrier (e.g., Diphtheria toxin), which effectively induced anti-RM2 immune responses and presence of an adjuvant significantly enhanced such immune responses.

Accordingly, the present invention provides synthetic glycan conjugates, immmunogenic compositions comprising such, and kits comprising the glycan conjugates or immunogenic compositions. The present invention further provides methods of using the synthetic glycan conjugates and/or immunogenic compositions thereof to treat or reduce the risk for proliferative diseases such as cancer. In certain embodiments, the cancer being treated is prostate cancer.

In one aspect, the present invention provides a compound of Formula (F-1) or Formula (F-2)

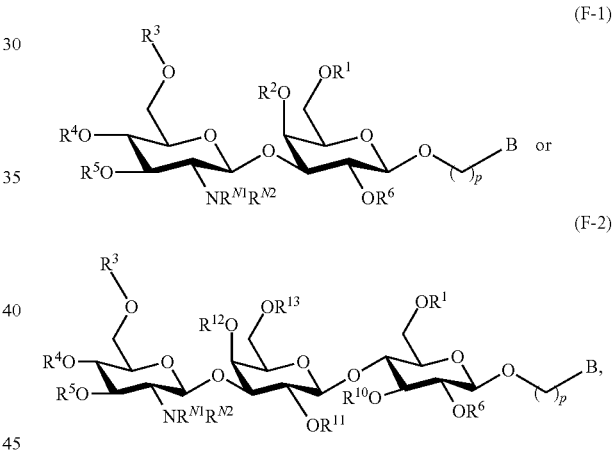

or a salt thereof, provided the compound is not of the formula

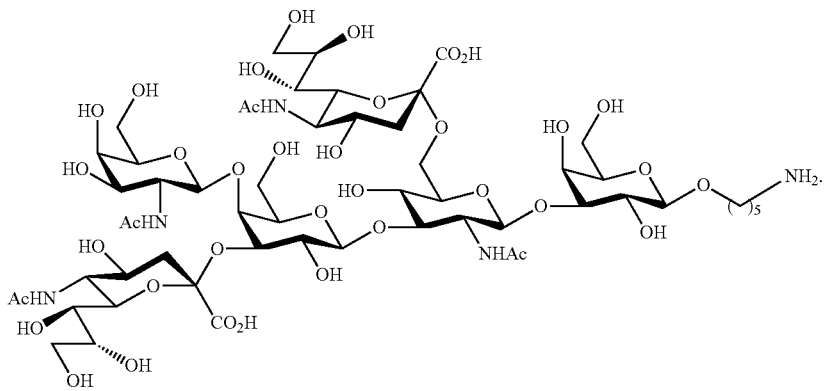

In one aspect, the present invention provides a glycan conjugate or a pharmaceutically acceptable salt thereof, comprising a carrier and a glycan moiety of Formula (I-i) or Formula (I-ii)

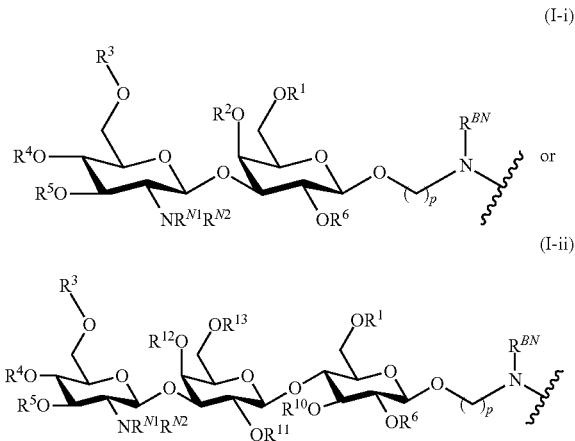

wherein the glycan moiety is covalently linked to the carrier. In some embodiments, the carrier is a protein, a lipid, a lipolized protein, a virus, a peptide comprising a T cell epitope, or a dendrimer of glycopeptides. In some embodiments, the carrier protein is a toxin protein selected from the group consisting of diphtheria toxin cross-reacting material 197 (DT-CRM197), diphtheria toxoid, tetanus toxoid, and outer-membrane protein (OMP). In some embodiments, the carrier is DT-CRM197.

In another aspect, the present invention provides a glycan conjugate mixture comprising at least two of the glycan conjugates as described herein.

In another aspect, the present invention provides methods of synthesizing the glycan conjugates as described herein.

In another aspect, the present invention provides immmunogenic compositions comprising a glycan conjugate or a glycan conjugate mixture as provided herein and a pharmaceutically acceptable excipient. In certain embodiments, the immmunogenic compositions further comprise an adjuvant. In certain embodiments, the adjuvant is C34, 7DW8-5, C17, C23, C30, α-galactoceramide, Aluminum salt, Squalene, MF59, or QS-21. In certain embodiments, the immmunogenic compositions described herein include an immunogenically effective amount of an inventive glycan conjugate. In certain embodiments, the immmunogenic compositions described herein include an pharmaceutically effective amount of an inventive glycan conjugate. The inventive glycan conjugates described herein are useful for inducing an immune response against the proliferative disease in a subject. The proliferative diseases include, but are not limited to, cancer (e.g., breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.), benign neoplasm, angiogenesis, inflammatory diseases, autoinflammatory diseases, and autoimmune diseases. In certain embodiments, the proliferative disease is prostate cancer. In certain embodiments, the immmunogenic compositions provided herein induce IgG and IgM antibodies and provided an immunogenicity in cancer models. In certain embodiments, the immmunogenic compositions induce more IgG antibodies and IgM antibodies. In certain embodiments, the cancer model is a prostate cancer model. In certain embodiments, the cancer tissue expresses a RM2 antigen on the surface of the cancer cell.

In another aspect, the present invention provides kits comprising the inventive glycan conjugates, or the inventive glycan conjugate mixture thereof, or immmunogenic compositions thereof. The kits of the invention may include a single dose or multiple doses of the inventive glycan conjugates, or immmunogenic compositions thereof, or vaccines thereof. The provided kits may be useful for the treatment or prevention of proliferative diseases such as cancer (e.g. breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer). The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

In another aspect, the present invention provides methods for treating and/or preventing proliferative diseases. Exemplary proliferative diseases include cancer (e.g., breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.), benign neoplasm, angiogenesis, inflammatory diseases, autoinflammatory diseases, and autoimmune diseases. In certain embodiments, the proliferative disease is prostate cancer.

The details of certain embodiments of the invention are set forth herein. Other features, objects, and advantages of the invention will be apparent from the Detailed Description, the Figures, the Examples, and the Claims.

BRIEF DESCRIPTION OF THE DRAWINGS

FIGS. 24A thru 24I shows the chemical structures of 96 various oligosaccharides for glycan array chip.

DETAILED DESCRIPTION OF THE INVENTION

Chemical Definitions

Figure 1:
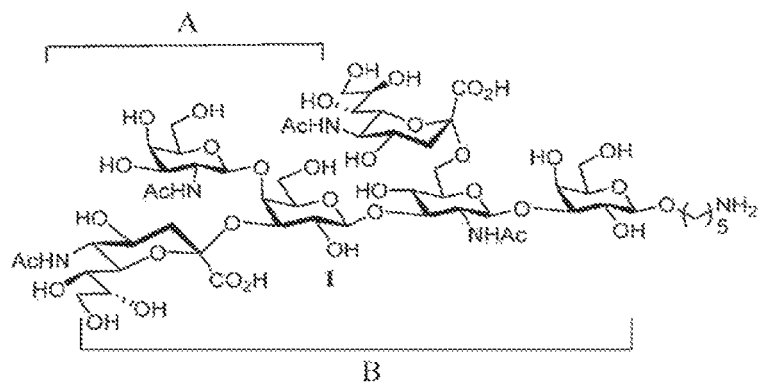
FIG. 1 shows the structure of a RM2 carbohydrate hapten 1. A: ganglio-series structure. B: disialyl lacto-series type 1 structure. This RM2 antigen is a glycosphingolipid (GSL) isolated and identified by Hakomari and colleagues from a renal cell carcinoma cell line TOS-1 and prostate cancer cell lines LNCap and PC-3. The structure of this RM2 antigen consists of a hybrid core with the "ganglio-series" and the "disialyl lacto-series type 1 chain" groups (Ito et al., *J. Biol. Chem.* 2001, 276, 16695).

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and subrange within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl").

In some embodiments, an alkyl group has 1 to 2 carbon atoms ("$C_{1-2}$ alkyl"). In some embodiments, an alkyl group has 1 carbon atom ("$C_{1-6}$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., $CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), 9ydroxy[2.2.1]heptanyl ($C_7$), 9ydroxy[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., it contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C (=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —Osi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$_{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^1$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —Osi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two R$^{dd}$ substituents can be joined to form =O or =S; each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups; each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —Osi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two R$^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{b}$)$_2$, —C(=O)NR$^{bb}$SO$_2$R$^{aa}$, —C(=S)N(R$^{bb}$)$_2$, —C(=O)SR$^{aa}$, and —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methylcarbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-Adamantyl)-1-methylethyl (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N, N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-hydroxyl, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)

phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxyamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

General Definitions

The following definitions are more general terms used throughout the present application:

As used herein, a "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers.

As used herein, the term "conjugated" or "conjugation" refers to an association of two molecules, for example, a glycan moiety and a protein carrier, with one another in a way that they are linked by a direct or indirect covalent or non-covalent interaction. In certain embodiments, the association is covalent, and the entities are said to be "conjugated" to one another.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds as described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual (e.g., an individual at risk for the disease) prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of refers to an amount sufficient to elicit a desired biological response, i.e., treating the condition. As will be appreciated by those of ordinary skill in this art, the effective amount of a compound may vary depending on such factors as the desired biological endpoint, the pharmacokinetics of the compound, the condition being treated, the mode of administration, and the age and health of the subject. An effective amount encompasses therapeutic and prophylactic treatment. In certain embodiments, the effective amount encompasses an amount effective in eliciting an immune responses specific to any RM2 antigen bearing disorder.

A "therapeutically effective amount" of a compound as described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound as described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

In certain embodiments, a compound of the present invention is provided as a salt. Salts are well known in the art. For example, Berge et al., describe pharmaceutically acceptable salts in detail in *J. Pharmaceutical Sciences*, 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, loweralkyl sulfonate and aryl sulfonate.

As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo. In certain embodiments, a probe compound of the present invention inhibits a glycosyltransferase protein.

As used herein, the term "effective amount" refers to the amount of a substance, compound, molecule, agent or composition that elicits the relevant response in vitro or in vivo. For example, in the case of a probe compound of the present invention used in an assay of the present invention, an effective amount of probe compound is an amount of probe compound that elicits the desired response, e.g., binding to a desired protein.

The term "independently" is used herein to indicate that the groups can be identical or different.

As used herein, the term "antigen" is defined as any substance capable of eliciting an immune response, e.g., a B-cell response or a T-cell response As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "epitope" is defined as the parts of an antigen molecule which contact the antigen binding site of an antibody or a T cell receptor.

As used herein, the term "immunogenic composition" is defined as a composition comprising at least one immunogenic agent and being capable of eliciting an immune response, e.g., an immune response specific to the immunogenic agent.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "immunologic adjuvant" refers to a substance used in conjunction with an immunogen which enhances or modifies the immune response to the immunogen. The α-GalCer analogs of the present disclosure are used as immunologic adjuvants to modify or augment the effects of a vaccine by stimulating the immune system of a patient who is administered the vaccine to respond to the vaccine more vigorously. In an exemplary implementation, the analog C34 is used as an adjuvant.

As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

Tumor-associated antigens (TAA) play an important role in the immunotherapy against proliferative diseases. Glycan antigen RM2 was identified as an antigen associated with cancer, e.g., prostate cancer. Thus, this TAA would be an attractive target for cancer immunotherapy.

Studies described herein indicate that RM2 analogs conjugated with a carrier are TD antigens, and able to induce IgG antibody titers higher than IgM antibody titers. In addition, the induced mouse antibodies were found to mediate effective complement-dependent cytotoxicity (CDC) against the prostate cancer cell line LNCap.

Compounds

The present invention provides a compound is of Formula (F-1) or Formula (F-2):

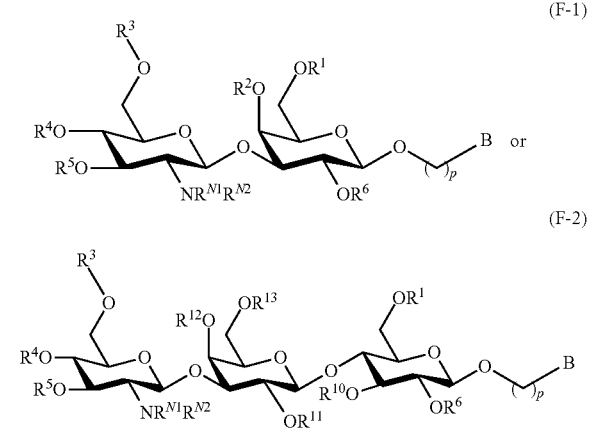

or a salt thereof, wherein each of $R^1$, $R^2$, $R^3$, $R^4$, $R^5$, $R^6$, $R^{10}$, $R^{11}$, $R^{12}$, and $R^{13}$ is independently hydrogen, optionally substituted $C_{1-6}$ alkyl, optionally substituted carbohydrate, or an oxygen protecting group; or optionally $R^1$ and $R^2$ are taken with the intervening atoms to form an optionally substituted heterocyclic ring; or optionally $R^3$ and $R^4$ are taken with the intervening atoms to form an optionally substituted heterocyclic ring; or optionally $R^4$ and $R^5$ are taken with the intervening atoms to form an optionally substituted heterocyclic ring; each instance of $R^{N1}$, $R^{N2}$, and $R^{BN}$ is independently hydrogen, optionally substituted $C^{1-6}$ alkyl, or a nitrogen protecting group; B is $N(R^{BN})_2$; and p is an integer of 1 to 10, inclusive; provided that the compound is not of the formula As generally defined herein, B is $N(R^{BN})_2$, wherein each instance of $R^{BN}$ is independently hydrogen, optionally substituted $C_{1-6}$ alkyl, or a nitrogen protecting group. In some embodiments, B is $NH_2$. In some embodiments, B is $NHR^{BN}$, wherein $R^{BN}$ is optionally substituted $C_{1-6}$ alkyl. In some embodiments, B is $NHR^{BN}$, wherein $R^{BN}$ is methyl, ethyl, or propyl. In some embodiments, B is $NHR^{BN}$, wherein $R^{BN}$ is a nitrogen protecting group. In some embodiments, B is $NHR^{BN}$, wherein $R^{BN}$ is Ac, Bn, BOC, Cbz, Troc, Fmoc, trifluoroacetyl, triphenylmethyl, or Ts. In some embodiments, B is $N(R^{BN})_2$, wherein $R^{BN}$ are the same. In some embodiments, B is $N(R^{BN})_2$, wherein $R^{BN}$ are different. In some embodiments, B is $N(R^{BN})_2$, wherein each instance of $R^{BN}$ is Ac, Bn, BOC, Cbz, Troc, Fmoc, trifluoroacetyl, triphenylmethyl, or Ts. In some embodiments, B is $NBnR^{BN}$, wherein $R^{BN}$ is Ac, Bn, BOC, Cbz, Troc, Fmoc, trifluoroacetyl, triphenylmethyl, or Ts. In some embodiments, B is NBnCbz.

As generally defined herein, p is an integer of 1 to 10, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

$R^1$, $R^2$, $R^3$, $R^4$, $R^5$, $R^6$, $R^{10}$, $R^{11}$, $R^{12}$, $R^{13}$, $R^{N1}$, and $R^{N2}$ are as defined herein.

In certain embodiments, a provided compound of the formula:

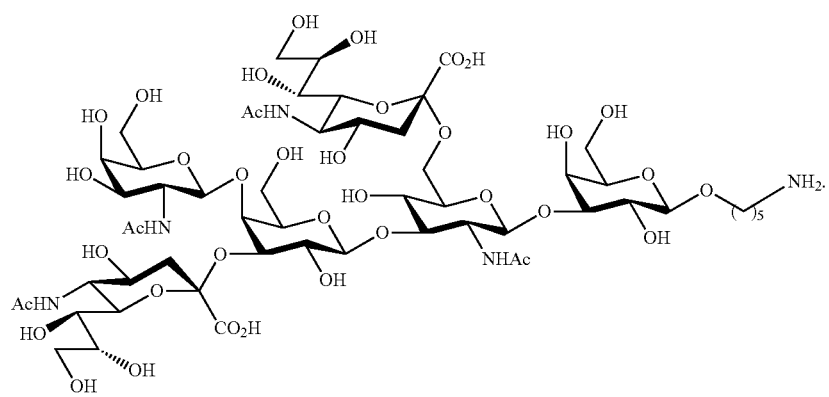

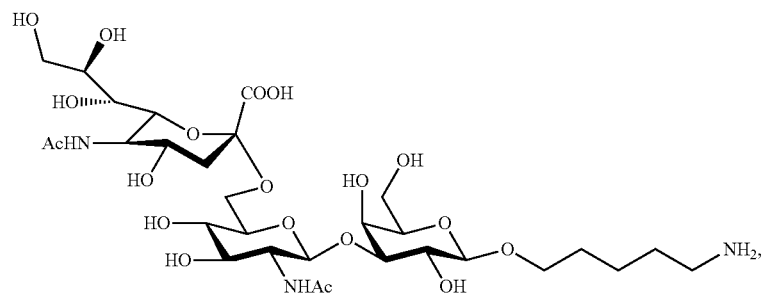
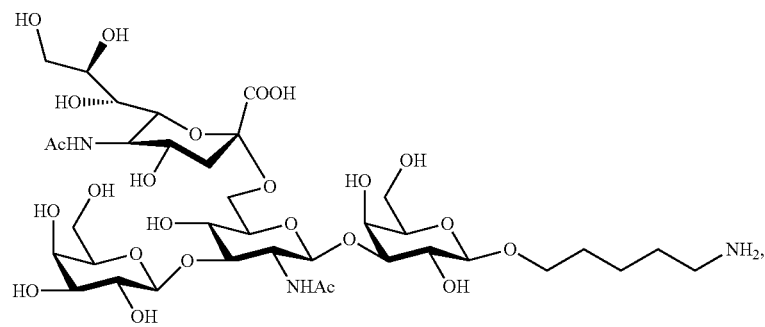
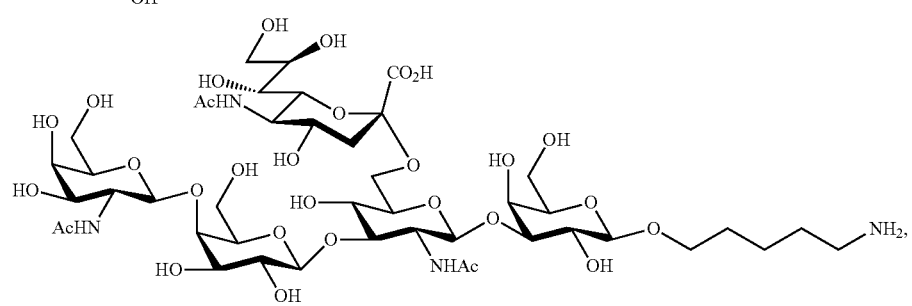
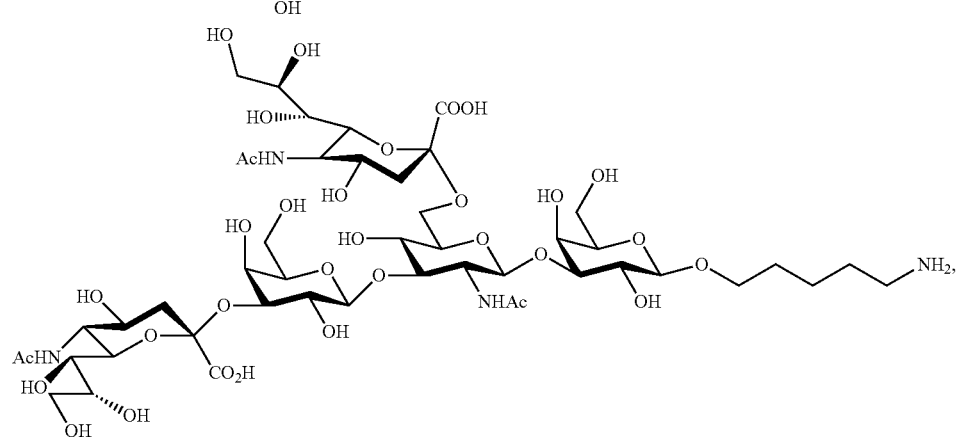
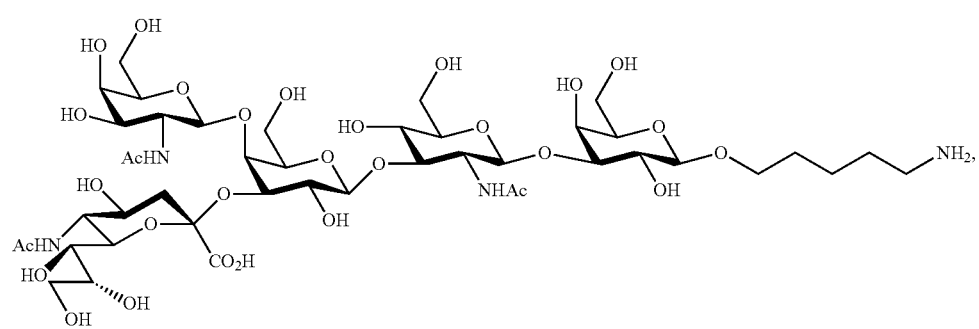

-continued
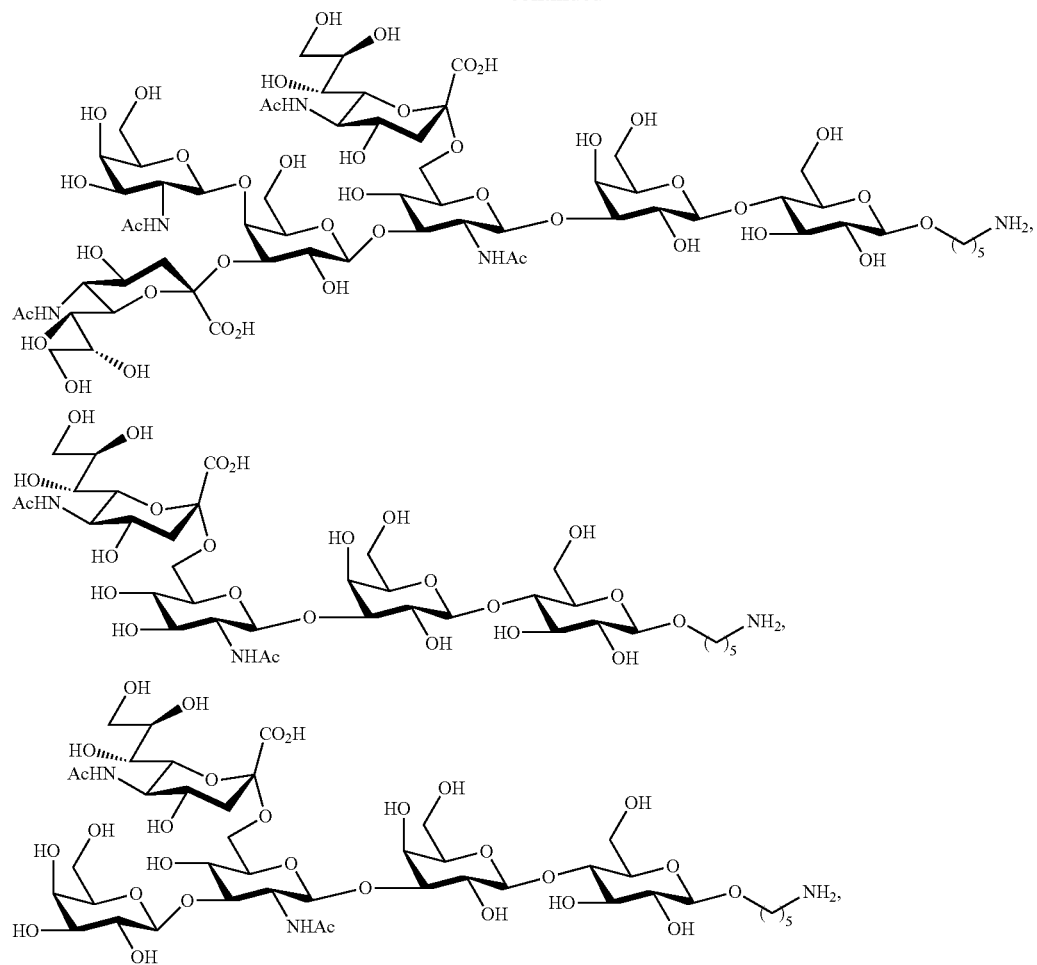
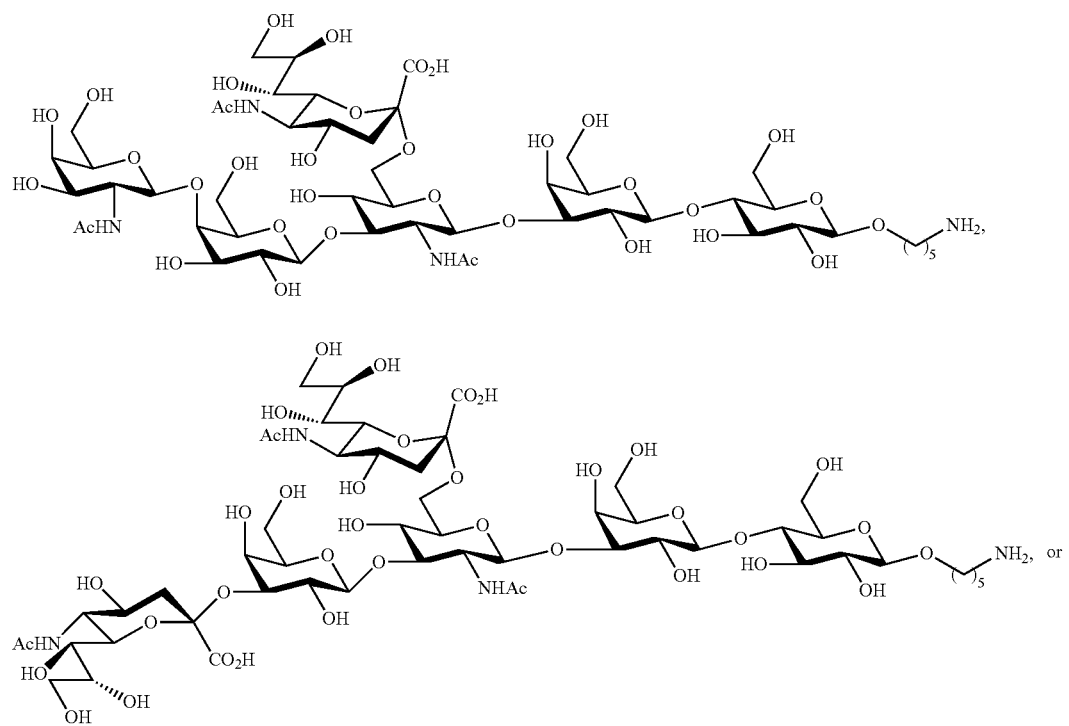

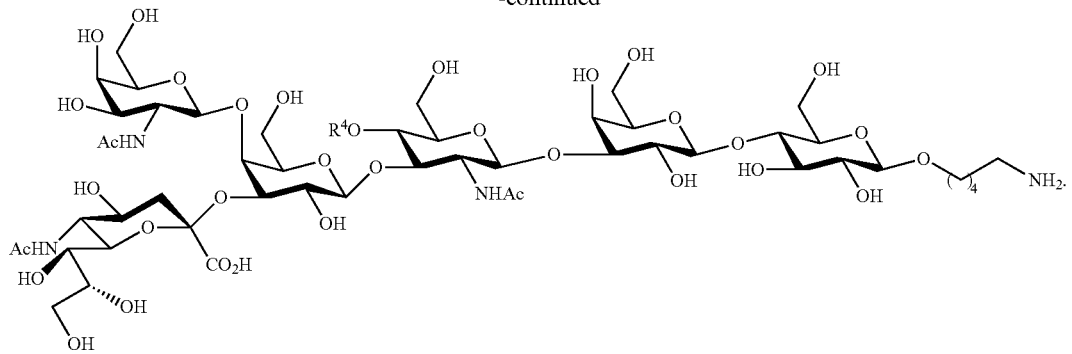
In certain embodiments, a provided compound is a synthetic intermediate of the formula:
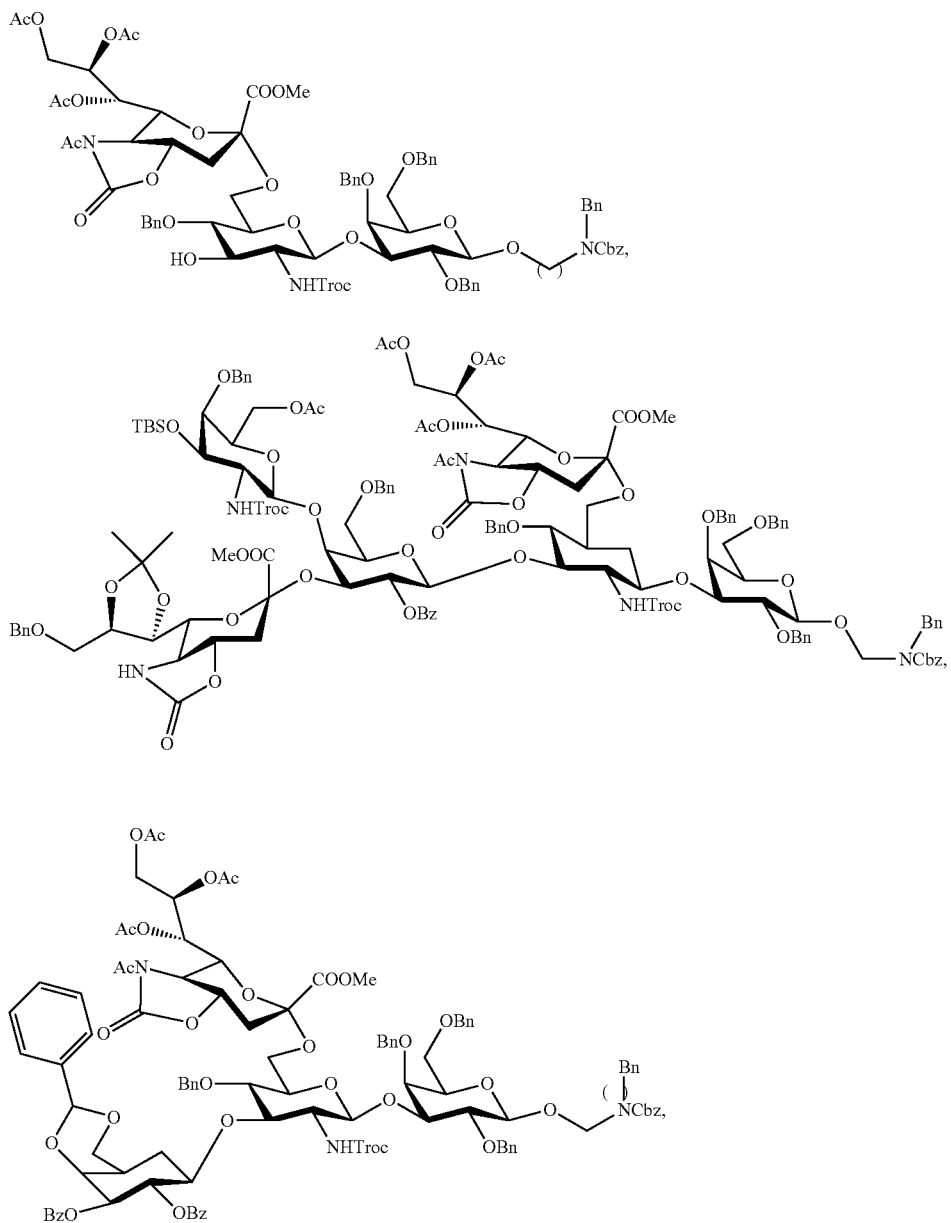

-continued

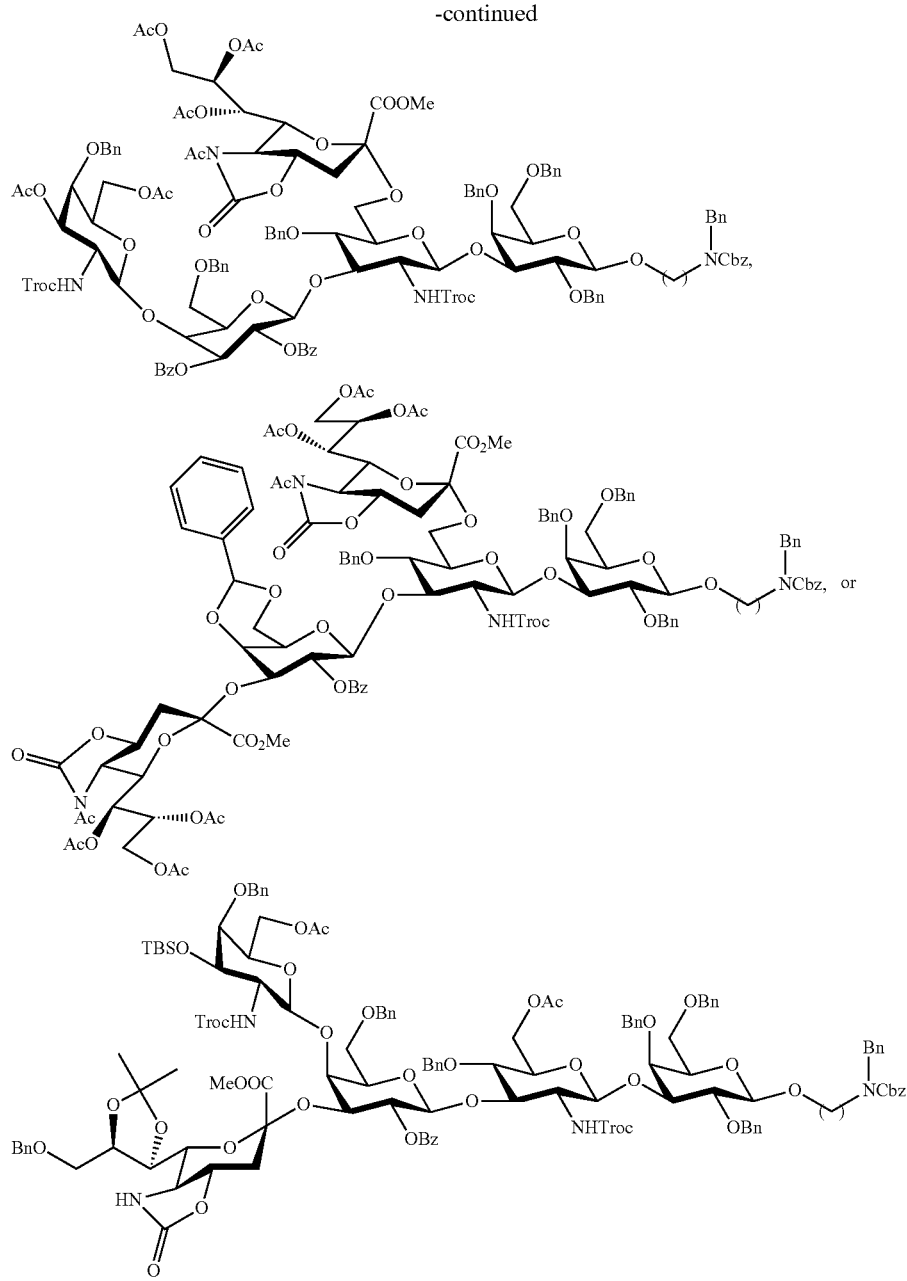

Glycan Conjugates

The present invention provides a glycan conjugate or a pharmaceutically acceptable salt thereof, comprising a carrier and a glycan moiety of Formula (I-i) or Formula (I-ii)

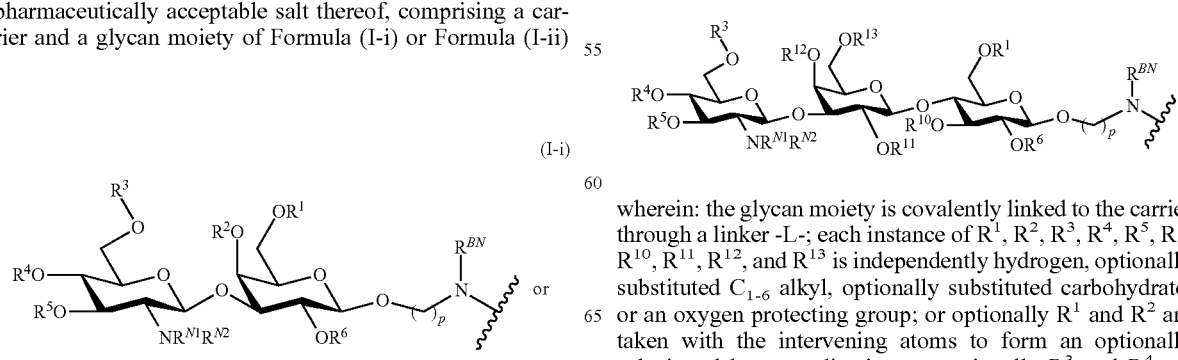

wherein: the glycan moiety is covalently linked to the carrier through a linker -L-; each instance of $R^1$, $R^2$, $R^3$, $R^4$, $R^5$, $R^6$, $R^{10}$, $R^{11}$, $R^{12}$, and $R^{13}$ is independently hydrogen, optionally substituted $C_{1-6}$ alkyl, optionally substituted carbohydrate, or an oxygen protecting group; or optionally $R^1$ and $R^2$ are taken with the intervening atoms to form an optionally substituted heterocyclic ring; or optionally $R^3$ and $R^4$ are taken with the intervening atoms to form an optionally substituted heterocyclic ring; or optionally $R^4$ and $R^5$ are taken with the intervening atoms to form an optionally substituted heterocyclic ring; each instance of $R^{N1}$, $R^{N2}$, and $R^{BN}$ is independently hydrogen, optionally substituted $C_{1-6}$ alkyl, optionally substituted acyl, or a nitrogen protecting group; each instance of L is independently a bond, —O—, —S—, —NR$^{La}$—, —C(=O)—, —NR$^{La}$C(=O)—, —NR$^{La}$C(=O)O—, —C(=O)NR$^{La}$—, —OC(=O)NR$^{La}$—, —SC(=O)—, —C(=O)S—, —OC(=O)—, —C(=O)O—, —NR$^{La}$C(=S)—, —C(=S)NR$^{La}$—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —C(R$^{Lb}$)$_2$S—, —S(=O)$_2$O—, —OS(=O)$_2$—, —S(=O)$_2$NR$^{La}$—, —NR$^{La}$S(=O)$_2$—, or an optionally substituted $C_{1-30}$ hydrocarbon chain, optionally wherein one or more carbon units of the hydrocarbon chain is replaced with —O—, —S—, —NR$^{La}$—, —C(=O)—, NR$^{La}$C(=O)—, —NR$^{La}$C(=O)O—, —C(=O)NR$^{La}$—, —OC(=O)NR$^{La}$—, —SC(=O)—, —C(=O)S—, —OC(=O)—, —C(=O)O—, —NR$^{La}$C(=S)—, —C(=S)NR$^{La}$—, trans-CR$^{Lb}$=CR$^{Lb}$—, cis-CR$^{Lb}$=CR$_{Lb}$—, —C≡C—, —S(=O)$_2$O—, —OS(=O)$_2$—, —S(=O)$_2$NR$^{La}$—, or —NR$^{La}$S(=O)$_2$—, wherein R$^{La}$ is hydrogen, optionally substituted $C_{1-15}$ alkyl, or a nitrogen protecting group, or R$^{La}$ is joined with the adjacent carbon atom to form an optionally substituted heterocyclic ring, and wherein each occurrence of R$^{Lb}$ is independently selected from the group consisting of hydrogen, halogen, optionally substituted $C_{1-15}$ alkyl, optionally substituted alkenyl, optionally substituted alkynyl, optionally substituted carbocyclyl, optionally substituted heterocyclyl, optionally substituted aryl, and optionally substituted heteroaryl, or R$^{Lb}$ is joined with the adjacent carbon or nitrogen or oxygen atom to form an optionally substituted carbocyclic or heterocyclic ring, or two R$^{Lb}$ groups are joined to form an optionally substituted carbocyclic or optionally substituted heterocyclic ring; and p is an integer of 1 to 10, inclusive.

As generally defined herein, $R^1$ is independently hydrogen, optionally substituted $C_{1-6}$ alkyl, optionally substituted carbohydrate, or an oxygen protecting group. In certain embodiments, $R^1$ is hydrogen. In certain embodiments, $R^1$ is optionally substituted $C_{1-6}$ alkyl, optionally substituted carbohydrate, or an oxygen protecting group. In certain embodiments, $R^1$ is optionally substituted $C_{1-6}$ alkyl. In certain embodiments, $R^1$ is unsubstituted $C_{1-6}$ alkyl. In certain embodiments, $R^1$ is methyl, ethyl, or propyl. In certain embodiments, $R^1$ is optionally substituted carbohydrate as defined herein. In certain embodiments, $R^1$ is an oxygen protecting group. In certain embodiments, $R^1$ is acyl. In certain embodiments, $R^1$ is acetyl or Bz. In certain embodiments, $R^1$ is Bn, PMB, In certain embodiments, $R^1$ is substituted silyl. In certain embodiments, $R^1$ is TBS.

As generally defined herein, $R^2$ is independently hydrogen, optionally substituted $C_{1-6}$ alkyl, optionally substituted carbohydrate, or an oxygen protecting group. In certain embodiments, $R^2$ is hydrogen. In certain embodiments, $R^2$ is optionally substituted $C_{1-6}$ alkyl, optionally substituted carbohydrate, or an oxygen protecting group. In certain embodiments, $R^2$ is optionally substituted $C_{1-6}$ alkyl. In certain embodiments, $R^2$ is unsubstituted $C_{1-6}$ alkyl. In certain embodiments, $R^2$ is methyl, ethyl, or propyl. In certain embodiments, $R^2$ is optionally substituted carbohydrate as defined herein. In certain embodiments, $R^2$ is an oxygen protecting group. In certain embodiments, $R^2$ is acyl. In certain embodiments, $R^2$ is acetyl or Bz. In certain embodiments, $R^2$ is Bn, PMB. In certain embodiments, $R^2$ is substituted silyl. In certain embodiments, $R^2$ is TBS.

As generally defined herein, $R^3$ is independently hydrogen, optionally substituted $C_{1-6}$ alkyl, optionally substituted carbohydrate, or an oxygen protecting group. In certain embodiments, $R^3$ is hydrogen. In certain embodiments, $R^3$ is optionally substituted $C_{1-6}$ alkyl, optionally substituted carbohydrate, or an oxygen protecting group. In certain embodiments, $R^3$ is optionally substituted $C_{1-6}$ alkyl. In certain embodiments, $R^3$ is unsubstituted $C_{1-6}$ alkyl. In certain embodiments, $R^3$ is methyl, ethyl, or propyl. In certain embodiments, $R^3$ is optionally substituted carbohydrate as defined herein. In certain embodiments, $R^3$ is an oxygen protecting group. In certain embodiments, $R^3$ is acyl. In certain embodiments, $R^3$ is acetyl or Bz. In certain embodiments, $R^3$ is Bn, PMB. In certain embodiments, $R^3$ is substituted silyl. In certain embodiments, $R^3$ is TBS.

As generally defined herein, $R^4$ is independently hydrogen, optionally substituted $C_{1-6}$ alkyl, optionally substituted carbohydrate, or an oxygen protecting group. In certain embodiments, $R^4$ is hydrogen. In certain embodiments, $R^4$ is optionally substituted $C_{1-6}$ alkyl, optionally substituted carbohydrate, or an oxygen protecting group. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl, ethyl, or propyl. In certain embodiments, $R^4$ is optionally substituted carbohydrate as defined herein. In certain embodiments, $R^4$ is an oxygen protecting group. In certain embodiments, $R^4$ is acyl. In certain embodiments, $R^4$ is acetyl or Bz. In certain embodiments, $R^4$ is Bn, PMB. In certain embodiments, $R^4$ is substituted silyl. In certain embodiments, $R^4$ is TBS.

As generally defined herein, $R^5$ is independently hydrogen, optionally substituted $C_{1-6}$ alkyl, optionally substituted carbohydrate, or an oxygen protecting group. In certain embodiments, $R^5$ is hydrogen. In certain embodiments, $R^5$ is optionally substituted $C_{1-6}$ alkyl, optionally substituted carbohydrate, or an oxygen protecting group. In certain embodiments, $R^5$ is optionally substituted $C_{1-6}$ alkyl. In certain embodiments, $R^5$ is unsubstituted $C_{1-6}$ alkyl. In certain embodiments, $R^5$ is methyl, ethyl, or propyl. In certain embodiments, $R^5$ is optionally substituted carbohydrate as defined herein. In certain embodiments, $R^5$ is an oxygen protecting group. In certain embodiments, $R^5$ is acyl. In certain embodiments, $R^5$ is acetyl or Bz. In certain embodiments, $R^5$ is Bn, PMB. In certain embodiments, $R^5$ is substituted silyl. In certain embodiments, $R^5$ is TBS.

As generally defined herein, $R^6$ is independently hydrogen, optionally substituted $C_{1-6}$ alkyl, optionally substituted carbohydrate, or an oxygen protecting group. In certain embodiments, $R^6$ is hydrogen. In certain embodiments, $R^6$ is optionally substituted $C_{1-6}$ alkyl, optionally substituted carbohydrate, or an oxygen protecting group. In certain embodiments, $R^6$ is optionally substituted $C_{1-6}$ alkyl. In certain embodiments, $R^6$ is unsubstituted $C_{1-6}$ alkyl. In certain embodiments, $R^6$ is methyl, ethyl, or propyl. In certain embodiments, $R^6$ is optionally substituted carbohydrate as defined herein. In certain embodiments, $R^6$ is an oxygen protecting group. In certain embodiments, $R^6$ is acyl. In certain embodiments, $R^6$ is acetyl or Bz. In certain embodiments, $R^6$ is Bn, PMB. In certain embodiments, $R^6$ is substituted silyl. In certain embodiments, $R^6$ is TBS.

As generally defined herein, $R^{10}$ is independently hydrogen, optionally substituted $C_{1-6}$ alkyl, optionally substituted carbohydrate, or an oxygen protecting group. In certain embodiments, $R^{10}$ is hydrogen. In certain embodiments, $R^{10}$ is optionally substituted $C_{1-6}$ alkyl, optionally substituted carbohydrate, or an oxygen protecting group. In certain embodiments, $R^{10}$ is optionally substituted $C_{1-6}$ alkyl. In certain embodiments, $R^{10}$ is unsubstituted $C_{1-6}$ alkyl. In certain embodiments, $R^{10}$ is methyl, ethyl, or propyl. In certain embodiments, $R^{10}$ is optionally substituted carbohydrate as defined herein. In certain embodiments, $R^{10}$ is an oxygen protecting group. In certain embodiments, $R^{10}$ is acyl. In certain embodiments, $R^{10}$ is acetyl or Bz. In certain embodiments, $R^{10}$ is Bn, PMB. In certain embodiments, $R^{10}$ is substituted silyl. In certain embodiments, $R^{10}$ is TBS.

As generally defined herein, $R^{11}$ is independently hydrogen, optionally substituted $C_{1-6}$ alkyl, optionally substituted carbohydrate, or an oxygen protecting group. In certain embodiments, $R^{11}$ is hydrogen. In certain embodiments, $R^{11}$ is optionally substituted $C_{1-6}$ alkyl, optionally substituted carbohydrate, or an oxygen protecting group. In certain embodiments, $R^{11}$ is optionally substituted $C_{1-6}$ alkyl. In certain embodiments, $R^{11}$ is unsubstituted $C_{1-6}$ alkyl. In certain embodiments, $R^{11}$ is methyl, ethyl, or propyl. In certain embodiments, $R^{11}$ is optionally substituted carbohydrate as defined herein. In certain embodiments, $R^{11}$ is an oxygen protecting group. In certain embodiments, $R^{11}$ is acyl. In certain embodiments, $R^{11}$ is acetyl or Bz. In certain embodiments, $R^{11}$ is Bn, PMB. In certain embodiments, $R^{11}$ is substituted silyl. In certain embodiments, $R^{11}$ is TBS.

As generally defined herein, $R^{12}$ is independently hydrogen, optionally substituted $C_{1-6}$ alkyl, optionally substituted carbohydrate, or an oxygen protecting group. In certain embodiments, $R^{12}$ is hydrogen. In certain embodiments, $R^{12}$ is optionally substituted $C_{1-6}$ alkyl, optionally substituted carbohydrate, or an oxygen protecting group. In certain embodiments, $R^{12}$ is optionally substituted $C_{1-6}$ alkyl. In certain embodiments, $R^{12}$ is unsubstituted $C_{1-6}$ alkyl. In certain embodiments, $R^{12}$ is methyl, ethyl, or propyl. In certain embodiments, $R^{12}$ is optionally substituted carbohydrate as defined herein. In certain embodiments, $R^{12}$ is an oxygen protecting group. In certain embodiments, $R^{12}$ is acyl. In certain embodiments, $R^{12}$ is acetyl or Bz. In certain embodiments, $R^{12}$ is Bn, PMB. In certain embodiments, $R^{12}$ is substituted silyl. In certain embodiments, $R^{12}$ is TBS.

As generally defined herein, $R^{13}$ is independently hydrogen, optionally substituted $C_{1-6}$ alkyl, optionally substituted carbohydrate, or an oxygen protecting group. In certain embodiments, $R^{13}$ is hydrogen. In certain embodiments, $R^{13}$ is optionally substituted $C_{1-6}$ alkyl, optionally substituted carbohydrate, or an oxygen protecting group. In certain embodiments, $R^{13}$ is optionally substituted $C_{1-6}$ alkyl. In certain embodiments, $R^{13}$ is unsubstituted $C_{1-6}$ alkyl. In certain embodiments, $R^{13}$ is methyl, ethyl, or propyl. In certain embodiments, $R^{13}$ is optionally substituted carbohydrate as defined herein. In certain embodiments, $R^{13}$ is an oxygen protecting group. In certain embodiments, $R^{13}$ is acyl. In certain embodiments, $R^{13}$ is acetyl or Bz. In certain embodiments, $R^{13}$ is Bn, PMB. In certain embodiments, $R^{13}$ is substituted silyl. In certain embodiments, $R^{13}$ is TBS.

In certain embodiments, $R^1$ and $R^2$ are taken with the intervening atoms to form an optionally substituted heterocyclic ring. In certain embodiments, $R^1$ and $R^2$ are taken with the intervening atoms to form an optionally substituted 5-membered heterocyclic ring. In certain embodiments, $R^1$ and $R^2$ are taken with the intervening atoms to form an optionally substituted 5-membered heterocyclic ring with two oxygen. In certain embodiments, $R^1$ and $R^2$ are taken with the intervening atoms to form a di-methylated 5-membered heterocyclic ring with two oxygen. In certain embodiments, $R^1$ and $R^2$ are taken with the intervening atoms to form a 5-membered heterocyclic ring of the formula

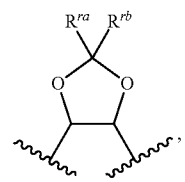

wherein $R^{ra}$ and $R^{rb}$ are each independently optionally substituted $C_{1-6}$ alkyl. In certain embodiments, $R^1$ and $R^2$ are taken with the intervening atoms to form a 5-membered heterocyclic ring of the formula

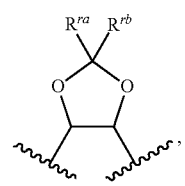

wherein $R^{ra}$ and $R^{rb}$ are each independently unsubstituted $C_{1-6}$ alkyl. In certain embodiments, $R^1$ and $R^2$ are taken with the intervening atoms to form a 5-membered heterocyclic ring of the formula

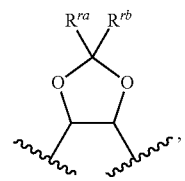

wherein $R^{ra}$ and $R^{rb}$ are each independently methyl, ethyl, or propyl.

In certain embodiments, $R^3$ and $R^4$ are taken with the intervening atoms to form an optionally substituted heterocyclic ring. In certain embodiments, $R^3$ and $R^4$ are taken with the intervening atoms to form an optionally substituted 5-membered heterocyclic ring. In certain embodiments, $R^3$ and $R^4$ are taken with the intervening atoms to form an optionally substituted 5-membered heterocyclic ring with two oxygen. In certain embodiments, $R^3$ and $R^4$ are taken with the intervening atoms to form a di-methylated 5-membered heterocyclic ring with two oxygen. In certain embodiments, $R^3$ and $R^4$ are taken with the intervening atoms to form a 5-membered heterocyclic ring of the formula

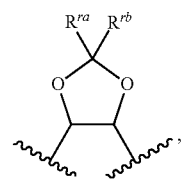

wherein $R^{ra}$ and $R^{rb}$ are each independently optionally substituted $C_{1-6}$ alkyl. In certain embodiments, $R^3$ and $R^4$ are taken with the intervening atoms to form a 5-membered heterocyclic ring of the formula

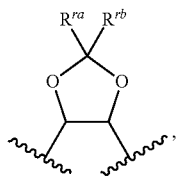

wherein $R^{ra}$ and $R^{rb}$ are each independently unsubstituted $C_{1-6}$ alkyl. In certain embodiments, $R^3$ and $R^4$ are taken with the intervening atoms to form a 5-membered heterocyclic ring of the formula

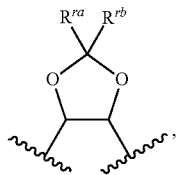

wherein $R^{ra}$ and $R^{rb}$ are each independently methyl, ethyl, or propyl.

In certain embodiments, $R^5$ and $R^6$ are taken with the intervening atoms to form an optionally substituted heterocyclic ring. In certain embodiments, $R^5$ and $R^6$ are taken with the intervening atoms to form an optionally substituted 5-membered heterocyclic ring. In certain embodiments, $R^5$ and $R^6$ are taken with the intervening atoms to form an optionally substituted 5-membered heterocyclic ring with two oxygen. In certain embodiments, $R^5$ and $R^6$ are taken with the intervening atoms to form a di-methylated 5-membered heterocyclic ring with two oxygen. In certain embodiments, $R^5$ and $R^6$ are taken with the intervening atoms to form a 5-membered heterocyclic ring of the formula

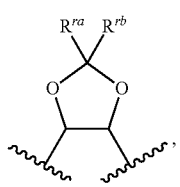

wherein $R^{ra}$ and $R^{rb}$ are each independently optionally substituted $C_{1-6}$ alkyl. In certain embodiments, $R^5$ and $R^6$ are taken with the intervening atoms to form a 5-membered heterocyclic ring of the formula

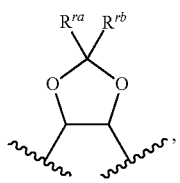

wherein $R^{ra}$ and $R^{rb}$ are each independently unsubstituted $C_{1-6}$ alkyl. In certain embodiments, $R^5$ and $R^6$ are taken with the intervening atoms to form a 5-membered heterocyclic ring of the formula

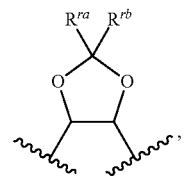

wherein $R^{ra}$ and $R^{rb}$ are each independently methyl, ethyl, or propyl.

As generally defined herein, $R^{7a}$ is independently hydrogen, halogen, or optionally substituted $C_{1-6}$ alkyl. In certain embodiments, $R^{7a}$ is hydrogen. In certain embodiments, $R^{7a}$ is halogen. In certain embodiments, $R^{7a}$ is F. In certain embodiments, $R^{7a}$ is Cl. In certain embodiments, $R^{7a}$ is Br. In certain embodiments, $R^{7a}$ is I. In certain embodiments, $R^{7a}$ is optionally substituted $C_{1-6}$ alkyl. In certain embodiments, $R^{7a}$ is optionally substituted $C_{1-6}$ alkyl. In certain embodiments, $R^{7a}$ is unsubstituted $C_{1-6}$ alkyl. In certain embodiments, $R^{7a}$ is methyl, ethyl, or propyl.

As generally defined herein, $R^{7b}$ is independently hydrogen, halogen, or optionally substituted $C_{1-6}$ alkyl. In certain embodiments, $R^{7b}$ is hydrogen. In certain embodiments, $R^{7b}$ is halogen. In certain embodiments, $R^{7b}$ is F. In certain embodiments, $R^{7b}$ is Cl. In certain embodiments, $R^{7b}$ is Br. In certain embodiments, $R^{7b}$ is I. In certain embodiments, $R^{7b}$ is optionally substituted $C_{1-6}$ alkyl. In certain embodiments, $R^{7b}$ is optionally substituted $C_{1-6}$ alkyl. In certain embodiments, $R^{7b}$ is unsubstituted $C_{1-6}$ alkyl. In certain embodiments, $R^{7b}$ is methyl, ethyl, or propyl.

As generally defined herein, $R^8$ is independently hydrogen, halogen, or optionally substituted $C_{1-6}$ alkyl. In certain embodiments, $R^8$ is hydrogen. In certain embodiments, $R^8$ is halogen. In certain embodiments, $R^8$ is F. In certain embodiments, $R^8$ is Cl. In certain embodiments, $R^8$ is Br. In certain embodiments, $R^8$ is I. In certain embodiments, $R^8$ is optionally substituted $C_{1-6}$ alkyl. In certain embodiments, $R^8$ is optionally substituted $C_{1-6}$ alkyl. In certain embodiments, $R^8$ is unsubstituted $C_{1-6}$ alkyl. In certain embodiments, $R^8$ is methyl, ethyl, or propyl.

As generally defined herein, $R^{N1}$ is hydrogen, optionally substituted $C_{1-6}$ alkyl, or a nitrogen protecting group. In some embodiments, $R^{N1}$ is hydrogen. In some embodiments, $R^{N1}$ is optionally substituted $C_{1-6}$ alkyl. In certain embodiments, $R^{N1}$ is methyl. In certain embodiments, $R^{N1}$ is ethyl. In certain embodiments, $R^{N1}$ is propyl. In certain embodiments, $R^{N1}$ is a nitrogen protecting group. In certain embodiments, $R^{N1}$ is acyl. In certain embodiments, $R^{N1}$ is acetyl. In certain embodiments, $R^{N1}$ is Bn, BOC, Cbz, Troc, Fmoc, trifluoroacetyl, triphenylmethyl, or Ts.

As generally defined herein, $R^{N2}$ is hydrogen, optionally substituted $C_{1-6}$ alkyl, or a nitrogen protecting group. In some embodiments, $R^{N2}$ is hydrogen. In some embodiments, $R^{N2}$ is optionally substituted $C_{1-6}$ alkyl. In certain embodiments, $R^{N2}$ is methyl. In certain embodiments, $R^{N2}$ is ethyl. In certain embodiments, $R^{N2}$ is propyl. In certain embodiments, $R^{N2}$ is a nitrogen protecting group. In certain embodiments, $R^{N2}$ is acyl. In certain embodiments, $R^{N2}$ is acetyl. In certain embodiments, $R^{N2}$ is Bn, BOC, Cbz, Troc, Fmoc, trifluoroacetyl, triphenylmethyl, or Ts.

In certain embodiments, $R^{N1}$ and $R^5$ are taken with the intervening atoms to form an optionally substituted heterocyclic ring. In certain embodiments, $R^{N1}$ and $R^5$ are taken with the intervening atoms to form an optionally substituted 5-membered heterocyclic ring. In certain embodiments, $R^{N1}$ and $R^5$ are taken with the intervening atoms to form an optionally substituted 5-membered heterocyclic ring of the formula

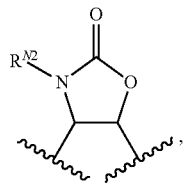

wherein $R^{N2}$ is defined herein. In certain embodiments, $R^{N1}$ and $R^5$ are taken with the intervening atoms to form an optionally substituted 5-membered heterocyclic ring of the formula

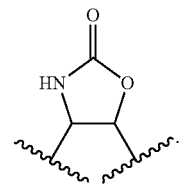 [SMILES: *C1NC(=O)OC1*]

As generally defined herein, p is an integer of 1 to 10, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

As generally defined herein, q is an integer of 1 to 8 inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8.

As generally defined herein, t is an integer of 1 to 8 inclusive. In certain embodiments, t is 1. In certain embodiments, t is 2. In certain embodiments, t is 3. In certain embodiments, t is 4. In certain embodiments, t is 5. In certain embodiments, t is 6. In certain embodiments, t is 7. In certain embodiments, t is 8.

In some embodiments, p is 1, q is an integer of 1 to 8 inclusive, and t is an integer of 1 to 8 inclusive. In some embodiments, p is 2, q is an integer of 1 to 8 inclusive, and t is an integer of 1 to 8 inclusive. In some embodiments, p is 3, q is an integer of 1 to 8 inclusive, and t is an integer of 1 to 8 inclusive. In some embodiments, p is 4, q is an integer of 1 to 8 inclusive, and t is an integer of 1 to 8 inclusive. In some embodiments, p is 5, q is an integer of 1 to 8 inclusive, and t is an integer of 1 to 8 inclusive. In some embodiments, p is 6, q is an integer of 1 to 8 inclusive, and t is an integer of 1 to 8 inclusive. In some embodiments, p is 7, q is an integer of 1 to 8 inclusive, and t is an integer of 1 to 8 inclusive. In some embodiments, p is 8, q is an integer of 1 to 8 inclusive, and t is an integer of 1 to 8 inclusive. In some embodiments, p is 4, q is 1, and t is an integer of 1 to 8 inclusive. In some embodiments, p is 4, q is 2, and t is an integer of 1 to 8 inclusive. In some embodiments, p is 4, q is 3, and t is an integer of 1 to 8 inclusive. In some embodiments, p is 4, q is 4, and t is an integer of 1 to 8 inclusive. In some embodiments, p is 4, q is 5, and t is an integer of 1 to 8 inclusive. In some embodiments, p is 4, q is 6, and t is an integer of 1 to 8 inclusive. In some embodiments, p is 4, q is 7, and t is an integer of 1 to 8 inclusive. In some embodiments, p is 4, q is 8, and t is an integer of 1 to 8 inclusive. In some embodiments, p is 4, q is 2, and t is an integer of 1 to 8 inclusive. In some embodiments, p is 4, q is 2, and t is 1. In some embodiments, p is 4, q is 2, and t is 3. In some embodiments, p is 4, q is 2, and t is 4. In some embodiments, p is 4, q is 2, and t is 5. In some embodiments, p is 4, q is 2, and t is 6. In some embodiments, p is 4, q is 2, and t is 7. In some embodiments, p is 4, q is 2, and t is 8.

In certain embodiments, each of $R^1$, $R^2$, $R^3$, $R^4$, $R^5$, and $R^6$ is independently a carbohydrate of Formula (s-1):

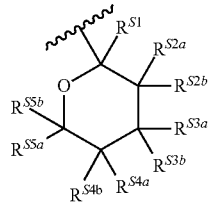

(s-1)

wherein: each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, —$OR^{SO}$, or —$N(R^{SN})_2$; each instance of $R^{SO}$ is independently hydrogen, optionally substituted alkyl, optionally substituted heterocyclyl, or an oxygen protecting group; and each instance of $R^{SN}$ is independently hydrogen, optionally substituted alkyl, or a nitrogen protecting group; or optionally two $R^{SN}$ are taken with the intervening atoms to form a heterocyclic ring.

As generally defined herein, each instance of $R^{S1}$ is independently hydrogen, optionally substituted alkyl, —$OR^{SO}$, or —$N(R^{SN})_2$. In certain embodiments, $R^{S1}$ is hydrogen. In certain embodiments, $R^{S1}$ is optionally substituted alkyl. In certain embodiments, $R^{S1}$ is substituted $C_{1-6}$ alkyl. In certain embodiments, $R^{S1}$ is unsubstituted $C_{1-6}$ alkyl. In certain embodiments, $R^{S1}$ is methyl, ethyl, propyl, butyl, pentyl, or hexyl.

In certain embodiments, $R^{S1}$ is —$OR^{SO}$, wherein $R^{SO}$ is independently hydrogen, optionally substituted alkyl, optionally substituted alkyl, optionally substituted heterocyclyl, or an oxygen protecting group. In certain embodiments, $R^{S1}$ is —OH. In certain embodiments, $R^{S1}$ is —$OR^{SO}$, wherein $R^{SO}$ is optionally substituted alkyl. In certain embodiments, $R^{S1}$ is —O-methyl, —O-ethyl, or —O-propyl. In certain embodiments, $R^{S1}$ is optionally substituted —O-alkylaryl. In certain embodiments, $R^{S1}$ is —O-Bn. In certain embodiments, $R^{S1}$ is —$OR^{SO}$, wherein $R^{SO}$ is an oxygen protecting group. In certain embodiments, $R^{S1}$ is —$OR^{SO}$, wherein $R^{SO}$ is acyl. In certain embodiments, $R^{S1}$ is —O-acetyl or —O-Bz. In certain embodiments, $R^{S1}$ is —$OR^{SO}$, wherein $R^{SO}$ is optionally substituted heterocyclyl. In certain embodiments, $R^{S1}$ is —$OR^{SO}$, wherein $R^{SO}$ is an oxygen protecting group. In certain embodiments, $R^{S1}$ is —$OR^{SO}$, wherein $R^{SO}$ is PMB, Bn, TBS, or TMS.

In certain embodiments $R^{S1}$ is —$N(R^{SN})_2$. In some embodiments, $R^{S1}$ is —$N(R^{SN})_2$, wherein each $R^{SN}$ is the same. In some embodiments, $R^{S1}$ is —$N(R^{SN})_2$, wherein each $R^{SN}$ is different. In certain embodiments, $R^{S1}$ is —$NH_2$. In certain embodiments, $R^{S1}$ is —$NHR^{SN}$. In certain embodiments, $R^{S1}$ is —$NHR^{SN}$, wherein $R^{SN}$ is optionally substituted $C_{1-6}$ alkyl. In certain embodiments, $R^{S1}$ is —NHR$^{SN}$, wherein R$^{SN}$ is unsubstituted C$_{1-6}$ alkyl. In certain embodiment, R$^{S1}$ is —NHR$^{SN}$, wherein R$^{SN}$ is substituted C$_{1-6}$ alkyl. In certain embodiments, R$^{S1}$ is —NH-benzyl. In certain embodiment, R$^{S1}$ is —NHR$^{SN}$, wherein R$^{SN}$ is a nitrogen protecting group. In certain embodiment, R$^{S1}$ is —NHAc, —NHBoc, Troc, Bn, or Cbz. In certain embodiments, R$^{S1}$ is —N(R$^{SN}$)$_2$, wherein each R$^{SN}$ is independently optionally substituted C$_{1-6}$ alkyl. In certain embodiments, R$^{S1}$ is —N(R$^{SN}$)$_2$, wherein each R$^{SN}$ is independently unsubstituted C$_{1-6}$ alkyl. In certain embodiments, R$^{S1}$ is —N(CH$_3$)R$^{SN}$, wherein each R$^{SN}$ is independently optionally substituted C$_{1-6}$ alkyl. In certain embodiments, R$^{S1}$ is —N(CH$_3$)R$^{SN}$, wherein each R$^{SN}$ is independently unsubstituted C$_{1-6}$ alkyl. In certain embodiments, R$^{S1}$ is —N(CH$_2$CH$_3$)R$^{SN}$, wherein each R$^{SN}$ is independently optionally substituted C$_{1-6}$ alkyl. In certain embodiments, R$^{S1}$ is —N(CH$_2$CH$_3$)R$^{SN}$, wherein each R$^{SN}$ is independently unsubstituted C$_{1-6}$ alkyl. In certain embodiments, R$^{S1}$ is —N(R$^{SN}$)$_2$, wherein each R$^{SN}$ is independently selected from the group consisting of methyl, ethyl, isopropyl, isobutyl, isoamyl, and benzyl. In some embodiments, R$^{S1}$ is —N(R$^{SN}$)$_2$, wherein two R$^{SN}$ groups are taken together with the intervening atoms to form an optionally substituted heterocyclic ring. For example, in certain embodiments, R$^{S1}$ is of the formula:

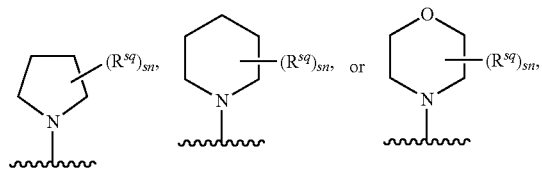

wherein R$^{sq}$ is as defined herein, and sn is 0, 1, 2, or 3.

As generally defined above, each instance of R$^{S2a}$ and R$^{S2b}$ is independently hydrogen, optionally substituted alkyl, —OR$^{SO}$, or —N(R$^{SN}$)$_2$. In certain embodiments, at least one instance of R$^{S2a}$ and R$^{S2b}$ is hydrogen. In certain embodiments, at least one instance of R$^{S2a}$ and R$^{S2b}$ is optionally substituted alkyl. In certain embodiments, at least one instance of R$^{S2a}$ and R$^{S2b}$ is substituted C$_{1-6}$ alkyl. In certain embodiments, at least one instance of R$^{S2a}$ and R$^{S2b}$ is unsubstituted C$_{1-6}$ alkyl. In certain embodiments, at least one instance of R$^{S2a}$ and R$^{S2b}$ is methyl, ethyl, propyl, butyl, pentyl, or hexyl. In certain embodiments, at least one instance of R$^{S2a}$ and R$^{S2b}$ is isopropyl, isobutyl, or isoamyl. In certain embodiments, at least one instance of R$^{S2a}$ and R$^{S2b}$ is isobutyl. In certain embodiments, at least one instance of R$^{S2a}$ and R$^{S2b}$ is tert-butyl. In certain embodiments, at least one instance of R$^{S2a}$ and R$^{S2b}$ is —OR$^{SO}$, wherein R$^{SO}$ is independently hydrogen, optionally substituted alkyl, optionally substituted alkyl, optionally substituted heterocyclyl, or an oxygen protecting group. In certain embodiments, at least one instance of R$^{S2a}$ and R$^{S2b}$ is —OH. In certain embodiments, at least one instance of R$^{S2a}$ and R$^{S2b}$ is —OR$^{SO}$, wherein R$^{SO}$ is optionally substituted alkyl. In certain embodiments, at least one instance of R$^{S2a}$ and R$^{S2b}$ is —O-methyl, —O-ethyl, or —O-propyl. In certain embodiments, at least one instance of R$^{S2a}$ and R$^{S2b}$ is optionally substituted —O-alkylaryl. In certain embodiments, at least one instance of R$^{S2a}$ and R$^{S2b}$ is —O-Bz. In certain embodiments, at least one instance of R$^{S2a}$ and R$^{S2b}$ is —OR$^{SO}$, wherein R$^{SO}$ is an oxygen protecting group. In certain embodiments, at least one instance of R$^{S2a}$ and R$^{S2b}$ is —OR$^{SO}$, wherein R$^{SO}$ is carbonyl. In certain embodiments, at least one instance of R$^{S2a}$ and R$^{S2b}$ is —OR$^{SO}$, wherein R$^{SO}$ is acetyl. In certain embodiments, at least one instance of R$^{S2a}$ and R$^{S2b}$ is —OR$^{SO}$, wherein R$^{SO}$ is optionally substituted heterocyclyl.

In certain embodiments, at least one instance of R$^{S2a}$ and R$^{S2b}$ is —N(R$^{SN}$)$_2$. In some embodiments, at least one instance of R$^{S2a}$ and R$^{S2b}$ is —N(R$^{SN}$)$_2$, wherein each R$^{SN}$ is the same. In some embodiments, at least one instance of R$^{S2a}$ and R$^{S2b}$ is —N(R$^{SN}$)$_2$, wherein each R$^{SN}$ is different. In certain embodiments, at least one instance of R$^{S2a}$ and R$^{S2b}$ is —NH$_2$. In certain embodiments, at least one instance of R$^{S2a}$ and R$^{S2b}$ is —NHR$^{SN}$. In certain embodiments, at least one instance of R$^{S2a}$ and R$^{S2b}$ is —NHR$^{SN}$, wherein R$^{SN}$ is optionally substituted C$_{1-6}$ alkyl. In certain embodiments, at least one instance of R$^{S2a}$ and R$^{S2b}$ is —NHR$^{SN}$, wherein R$^{SN}$ is unsubstituted C$_{1-6}$ alkyl. In certain embodiment, at least one instance of R$^{S2a}$ and R$^{S2b}$ is —NHR$^{SN}$, wherein R$^{SN}$ is substituted C$_{1-6}$ alkyl. In certain embodiments, at least one instance of R$^{S2a}$ and R$^{S2b}$ is —NH-benzyl. In certain embodiment, at least one instance of R$^{S2a}$ and R$^{S2b}$ is —NHR$^{SN}$, wherein R$^{SN}$ is a nitrogen protecting group. In certain embodiment, at least one instance of R$^{S2a}$ and R$^{S2b}$ is —NHFmoc. In certain embodiment, at least one instance of R$^{S2a}$ and R$^{S2b}$ is —NHBoc. In certain embodiments, at least one instance of R$^{S2a}$ and R$^{S2b}$ is —N(R$^{SN}$)$_2$, wherein each R$^{SN}$ is independently optionally substituted C$_{1-6}$ alkyl. In certain embodiments, at least one instance of R$^{S2a}$ and R$^{S2b}$ is —N(R$^{SN}$)$_2$, wherein each R$^{SN}$ is independently unsubstituted C$_{1-6}$ alkyl. In certain embodiments, at least one instance of R$^{S2a}$ and R$^{S2b}$ is —N(CH$_3$)R$^{SN}$, wherein each R$^{SN}$ is independently optionally substituted C$_{1-6}$ alkyl. In certain embodiments, at least one instance of R$^{S2a}$ and R$^{S2b}$ is —N(CH$_3$)R$^{SN}$, wherein each R$^{SN}$ is independently unsubstituted C$_{1-6}$ alkyl. In certain embodiments, at least one instance of R$^{S2a}$ and R$^{S2b}$ is —N(CH$_2$CH$_3$)R$^{SN}$, wherein each R$^{SN}$ is independently optionally substituted C$_{1-6}$ alkyl. In certain embodiments, at least one instance of R$^{S2a}$ and R$^{S2b}$ is —N(CH$_2$CH$_3$)R$^{SN}$, wherein each R$^{SN}$ is independently unsubstituted C$_{1-6}$ alkyl. In certain embodiments, at least one instance of R$^{S2a}$ and R$^{S2b}$ is —N(R$^{SN}$)$_2$, wherein each R$^{SN}$ is independently selected from the group consisting of methyl, ethyl, isopropyl, isobutyl, isoamyl, and benzyl. In some embodiments, at least one instance of R$^{S2a}$ and R$^{S2b}$ is —N(R$^{SN}$)$_2$, wherein two R$^{SN}$ groups are taken together with the intervening atoms to form an optionally substituted heterocyclic ring. For example, in certain embodiments, at least one instance of R$^{S2a}$ and R$^{S2b}$ is of the formula:

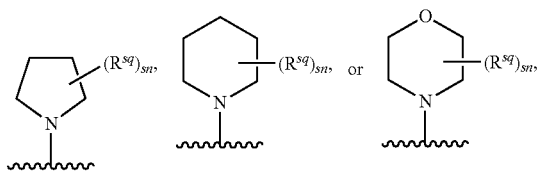

wherein R$^{sq}$ is as defined herein, and sn is 0, 1, 2, or 3.

As generally defined above, each instance of R$^{S3a}$ and R$^{S3b}$ is independently hydrogen, optionally substituted alkyl, —OR$^{SO}$, or —N(R$^{SN}$)$_2$. In certain embodiments, at least one instance of R$^{S3a}$ and R$^{S3b}$ is hydrogen. In certain embodiments, at least one instance of R$^{S3a}$ and R$^{S3b}$ is optionally substituted alkyl. In certain embodiments, at least one instance of R$^{S3a}$ and R$^{S3b}$ is substituted C$_{1-6}$ alkyl. In certain embodiments, at least one instance of R$^{S3a}$ and R$^{S3b}$ is unsubstituted $C_{1-6}$ alkyl. In certain embodiments, at least one instance of $R^{S3a}$ and $R^{S3b}$ is methyl, ethyl, propyl, butyl, pentyl, or hexyl. In certain embodiments, at least one instance of $R^{S3a}$ and $R^{S3b}$ is isopropyl, isobutyl, or isoamyl. In certain embodiments, at least one instance of $R^{S3a}$ and $R^{S3b}$ is isobutyl. In certain embodiments, at least one instance of $R^{S3a}$ and $R^{S3b}$ is tert-butyl. In certain embodiments, at least one instance of $R^{S3a}$ and $R^{S3b}$ is —$OR^{SO}$, wherein $R^{SO}$ is independently hydrogen, optionally substituted alkyl, optionally substituted alkyl, optionally substituted heterocyclyl, or an oxygen protecting group. In certain embodiments, at least one instance of $R^{S3a}$ and $R^{S3b}$ is —OH. In certain embodiments, at least one instance of $R^{S3a}$ and $R^{S3b}$ is —$OR^{SO}$, wherein $R^{SO}$ is optionally substituted alkyl. In certain embodiments, at least one instance of $R^{S3a}$ and $R^{S3b}$ is —O-methyl, —O-ethyl, or —O-propyl. In certain embodiments, at least one instance of $R^{S3a}$ and $R^{S3b}$ is optionally substituted —O-alkylaryl. In certain embodiments, at least one instance of $R^{S3a}$ and $R^{S3b}$ —O-Bz. In certain embodiments, at least one instance of $R^{S3a}$ and $R^{S3b}$ is —$OR^{SO}$, wherein $R^{SO}$ is an oxygen protecting group. In certain embodiments, at least one instance of $R^{S3a}$ and $R^{S3b}$ is —$OR^{SO}$, wherein $R^{SO}$ is carbonyl. In certain embodiments, at least one instance of $R^{S3a}$ and $R^{S3b}$ is —$OR^{SO}$, wherein $R^{SO}$ is acetyl. In certain embodiments, at least one instance of $R^{S3a}$ and $R^{S3b}$ is —$OR^{SO}$, wherein $R^{SO}$ is optionally substituted heterocyclyl. In certain embodiments, at least one instance of $R^{S3a}$ and $R^{S3b}$ is $N(R^{SN})_2$. In some embodiments, at least one instance of $R^{S3a}$ and $R^{S3b}$ is —$N(R^{SN})_2$, wherein each $R^{SN}$ is the same. In some embodiments, at least one instance of $R^{S3a}$ and $R^{S3b}$ is —$N(R^{SN})_2$, wherein each $R^{SN}$ is different. In certain embodiments, at least one instance of $R^{S3a}$ and $R^{S3b}$ is —$NH_2$. In certain embodiments, at least one instance of $R^{S3a}$ and $R^{S3b}$ is —$NHR^{SN}$. In certain embodiments, at least one instance of $R^{S3a}$ and $R^{S3b}$ is —$NHR^{SN}$, wherein $R^{SN}$ is optionally substituted $C_{1-6}$ alkyl. In certain embodiments, at least one instance of $R^{S3a}$ and $R^{S3b}$ is —$NHR^{SN}$, wherein $R^{SN}$ is unsubstituted $C_{1-6}$ alkyl. In certain embodiment, at least one instance of $R^{S3a}$ and $R^{S3b}$ is —$NHR^{SN}$, wherein $R^{SN}$ is substituted $C_{1-6}$ alkyl. In certain embodiments, at least one instance of $R^{S3a}$ and $R^{S3b}$ is —NH-benzyl. In certain embodiment, at least one instance of $R^{S3a}$ and $R^{S3b}$ is —$NHR^{SN}$, wherein $R^{SN}$ is a nitrogen protecting group. In certain embodiment, at least one instance of $R^{S3a}$ and $R^{S3b}$ is —NHFmoc. In certain embodiment, at least one instance of $R^{S3a}$ and $R^{S3b}$ is —NHBoc. In certain embodiments, at least one instance of $R^{S3a}$ and $R^{S3b}$ is —$N(R^{SN})_2$, wherein each $R^{SN}$ is independently optionally substituted $C_{1-6}$ alkyl. In certain embodiments, at least one instance of $R^{S3a}$ and $R^{S3b}$ is —$N(R^{SN})_2$, wherein each $R^{SN}$ is independently unsubstituted $C_{1-6}$ alkyl. In certain embodiments, at least one instance of $R^{S4a}$ and $R^{S4b}$ is —$N(CH_3)R^{SN}$, wherein each $R^{SN}$ is independently optionally substituted $C_{1-6}$ alkyl. In certain embodiments, at least one instance of $R^{S3a}$ and $R^{S3b}$ is —$N(CH_3)R^{SN}$, wherein each $R^{SN}$ is independently unsubstituted $C_{1-6}$ alkyl. In certain embodiments, at least one instance of $R^{S3a}$ and $R^{S3b}$ is —$N(CH_2CH_3)R^{SN}$, wherein each $R^{SN}$ is independently optionally substituted $C_{1-6}$ alkyl. In certain embodiments, at least one instance of $R^{S3a}$ and $R^{S3b}$ is —$N(CH_2CH_3)R^{SN}$, wherein each $R^{SN}$ is independently unsubstituted $C_{1-6}$ alkyl. In certain embodiments, at least one instance of $R^{S3a}$ and $R^{S3b}$ is —$N(R^{SN})_2$, wherein each $R^{SN}$ is independently selected from the group consisting of methyl, ethyl, isopropyl, isobutyl, isoamyl, and benzyl. In some embodiments, at least one instance of $R^{S3a}$ and $R^{S3b}$ is —$N(R^{SN})_2$, wherein two $R^{SN}$ groups are taken together with the intervening atoms to form an optionally substituted heterocyclic ring. For example, in certain embodiments, at least one instance of $R^{S3a}$ and $R^{S3b}$ is of the formula:

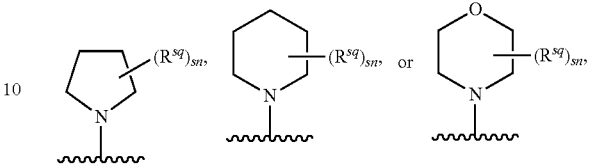

wherein $R^{sq}$ is as defined herein, and sn is 0, 1, 2, or 3.

As generally defined above, each instance of $R^{S4a}$ and $R^{S4b}$ is independently hydrogen, optionally substituted alkyl, —$OR^{SO}$, or —$N(R^{SN})_2$. In certain embodiments, at least one instance of $R^{S4a}$ and $R^{S4b}$ is hydrogen. In certain embodiments, at least one instance of $R^{S4a}$ and $R^{S4b}$ is optionally substituted alkyl. In certain embodiments, at least one instance of $R^{S4a}$ and $R^{S4b}$ is substituted $C_{1-6}$ alkyl. In certain embodiments, at least one instance of $R^{S4a}$ and $R^{S4b}$ is unsubstituted $C_{1-6}$ alkyl. In certain embodiments, at least one instance of $R^{S4a}$ and $R^{S4b}$ is methyl, ethyl, propyl, butyl, pentyl, or hexyl. In certain embodiments, at least one instance of $R^{S4a}$ and $R^{S4b}$ is isopropyl, isobutyl, or isoamyl. In certain embodiments, at least one instance of $R^{S4a}$ and $R^{S4b}$ is isobutyl. In certain embodiments, at least one instance of $R^{S4a}$ and $R^{S4b}$ is tert-butyl.

In certain embodiments, at least one instance of $R^{S4a}$ and $R^{S4b}$ is —$OR^{SO}$, wherein $R^{SO}$ is independently hydrogen, optionally substituted alkyl, optionally substituted alkyl, optionally substituted heterocyclyl, or an oxygen protecting group. In certain embodiments, at least one instance of $R^{S4a}$ and $R^{S4b}$ is —OH. In certain embodiments, at least one instance of $R^{S4a}$ and $R^{S4b}$ is —$OR^{SO}$, wherein $R^{SO}$ is optionally substituted alkyl. In certain embodiments, at least one instance of $R^{S4a}$ and $R^{S4b}$ is —O-methyl, —O-ethyl, or —O-propyl. In certain embodiments, at least one instance of $R^{S4a}$ and $R^{S4b}$ is optionally substituted —O-alkylaryl. In certain embodiments, at least one instance of $R^{S4a}$ and $R^{S4b}$ is —O-Bz. In certain embodiments, at least one instance of $R^{S4a}$ and $R^{S4b}$ is —$OR^{SO}$, wherein $R^{SO}$ is an oxygen protecting group. In certain embodiments, at least one instance of $R^{S4a}$ and $R^{S4b}$ is —$OR^{SO}$, wherein $R^{SO}$ is carbonyl. In certain embodiments, at least one instance of $R^{S4a}$ and $R^{S4b}$ is —$OR^{SO}$, wherein $R^{SO}$ is acetyl. In certain embodiments, at least one instance of $R^{S4a}$ and $R^{S4b}$ is —$OR^{SO}$, wherein $R^{SO}$ is optionally substituted heterocyclyl.

In certain embodiments, at least one instance of $R^{S4a}$ and $R^{S4b}$ is —$N(R^{SN})_2$. In some embodiments, at least one instance of $R^{S4a}$ and $R^{S4b}$ is —$N(R^{SN})_2$, wherein each $R^{SN}$ is the same. In some embodiments, at least one instance of $R^{S4a}$ and $R^{S4b}$ is —$N(R^{SN})_2$, wherein each $R^{SN}$ is different. In certain embodiments, at least one instance of $R^{S4a}$ and $R^{S4b}$ is —$NH_2$. In certain embodiments, at least one instance of $R^{S4a}$ and $R^{S4b}$ is —$NHR^{SN}$. In certain embodiments, at least one instance of $R^{S4a}$ and $R^{S4b}$ is —$NHR^{SN}$, wherein $R^{SN}$ is optionally substituted $C_{1-6}$ alkyl. In certain embodiments, at least one instance of $R^{S4a}$ and $R^{S4b}$ is —$NHR^{SN}$, wherein $R^{SN}$ is unsubstituted $C_{1-6}$ alkyl. In certain embodiment, at least one instance of $R^{S4a}$ and $R^{S4b}$ is —$NHR^{SN}$, wherein $R^{SN}$ is substituted $C_{1-6}$ alkyl. In certain embodiments, at least one instance of $R^{S4a}$ and $R^{S4b}$ is —NH-benzyl. In certain embodiment, at least one instance of $R^{S4a}$ and $R^{S4b}$ is —$NHR^{SN}$, wherein $R^{SN}$ is a nitrogen protecting group. In certain embodiment, at least one instance of $R^{S4a}$ and $R^{S4b}$ is —NHFmoc. In certain embodiment, at least one instance of $R^{S4a}$ and $R^{S4b}$ is —NHBoc. In certain embodiments, at least one instance of $R^{S4a}$ and $R^{S4b}$ is —N($R^{SN}$)$_2$, wherein each $R^{SN}$ is independently optionally substituted $C_{1-6}$ alkyl. In certain embodiments, at least one instance of $R^{S4a}$ and $R^{S4b}$ is —N($R^{SN}$)$_2$, wherein each $R^{SN}$ is independently unsubstituted $C_{1-6}$ alkyl. In certain embodiments, at least one instance of $R^{S4a}$ and $R^{S4b}$ is —N(CH$_3$)$R^{SN}$, wherein each $R^{SN}$ is independently optionally substituted $C_{1-6}$ alkyl. In certain embodiments, at least one instance of $R^{S4a}$ and $R^{S4b}$ is —N(CH$_3$)$R^{SN}$, wherein each $R^{SN}$ is independently unsubstituted $C_{1-6}$ alkyl. In certain embodiments, at least one instance of $R^{S4a}$ and $R^{S4b}$ is —N(CH$_2$CH$_3$)$R^{SN}$, wherein each $R^{SN}$ is independently optionally substituted $C_{1-6}$ alkyl. In certain embodiments, at least one instance of $R^{S4a}$ and $R^{S4b}$ is —N(CH$_2$CH$_3$)$R^{SN}$, wherein each $R^{SN}$ is independently unsubstituted $C_{1-6}$ alkyl. In certain embodiments, at least one instance of $R^{S4a}$ and $R^{S4b}$ is —N($R^{SN}$)$_2$, wherein each $R^{SN}$ is independently selected from the group consisting of methyl, ethyl, isopropyl, isobutyl, isoamyl, and benzyl.

In some embodiments, at least one instance of $R^{S4a}$ and $R^{S4b}$ is —N($R^{SN}$)$_2$, wherein two $R^{SN}$ groups are taken together with the intervening atoms to form an optionally substituted heterocyclic ring. For example, in certain embodiments, at least one instance of $R^{S4a}$ and $R^{S4b}$ is of the formula:

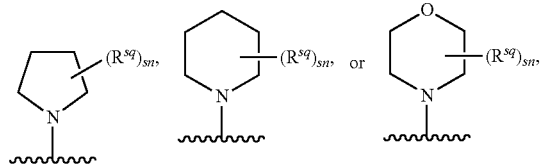

wherein $R^{sq}$ is as defined herein, and sn is 0, 1, 2, or 3.

As generally defined above, each instance of $R^{S5a}$ and $R^{S5b}$ is independently hydrogen, optionally substituted alkyl, —OR$^{SO}$, or —N($R^{SN}$)$_2$. In certain embodiments, at least one instance of $R^{S5a}$ and $R^{S5b}$ is hydrogen. In certain embodiments, at least one instance of $R^{S5a}$ and $R^{S5b}$ is optionally substituted alkyl. In certain embodiments, at least one instance of $R^{S5a}$ and $R^{S5b}$ is substituted $C_{1-6}$ alkyl. In certain embodiments, at least one instance of $R^{S5a}$ and $R^{S5b}$ is unsubstituted $C_{1-6}$ alkyl. In certain embodiments, at least one instance of $R^{S5a}$ and $R^{S5b}$ is methyl, ethyl, propyl, butyl, pentyl, or hexyl. In certain embodiments, at least one instance of $R^{S5a}$ and $R^{S5b}$ is isopropyl, isobutyl, or isoamyl. In certain embodiments, at least one instance of $R^{S5a}$ and $R^{S5b}$ is isobutyl. In certain embodiments, at least one instance of $R^{S5a}$ and $R^{S5b}$ is tert-butyl.

In certain embodiments, at least one instance of $R^{S5a}$ and $R^{S5b}$ is —OR$^{SO}$, wherein $R^{SO}$ is independently hydrogen, optionally substituted alkyl, optionally substituted alkyl, optionally substituted heterocyclyl, or an oxygen protecting group. In certain embodiments, at least one instance of $R^{S5a}$ and $R^{S5b}$ is —OH. In certain embodiments, at least one instance of $R^{S4a}$ and $R^{S4b}$ is —OR$^{SO}$, wherein $R^{SO}$ is optionally substituted alkyl. In certain embodiments, at least one instance of $R^{S5a}$ and $R^{S5b}$ is —O-methyl, —O-ethyl, or —O-propyl. In certain embodiments, at least one instance of $R^{S5a}$ and $R^{S5b}$ is optionally substituted —O-alkyl-aryl. In certain embodiments, at least one instance of $R^{S5a}$ and $R^{S5b}$ is —O-Bz. In certain embodiments, at least one instance of $R^{S5a}$ and $R^{S5b}$ is —OR$^{SO}$, wherein $R^{SO}$ is an oxygen protecting group. In certain embodiments, at least one instance of $R^{S5a}$ and $R^{S5b}$ is —OR$^{SO}$, wherein $R^{SO}$ is carbonyl. In certain embodiments, at least one instance of $R^{S5a}$ and $R^{S5b}$ is —OR$^{SO}$, wherein $R^{SO}$ is acetyl. In certain embodiments, at least one instance of $R^{S5a}$ and $R^{S5b}$ is —OR$^{SO}$, wherein $R^{SO}$ is optionally substituted heterocyclyl.

In certain embodiments, at least one instance of $R^{S5a}$ and $R^{S5b}$ is —N($R^{SN}$)$_2$. In some embodiments, at least one instance of $R^{S5a}$ and $R^{S5b}$ is —N($R^{SN}$)$_2$, wherein each $R^{SN}$ is the same. In some embodiments, at least one instance of $R^{S5a}$ and $R^{S5b}$ is —N($R^{SN}$)$_2$, wherein each $R^{SN}$ is different. In certain embodiments, at least one instance of $R^{S5a}$ and $R^{S5b}$ is —NH$_2$. In certain embodiments, at least one instance of $R^{S5a}$ and $R^{S5b}$ is —NHR$^{SN}$. In certain embodiments, at least one instance of $R^{S5a}$ and $R^{S5b}$ is —NHR$^{SN}$, wherein $R^{SN}$ is optionally substituted $C_{1-6}$ alkyl. In certain embodiments, at least one instance of $R^{S5a}$ and $R^{S5b}$ is —NHR$^{SN}$, wherein $R^{SN}$ is unsubstituted $C_{1-6}$ alkyl. In certain embodiment, at least one instance $R^{S5a}$ and $R^{S5b}$ is —NHR$^{SN}$, wherein $R^{SN}$ is substituted $C_{1-6}$ alkyl. In certain embodiments, at least one instance of $R^{S5a}$ and $R^{S5b}$ is —NH-benzyl. In certain embodiment, at least one instance of $R^{S5a}$ and $R^{S5b}$ is —NHR$^{SN}$, wherein $R^{SN}$ is a nitrogen protecting group. In certain embodiment, at least one instance of $R^{S4a}$ and $R^{S4b}$ is —NHFmoc. In certain embodiment, at least one instance of $R^{S5a}$ and $R^{S5b}$ is —NHBoc.

In certain embodiments, at least one instance of $R^{S5a}$ and $R^{S5b}$ is —N($R^{SN}$)$_2$, wherein each $R^{SN}$ is independently optionally substituted $C_{1-6}$ alkyl. In certain embodiments, at least one instance of $R^{S5a}$ and $R^{S5b}$ is —N($R^{SN}$)$_2$, wherein each $R^{SN}$ is independently unsubstituted $C_{1-6}$ alkyl. In certain embodiments, at least one instance of $R^{S5a}$ and $R^{S5b}$ is —N(CH$_3$)$R^{SN}$, wherein each $R^{SN}$ is independently optionally substituted $C_{1-6}$ alkyl. In certain embodiments, at least one instance of $R^{S5a}$ and $R^{S5b}$ is —N(CH$_3$)$R^{SN}$, wherein each $R^{SN}$ is independently unsubstituted $C_{1-6}$ alkyl. In certain embodiments, at least one instance of $R^{S5a}$ and $R^{S5b}$ is —N(CH$_2$CH$_3$)$R^{SN}$, wherein each $R^{SN}$ is independently optionally substituted $C_{1-6}$ alkyl. In certain embodiments, at least one instance of $R^{S5a}$ and $R^{S5b}$ is —N(CH$_2$CH$_3$)$R^{SN}$, wherein each $R^{SN}$ is independently unsubstituted $C_{1-6}$ alkyl. In certain embodiments, at least one instance of $R^{S5a}$ and $R^{S5b}$ is —N($R^{SN}$)$_2$, wherein each $R^{SN}$ is independently selected from the group consisting of methyl, ethyl, isopropyl, isobutyl, isoamyl, and benzyl.

In some embodiments, at least one instance of $R^{S5a}$ and $R^{S5b}$ is —N($R^{SN}$)$_2$, wherein two $R^{SN}$ groups are taken together with the intervening atoms to form an optionally substituted heterocyclic ring. For example, in certain embodiments, at least one instance of $R^{S5a}$ and $R^{S5b}$ is of the formula:

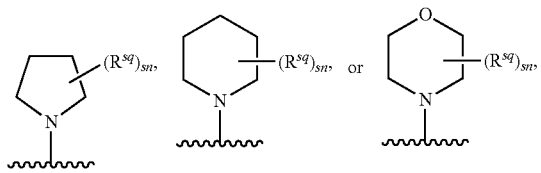

wherein $R^{sq}$ is as defined herein, and sn is 0, 1, 2, or 3.

As used herein, each instance $R^{sq}$ is independently halogen, optionally substituted alkyl, —OR$^{SO1}$, or —N($R^{SN1}$)$_2$, wherein $R^{SO1}$ is independently hydrogen, optionally substituted alkyl, or an oxygen protecting group; and $R^{SN1}$ is independently hydrogen, optionally substituted alkyl, or a nitrogen protecting group; or optionally two $R^{SN1}$ are taken together with the intervening atoms to form an optionally substituted heterocyclic ring.

As generally defined herein, each instance of $R^{SO}$ is independently hydrogen, optionally substituted alkyl, carbonyl, optionally substituted heterocyclyl, or an oxygen protecting group.

In certain embodiments, $R^{SO}$ is hydrogen. In certain embodiments, $R^{SO}$ is optionally substituted alkyl. In certain embodiments, $R^{SO}$ is optionally substituted $C_{1-6}$ alkyl. In certain embodiments, $R^{SO}$ is methyl, ethyl, or propyl. In certain embodiments, $R^{SO}$ is optionally substituted aralkyl, e.g., optionally substituted benzyl (Bn). In certain embodiments, $R^{SO}$ is optionally substituted heterocyclyl. In certain embodiments, RSO is carbonyl. In certain embodiments, $R^{SO}$ is —C(=O)CH$_3$ (acetyl, Ac). In certain embodiments, $R^{SO}$ is —C(=O)Ph (benzoyl, Bz). In certain embodiments, $R^{SO}$ is an oxygen protecting group.

As generally defined herein, each instance of $R^{SN}$ is independently hydrogen, optionally substituted alkyl, optionally substituted heterocyclyl, or a nitrogen protecting group; or optionally two $R^{SN}$ are taken together with the intervening atoms to form an optionally substituted heterocyclic ring. In certain embodiments, $R^{SN}$ is hydrogen. In certain embodiments, $R^{SN}$ is optionally substituted alkyl. In certain embodiments, $R^{SN}$ is optionally substituted $C_{1-6}$ alkyl. In certain embodiments, $R^{SN}$ is methyl, ethyl, or propyl. In certain embodiments, $R^{SN}$ is substituted aralkyl, e.g., optionally substituted benzyl (Bn). In certain embodiments, RSN is optionally substituted heterocyclyl. In certain embodiments, $R^{SN}$ is carbonyl. In certain embodiments, $R^{SN}$ is carbonyl. In certain embodiments, $R^{SN}$ is —C(=O)CH$_3$ (acetyl, Ac). In certain embodiments, $R^{SN}$ is —C(=O)Ph (benzoyl, Bz). In certain embodiments, $R^{SN}$ is a nitrogen protecting group.

In some embodiments, $R^3$ is of Formula (i)

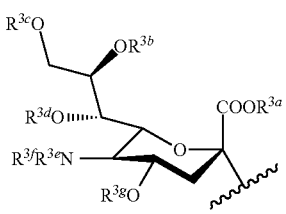

(i)

wherein: each of $R^{3a}$, $R^{3b}$, $R^{3c}$, $R^{3d}$, and $R^{3g}$ is independently hydrogen, optionally substituted $C_{1-6}$ alkyl, optionally substituted carbohydrate, or an oxygen protecting group; or optionally $R^{3c}$ and $R^{3b}$ are taken with the intervening atoms to form an optionally substituted heterocyclic ring; or optionally $R^{3b}$ and $R^{3d}$ are taken with the intervening atoms to form an optionally substituted heterocyclic ring; or optionally $R^{3f}$ and $R^{3g}$ are taken with the intervening atoms to form an optionally substituted heterocyclic ring; and $R^{3f}$ and $R^{3e}$ are each independently hydrogen, optionally substituted $C_{1-6}$ alkyl, or a nitrogen protecting group.

As generally defined herein, $R^{3a}$ is independently hydrogen, optionally substituted $C_{1-6}$ alkyl, optionally substituted carbohydrate, or an oxygen protecting group. In certain embodiments, $R^{3a}$ is hydrogen. In certain embodiments, $R^{3a}$ is optionally substituted $C_{1-6}$ alkyl, optionally substituted carbohydrate, or an oxygen protecting group. In certain embodiments, $R^{3a}$ is optionally substituted $C_{1-6}$ alkyl. In certain embodiments, $R^{3a}$ is unsubstituted $C_{1-6}$ alkyl. In certain embodiments, $R^{3a}$ is methyl, ethyl, or propyl. In certain embodiments, $R^{3a}$ is optionally substituted carbohydrate as defined herein. In certain embodiments, $R^{3a}$ is an oxygen protecting group. In certain embodiments, $R^{3a}$ is acyl. In certain embodiments, $R^{3a}$ is acetyl or Bz. In certain embodiments, $R^{3a}$ is Bn, PMB, In certain embodiments, $R^{3a}$ is substituted silyl. In certain embodiments, $R^{3a}$ is TBS.

As generally defined herein, $R^{3b}$ is independently hydrogen, optionally substituted $C_{1-6}$ alkyl, optionally substituted carbohydrate, or an oxygen protecting group. In certain embodiments, $R^{3b}$ is hydrogen. In certain embodiments, $R^{3b}$ is optionally substituted $C_{1-6}$ alkyl, optionally substituted carbohydrate, or an oxygen protecting group. In certain embodiments, $R^{3b}$ is optionally substituted $C_{1-6}$ alkyl. In certain embodiments, $R^{3b}$ is unsubstituted $C_{1-6}$ alkyl. In certain embodiments, $R^{3b}$ is methyl, ethyl, or propyl. In certain embodiments, $R^{3b}$ is optionally substituted carbohydrate as defined herein. In certain embodiments, $R^{3b}$ is an oxygen protecting group. In certain embodiments, $R^{3b}$ is acyl. In certain embodiments, $R^{3b}$ is acetyl or Bz. In certain embodiments, $R^{3b}$ is Bn, PMB, In certain embodiments, $R^{3b}$ is substituted silyl. In certain embodiments, $R^{3b}$ is TBS.

As generally defined herein, $R^{3c}$ is independently hydrogen, optionally substituted $C_{1-6}$ alkyl, optionally substituted carbohydrate, or an oxygen protecting group. In certain embodiments, $R^{3c}$ is hydrogen. In certain embodiments, $R^{3c}$ is optionally substituted. $C_{1-6}$ alkyl, optionally substituted carbohydrate, or an oxygen protecting group. In certain embodiments, $R^{3c}$ is optionally substituted $C_{1-6}$ alkyl. In certain embodiments, $R^{3c}$ is unsubstituted $C_{1-6}$ alkyl. In certain embodiments, $R^{3c}$ is methyl, ethyl, or propyl. In certain embodiments, $R^{3c}$ is optionally substituted carbohydrate as defined herein. In certain embodiments, $R^{3c}$ is an oxygen protecting group. In certain embodiments, $R^{3c}$ is acyl. In certain embodiments, $R^{3c}$ is acetyl or Bz. In certain embodiments, $R^{3c}$ is Bn, PMB, In certain embodiments, $R^{3c}$ is substituted silyl. In certain embodiments, $R^{3c}$ is TBS.

As generally defined herein, $R^{3d}$ is independently hydrogen, optionally substituted $C_{1-6}$ alkyl, optionally substituted carbohydrate, or an oxygen protecting group. In certain embodiments, $R^{3d}$ is hydrogen. In certain embodiments, $R^{3d}$ is optionally substituted $C_{1-6}$ alkyl, optionally substituted carbohydrate, or an oxygen protecting group. In certain embodiments, $R^{3d}$ is optionally substituted $C_{1-6}$ alkyl. In certain embodiments, $R^{3d}$ is unsubstituted $C_{1-6}$ alkyl. In certain embodiments, $R^{3d}$ is methyl, ethyl, or propyl. In certain embodiments, $R^{3d}$ is optionally substituted carbohydrate as defined herein. In certain embodiments, $R^{3d}$ is an oxygen protecting group. In certain embodiments, $R^{3d}$ is acyl. In certain embodiments, $R^{3d}$ is acetyl or Bz. In certain embodiments, $R^{3d}$ is Bn, PMB, In certain embodiments, $R^{3d}$ is substituted silyl. In certain embodiments, $R^{3d}$ is TBS.

As generally defined herein, $R^{3g}$ is independently hydrogen, optionally substituted $C_{1-6}$ alkyl, optionally substituted carbohydrate, or an oxygen protecting group. In certain embodiments, $R^{3g}$ is hydrogen. In certain embodiments, $R^{3g}$ is optionally substituted $C_{1-6}$ alkyl, optionally substituted carbohydrate, or an oxygen protecting group. In certain embodiments, $R^{3g}$ is optionally substituted $C_{1-6}$ alkyl. In certain embodiments, $R^{3g}$ is unsubstituted $C_{1-6}$ alkyl. In certain embodiments, $R^{3g}$ is methyl, ethyl, or propyl. In certain embodiments, $R^{3g}$ is optionally substituted carbohydrate as defined herein. In certain embodiments, $R^{3g}$ is an oxygen protecting group. In certain embodiments, $R^{3g}$ is acyl. In certain embodiments, $R^{3g}$ is acetyl or Bz. In certain embodiments, $R^{3g}$ is Bn, PMB, In certain embodiments, $R^{3g}$ is substituted silyl. In certain embodiments, $R^{3g}$ is TBS.

In certain embodiments, $R^{3c}$ and $R^{3b}$ are taken with the intervening atoms to form an optionally substituted heterocyclic ring. In certain embodiments, $R^{3c}$ and $R^{3b}$ are taken with the intervening atoms to form an optionally substituted 5-membered heterocyclic ring. In certain embodiments, $R^{3c}$ and $R^{3b}$ are taken with the intervening atoms to form an optionally substituted 5-membered heterocyclic ring with two oxygen. In certain embodiments, $R^{3c}$ and $R^{3b}$ are taken with the intervening atoms to form a di-methylated 5-membered heterocyclic ring with two oxygen. In certain embodiments, $R^{3c}$ and $R^{3b}$ are taken with the intervening atoms to form a 5-membered heterocyclic ring of the formula

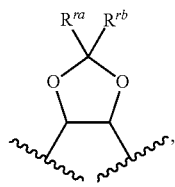

wherein $R^{ra}$ and $R^{rb}$ are each independently optionally substituted $C_{1-6}$ alkyl. In certain embodiments, $R^{3c}$ and $R^{3b}$ are taken with the intervening atoms to form a 5-membered heterocyclic ring of the formula

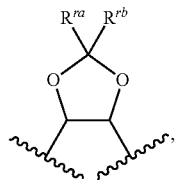

wherein $R^{ra}$ and $R^{rb}$ are each independently unsubstituted $C_{1-6}$ alkyl. In certain embodiments, $R^{3c}$ and $R^{3b}$ are taken with the intervening atoms to form a 5-membered heterocyclic ring of the formula

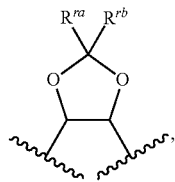

wherein $R^{ra}$ and $R^{rb}$ are each independently methyl, ethyl, or propyl.

In certain embodiments, $R^{3b}$ and $R^{3d}$ are taken with the intervening atoms to form an optionally substituted heterocyclic ring. In certain embodiments, $R^{3b}$ and $R^{3d}$ are taken with the intervening atoms to form an optionally substituted 5-membered heterocyclic ring. In certain embodiments, $R^{3b}$ and R3d are taken with the intervening atoms to form an optionally substituted 5-membered heterocyclic ring with two oxygen. In certain embodiments, R3b and R3d are taken with the intervening atoms to form a di-methylated 5-membered heterocyclic ring with two oxygen. In certain embodiments, $R^{3b}$ and $R^{3d}$ are taken with the intervening atoms to form a 5-membered heterocyclic ring of the formula

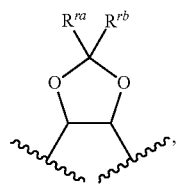

wherein $R^{ra}$ and $R^{rb}$ are each independently optionally substituted $C_{1-6}$ alkyl. In certain embodiments, $R^{3b}$ and $R^{3d}$ are taken with the intervening atoms to form a 5-membered heterocyclic ring of the formula

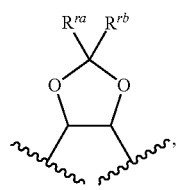

wherein $R^{ra}$ and $R^{rb}$ are each independently unsubstituted $C_{1-6}$ alkyl. In certain embodiments, $R^{3b}$ and $R^{3d}$ are taken with the intervening atoms to form a 5-membered heterocyclic ring of the formula

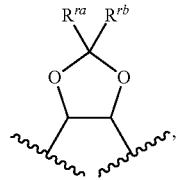

wherein $R^{ra}$ and $R^{rb}$ are each independently methyl, ethyl, or propyl.

In certain embodiments, $R^{3f}$ and $R^{3g}$ are taken with the intervening atoms to form an optionally substituted heterocyclic ring. In certain embodiments, $R^{3f}$ and $R^{3g}$ are taken with the intervening atoms to form an optionally substituted 5-membered heterocyclic ring. In certain embodiments, $R^{3f}$ and $R^{3g}$ are taken with the intervening atoms to form an optionally substituted 5-membered heterocyclic ring with two oxygen. In certain embodiments, $R^{3f}$ and $R^{3g}$ are taken with the intervening atoms to form a di-methylated 5-membered heterocyclic ring with two oxygen. In certain embodiments, $R^{3f}$ and $R^{3g}$ are taken with the intervening atoms to form a 5-membered heterocyclic ring of the formula

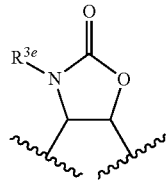

In certain embodiments, $R^{3f}$ and $R^{3g}$ are taken with the intervening atoms to form a 5-membered heterocyclic ring of the formula

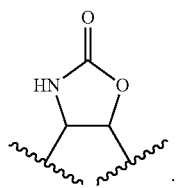 [SMILES: *C1NC(=O)OC1*]

As generally defined herein, $R^{3f}$ is hydrogen, optionally substituted $C_{1-6}$ alkyl, or a nitrogen protecting group. In some embodiments, $R^{3f}$ is hydrogen. In some embodiments, $R^{3f}$ is optionally substituted $C_{1-6}$ alkyl. In certain embodiments, $R^{3f}$ is methyl. In certain embodiments, $R^{3f}$ is ethyl. In certain embodiments, $R^{3f}$ is propyl. In certain embodiments, $R^{3f}$ is a nitrogen protecting group. In certain embodiments, $R^{3f}$ is acyl. In certain embodiments, $R^{3f}$ is acetyl. In certain embodiments, $R^{3f}$ is Bn, BOC, Cbz, Troc, Fmoc, trifluoroacetyl, triphenylmethyl, or Ts.

As generally defined herein, $R^{3e}$ is hydrogen, optionally substituted $C_{1-6}$ alkyl, or a nitrogen protecting group. In some embodiments, $R^{3e}$ is hydrogen. In some embodiments, $R^{3e}$ is optionally substituted $C_{1-6}$ alkyl. In certain embodiments, $R^{3e}$ is methyl. In certain embodiments, $R^{3e}$ is ethyl. In certain embodiments, $R^{3e}$ is propyl. In certain embodiments, $R^{3e}$ is a nitrogen protecting group. In certain embodiments, $R^{3e}$ is acyl. In certain embodiments, $R^{3e}$ is acetyl. In certain embodiments, $R^{3e}$ is Bn, BOC, Cbz, Troc, Fmoc, trifluoroacetyl, triphenylmethyl, or Ts.

In some embodiments, $R^5$ is of one of the following formulae:

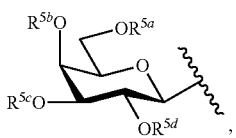
(ii)

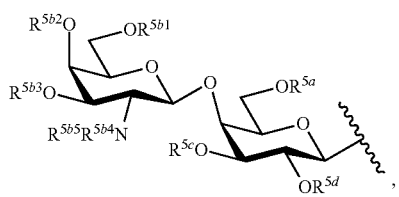
(ii)

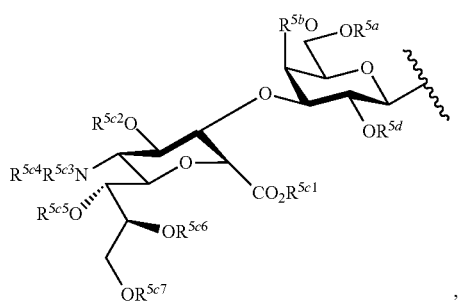
(iii)
, and

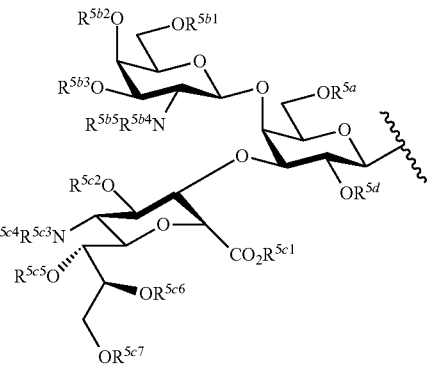
(iv)

wherein each of $R^{5a}$, $R^{5b}$, $R^{5c}$, $R^{5d}$, $R^{5b1}$, $R^{5b2}$, $R^{5b3}$, $R^{5c1}$, $R^{5c2}$, $R^{5c5}$, $R^{5c6}$, and $R^{5c7}$ is independently hydrogen, optionally substituted $C_{1-6}$ alkyl, optionally substituted carbohydrate, or an oxygen protecting group; or optionally $R^{5a}$ and $R^{5b}$ are taken with the intervening atoms to form an optionally substituted heterocyclic ring; or optionally $R^{5b}$ and $R^{5c}$ are taken with the intervening atoms to form an optionally substituted heterocyclic ring; or optionally $R^{5c}$ and $R^{5d}$ are taken with the intervening atoms to form an optionally substituted heterocyclic ring; or optionally $R^{5b1}$ and $R^{5b2}$ are taken with the intervening atoms to form an optionally substituted heterocyclic ring; or optionally $R^{5b2}$ and $R^{5b3}$ are taken with the intervening atoms to form an optionally substituted heterocyclic ring; or optionally $R^{5b3}$ and $R^{5b4}$ are taken with the intervening atoms to form an optionally substituted heterocyclic ring; or optionally $R^{5c2}$ and $R^{5c4}$ are taken with the intervening atoms to form an optionally substituted heterocyclic ring; or optionally $R^{5c5}$ and $R^{5c6}$ are taken with the intervening atoms to form an optionally substituted heterocyclic ring; or optionally $R^{5c6}$ and $R^{5c7}$ are taken with the intervening atoms to form an optionally substituted heterocyclic ring; and each of $R^{5b4}$, $R^{5b5}$, $R^{5a3}$, and $R^{5c4}$ is independently hydrogen, optionally substituted $C_{1-6}$ alkyl, or a nitrogen protecting group.

As generally defined herein, $R^{5a}$ is independently hydrogen, optionally substituted $C_{1-6}$ alkyl, optionally substituted carbohydrate, or an oxygen protecting group. In certain embodiments, $R^{5a}$ is hydrogen. In certain embodiments, $R^{5a}$ is optionally substituted $C_{1-6}$ alkyl, optionally substituted carbohydrate, or an oxygen protecting group. In certain embodiments, $R^{5a}$ is optionally substituted $C_{1-6}$ alkyl. In certain embodiments, $R^{5a}$ is unsubstituted $C_{1-6}$ alkyl. In certain embodiments, $R^{5a}$ is methyl, ethyl, or propyl. In certain embodiments, $R^{5a}$ is optionally substituted carbohydrate as defined herein. In certain embodiments, $R^{5a}$ is an oxygen protecting group. In certain embodiments, $R^{5a}$ is acyl. In certain embodiments, $R^{5a}$ is acetyl or Bz. In certain embodiments, $R^{5a}$ is Bn, PMB, In certain embodiments, $R^{5a}$ is substituted silyl. In certain embodiments, $R^{5a}$ is TBS.

As generally defined herein, $R^{5b}$ is independently hydrogen, optionally substituted $C_{1-6}$ alkyl, optionally substituted carbohydrate, or an oxygen protecting group. In certain embodiments, $R^{5b}$ is hydrogen. In certain embodiments, $R^{5b}$ is optionally substituted $C_{1-6}$ alkyl, optionally substituted carbohydrate, or an oxygen protecting group. In certain embodiments, $R^{5b}$ is optionally substituted $C_{1-6}$ alkyl. In certain embodiments, $R^{5b}$ is unsubstituted $C_{1-6}$ alkyl. In certain embodiments, $R^{5b}$ is methyl, ethyl, or propyl. In certain embodiments, $R^{5b}$ is optionally substituted carbohydrate as defined herein. In certain embodiments, $R^{5b}$ is an oxygen protecting group. In certain embodiments, $R^{5b}$ is acyl. In certain embodiments, $R^{5b}$ is acetyl or Bz. In certain embodiments, $R^{5b}$ is Bn, PMB, In certain embodiments, $R^{5b}$ is substituted silyl. In certain embodiments, $R^{5b}$ is TBS.

As generally defined herein, $R^{5c}$ is independently hydrogen, optionally substituted $C_{1-6}$ alkyl, optionally substituted carbohydrate, or an oxygen protecting group. In certain embodiments, $R^{5c}$ is hydrogen. In certain embodiments, $R^{5c}$ is optionally substituted $C_{1-6}$ alkyl, optionally substituted carbohydrate, or an oxygen protecting group. In certain embodiments, $R^{5c}$ is optionally substituted $C_{1-6}$ alkyl. In certain embodiments, $R^{5c}$ is unsubstituted $C_{1-6}$ alkyl. In certain embodiments, $R^{5c}$ is methyl, ethyl, or propyl. In certain embodiments, $R^{5c}$ is optionally substituted carbohydrate as defined herein. In certain embodiments, $R^{5c}$ is an oxygen protecting group. In certain embodiments, $R^{5c}$ is acyl. In certain embodiments, $R^{5c}$ is acetyl or Bz. In certain embodiments, $R^{5c}$ is Bn, PMB, In certain embodiments, $R^{5c}$ is substituted silyl. In certain embodiments, $R^{5c}$ is TBS.

As generally defined herein, $R^{5d}$ is independently hydrogen, optionally substituted $C_{1-6}$ alkyl, optionally substituted carbohydrate, or an oxygen protecting group. In certain embodiments, $R^{5d}$ is hydrogen. In certain embodiments, $R^{5d}$ is optionally substituted $C_{1-6}$ alkyl, optionally substituted carbohydrate, or an oxygen protecting group. In certain embodiments, $R^{5d}$ is optionally substituted $C_{1-6}$ alkyl. In certain embodiments, $R^{5d}$ is unsubstituted $C_{1-6}$ alkyl. In certain embodiments, $R^{5d}$ is methyl, ethyl, or propyl. In certain embodiments, $R^{5d}$ is optionally substituted carbohydrate as defined herein. In certain embodiments, $R^{5d}$ is an oxygen protecting group. In certain embodiments, $R^{5d}$ is acyl. In certain embodiments, $R^{5d}$ is acetyl or Bz. In certain embodiments, $R^{5d}$ is Bn, PMB, In certain embodiments, $R^{5d}$ is substituted silyl. In certain embodiments, $R^{5d}$ is TBS.

As generally defined herein, $R^{5b1}$ is independently hydrogen, optionally substituted $C_{1-6}$ alkyl, optionally substituted carbohydrate, or an oxygen protecting group. In certain embodiments, $R^{5b1}$ is hydrogen. In certain embodiments, $R^{5b1}$ is optionally substituted $C_{1-6}$ alkyl, optionally substituted carbohydrate, or an oxygen protecting group. In certain embodiments, $R^{5b1}$ is optionally substituted $C_{1-6}$ alkyl. In certain embodiments, $R^{5b1}$ is unsubstituted $C_{1-6}$ alkyl. In certain embodiments, $R^{5b1}$ is methyl, ethyl, or propyl. In certain embodiments, $R^{5b1}$ is optionally substituted carbohydrate as defined herein. In certain embodiments, $R^{5b1}$ is an oxygen protecting group. In certain embodiments, $R^{5b1}$ is acyl. In certain embodiments, $R^{5b1}$ is acetyl or Bz. In certain embodiments, $R^{5b1}$ is Bn, PMB, In certain embodiments, $R^{5b1}$ is substituted silyl. In certain embodiments, $R^{5b1}$ is TBS.

As generally defined herein, $R^{5b2}$ is independently hydrogen, optionally substituted $C_{1-6}$ alkyl, optionally substituted carbohydrate, or an oxygen protecting group. In certain embodiments, $R^{5b2}$ is hydrogen. In certain embodiments, $R^{5b2}$ is optionally substituted $C_{1-6}$ alkyl, optionally substituted carbohydrate, or an oxygen protecting group. In certain embodiments, $R^{5b2}$ is optionally substituted $C_{1-6}$ alkyl. In certain embodiments, $R^{5b2}$ is unsubstituted $C_{1-6}$ alkyl. In certain embodiments, $R^{5b2}$ is methyl, ethyl, or propyl. In certain embodiments, $R^{5b2}$ is optionally substituted carbohydrate as defined herein. In certain embodiments, $R^{5b2}$ is an oxygen protecting group. In certain embodiments, $R^{5b2}$ is acyl. In certain embodiments, $R^{5b2}$ is acetyl or Bz. In certain embodiments, $R^{5b2}$ is Bn, PMB, In certain embodiments, $R^{5b2}$ is substituted silyl. In certain embodiments, $R^{5b2}$ is TBS.

As generally defined herein, $R^{5b3}$ is independently hydrogen, optionally substituted $C_{1-6}$ alkyl, optionally substituted carbohydrate, or an oxygen protecting group. In certain embodiments, $R^{5b3}$ is hydrogen. In certain embodiments, $R^{5b3}$ is optionally substituted $C_{1-6}$ alkyl, optionally substituted carbohydrate, or an oxygen protecting group. In certain embodiments, $R^{5b3}$ is optionally substituted $C_{1-6}$ alkyl. In certain embodiments, $R^{5b3}$ is unsubstituted $C_{1-6}$ alkyl. In certain embodiments, $R^{5b3}$ is methyl, ethyl, or propyl. In certain embodiments, $R^{5b3}$ is optionally substituted carbohydrate as defined herein. In certain embodiments, $R^{5b3}$ is an oxygen protecting group. In certain embodiments, $R^{5b3}$ is acyl. In certain embodiments, $R^{5b3}$ is acetyl or Bz. In certain embodiments, $R^{5b3}$ is Bn, PMB, In certain embodiments, $R^{5b3}$ is substituted silyl. In certain embodiments, $R^{5b3}$ is TBS.

As generally defined herein, $R^{5c1}$ is independently hydrogen, optionally substituted $C_{1-6}$ alkyl, optionally substituted carbohydrate, or an oxygen protecting group. In certain embodiments, $R^{5c1}$ is hydrogen. In certain embodiments, $R^{5c1}$ is optionally substituted $C_{1-6}$ alkyl, optionally substituted carbohydrate, or an oxygen protecting group. In certain embodiments, $R^{5c1}$ is optionally substituted $C_{1-6}$ alkyl. In certain embodiments, $R^{5c1}$ is unsubstituted $C_{1-6}$ alkyl. In certain embodiments, $R^{5c1}$ is methyl, ethyl, or propyl. In certain embodiments, $R^{5c1}$ is optionally substituted carbohydrate as defined herein. In certain embodiments, $R^{5c1}$ is an oxygen protecting group. In certain embodiments, $R^{5c1}$ is acyl. In certain embodiments, $R^{5c1}$ is acetyl or Bz. In certain embodiments, $R^{5c1}$ is Bn, PMB, In certain embodiments, $R^{5c1}$ is substituted silyl. In certain embodiments, $R^{5c1}$ is TBS.

As generally defined herein, $R^{5c2}$ is independently hydrogen, optionally substituted $C_{1-6}$ alkyl, optionally substituted carbohydrate, or an oxygen protecting group. In certain embodiments, $R^{5c2}$ is hydrogen. In certain embodiments, $R^{5c2}$ is optionally substituted $C_{1-6}$ alkyl, optionally substituted carbohydrate, or an oxygen protecting group. In certain embodiments, $R^{5c2}$ is optionally substituted $C_{1-6}$ alkyl. In certain embodiments, $R^{5c2}$ is unsubstituted $C_{1-6}$ alkyl. In certain embodiments, $R^{5c2}$ is methyl, ethyl, or propyl. In certain embodiments, $R^{5c2}$ is optionally substituted carbohydrate as defined herein. In certain embodiments, $R^{5c2}$ is an oxygen protecting group. In certain embodiments, $R^{5c2}$ is acyl. In certain embodiments, $R^{5c2}$ is acetyl or Bz. In certain embodiments, $R^{5c2}$ is Bn, PMB. In certain embodiments, $R^{5c2}$ is substituted silyl. In certain embodiments, $R^{5c2}$ is TBS.

As generally defined herein, $R^{5c5}$ is independently hydrogen, optionally substituted $C_{1-6}$ alkyl, optionally substituted carbohydrate, or an oxygen protecting group. In certain embodiments, $R^{5c5}$ is hydrogen. In certain embodiments, $R^{5c5}$ is optionally substituted $C_{1-6}$ alkyl, optionally substituted carbohydrate, or an oxygen protecting group. In certain embodiments, $R^{5c5}$ is optionally substituted $C_{1-6}$ alkyl. In certain embodiments, $R^{5c5}$ is unsubstituted $C_{1-6}$ alkyl. In certain embodiments, $R^{5c5}$ is methyl, ethyl, or propyl. In certain embodiments, $R^{5c5}$ is optionally substituted carbohydrate as defined herein. In certain embodiments, $R^{5c5}$ is an oxygen protecting group. In certain embodiments, $R^{5c5}$ is acyl. In certain embodiments, $R^{5c5}$ is acetyl or Bz. In certain embodiments, $R^{5c5}$ is Bn, PMB, In certain embodiments, $R^{5c5}$ is substituted silyl. In certain embodiments, $R^{5c5}$ is TBS.

As generally defined herein, $R^{5c6}$ is independently hydrogen, optionally substituted $C_{1-6}$ alkyl, optionally substituted carbohydrate, or an oxygen protecting group. In certain embodiments, $R^{5c6}$ is hydrogen. In certain embodiments, $R^{5c6}$ is optionally substituted $C_{1-6}$ alkyl, optionally substituted carbohydrate, or an oxygen protecting group. In certain embodiments, $R^{5c6}$ is optionally substituted $C_{1-6}$ alkyl. In certain embodiments, $R^{5c6}$ is unsubstituted $C_{1-6}$ alkyl. In certain embodiments, $R^{5c6}$ is methyl, ethyl, or propyl. In certain embodiments, $R^{5c6}$ is optionally substituted carbohydrate as defined herein. In certain embodiments, $R^{5c6}$ is an oxygen protecting group. In certain embodiments, $R^{5c6}$ is acyl. In certain embodiments, $R^{5c6}$ is acetyl or Bz. In certain embodiments, $R^{5c6}$ is Bn, PMB, In certain embodiments, $R^{5c6}$ is substituted silyl. In certain embodiments, $R^{5c6}$ is TBS.

As generally defined herein, $R^{5c7}$ is independently hydrogen, optionally substituted $C_{1-6}$ alkyl, optionally substituted carbohydrate, or an oxygen protecting group. In certain embodiments, $R^{5c7}$ is hydrogen. In certain embodiments, $R^{5c7}$ is optionally substituted $C_{1-6}$ alkyl, optionally substituted carbohydrate, or an oxygen protecting group. In certain embodiments, $R^{5c7}$ is optionally substituted $C_{1-6}$ alkyl. In certain embodiments, $R^{5c7}$ is unsubstituted. $C_{1-6}$ alkyl. In certain embodiments, $R^{5c7}$ is methyl, ethyl, or propyl. In certain embodiments, $R^{5c7}$ is optionally substituted carbohydrate as defined herein. In certain embodiments, $R^{5c7}$ is an oxygen protecting group. In certain embodiments, $R^{5c7}$ is acyl. In certain embodiments, $R^{5c7}$ is acetyl or Bz. In certain embodiments, $R^{5c7}$ is Bn, PMB, In certain embodiments, $R^{5c7}$ is substituted silyl. In certain embodiments, $R^{5c7}$ is TBS.

In certain embodiments, $R^{5a}$ and $R^{5b}$ are taken with the intervening atoms to form an optionally substituted heterocyclic ring. In certain embodiments, $R^{5a}$ and $R^{5b}$ are taken with the intervening atoms to form an optionally substituted heterocyclic ring of formula

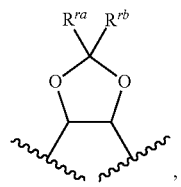

wherein $R^{ra}$ and $R^{rb}$ are each independently optionally substituted $C_{1-6}$ alkyl. In certain embodiments, $R^{5a}$ and $R^{5b}$ are taken with the intervening atoms to form an optionally substituted heterocyclic ring of formula formula

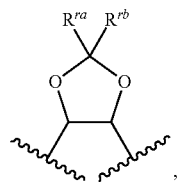

wherein $R^{ra}$ and $R^{rb}$ are each independently optionally methyl, ethyl, or propyl.

In certain embodiments, $R^{5b}$ and $R^{5c}$ are taken with the intervening atoms to form an optionally substituted heterocyclic ring. In certain embodiments, $R^{5b}$ and $R^{5c}$ are taken with the intervening atoms to form an optionally substituted heterocyclic ring of formula

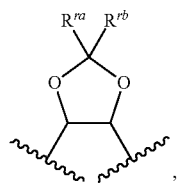

wherein $R^{ra}$ and $R^{rb}$ are each independently optionally substituted $C_{1-6}$ alkyl. In certain embodiments, $R^{5b}$ and $R^{5c}$ are taken with the intervening atoms to form an optionally substituted heterocyclic ring of formula

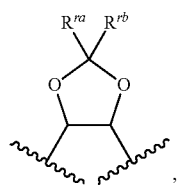

wherein $R^{ra}$ and $R^{rb}$ are each independently optionally methyl, ethyl, or propyl.

In certain embodiments, $R^{5c}$ and $R^{5d}$ are taken with the intervening atoms to form an optionally substituted heterocyclic ring. In certain embodiments, $R^{5c}$ and $R^{5d}$ are taken with the intervening atoms to form an optionally substituted heterocyclic ring of formula

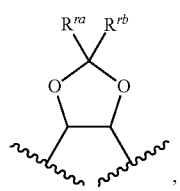

wherein $R^{ra}$ and $R^{rb}$ are each independently optionally substituted $C_{1-6}$ alkyl. In certain embodiments, $R^{5c}$ and $R^{5d}$ are taken with the intervening atoms to form an optionally substituted heterocyclic ring of formula formula

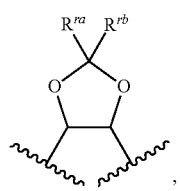

wherein $R^{ra}$ and $R^{rb}$ are each independently optionally methyl, ethyl, or propyl.

In certain embodiments, $R^{5b1}$ and $R^{5b2}$ are taken with the intervening atoms to form an optionally substituted heterocyclic ring. In certain embodiments, $R^{5b1}$ and $R^{5b2}$ are taken with the intervening atoms to form an optionally substituted heterocyclic ring of formula

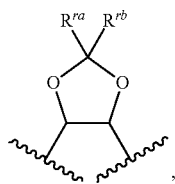

, wherein $R^{ra}$ and $R^{rb}$ are each independently optionally substituted $C_{1-6}$ alkyl. In certain embodiments, $R^{5b1}$ and $R^{5b2}$ are taken with the intervening atoms to form an optionally substituted heterocyclic ring of formula formula

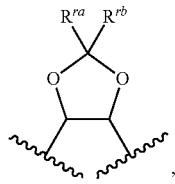

, wherein $R^{ra}$ and $R^{rb}$ are each independently optionally methyl, ethyl, or propyl.

In certain embodiments, $R^{5b2}$ and $R^{5b3}$ are taken with the intervening atoms to form an optionally substituted heterocyclic ring. In certain embodiments, $R^{5b2}$ and $R^{5b3}$ are taken with the intervening atoms to form an optionally substituted heterocyclic ring of formula

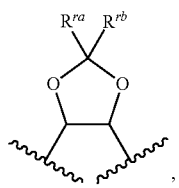

, wherein $R^{ra}$ and $R^{rb}$ are each independently optionally substituted $C_{1-6}$ alkyl. In certain embodiments, $R^{5b2}$ and $R^{5b3}$ are taken with the intervening atoms to form an optionally substituted heterocyclic ring of formula formula

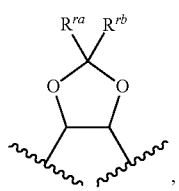

, wherein $R^{ra}$ and $R^{rb}$ are each independently optionally methyl, ethyl, or propyl.

In certain embodiments, $R^{5b3}$ and $R^{5b4}$ are taken with the intervening atoms to form an optionally substituted heterocyclic ring. In certain embodiments, $R^{5b3}$ and $R^{5b4}$ are taken with the intervening atoms to form an optionally substituted heterocyclic ring of formula

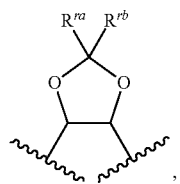

, wherein $R^{ra}$ and $R^{rb}$ are each independently optionally substituted $C_{1-6}$ alkyl. In certain embodiments, $R^{5b3}$ and $R^{5b4}$ are taken with the intervening atoms to form an optionally substituted heterocyclic ring of formula formula wherein $R^{ra}$ and $R^{rb}$ are each independently optionally methyl, ethyl, or propyl.

In certain embodiments, $R^{5c2}$ and $R^{5c4}$ are taken with the intervening atoms to form an optionally substituted heterocyclic ring. In certain embodiments, $R^{5c2}$ and $R^{5c4}$ are taken with the intervening atoms to form an optionally substituted heterocyclic ring of formula

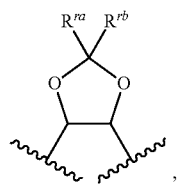

, wherein $R^{ra}$ and $R^{rb}$ are each independently optionally substituted $C_{1-6}$ alkyl. In certain embodiments, $R^{5c2}$ and $R^{5c4}$ are taken with the intervening atoms to form an optionally substituted heterocyclic ring of formula formula

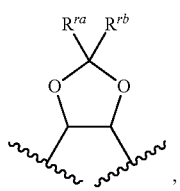

, wherein $R^{ra}$ and $R^{rb}$ are each independently optionally methyl, ethyl, or propyl.

In certain embodiments, $R^{5c5}$ and $R^{5c6}$ are taken with the intervening atoms to form an optionally substituted heterocyclic ring. In certain embodiments, $R^{5c5}$ and $R^{5c6}$ are taken with the intervening atoms to form an optionally substituted heterocyclic ring of formula

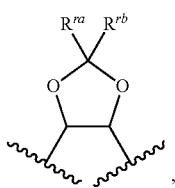

wherein $R^{ra}$ and $R^{rb}$ are each independently optionally substituted $C_{1-6}$ alkyl. In certain embodiments, $R^{5c5}$ and $R^{5c6}$ are taken with the intervening atoms to form an optionally substituted heterocyclic ring of formula formula

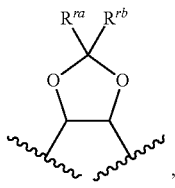

wherein $R^{ra}$ and $R^{rb}$ are each independently optionally methyl, ethyl, or propyl.

In certain embodiments, $R^{5c6}$ and $R^{5c7}$ are taken with the intervening atoms to form an optionally substituted heterocyclic ring. In certain embodiments, $R^{5c6}$ and $R^{5c7}$ are taken with the intervening atoms to form an optionally substituted heterocyclic ring of formula

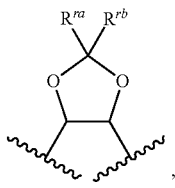

wherein $R^{ra}$ and $R^{rb}$ are each independently optionally substituted $C_{1-6}$ alkyl. In certain embodiments, $R^{5c6}$ and $R^{5c7}$ are taken with the intervening atoms to form an optionally substituted heterocyclic ring of formula formula

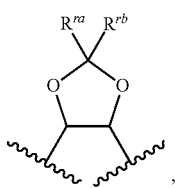

wherein $R^{ra}$ and $R^{rb}$ are each independently optionally methyl, ethyl, or propyl.

As generally defined herein, $R^{5b4}$ is hydrogen, optionally substituted $C_{1-6}$ alkyl, or a nitrogen protecting group. In some embodiments, $R^{5b4}$ is hydrogen. In some embodiments, $R^{5b4}$ is optionally substituted $C_{1-6}$ alkyl. In certain embodiments, $R^{5b4}$ is methyl. In certain embodiments, $R^{5b4}$ is ethyl. In certain embodiments, $R^{5b4}$ is propyl. In certain embodiments, $R^{5b4}$ is a nitrogen protecting group. In certain embodiments, $R^{5b4}$ is acyl. In certain embodiments, $R^{5b4}$ is acetyl. In certain embodiments, $R^{5b4}$ is Bn, BOC, Cbz, Troc, Fmoc, trifluoroacetyl, triphenylmethyl, or Ts.

As generally defined herein, $R^{5b5}$ is hydrogen, optionally substituted $C_{1-6}$ alkyl, or a nitrogen protecting group. In some embodiments, $R^{5b5}$ is hydrogen. In some embodiments, $R^{5b5}$ is optionally substituted $C_{1-6}$ alkyl. In certain embodiments, $R^{5b5}$ is methyl. In certain embodiments, $R^{5b5}$ is ethyl. In certain embodiments, $R^{5b5}$ is propyl. In certain embodiments, $R^{5b5}$ is a nitrogen protecting group. In certain embodiments, $R^{5b5}$ is acyl. In certain embodiments, $R^{5b5}$ is acetyl. In certain embodiments, $R^{5b5}$ is Bn, BOC, Cbz, Troc, Fmoc, trifluoroacetyl, triphenylmethyl, or Ts.

As generally defined herein, $R^{5c3}$ is hydrogen, optionally substituted $C_{1-6}$ alkyl, or a nitrogen protecting group. In some embodiments, $R^{5c3}$ is hydrogen. In some embodiments, $R^{5c3}$ is optionally substituted $C_{1-6}$ alkyl. In certain embodiments, $R^{5c3}$ is methyl. In certain embodiments, $R^{5c3}$ is ethyl. In certain embodiments, $R^{5c3}$ is propyl. In certain embodiments, $R^{5c3}$ is a nitrogen protecting group. In certain embodiments, $R^{5c3}$ is acyl. In certain embodiments, $R^{5c3}$ is acetyl. In certain embodiments, $R^{5c3}$ is Bn, BOC, Cbz, Troc, Fmoc, trifluoroacetyl, triphenylmethyl, or Ts.

As generally defined herein, $R^{5c4}$ is hydrogen, optionally substituted $C_{1-6}$ alkyl, or a nitrogen protecting group. In some embodiments, $R^{5c4}$ is hydrogen. In some embodiments, $R^{5c4}$ is optionally substituted $C_{1-6}$ alkyl. In certain embodiments, $R^{5c4}$ is methyl. In certain embodiments, $R^{5c4}$ is ethyl. In certain embodiments, $R^{5c4}$ is propyl. In certain embodiments, $R^{5c4}$ is a nitrogen protecting group. In certain embodiments, $R^{5c4}$ is acyl. In certain embodiments, $R^{5c4}$ is acetyl. In certain embodiments, $R^{5c4}$ is Bn, BOC, Cbz, Troc, Fmoc, trifluoroacetyl, triphenylmethyl, or Ts.

In some embodiments, the glycan conjugate is of Formula (I-a)

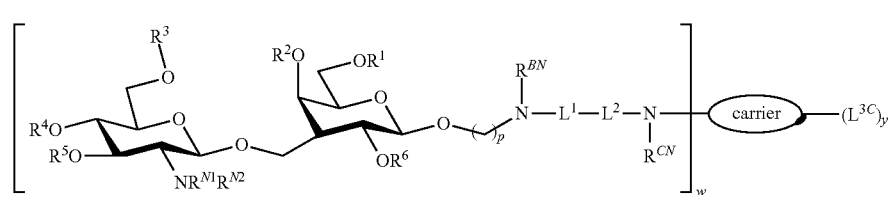

wherein: each instance of $L^1$ is independently a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —OC(R$^{L1b}$)$_2$—, —C(R$^{L1b}$)$_2$O—, —NR$^{L1a}$C(R$^{L1b}$)$_2$—, —C(R$^{L1b}$)$_2$NR$^{L1a}$—, —SC(R$^{L1b}$)$_2$—, —C(R$^{L1b}$)$_2$S—, —S(=O)$_2$O—, —OS(=O)$_2$—, —S(=O)$_2$NR$^{L1a}$—, —NR$^{L1a}$S(=O)$_2$—, or an optionally substituted $C_{1-20}$ hydrocarbon chain, optionally wherein one or more carbon units of the hydrocarbon chain is replaced with —O—, —S—, —NR$^{L1a}$—, —C(=O)—, NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{Lib}$—, cis-CR$^{L1b}$=CR$^{L1b}$—, —C≡C—, —S(=O)$_2$—, —OS(=O)$_2$—, —S(=O)$_2$NR$^{L1a}$—, or —NR$^{L1a}$S(=O)$^2$—, wherein R$^{L1a}$ is hydrogen, optionally substituted $C_{1-6}$ alkyl, or a nitrogen protecting group, or R$^{L1a}$ joined with the adjacent carbon atom to form an optionally substituted heterocyclic ring, and wherein each occurrence of R$^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or R$^{L1b}$ is joined with the adjacent carbon or nitrogen or oxygen atom to form an optionally substituted carbocyclic or heterocyclic ring, or two R$^{L1b}$ groups are joined to form an optionally substituted carbocyclic or optionally substituted heterocyclic ring; and each instance of L$^2$ is independently a moiety derived from a crosslinking reagent capable of crosslinking the carrier and L$^1$-H; each instance of L$^{3C}$ is independently a crosslinking reagent capable of crosslinking the carrier and L$^1$-H; each instance of R$^{CN}$ is independently hydrogen, optionally substituted $C_{1-6}$ alkyl, optionally substituted acyl, or a nitrogen protecting group; w is a integer of 1 to 100, inclusive; and y is 0 or an integer of 1 to 100, inclusive.

As generally defined herein, each instance of L$^1$ is independently a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$_{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —OC(R$^{L1b}$)$_2$—, —C(R$^{L1b}$)$_2$O—, —NR$^{L1a}$C(R$^{L1b}$)$_2$—, —C(R$^{L1b}$)$_2$NR$^{L1a}$—, —SC(R$^{L1b}$)$_2$—, —C(R$^{L1b}$)$_2$S—, —S(=O)$_2$O—, —OS(=O)$_2$—, —S(=O)$_2$NR$^{L1a}$—, —NR$^{L1a}$S(=O)$_2$—, or an optionally substituted $C_{1-20}$ hydrocarbon chain, optionally wherein one or more carbon units of the hydrocarbon chain is replaced with —O—, —S—, —NR$^{L1a}$—, —C(=O)—, NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —S(=O)$_2$O—, —OS(=O)$_2$—, —S(=O)$_2$NR$^{L1a}$—, or —NR$^{L1a}$S(=O)$_2$—, wherein R$^{L1a}$ is hydrogen, optionally substituted $C_{1-6}$ alkyl, or a nitrogen protecting group, or R$^{L1a}$ is joined with the adjacent carbon atom to form an optionally substituted heterocyclic ring, and wherein each occurrence of R$^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or R$^{L1b}$ is joined with the adjacent carbon or nitrogen or oxygen atom to form an optionally substituted carbocyclic or heterocyclic ring, or two R$^{L1b}$ groups are joined to form an optionally substituted carbocyclic or optionally substituted heterocyclic ring. In certain embodiments, L$^1$ is a bond. In certain embodiments, L$^1$ is an optionally substituted $C_{1-20}$ hydrocarbon chain, optionally wherein one or more carbon units of the hydrocarbon chain is replaced with —O—, —S—, —NR$^{L1a}$—, —C(=O)—, NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —S(=O)$_2$O—, —OS(=O)$_2$—, —S(=O)$_2$NR$^{L1a}$—, or —NR$^{L1a}$S(=O)$_2$—. In certain embodiments, L$^1$ is of the formula —C(=O)—(CH$_2$)$_q$—S— or —C(=O)—(CH$_2$)$_q$—C(=O)—, wherein q is an integer of 1 to 8, inclusive. In certain embodiments, q is 1.

In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8.

In certain embodiments, R$^{L1a}$ is hydrogen or optionally substituted $C_{1-6}$ alkyl. In certain embodiments, R$^{L1a}$ is hydrogen. In certain embodiments, R$^{L1a}$ is methyl, ethyl, or propyl.

In certain embodiments, R$^{L1b}$ is hydrogen or optionally substituted $C_{1-6}$ alkyl. In certain embodiments, R$^{L1b}$ is hydrogen. In certain embodiments, R$^{L1b}$ is methyl, ethyl, or propyl.

As generally defined herein, each instance of L$^2$ is a moiety derived from a crosslinking reagent capable of crosslinking the carrier and L$^1$-H. Crosslinking reagents suited to the invention are widely known in the art (see, for example, 1994 Pierce Technical Handbook: cross-linking available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain embodiments, each instance of L$^2$ is a moiety derived from a crosslinking reagent capable of crosslinking the amino group on the surface of the carrier and L$^1$-H. In certain embodiments, L$^2$ is of the formula

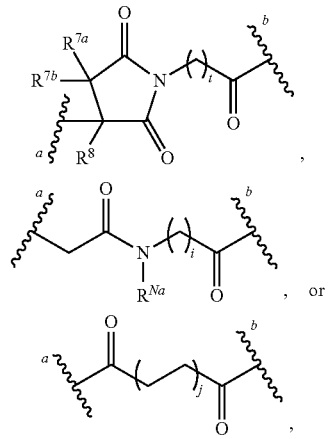

wherein R$^{7a}$, R$^{7b}$ and R$^8$ are each independently hydrogen, halogen, or optionally substituted $C_{1-6}$ alkyl; R$^{Na}$ is independently hydrogen, optionally substituted $C_{1-6}$ alkyl, optionally substituted acyl, or a nitrogen protecting group; i is an integer from 1 to 8, inclusive; and j is an integer from 1 to 8, inclusive, end a is linked to L$^1$-H; and end b is linked to the amino group on the surface of the carrier. In certain embodiments, L$^2$ is of the formula

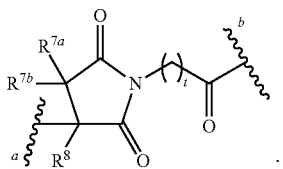

In certain embodiments, $L^2$ is of the formula

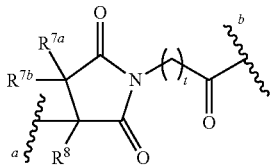

wherein $R^{7a}$, $R^{7b}$ and $R^8$ are hydrogen. In certain embodiments, $L^2$ is of the formula

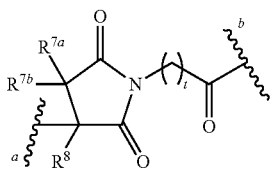

wherein $R^{7a}$, $R^{7b}$ and $R^8$ are hydrogen and t is 5.

As generally defined herein, $R^{CN}$ is independently hydrogen, optionally substituted $C_{1-6}$ alkyl, optionally substituted acyl, or a nitrogen protecting group. In some embodiments, $R^{CN}$ is hydrogen. In some embodiments, $R^{CN}$ is optionally substituted $C_{1-6}$ alkyl. In certain embodiments, $R^{CN}$ is methyl. In certain embodiments, $R^{CN}$ is ethyl. In certain embodiments, $R^{CN}$ is propyl. In certain embodiments, $R^{CN}$ is a nitrogen protecting group. In certain embodiments, $R^{CN}$ is acyl. In certain embodiments, $R^{CN}$ is acetyl. In certain embodiments, $R^{CN}$ is Bn, BOC, Cbz, Troc, Fmoc, trifluoroacetyl, triphenylmethyl, or Ts.

As generally defined herein, w is a integer of 1 to 100, inclusive. In certain embodiments, w is a integer of 1 to 80, inclusive. In certain embodiments, w is a integer of 1 to 60, inclusive. In certain embodiments, w is a integer of 1 to 40, inclusive. In certain embodiments, w is a integer of 1 to 20, inclusive. In certain embodiments, w is a integer of 1 to 10, inclusive. In certain embodiments, w is a integer of 1 to 5, inclusive.

As generally defined herein, y is 0 or an integer of 1 to 100, inclusive. In certain embodiments, y is 0. In certain embodiments, y is a integer of 1 to 80, inclusive. In certain embodiments, y is a integer of 1 to 60, inclusive. In certain embodiments, y is a integer of 1 to 40, inclusive. In certain embodiments, y is a integer of 1 to 20, inclusive. In certain embodiments, y is a integer of 1 to 10, inclusive. In certain embodiments, y is a integer of 1 to 5, inclusive.

As generally defined herein, $L^{3C}$ is independently a crosslinking reagent or a crosslinking reagent moiety wherein the crosslinking reagent is capable of crosslinking the carrier and $L^1$-H. In certain embodiments, $L^{3C}$ is one of the following formulae:

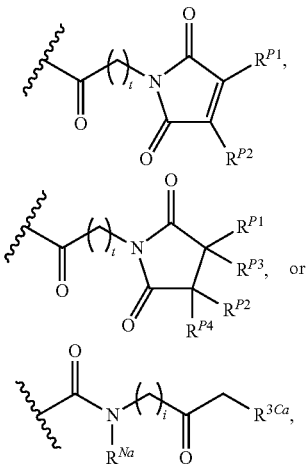

wherein $R^{P1}$, $R^{P2}$, and $R^{3ca}$ are each independently hydrogen, halogen, or optionally substituted $C_{1-6}$ alkyl; each of $R^{P3}$ and $R^{P4}$ independently optionally substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, —$OR^{3CO}$, —$SR^{3CS}$, or —$N(R^{3CN})_2$; $R^{3CO}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or an oxygen protecting group; $R^{2CS}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or a sulfur protecting group; each instance of $R^{3CN}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or a nitrogen protecting group.

In certain embodiments, $R^{P1}$ is hydrogen. In certain embodiments, $R^{P1}$ is halogen. In certain embodiments, $R^{P1}$ is optionally substituted $C_{1-6}$ alkyl. In certain embodiments, $R^{P2}$ is methyl, ethyl, or propyl.

In certain embodiments, $R^{P2}$ is hydrogen. In certain embodiments, $R^{P2}$ is halogen. In certain embodiments, $R^{P2}$ is optionally substituted $C_{1-6}$ alkyl. In certain embodiments, $R^{P2}$ is methyl, ethyl, or propyl.

In certain embodiments, $R^{P3}$ is hydrogen. In certain embodiments, $R^{P3}$ is halogen. In certain embodiments, $R^{P3}$ is optionally substituted $C_{1-6}$ alkyl. In certain embodiments, $R^{P3}$ is methyl, ethyl, or propyl. In certain embodiments, $R^{P3}$ is —$SR^{3CS}$, wherein $R^{3CS}$ is optionally substituted alkyl.

In certain embodiments, $R^{P4}$ is hydrogen. In certain embodiments, $R^{P4}$ is halogen. In certain embodiments, $R^{P4}$ is optionally substituted $C_{1-6}$ alkyl. In certain embodiments, $R^{P4}$ is methyl, ethyl, or propyl. In certain embodiments, $R^{P4}$ is —$SR^{3CS}$, wherein $R^{3CS}$ is optionally substituted alkyl.

In certain embodiments, $R^{3Ca}$ is hydrogen. In certain embodiments, $R^{3Ca}$ is halogen. In certain embodiments, $R^{3Ca}$ is optionally substituted $C_{1-6}$ alkyl. In certain embodiments, $R^{3Ca}$ is methyl, ethyl, or propyl.

In certain embodiments, $L^{3C}$ is one of the following formulae:

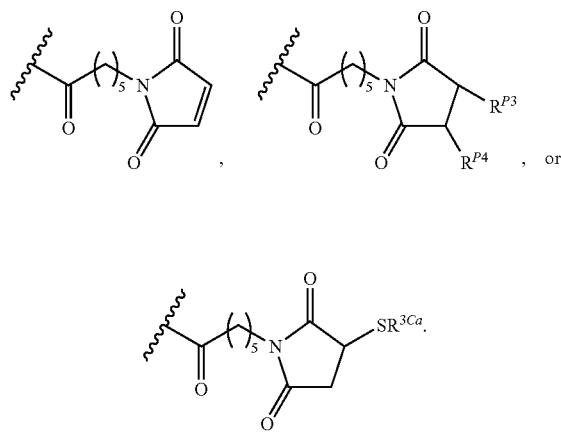

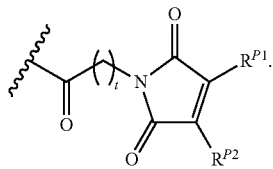

In certain embodiments, $L^{3C}$ is a crosslinking reagent of the formula

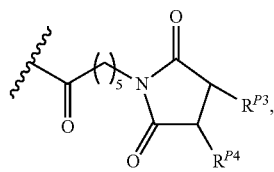

prepared a nucleophilic reaction with the crosslinking reagent of the formula

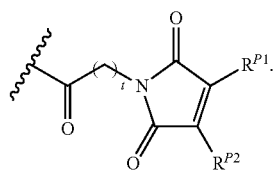

In certain embodiments, $L^{3C}$ is a crosslinking reagent moiety of the formula

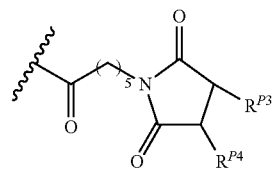

wherein $R^{P3}$ is hydrogen and $R^{P4}$ is —$SR^{3CS}$; or $R^{P3}$ is —$SR^{3CS}$ and $R^{P4}$ is hydrogen.

In some embodiments, the glycan moiety is of Formula (II-a)

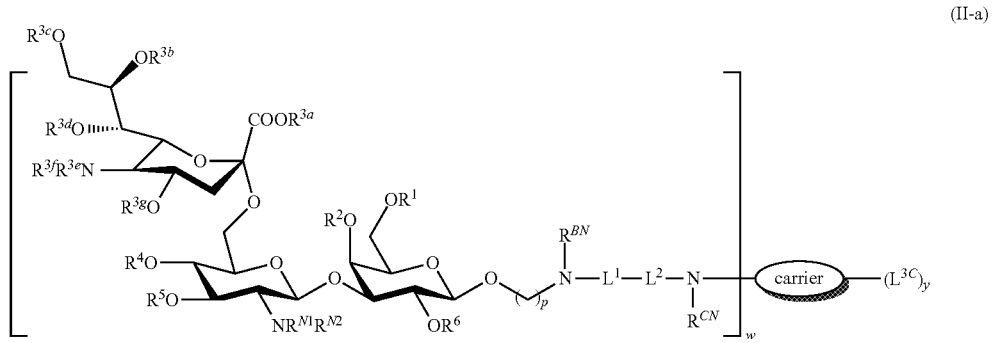

or a pharmaceutically acceptable salt thereof.

In some embodiments, the glycan moiety is of Formula (II-b)
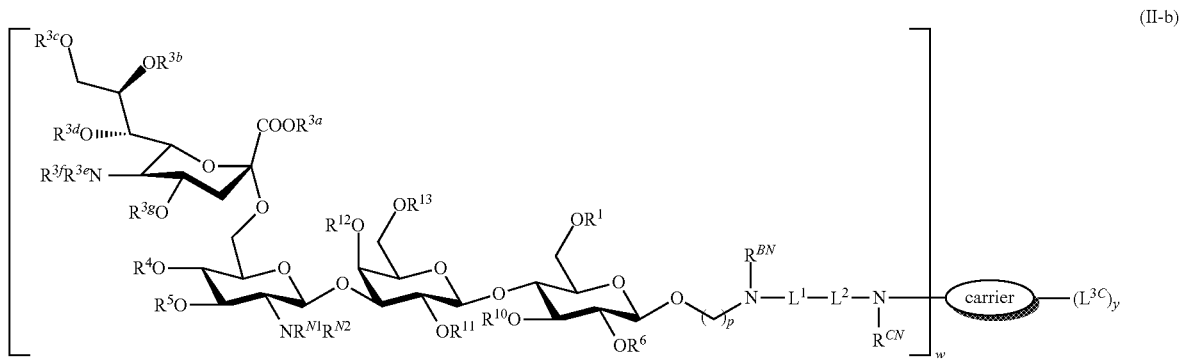
or a pharmaceutically acceptable salt thereof.
In some embodiments, the glycan moiety is of Formula (III-a)
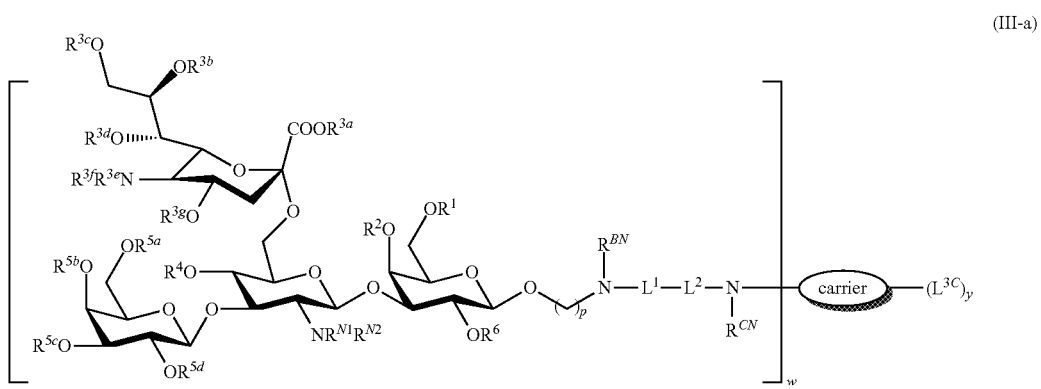
or a pharmaceutically acceptable salt thereof.
In some embodiments, the glycan moiety is of Formula (III-b)
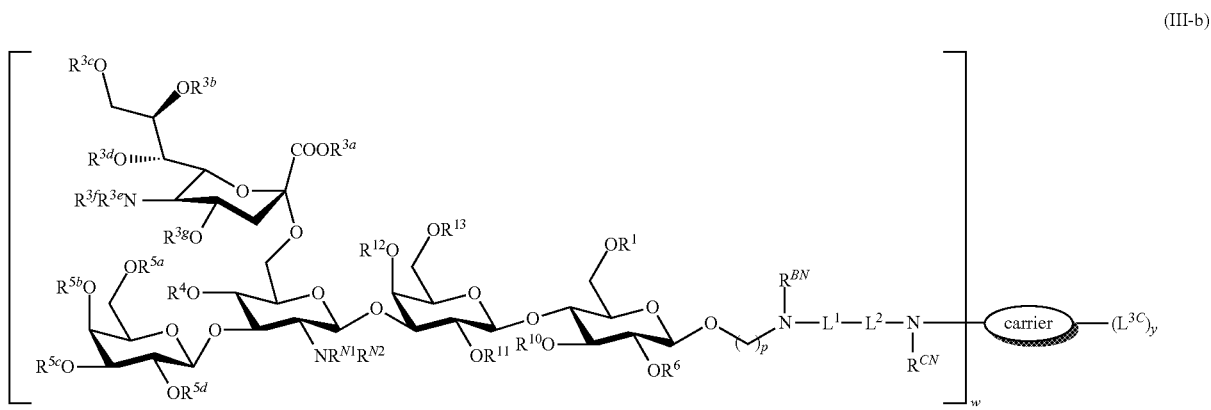
or a pharmaceutically acceptable salt thereof.

In some embodiments, the glycan moiety is of Formula (IV-a)
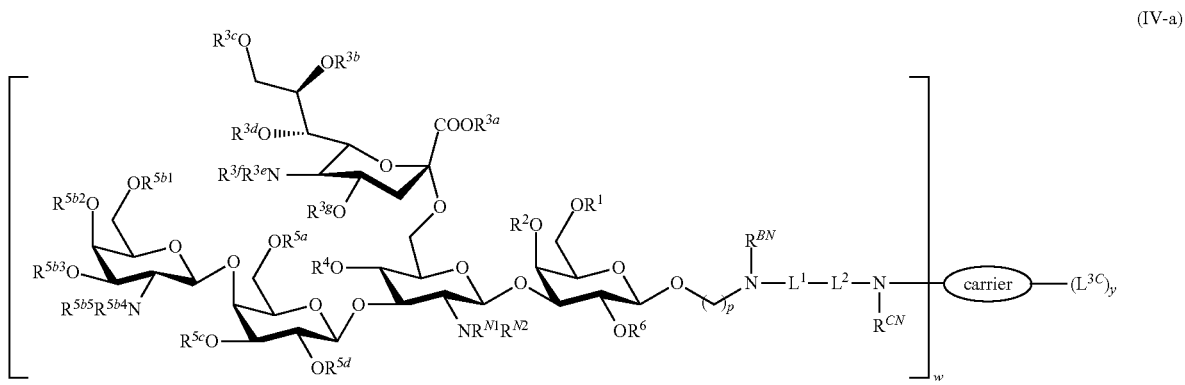
or a pharmaceutically acceptable salt thereof.
In some embodiments, the glycan moiety is of Formula (IV-b)
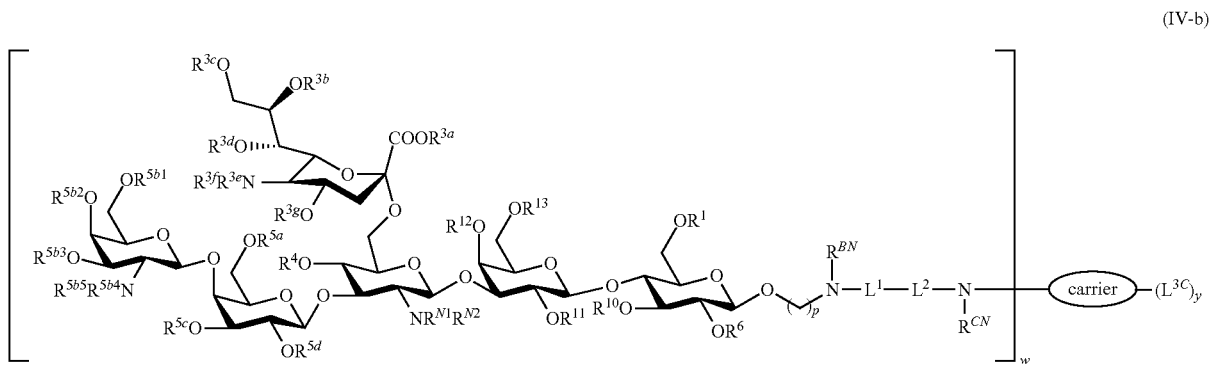
or a pharmaceutically acceptable salt thereof.
In some embodiments, the glycan moiety is of Formula (V-a)
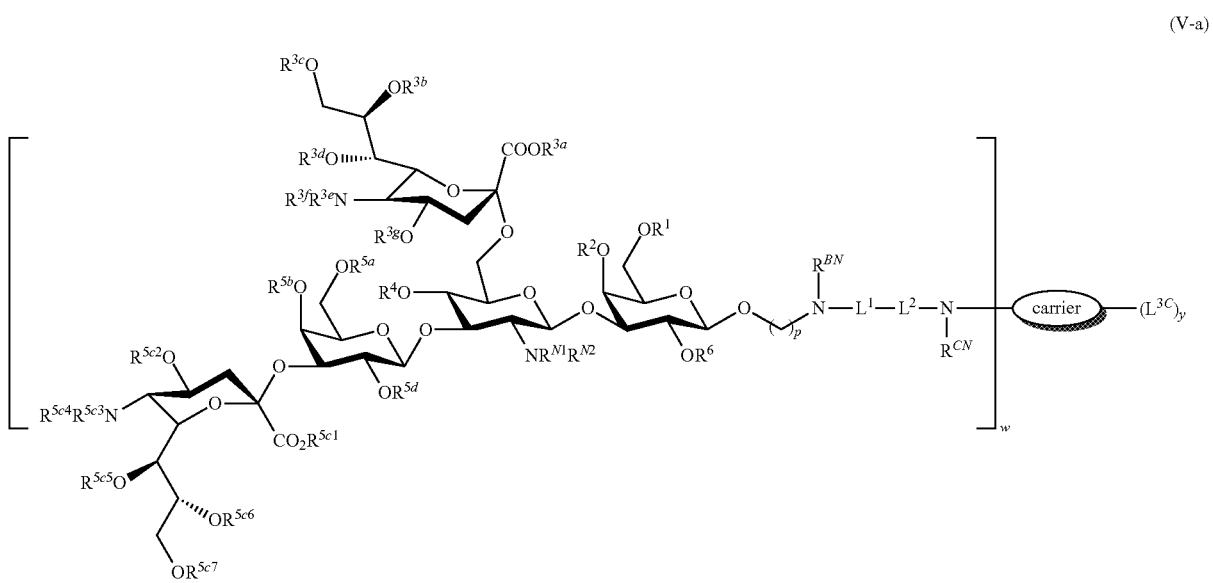
or a pharmaceutically acceptable salt thereof.

In some embodiments, the glycan moiety is of Formula (V-b)
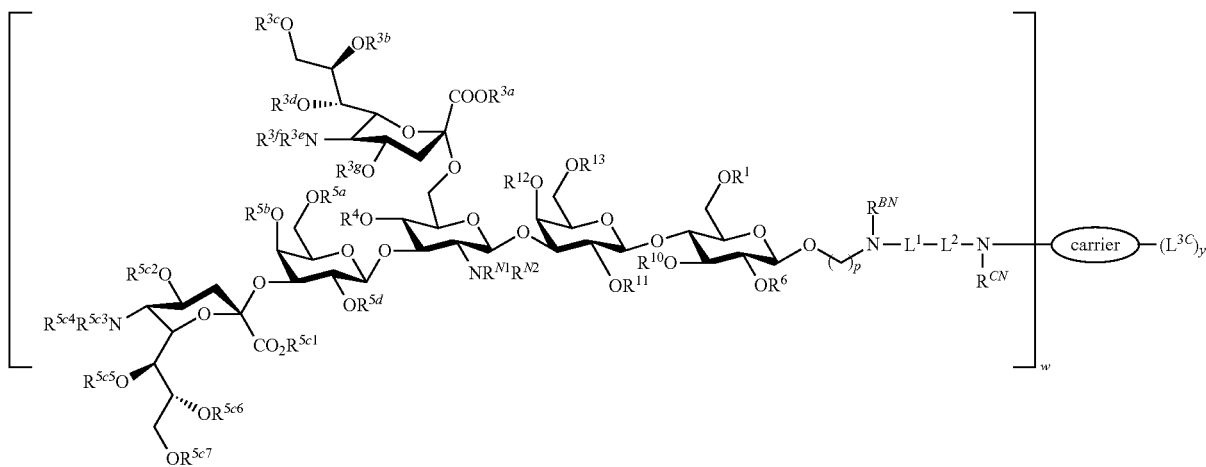
or a pharmaceutically acceptable salt thereof.
In some embodiments, the glycan moiety is of Formula (VI-a)
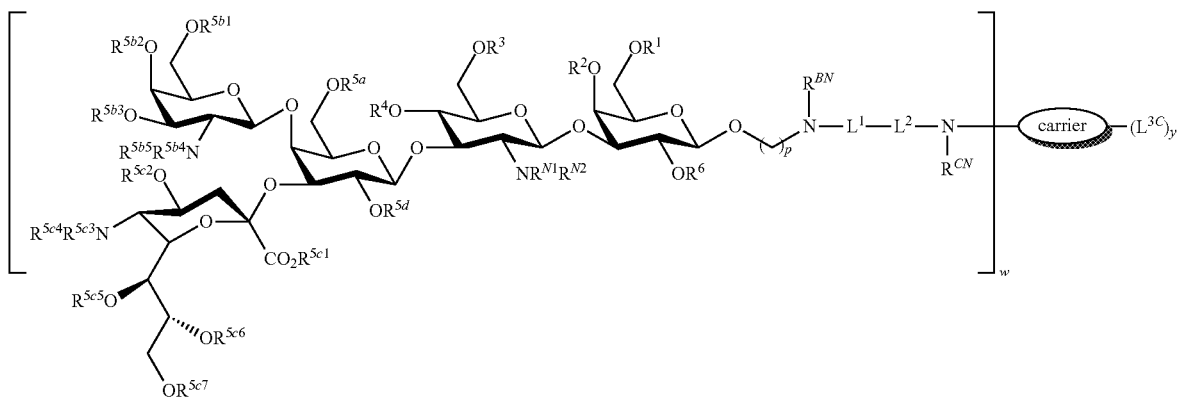
or a pharmaceutically acceptable salt thereof.
In some embodiments, the glycan moiety is of Formula (VI-b)
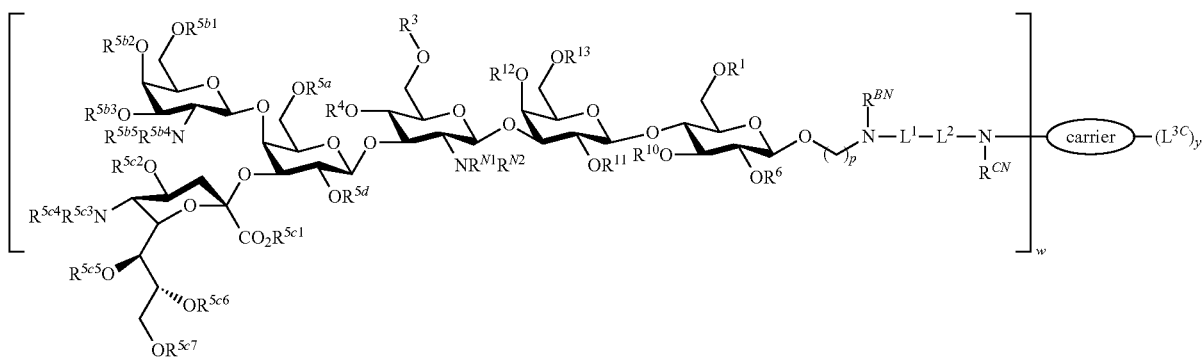
or a pharmaceutically acceptable salt thereof.

In some embodiments, the glycan moiety is of Formula (VII-a)

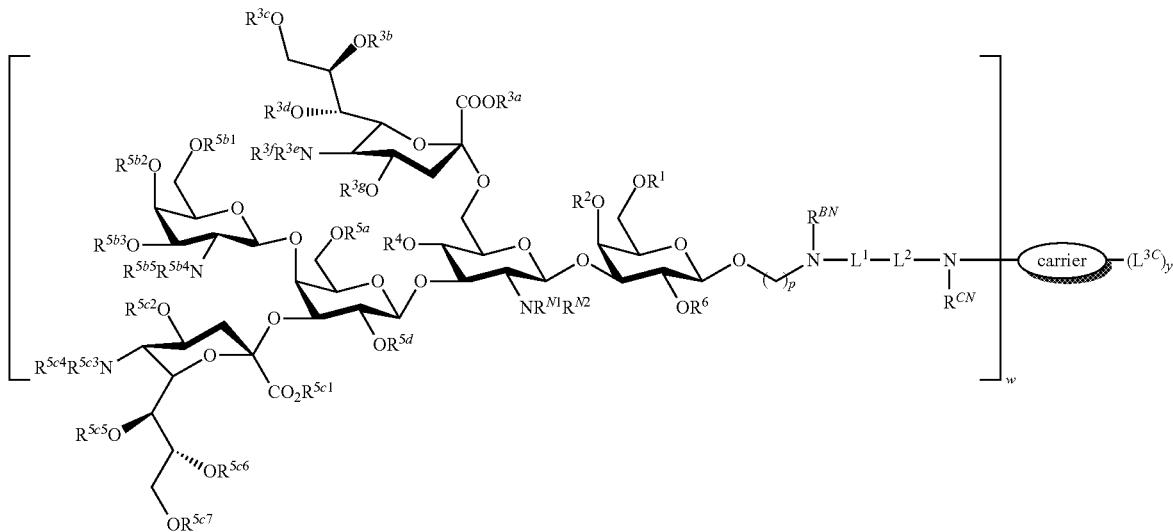

(VII-a)

or a pharmaceutically acceptable salt thereof.

In some embodiments, the glycan moiety is of Formula (VII-b)

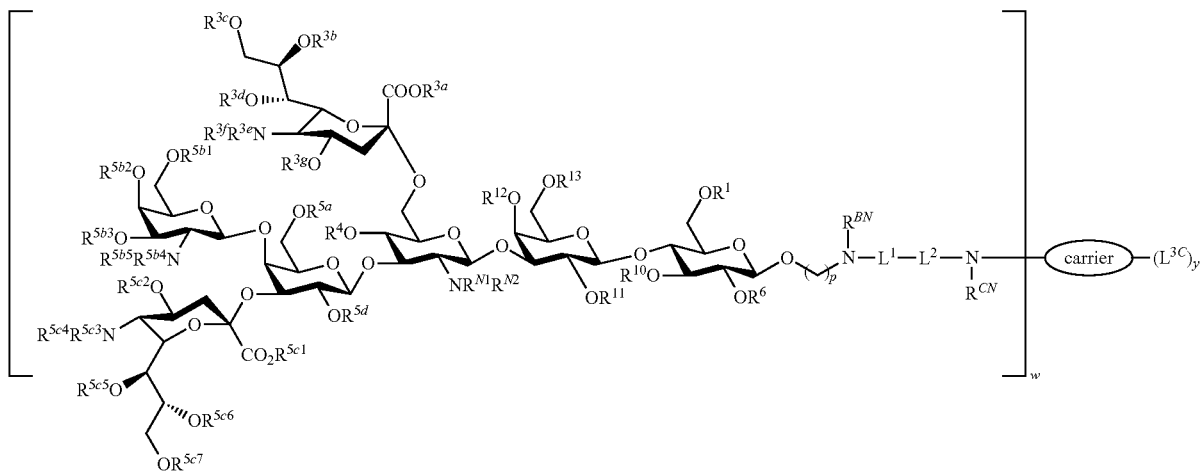

(VII-b)

or a pharmaceutically acceptable salt thereof.

In certain embodiments, $R^1$ and $R^2$ are hydrogen. In certain embodiments, $R^1$, $R^2$, and $R^6$ are all hydrogen. In certain embodiments, $R^1$ and $R^2$ are acetyl. In certain embodiments, $R^1$, $R^2$, and $R^6$ are acetyl. In certain embodiments, $R^1$ and $R^2$ are Bn. In certain embodiments, $R^1$, $R^2$, and $R^6$ are Bn.

In certain embodiments, $R^3$ and $R^4$ are hydrogen. In certain embodiments, $R^3$, $R^4$, and $R^5$ are all hydrogen. In certain embodiments, $R^3$ and $R^4$ are acetyl. In certain embodiments, $R^3$, $R^4$, and $R^5$ are acetyl. In certain embodiments, $R^3$ and $R^4$ are Bn. In certain embodiments, $R^3$, $R^4$, and $R^5$ are Bn. In certain embodiments, $R^3$ is acetyl and $R^4$ is Bn.

In certain embodiments, $R^{3b}$ and $R^{3c}$ are hydrogen. In certain embodiments, $R^{3b}$, $R^{3c}$, and $R^{3d}$ are all hydrogen. In certain embodiments, $R^{3b}$, $R^{3c}$, and $R^{3d}$ are acetyl. In certain embodiments, $R^{3b}$, $R^{3c}$, and $R^{3d}$ are acetyl and $R^{3d}$ and are taken with the intervening atoms to form an optionally substituted heterocyclic ring of formula formula

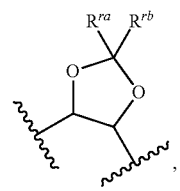

, wherein $R^{ra}$ and $R^{rb}$ are each independently optionally substituted $C_{1-6}$ alkyl. In certain embodiments, $R^{3b}$, $R^{3c}$, and $R^{3d}$ are acetyl and $R^{3d}$ and are taken with the intervening atoms to form an optionally substituted heterocyclic ring of formula formula

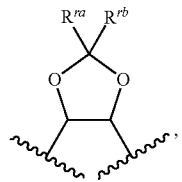

wherein $R^{ra}$ and $R^{rb}$ are each independently optionally methyl, ethyl, or propyl.

In certain embodiments, $R^{5a}$ and $R^{5b}$ are hydrogen. In certain embodiments, $R^{5a}$, $R^{5b}$, and $R^{5c}$ are hydrogen. In certain embodiments, $R^{5a}$, $R^{5b}$, $R^{5c}$, and $R^{5d}$ are hydrogen. In certain embodiments, $R^{5a}$, $R^{5b}$, and $R^{5c}$ are acetyl. In certain embodiments, $R^{5a}$, $R^{5b}$, $R^{5c}$, and $R^{5d}$ are acetyl. In certain embodiments, $R^{5a}$ is Bn and $R^{5d}$ is Bz.

In certain embodiments, $R^{5b1}$ and $R^{5b2}$ are hydrogen. In certain embodiments, $R^{5b1}$, $R^{5b2}$, $R^{5b3}$, and $R^{5b4}$ are hydrogen. In certain embodiments, $R^{5b1}$, $R^{5b2}$, $R^{5b3}$, and $R^{5b4}$ are hydrogen and $R^{5b5}$ is acetyl. In certain embodiments, $R^{5b1}$ is acetyl; $R^{5b2}$ is Bn; $R^{5b3}$ is acetyl. In certain embodiments, $R^{5b1}$ is acetyl; $R^{5b2}$ is Bn; $R^{5b3}$ is acetyl; $R^{5b5}$ is Troc. In certain embodiments, $R^{5b1}$ is acetyl; $R^{5b2}$ is Bn; $R^{5b3}$ is TBS. In certain embodiments, $R^{5b1}$ is acetyl; $R^{5b2}$ is Bn; $R^{5b3}$ is TBS; $R^{5b5}$ is Troc.

In certain embodiments, $R^{5c6}$ and $R^{5c7}$ are hydrogen. In certain embodiments, $R^{5c5}$, $R^{5c6}$, and $R^{5c7}$ are all hydrogen. In certain embodiments, $R^{5c2}$, $R^{5c3}$, $R^{5c5}$, $R^{5c6}$, and $R^{5c7}$ are all hydrogen. In certain embodiments, $R^{5c2}$, $R^{5c3}$, $R^{5c5}$, $R^{5c6}$, and $R^{5c7}$ are all hydrogen and $R^{5c4}$ is acetyl. In certain embodiments, $R^{5c5}$, $R^{5c6}$, and $R^{5c7}$ are acetyl. In certain embodiments, $R^{5c5}$, $R^{5c6}$, and $R^{5c7}$ are acetyl and $R^{5c4}$ is hydrogen. In certain embodiments, $R^{5c5}$, $R^{5c6}$, and $R^{5c7}$ are acetyl; $R^{5c4}$ is hydrogen; $R^{5c2}$ and $R^{5c3}$ are taken with the intervening atoms to form an optionally substituted heterocyclic ring of formula formula

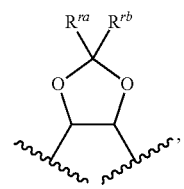

wherein $R^{ra}$ and $R^{rb}$ are each independently optionally substituted $C_{1-6}$ alkyl. In certain embodiments, $R^{5c5}$, $R^{5c6}$, and $R^{5c7}$ are acetyl; $R^{5c4}$ is hydrogen; $R^{5c2}$ and $R^{5c3}$ are taken with the intervening atoms to form an optionally substituted heterocyclic ring of formula formula wherein $R^{ra}$ and $R^{rb}$ are each independently optionally methyl, ethyl, or propyl.

In certain embodiments, $R^{N1}$ is acetyl and $R^{N2}$ is hydrogen. In certain embodiments, $R^{N1}$ and $R^{N2}$ are hydrogen.

In certain embodiments, $R^{BN}$ and $R^{CN}$ are hydrogen.

In certain embodiments, $R^{10}$, $R^{11}$, $R^{12}$, and $R^{13}$ are hydrogen.

Any of the glycan moieties described herein may be conjugated with a carrier to enhance the immunogenicity of the glycan moieties. Such carriers include, but are not limited to, a protein, a lipid, a lipolized protein, a virus, a peptide comprising a T cell epitope, or a dendrimer of glycopeptides. In some embodiments, the carrier is a toxin protein selected from the group consisting of diphtheria toxin cross-reacting material 197 (DT-CRM197), diphtheria toxoid, tetanus toxoid, and outer-membrane protein (OMP). In other examples, the carrier is the toxin protein is DT-CRM197.

In certain embodiments, the glycan conjugate described herein is of one of the following formulae:

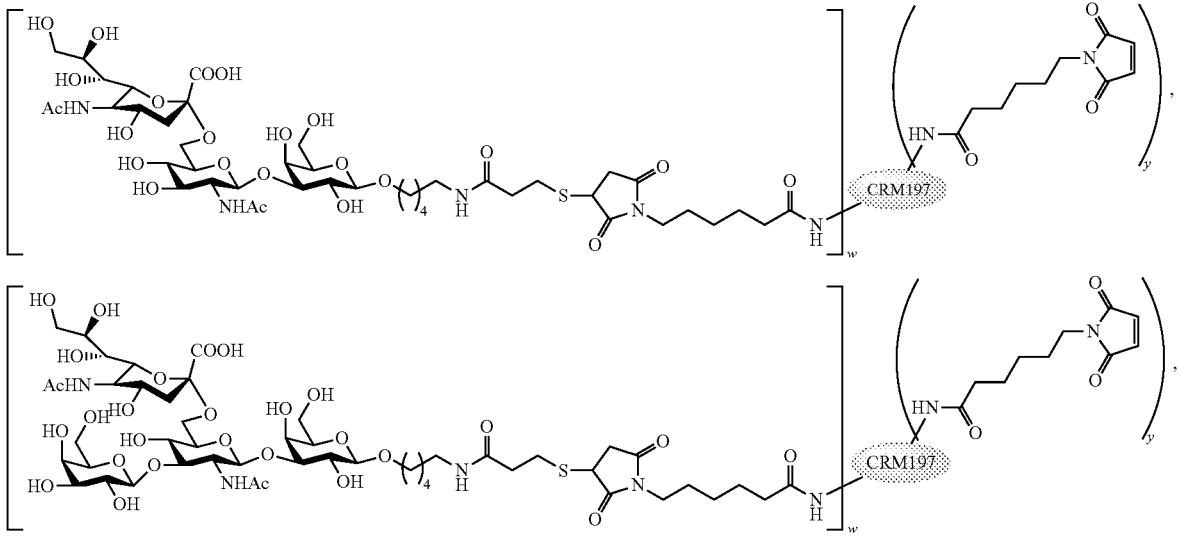

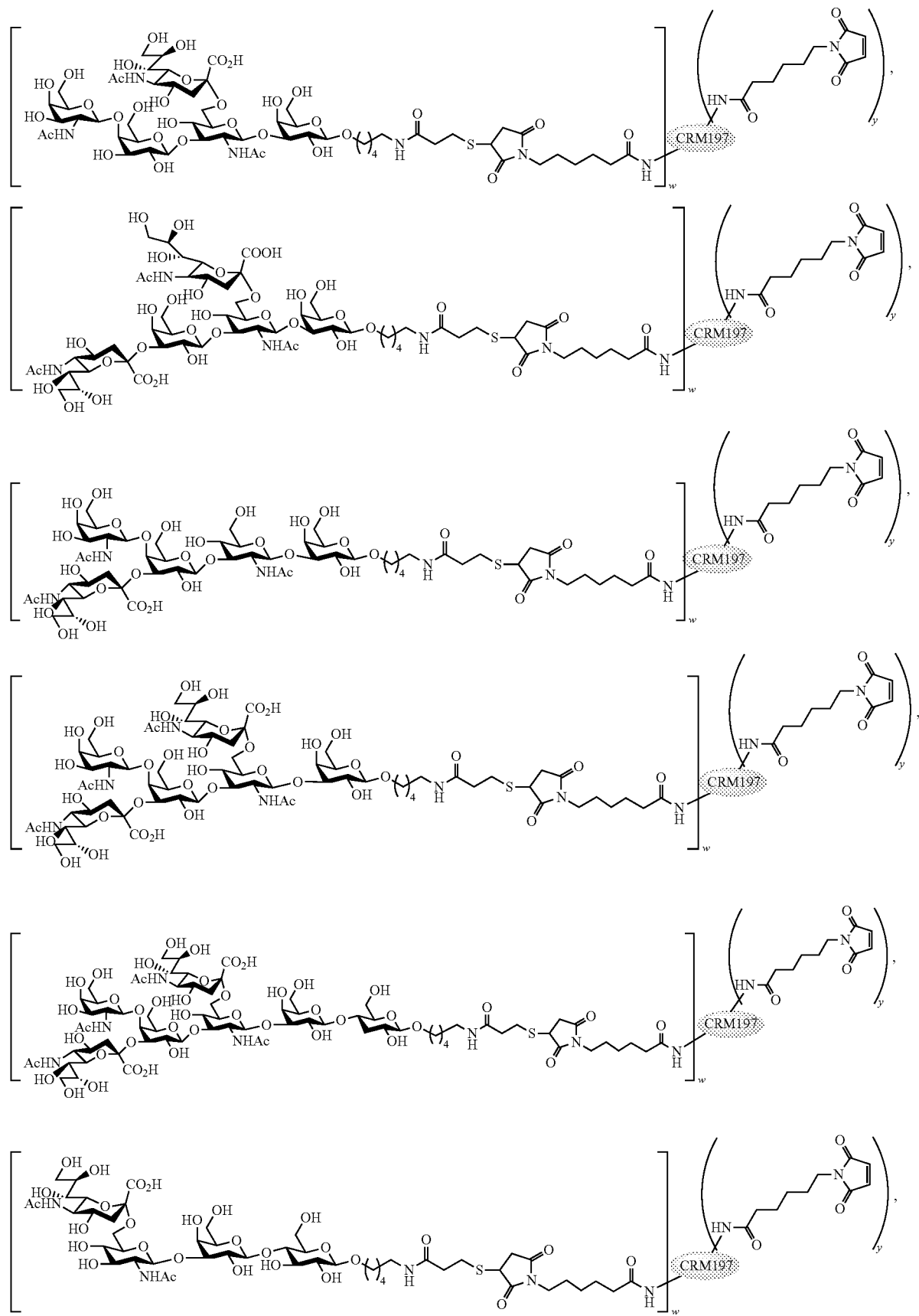

-continued

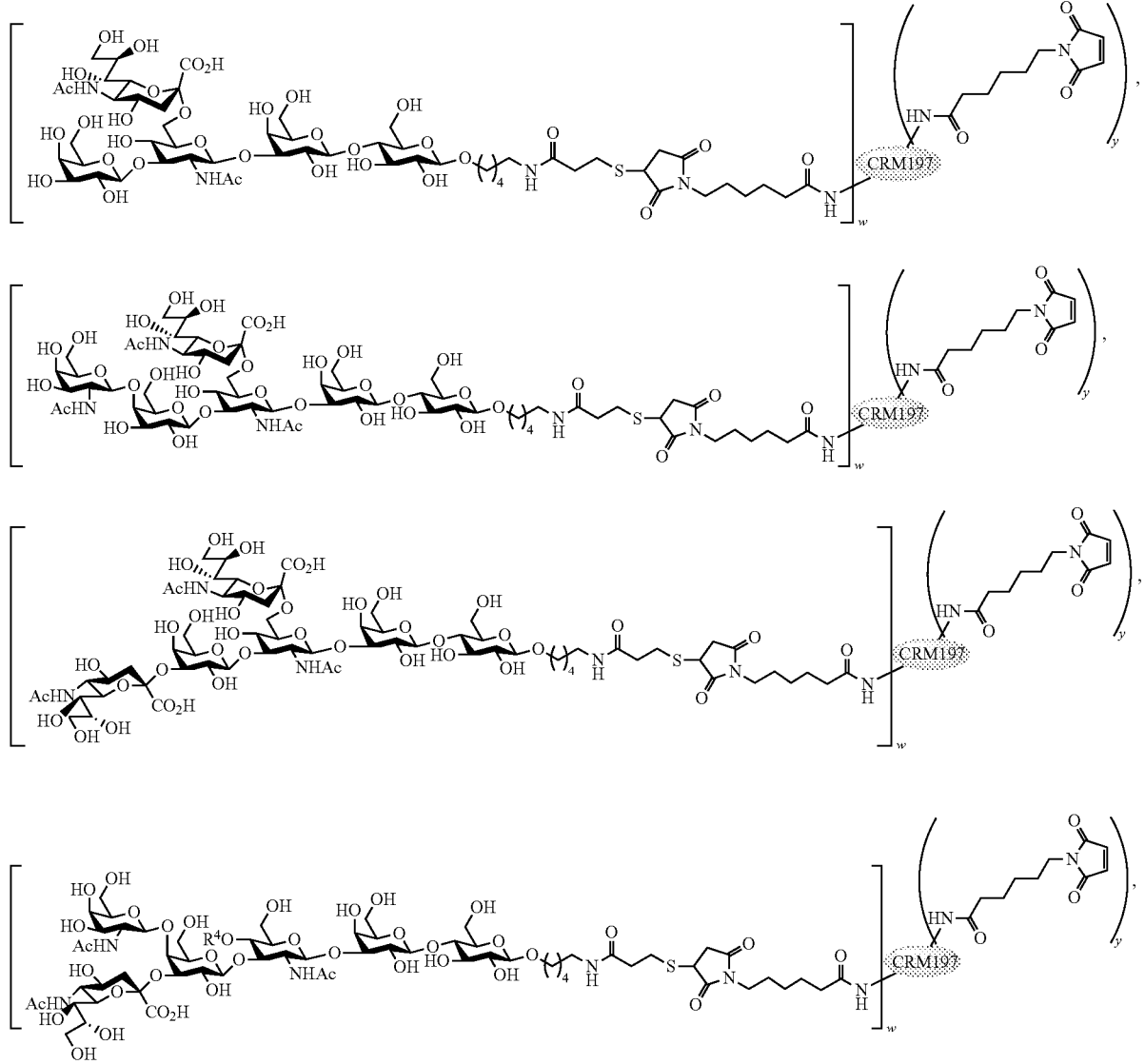

In another aspect, the present invention provides a glycan conjugate mixture comprising at least two of the glycan conjugates described herein. In certain embodiments, the glycan conjugate mixture has an average value of w from about 1.0 to about 100.0. In certain embodiments, the glycan conjugate mixture has an average value of w from about 1.0 to about 20.0. In certain embodiments, the glycan conjugate mixture has an average value of w from about 1.0 to about 10.0. In certain embodiments, the glycan conjugate mixture has an average value of w from about 1.0 to about 5.0. In certain embodiments, the glycan conjugate mixture has an average value of w of 1.0, 3.0, 4.7, 10.0, or 12.7. In certain embodiments, the glycan conjugate mixture has an average value of w of 4.7.

Method of Synthesis

The present invention provides methods of preparing glycan conjugates comprising a carrier and a glycan moiety of Formula (I). The method of preparing the inventive glycan conjugates comprising coupling a compound of Formula (C-1)

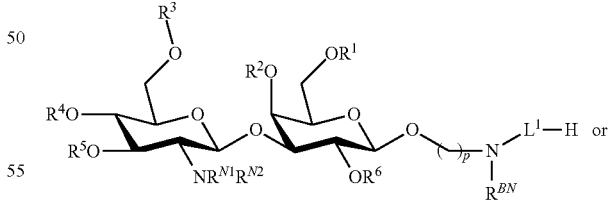
(C-1a)

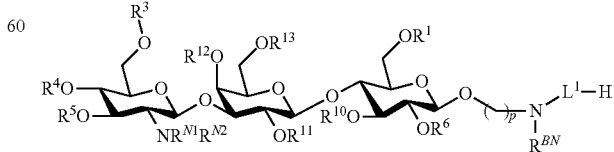
(C-1b)

or a salt thereof, with a compound of Formula (C-2)

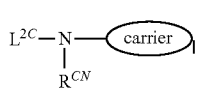
(C-2)

or a salt thereof,
wherein $L^1$, $R^1$, $R^2$, $R^3$, $R^4$, $R^5$, $R^6$, $R^{10}$, $R^{11}$, $R^{12}$, $R^{13}$, $R^{N1}$, $R^{CN}$, $R^{BN}$, and p are as defined herein; and $L^{2C}$ is a crosslinking reagent capable of crosslinking the carrier and $L^1$-H.

As generally defined herein, $L^{2C}$ is independently a crosslinking reagent capable of crosslinking the carrier and $L^1$-H. In certain embodiments, $L^{2C}$ is one of the following formulae:

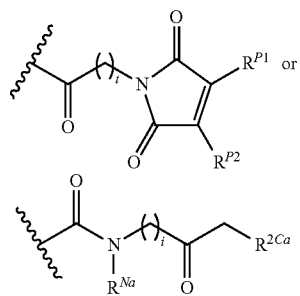

or a salt thereof,
wherein each instance of $R^{P1}$ and $R^{P2}$ are each independently hydrogen, halogen, or optionally substituted C1-6 alkyl; each instance of $R^{2Ca}$ is a leaving group selected from selected from —Br, —Cl, —I, —OS($=$O)$_2R^{2CO}$, or —OS($=$O)$R^{2CO}$, wherein $R^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and each of t and i is independently an integer of 1 to 8, inclusive;

As generally used herein, $R^{P1}$ and $R^{P2}$ are each independently hydrogen or optionally substituted $C_{1-6}$ alkyl. In certain embodiments, $R^{P1}$ is hydrogen. In certain embodiments, $R^{P1}$ is optionally substituted $C_{1-6}$ alkyl. In certain embodiments, $R^{P1}$ is unsubstituted $C_{1-6}$ alkyl. In certain embodiments, $R^{P1}$ is methyl, ethyl, or propyl. In certain embodiments, $R^{P2}$ is hydrogen. In certain embodiments, $R^{P2}$ is optionally substituted $C_{1-6}$ alkyl. In certain embodiments, $R^{P2}$ is unsubstituted $C_{1-6}$ alkyl. In certain embodiments, $R^{P2}$ is methyl, ethyl, or propyl. In certain embodiments, both $R^{P1}$ and $R^{P2}$ are hydrogen. In certain embodiments, $R^{P1}$ and $R^{P2}$ are each independently optionally substituted $C_{1-6}$ alkyl.

As generally used herein, $R^{2Ca}$ is a leaving group. In certain embodiments, $R^{2Ca}$ is a leaving group selected from selected from the group consisting of —Br, —Cl, —I, —OS($=$O)$^2R^{2CO}$, or —OS($=$O)$R^{2CO}$, wherein $R^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^{2Ca}$ is —Br, —Cl, or —I. In certain embodiments, $R^{2Ca}$ is —OS($=$O)$_2R^{2CO}$, or —OS($=$O)$R^{2CO}$, wherein $R^{2CO}$ is optionally substituted alkyl such as methyl, ethyl, or propyl.

Figure 18:
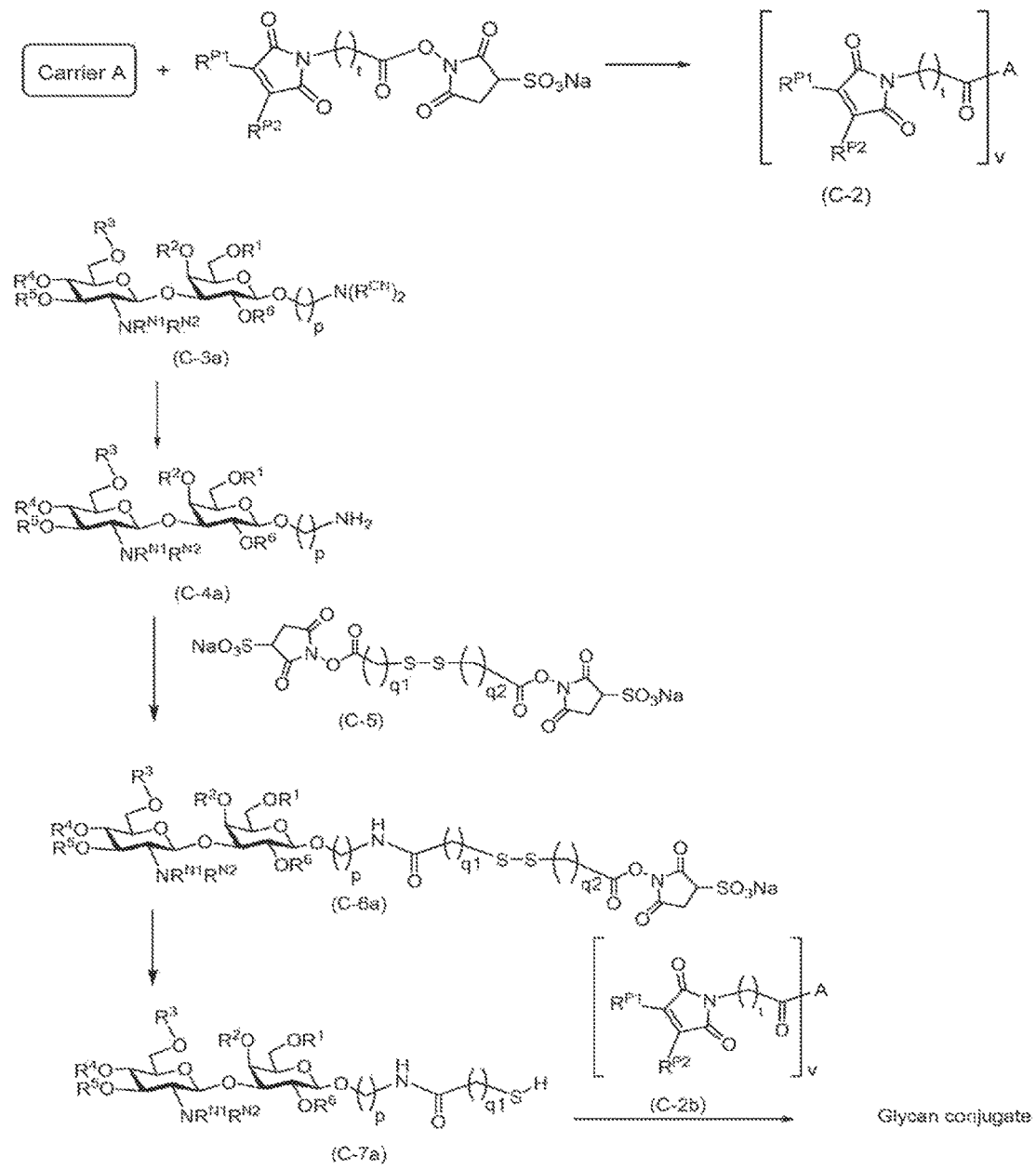
FIG. 18 shows general synthetic route to prepare the inventive glycan conjugates.
Figure 19:
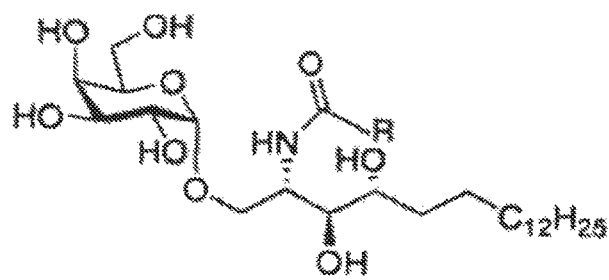
FIG. 19 shows exemplary adjuvants.

The synthesis of the glycan conjugates as described herein generally starts from coupling compounds of Formula (C-1a) or Formula (C-1b) with Formula (C-2). An exemplary scheme is shown in FIG. 18. Generally, a compound of Formula (C-3a) is deprotected to give a a compound of Formula (C-4a). The compound of Formula (C-4a) is activated to give a compound of Formula (C-6a). Cleavage of the the S—S bond in Formula (C-6a) gives a compound of Formula (C-7a). Carrier A is activated to give a compound of Formula (C-2). Coupling the compound of Formula (C-1a) and the compound of Formula (C-2b) gives a glycan conjugate. As used herein, v is an integer of 1 to 100, inclusive. In certain embodiments, v is an integer of 1 to 80, inclusive. In certain embodiments, v is an integer of 1 to 60, inclusive. In certain embodiments, v is an integer of 1 to 40, inclusive. In certain embodiments, v is an integer of 1 to 20, inclusive. In certain embodiments, v is an integer of 1 to 10, inclusive. In certain embodiments, v is an integer of 1 to 5, inclusive.

In certain embodiments, the activating agent for compound of Formula (C-4a) is a compound of Formula (C-5) (FIG. 18) wherein $R^{P1}$, $R^{P2}$, and t are as defined herein. In certain embodiments, the activating reaction is carried out under pH from about 6.0 to 9.0. In certain embodiments, the activating reaction is carried out under pH from about 6.0 to 8.0. In certain embodiments, the activating reaction is carried out under pH from about 7.0 to 9.0. In certain embodiments, the activating reaction is carried out under pH from about 7.5 to 8.0. In certain embodiments, the activating reaction is carried out under pH from about 7.0 to 7.5. In certain embodiments, the activating reaction is carried out in the presence of a buffer. In certain embodiments, the activating reaction is carried out in the presence of phosphate buffered saline (PBS).

As used herein, an activating reagent denotes a reagent which can react with one of the starting materials of a chemical reaction to form one or more active intermediate which subsequently facilitates the completion of the reaction. The active intermediate may not be stable enough to be separated and characterized. Examples of the activating reagent include, but are not limited to the coupling reagents used in amide/peptide synthesis, such as carbodiimide compound (EDC, DCC, DIC, and the like) and benzotriazole compounds (such as HOBt and HOAt); certain oxides and chloride (such as $P_2O_5$ and $POCl_3$); a reagent which react with a molecule to form a leaving group (such as MsCl, $Tf_2O$, and reagents for Mitsunobu reaction); and etc. In certain embodiments, the activating reagent is 3,3'-Dithiobis (sulfosuccinimidyl propionate) (DTSSP) and/or N-[ε-maleimidocaproyloxy]sulfosuccinimide ester) (sulfo-EMCS).

As used herein, each instance of $R^{CN}$ is optionally substituted alkyl, or a nitrogen protecting group. In some embodiments, $R^{CN}$ is methyl, ethyl, or propyl. In certain embodiments, $R^{CN}$ is a nitrogen protecting group. In certain embodiments, $R^{CN}$ is acyl. In certain embodiments, $R^{CN}$ is acetyl. In certain embodiments, $R^{CN}$ is Bn, BOC, Cbz, Troc, Fmoc, trifluoroacetyl, triphenylmethyl, or Ts. In certain embodiments, $R^{CN}$ is Bn or Cbz.

Figure 25:
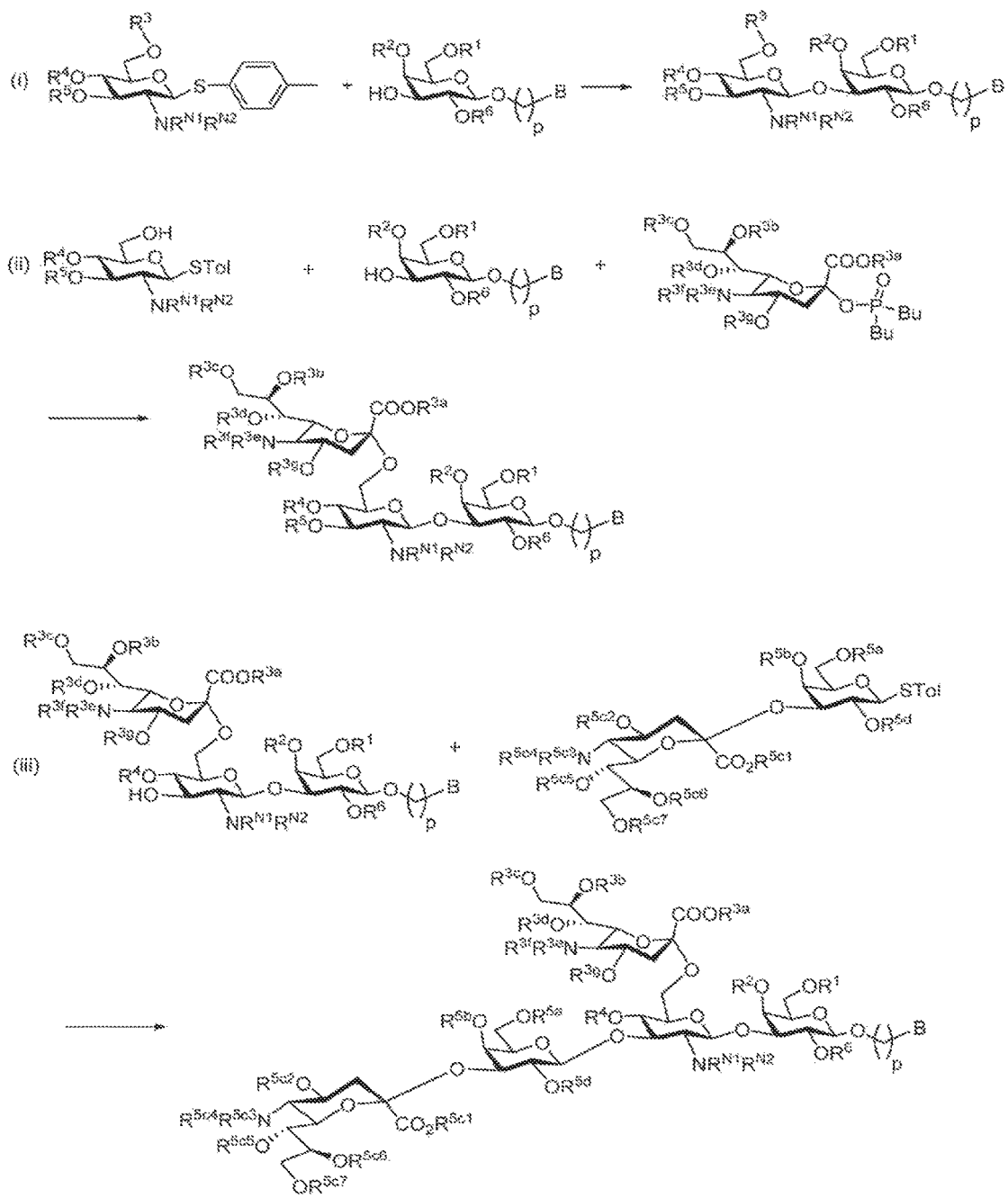
FIG. 25 shows exemplary synthetic scheme of compounds of Formula (F-1).
Figure 26:
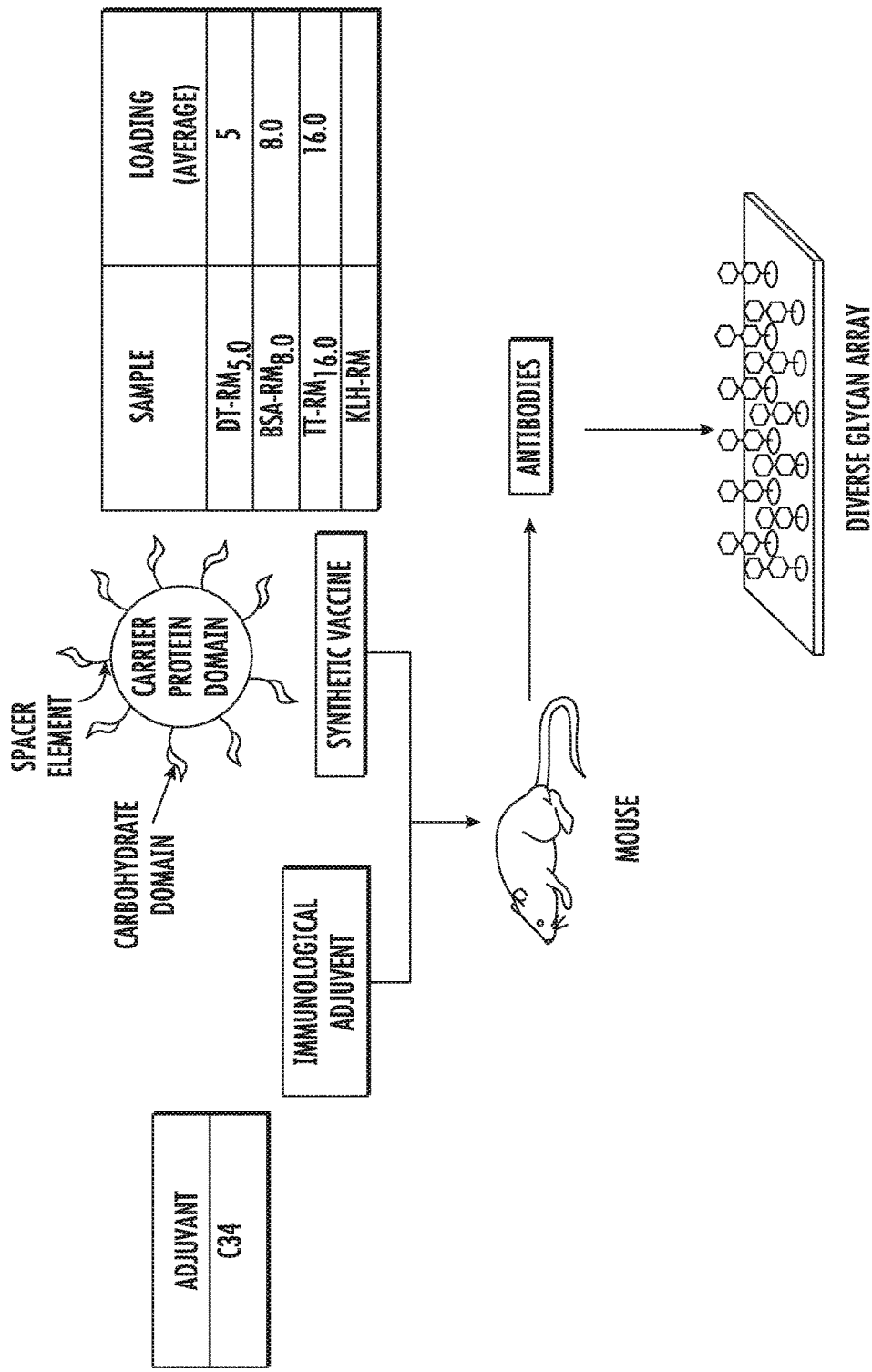
FIG. 26 shows exemplary synthetic glycan conjugates with different epitope ratio loading. The synthesized RM2 antigen was reacted with maleimide modified carrier proteins, including BSA, TT, DT, and KLH. The molecular weights of RM2-protein conjugates including RM2-BSA, RM2-TT, RM2-DT were determined by MALDI-TOF to calculate the average numbers of RM2 epitope on each carrier protein. Glycoconjugate RM2-DT showed an average of 5 RM2 incorporated into the protein, RM2-BSA and RM2-TT showed an average of 8 and 16 RM2 epitope, respectively, per protein molecule.
Figure 27:
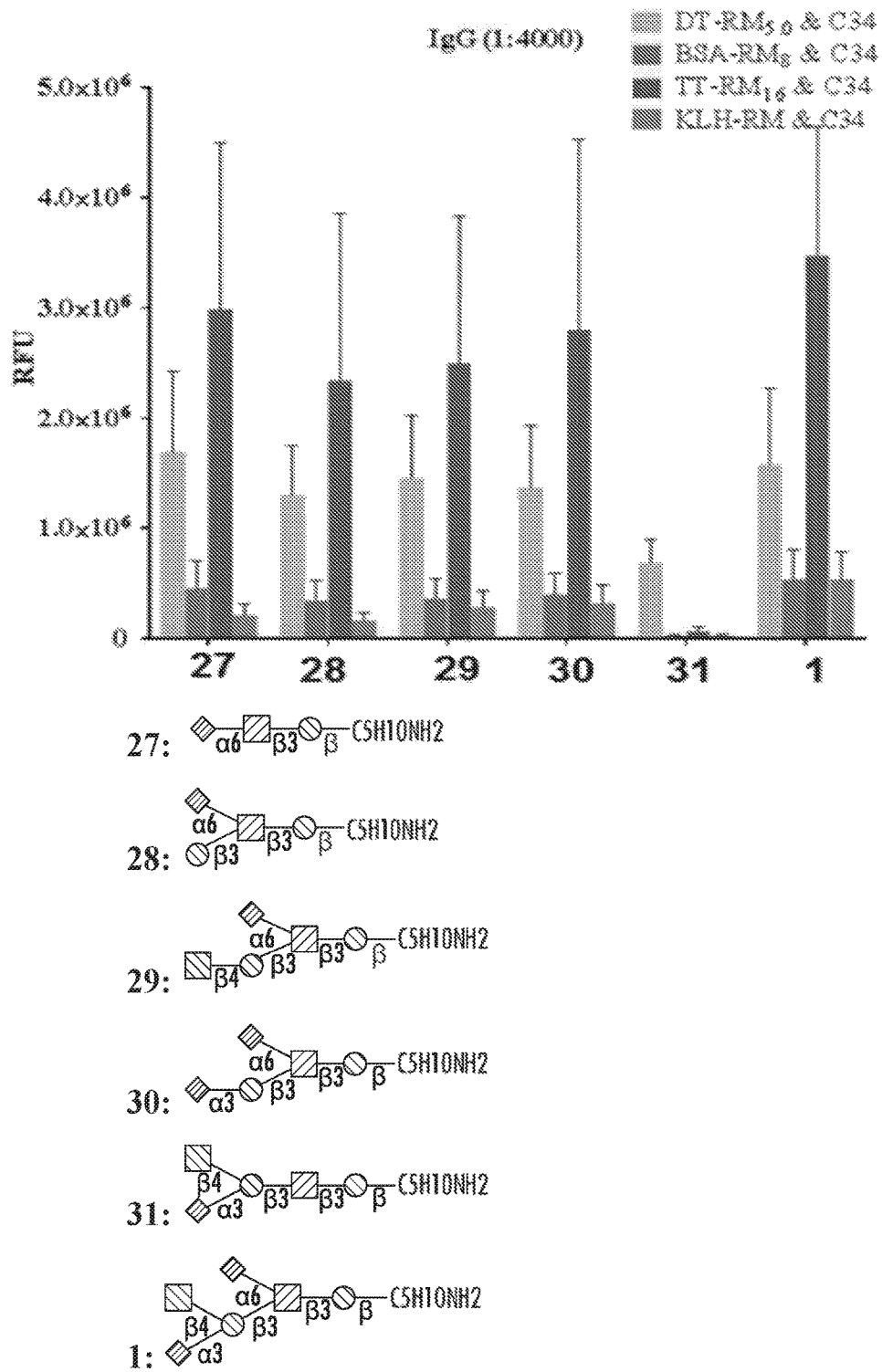
FIG. 27 shows exemplary synthetic glycan conjugates with different carriers. Mice were intramuscularly immunized with synthetic RM2 conjugated to different carriers (2 µg RM2) in the presence or absence of the glycolipid adjuvant C34 (2 µg). Three vaccinations were given at two weeks intervals. Ten days after the last injection, mice sera were collected and subsequently tested with a glycan microarray to evaluate the level and diversity of anti-RM2 related Ab. It was found that RM2-TT and RM2-DT could induce higher levels of anti-RM2 IgG than RM2-KLH and RM2-BSA.

Synthesis of the compound of (C-3a) follows the pattern of preparing a compound of Formula (F-1a). Compounds of Formula (F-1a) can be prepared following the exemplary scheme in FIG. 25. In certain embodiments, a compound of Formula (F-1a) is prepared by coupling a carbohydrate having the α-carbon substituted by STol with a carbohydrate having an hydroxyl group. In certain embodiments, the coupling reaction is carried out in the presence of NIS and TfOH. In certain embodiments, a compound of Formula (F-1a) is prepared by coupling (i) a carbohydrate having the α-carbon substituted by STol with (ii) a carbohydrate having an hydroxyl group in the presence of (iii) a carbohydrate having the α-carbon substituted by —OP(=O)(Bu)$_2$. In certain embodiments, the coupling reaction of carbohydrates (i)-(iii) is carried out in the presence of TMSOTf. In certain embodiments, the coupling reaction is carried out at a temperature of about −80° C. to about 25° C. In certain embodiments, the coupling reaction is carried out at a temperature of about −80° C. to −50° C. In certain embodiments, the coupling reaction is carried out at a temperature of about −60° C. In certain embodiments, the coupling reaction is carried out at a temperature of about −50° C. to 25° C. In certain embodiments, the coupling reaction is carried out at a temperature of about −20° C. to 25° C. In certain embodiments, the coupling reaction is carried out at a temperature of about −10° C. to 15° C. In certain embodiments, the coupling reaction is carried out at a temperature of about −0° C.

Figure 2:
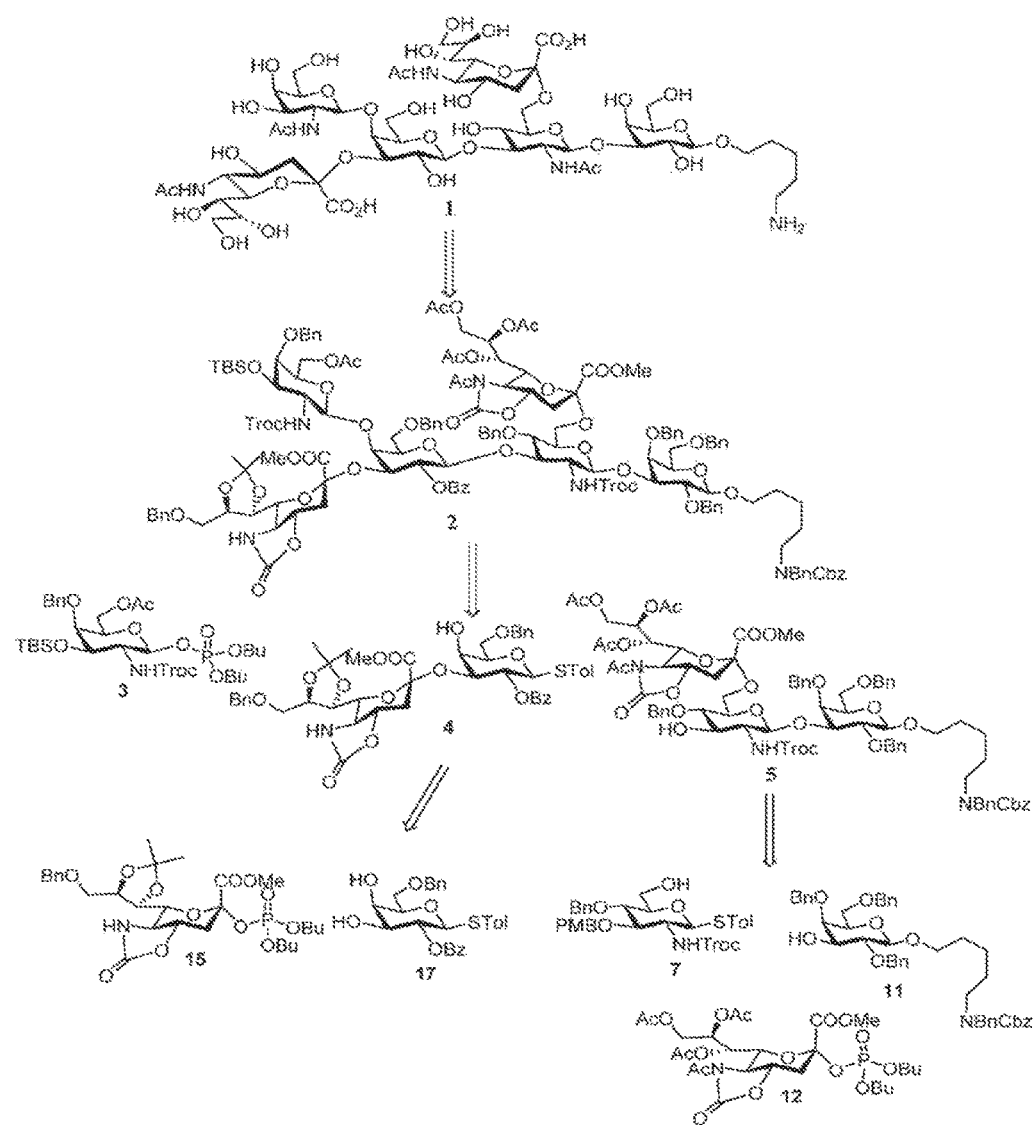
FIG. 2 shows retrosynthetic analysis of the RM2 hapten.

An exemplary compound of Formula (F-1a) is shown in FIG. 1. FIG. 2 shows the retrosynthesis analysis of compound 1. Specifically, the synthesis of compound 1 starts from a suitably protected hexasaccharide 2. The hydroxyl-pentamine linker at the reducing end of the galactose residue was designed for immobilizing hexasaccharide 1 onto the NHS-coated slides or conjugating to a carrier to form a vaccine candidate. To use the step by step protocol for oligosaccharide synthesis, orthogonal protecting groups were required to provide potential acceptor sites for later glycosylation. Overall, the target hexasaccharide can be divided into three parts, monosaccharide 3, disaccharide 4, and trisaccharide 5, which are further divided into six monosaccharide building blocks 3, 7, 11, 12, 15, and 17.

Immunogenic Compositions

The present invention provides immunogenic compositions comprising a glycan conjugate described herein and a pharmaceutically acceptable excipient. In certain embodiments, the provided immunogenic composition further comprise an adjuvant. Such immunogenic compositions can be used to elicit desired immune responses, such as immune responses specific to the glycan conjugate, particularly the glycan moiety in the conjugate. In certain embodiments, a provided composition comprises two or more glycan conjugates described herein.

The immunogenic compositions described herein can be prepared by any method known in the art of pharmacology, for example, as described in U.S. Pat. Nos. 4,601,903; 4,599,231; 4,599,230; and 4,596,792, all of which are incorporated by reference herein. In general, such preparatory methods include the steps of bringing an the glycan conjugate described herein into association with an adjuvant and/or a pharmaceutically acceptable excipient and/or one or more other accessory ingredients, and then, if necessary and/or desirable, shaping and/or packaging the product into a desired single- or multi-dose unit.

The immunogenic compositions disclosed herein can be included in a pharmaceutical or nutraceutical composition together with additional active agents, carriers, vehicles, excipients, or auxiliary agents identifiable by a person skilled in the art upon reading of the present disclosure.

The immunogenic compositions described herein may further comprises an adjuvant. An adjuvant is an agent that modifies the immunogenicity of the glycan conjugate in the composition. Adjuvant typically does not elicit immune responses specific to it but enhances immune responses specific to a given immunogenic agent (an antigen). Adjuvant can be inorganic or organic chemical, macromolecule or whole cells of certain killed bacteria which enhance the immune response to a given antigen. In certain embodiments, the adjuvant is a mineral salt/gel, e.g., aluminium hydroxide and aluminium or calcium phosphate gels. In certain embodiments, the adjuvant is an oil-in water and water-in-oil emulsion, amphiphilic molecule and surfactant based formulation, e.g., MF59 (microfluidised detergent stabilised oil-in-water emulsion), QS-21 (purified saponin, which is plant-derived), AS03 (consisting of an oil-in-water emulsion plus alpha-tocopherol), Montanide ISA-51, and Montanide ISA-720. In certain embodiments, the adjuvant is liposome, virosome (unilamellar liposomal vehicles incorporating influenza haemagglutinin), ISCOMS (structured complex of saponins and lipids), and polylactide co-glycolide (PLG), PLG-Dimethylaminoethane-carbamoyl-Cholesterol (PLGA/DC-cholesterol) particles, and Iscomatrix. In certain embodiments, the adjuvant isaicrobial derivative (natural and synthetic), e.g., monophosphoryl lipid A (MPL), Detox (MPL+M. Phlei cell wall skeleton), AGP [RC-529] (synthetic acylatedmonosaccharide), DC_Chol (lipoidal immunostimulators able to self-organise intoliposomes), OM-174 (lipid A derivative), CpG motifs (synthetic oligodeoxynucleotides containing immunostimulatory CpG motifs), modified heat labile enterotoxin (LT) and cholera toxin (CT) (genetically modified bacterial toxins that have been genetically modified to provide non-toxic adjuvant effects); synthetic dsRNA, Poly IC:LC (Hiltonol) and Poly I: Poly C12U (Ampligen®). In certain embodiments, the adjuvant is an endogenous human immunostimulator, e.g., hGM-CSF or hIL-12 (cytokines that can be administered either as protein or plasmid encoded), Immudaptin (C3d tandem array). In certain embodiments, the adjuvant is an inert vehicles, e.g., gold particle. In certain embodiments, the adjuvant is an inert polysaccharides, e.g., Advax (delta-inulin), derived from plants (dahlias). In certain embodiments, combination adjuvants or adjuvant systems can used in the immunogenic compositions described herein, for example, combinations of vaccine delivery systems and immunostimulatory agents. Combination adjuvants or adjuvant systems may result in more effective delivery of the immunostimulatory adjuvant as well as the antigen, e.g., AS01 consisting of liposomes, MPL, and QS-21; AS02 consisting of an oil-in-water emulsion plus MPL and QS-21; AS03 consisting of an oil-in-water emulsion plus alpha-tocopherol; AS04 consisting of MPL and aluminum hydroxide; AS15 consisting of liposomes, MPL, QS-21 and a CpG oligodeoxynucleotide; and GLA-SE consisting of a synthetic acylated monosaccharide in a stable oil in-water emulsion.

In some embodiments, the adjuvant used in the immunogenic compositions described herein is C34, 7DW8-5, C17, C23, C30, α-galactoceramide, Aluminum salt, Squalene, MF59, or QS-21 (see U.S. Pat. No. 8,268,969 and U.S. Publication No. 2008-0260774, both of which are incorporated into reference in the present application).

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Immunogenic compositions described herein can be prepared, packaged, and/or sold in bulk, as a single unit dose, and/or as a plurality of single unit doses. As used herein, a "unit dose" is discrete amount of the immunogenic compositions or vaccines described herein comprising a predetermined amount of the glycan conjugate described herein.

Relative amounts of the glycan conjugate, the pharmaceutically acceptable excipient, and/or any additional ingredients in a immunogenic compositions or vaccines described herein will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided immunogenic compositions or vaccines described herein include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cationexchange resins, calcium carbonate, silicates, sodium carbonate, crosslinked poly(vinylpyrrolidone) (crospovidone), sodium carboxymethyl starch (sodium starch glycolate), carboxymethyl cellulose, crosslinked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinylpyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinylpyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, betacarotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogenfree water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene lycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the glycan conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacterial retaining filter, or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing the glycan conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The glycan conjugates can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the glycan conjugates only, or preferentially, in a certain part of the intestinal tract, optionally, in a delayed manner. Examples of embedding compositions which can be used include polymeric substances and waxes.

Dosage forms for topical and/or transdermal administration of immunogenic compositions or vaccines described herein may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required.

Suitable devices for use in delivering intradermal immunogenic compositions or vaccines described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) of the glycan conjugates described herein, although the concentration of the glycan conjugates can be as high as the solubility limit of the active ingredient in the solvent. Formulations for topical administration may further comprise one or more of the additional ingredients described herein.

Immunogenic compositions described herein of the invention can be prepared, packaged, and/or sold in a formulation suitable for pulmonary administration via the buccal cavity. Such a formulation may comprise dry particles which comprise the glycan conjugates and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the glycan conjugates may constitute 0.1 to 20% (w/w) of the composition. The propellant may further comprise additional ingredients such as a liquid non ionic and/or solid anionic surfactant and/or a solid diluent (which may have a particle size of the same order as particles comprising the active ingredient).

Immunogenic compositions or vaccines described herein of the invention formulated for pulmonary delivery may provide the glycan conjugates in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Immunogenic compositions described herein can be useful for pulmonary delivery are useful for intranasal delivery of a immunogenic compositions or vaccines described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the glycan conjugates provided herein, and may comprise one or more of the additional ingredients described herein. An immunogenic compositions or vaccines described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

An immunogenic compositions described herein can be prepared, packaged, and/or sold in a formulation for ophthalmic administration. Such formulations may, for example, be in the form of eye drops including, for example, a 0.1/1.0% (w/w) solution and/or suspension of the glycan conjugate in an aqueous or oily liquid carrier. Such drops may further comprise buffering agents, salts, and/or one or more other of the additional ingredients described herein.

Although the descriptions of immunogenic compositions or vaccines described herein are principally suitable for administration to humans, it will be understood by the skilled artisan that such compositions are generally suitable for administration to animals of all sorts. Modification of immunogenic compositions or vaccines described herein suitable for administration to humans in order to render the compositions suitable for administration to various animals is well understood, and the ordinarily skilled veterinary pharmacologist can design and/or perform such modification with ordinary experimentation.

Immunogenic compositions or vaccines described herein provided herein are typically formulated in dosage unit form for ease of administration and uniformity of dosage. It will be understood, however, that the total daily usage of the immunogenic compositions or vaccines described herein will be decided by the attending physician within the scope of sound medical judgment. The quantity to be administered also depends on the subject to be treated, including, for example, the capacity of the individual's immune system to synthesize antibodies, and if needed, to produce a cell-mediated immune response. Suitable regimes for initial administration and booster doses are also variable, but may include an initial administration followed by subsequent administrations. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the invention are kits (e.g., pharmaceutical packs) to treat or prevent bacterial infections. The kits provided may comprise an inventive pharmaceutical composition or compound and a container (e.g., a vial, ampule, bottle, syringe, and/or dispenser package, or other suitable container). The kits provided may comprise an additional therapeutically active agents include, but are not limited to, antibiotics, antiviral agents, anesthetics, anticoagulants, inhibitors of an enzyme, steroidal agents, steroidal or nonsteroidal anti-inflammatory agents, antihistamine, immunosuppressant agents, antigens, vaccines, antibodies, decongestant, sedatives, opioids, pain-relieving agents, analgesics, antipyretics, hormones, and prostaglandins, etc. In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses of Glycan Conjugates Described Herein

The present invention provides glycan conjugates, immunogenic compositions or vaccines useful for the treatment of a proliferative disease such as cancer (e.g. lung cancer, large bowel cancer, pancreas cancer, biliary tract cancer, or endometrial cancer), benign neoplasm, or angiogenesis in a subject.

The immunogenic compositions or vaccines described herein can also be used to generate antibodies in human or animals for production of antibodies, which can be used in both cancer treatment and diagnosis. In some embodiments, the immunogenic compositions or vaccines described herein can also be used to generate antibodies for production of RM2 antibodies. Methods of making monoclonal and polyclonal antibodies and fragments thereof in human and/or animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab').sub.2, Fv, scFv (single chain antibody), and dAb (domain antibody; Ward, et. al. (1989) Nature, 341, 544).

In some embodiments, the provided glycan conjugates, immunogenic compositions or vaccines are useful in treating, or diagnosing a cancer, including, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the provided glycan conjugates, immunogenic compositions or vaccines are useful for treating prostate cancer.

To perform the treatment methods described herein, an effective amount of any of the glycan conjugates or immunogenic compositions described herein may be administered to a subject in need of the treatment via a suitable route, as described above. The subject, such as a human subject, can be a patient having cancer (e.g., prostate cancer), suspected of having cancer, or susceptible to cancer. The amount of the glycan conjugate or immunogenic composition administered to the subject may be effective in eliciting immune responses specific to the glycan moiety in the conjugate or composition. In some embodiments, the amount of the glycan conjugate or immunogenic composition is sufficient to elicit immune responses leading to the inhibition of cancer growth and/or reduction of tumor mass. In other embodiments, the amount of the glycan conjugate or immunogenic composition may be effective in delaying the onset of the target cancer or reducing the risk for developing the cancer. The exact amount of the provided glycan conjugates, immunogenic compositions or vaccines required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount, of the provided glycan conjugates, immunogenic compositions or vaccines for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the provided glycan conjugates, immunogenic compositions or vaccines may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the provided glycan conjugates, immunogenic compositions or vaccines to an adult. The amount to be administered to, for example, a child or an adolescent can be determined by a medical practitioner or person skilled in the art and can be lower or the same as that administered to an adult.

It will be also appreciated that the provided glycan conjugates, immunogenic compositions or vaccines can be administered in combination with one or more additional therapeutically active agents. The the provided glycan conjugates, immunogenic compositions or vaccines can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The the provided glycan conjugates, immunogenic compositions or vaccines can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the provided glycan conjugate, immunogenic composition or vaccine is administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon $\alpha$, interferon $\gamma$), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZAC- TIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

EXAMPLES

In order that the invention described herein may be more fully understood, the following examples are set forth. It should be understood that these examples are for illustrative purposes only and are not to be construed as limiting this invention in any manner.

Materials.

Commercial solvents and reagents were purchased from Sigma-Aldrich and Acros and used as received without further purification. Monoclonal antibody RM2 was given by Professor Seiichi Saito (Department of Urology, Graduate School of Medicine, University of Ryukyus, Nishihara 903-0215, Japan), and Cy3-conjugated anti-mouse IgG (IgG, IgG1, IgG2a, IgG2b, IgG2c, and IgG3) and IgM antibodies were form Jackson IMMUNO Research. Diphtheria toxoid (CRM 197) was purchase from PFenex Incorporation. Aluminum phosphate ($AlPO_4$) was from Brenntag Biosector, and Glycolipid derivatives (C1 and C34) were from Dr. Chi-Huey Wong's lab.

General.

Molecular sieves 4 Å (Reidel-deHaen No. 31812) for glycosylations were crushed and activated by heating at 350° C. for 10 h before use. Reactions were monitored with analytical TLC plates (PLC silica gel-60, $F_{254}$, 2 mm, Merck) and visualized under UV (254 nm) or by staining with acidic ceric ammonium molybdate or p-anisaldehyde. Flash column chromatography was performed on silica gel (40-63 μm, Merck), LiChroprep RP8 (40-63 μm), and LiChroprep RP18 (40-63 μm).

Instrumentation.

Proton nuclear magnetic resonance ($^1$H NMR) spectra and carbon nuclear magnetic resonance ($^{13}$C NMR) spectra were recorded on a Broker Advance 600 (600 MHz/150 MHz) NMR spectrometers. Chemical shifts of protons were reported in ppm (δ scale) and referenced to tetramethylsilane (δ=0). Chemical shifts of carbon were also reported in parts per million (ppm, δ scale) and were calibrated with tetramethylsilane (δ=0). DEPT 135 (distortionless enhancement by polarization transfer) was employed for determination of multiplicity. Data were represented as follows: chemical shift, multiplicity (s=singlet, d=doublet, t=triplet, q=quartet, m=multiplet, br=broad), coupling constant (J) in Hz, and integration. High resolution mass spectra were obtained using BioTOF III, and MALDI-TOF MS were obtained using Ultraflex II TOF/TOF.

Chemical Syntheses

In order that the invention described herein may be more fully understood, the following examples are set forth. It should be understood that these examples are for illustrative purposes only and are not to be construed as limiting this invention in any manner.

Retrosynthesis.

Two main problems in the synthesis of the exemplary compound 1 are encountered: α-stereo- and regio-selective sialylation at O-6 of the GlcNAc residue and O-3 of the Gal residue; and β-selective glycosylation of GalNAc at the O-4 position of the sialyl-α-(2,3)-D-galactose unit. Synthesis of hexasaccharide 1 starts from a suitably protected hexasaccharide 2 (FIG. 2). The hydroxylpentamine linker at the reducing end of the galactose residue was designed for immobilizing hexasaccharide 1 onto the NHS-coated slides or conjugating to a carrier protein to form a vaccine candidate. To use the step by step protocol for oligosaccharide synthesis, orthogonal protecting groups were required to provide potential acceptor sites for later glycosylation. Overall, the target hexasaccharide can be divided into three parts, monosaccharide 3, disaccharide 4, and trisaccharide 5, which are further divided into six monosaccharide building blocks 3, 7, 11, 12, 15, and 17.

Synthesis of GlcNAc Building Block 7

Figure 3:
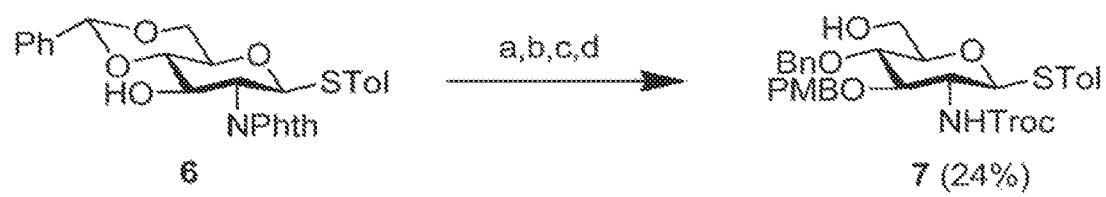
FIG. 3 shows synthesis of GlcNAc building block 7. a. NaH, PMBCl, DMF, rt, 1 h; b. BH$_3$, Bu$_2$BOTf, 0° C., 2 h; c. Ethylenediamine, ethanol, 80° C., 16 h; d. TrocCl, NaHCO$_3$, THF, rt, 16 h.

The synthesis of monosaccharide 7 can be achieved from the known 4,6-O-benzylidene acetal 6 (FIG. 3) (Huang et al., *Carbohydr. Res.* 2006, 341, 1669). The p-methoxybenzylation of 6 was carried out by p-methoxybenzyl choride (PMBCl) and sodium hydride (NaH) in DMF, followed by selective ring-opening of the 4,6-O-benzylidene group with dibutylboranetriflate ($Bu_2BOTf$) and borane-tetrahydrofuran complex ($BH_3$.THF). After sequential removal of the phthalimido group and Troc formation, the desired product 7 was produced in four steps in 24% yield.

Synthesis of Galactose Building Block 11

Figure 4:
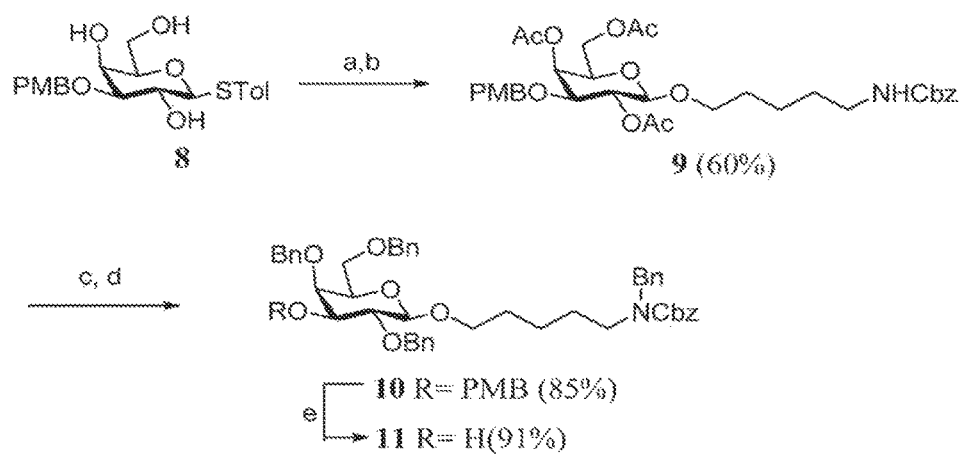
FIG. 4 shows synthesis of galactose building block 11. a. Ac$_2$O, pyridine, rt, 12 h; b. NIS, cat. TfOH, benzyl 5-hydroxypentylcarbamate, CH$_2$Cl$_2$, −30° C., 3 h; c. NaOMe, MeOH, rt, 10 h; d. BnBr, NaH, rt, 2 h; e. DDQ, CH$_2$Cl$_2$/H$_2$O, rt, 2 h.

Compound 8 was acetylated by the standard acetylation procedure (FIG. 4), and the acetylated compound was glycosylated with the benzyl-5-hydroxypentylcarbamate in dichloromethane using NIS/TfOH as a promoter to afford 9 in 60% yield (Wang et al., *J. Org. Chem.* 2007, 72, 6409). Compound 9 was de-acetylated under the Zemplen condition; then, benzylation of the triol intermediate afforded 10 in 85% yield. The acetyl group was replaced by the benzyl group to increase the reactivity of the galactose building block, followed by selective removal of the PMB protecting group with DDQ to give 11 in 77% yield.

Synthesis of Trisaccharide 5

Figure 5:
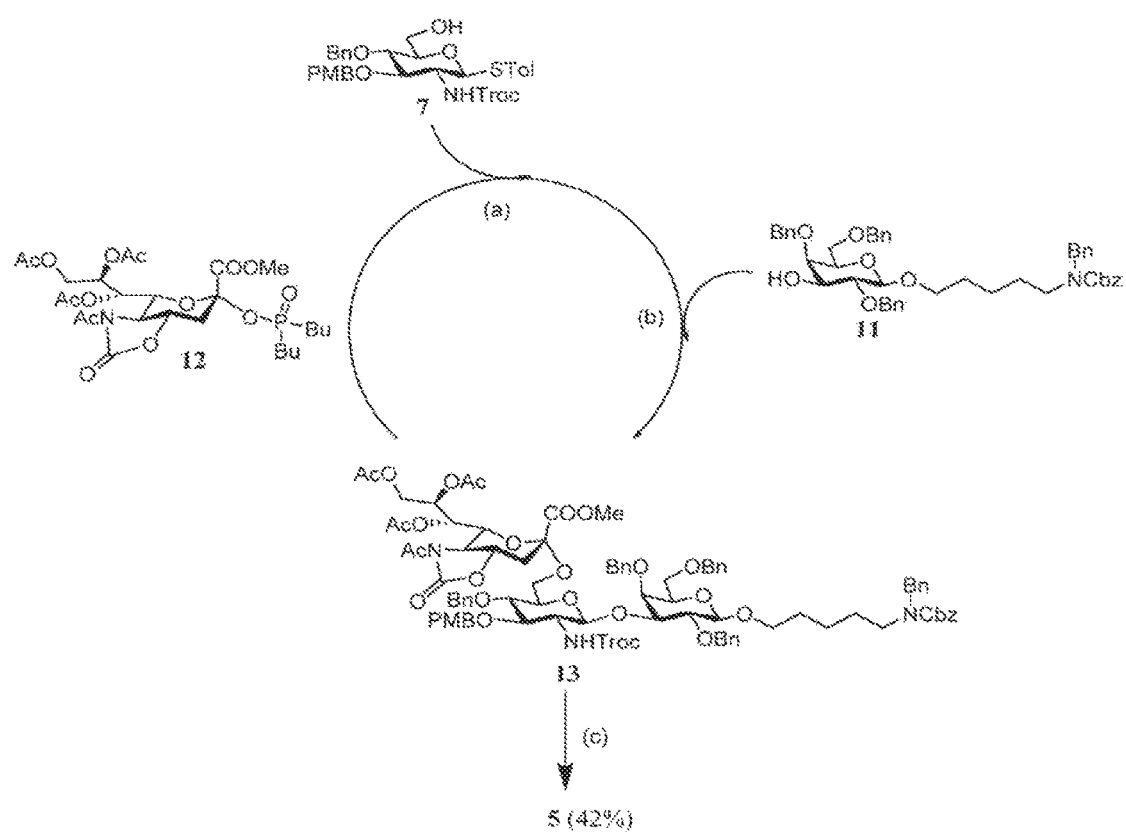
FIG. 5 shows orthogonal one-pot synthesis of trisaccharide 5. a. 7, 12, TMSOTf, MS 4 Å.

Compounds 7, 11, and 12 were used as starting materials for the synthesis of trisaccharide building block 5 using an orthogonal one-pot synthetic strategy (FIG. 5). The one-pot synthetic operation was performed by sialyl phosphate donor 12 (1.5 eq.) and GlcNAc acceptor 7 (1.0 eq.) in the presence of TMSOTf at −60° C.

The second glycosylation between 7 and 11 was carried out by adding NIS (2.0 eq.) to the reaction solution at higher temperature (−20° C.). Finally, removal of the PMB group by DDQ produced trisaccharide 5 in 41% yield.

Synthesis of Disaccharide 4

Figure 6:
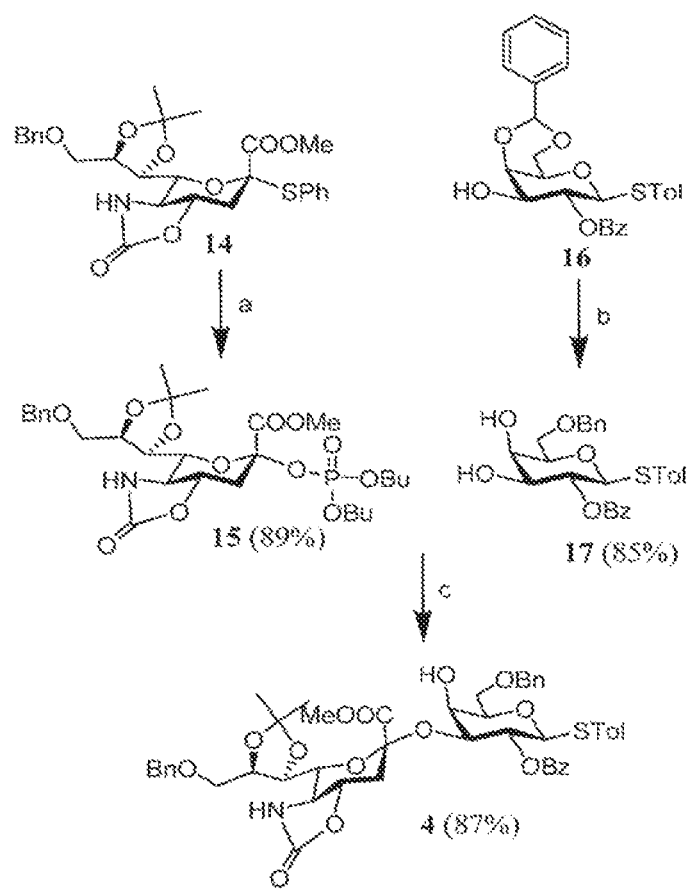
FIG. 6 shows synthesis of disaccharide 4. a. NIS, TfOH, dibutylphosphate, MS4 Å, CH$_2$Cl$_2$, 0° C., 10 h, 89%; b. Et$_3$SiH, TfOH, MS4 Å, CH$_2$Cl$_2$, −78° C., 1 h, 85%; c. TMSOTf, CH$_2$Cl$_2$, MS4 Å, −78° C., 2 h, 87%.

In order to synthesize the Neu5Acα2→3Gal disaccharide with high α-stereoselectivity and yield, the thiophenyl group in the anomeric center of 5-N,4-O-carbonyl-protected thiosialoside 14 was replaced by the dibutyl phosphate group at 0° C. under N-iodosuccinimide (NIS) and trifluoromethansulfonic acid (TfOH) activation for 10 h to obtain 15 in 89% yield (α:β=13:1) (Tanaka et al., *J. Am. Chem. Soc.* 2008, 130, 17244). In addition, compound 16 was efficiently converted to the corresponding 6-O-benzyl-4-hydroxy derivative 17 using triethylsilane (Et₃SiH) and trifluorosulfonic acid (TfOH) in a high yield with excellent regionselectivity (Hsu et al., *Chem-Eur. J.* 2010, 16, 1754). With the α-sialyl phosphate donor 15 and 3,4-dihydroxyl galactose acceptor 17 in hand, glycosylation of 15 and 17 under the activation of TMSOTf in CH₂Cl₂ at −78° C. for 2 h gave Neu5Acα→3Gal disaccharide 4 as a single isomer in 87% yield (FIG. 6). The configuration of the disaccharide 4 was examined by NMR spectrometry, and the new formed α-glycosidic bond was confirmed by coupling constant $^3J(C_1-H_{3ax})$=6.1 Hz.

Synthesis of Compound 2

Figure 7:
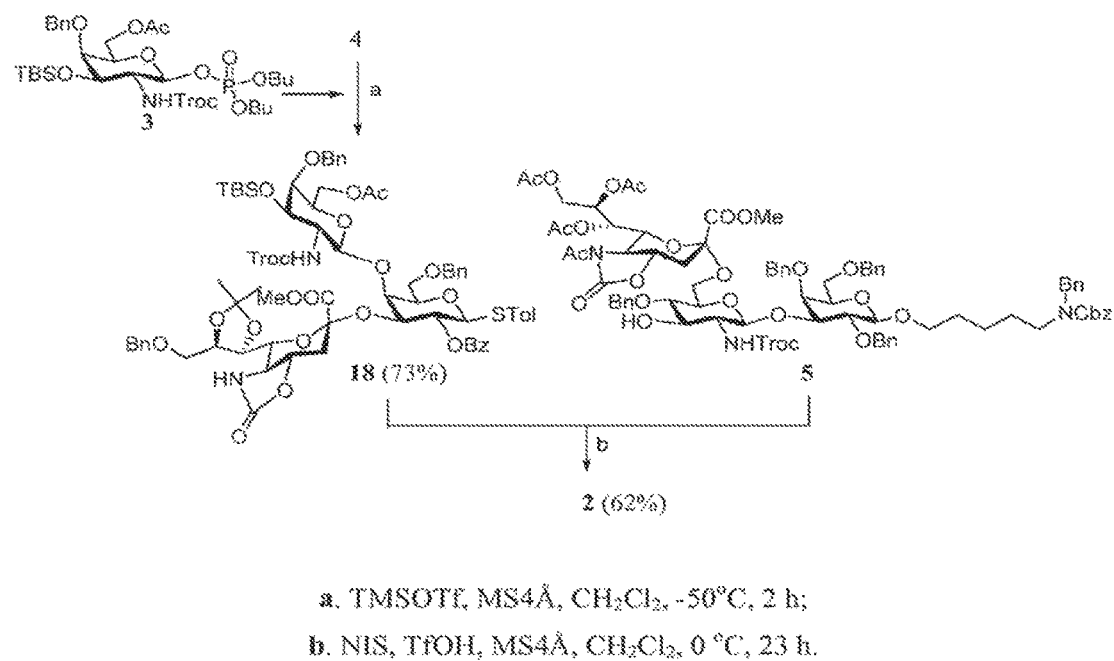
FIG. 7 shows synthesis of hexasaccharide 2.
Figure 8:
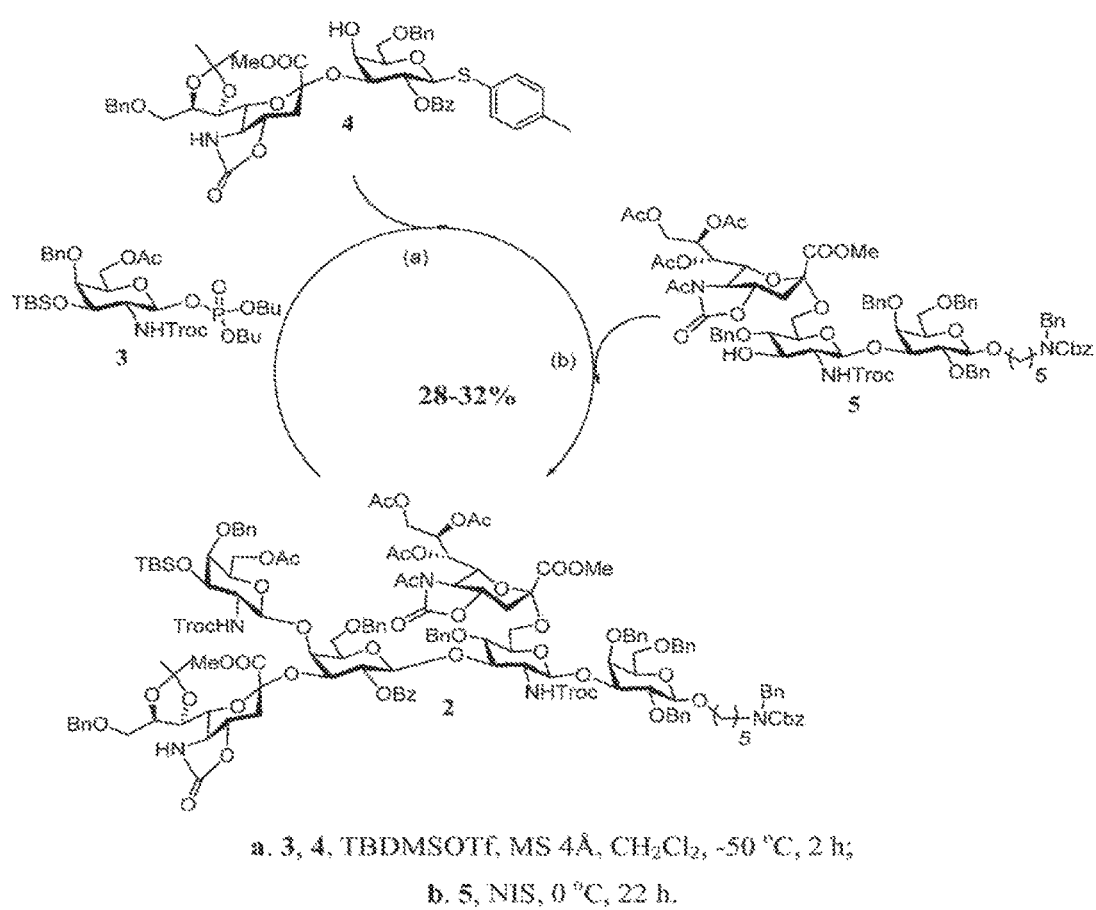
FIG. 8 shows one-pot synthesis of hexasaccharide 2.

The preparation of the target hexasaccharide 2 was started from the TMSOTf-promoted coupling of the GalNAc donor 3 with disaccharide 4 (Komori et al., *Carbohydr. Res.* 2009, 344, 1453). After glycosylation, the fully protected trisaccharide compound 18 was isolated in 73% as a 6 to 1 mixture of rotamers (determined by ¹H NMR spectroscopic analysis of the crude reaction). Convergent synthesis of hexasaccharide 2 was achieved in good yield (62%) by glycosylation of trisaccharide acceptor 5 with trisaccharide donor 18 in the NIS/TfOH promoting system at 0° C. for 23 h (FIG. 7). Orthogonal one-pot [1+2+3] glycosylation was also experimented and the target hexasaccharide 2 was successfully synthesized (FIG. 8). Chemoselective glycosylation of the phosphate donor 3 with the thioglycoside 4 under the TBDMSOTf activation in CH₂Cl₂ at −50° C. provided trisaccharide 18. Without isolation, the acceptor 5 and NIS were subsequently added to the reaction vessel at 0° C. and the reaction was finished in 23 h to afford the protected hexasaccharide 2 in an overall yield of 32% based on 5.

Syntheses of Compounds 20, 22, 24, and 26

Figure 9:
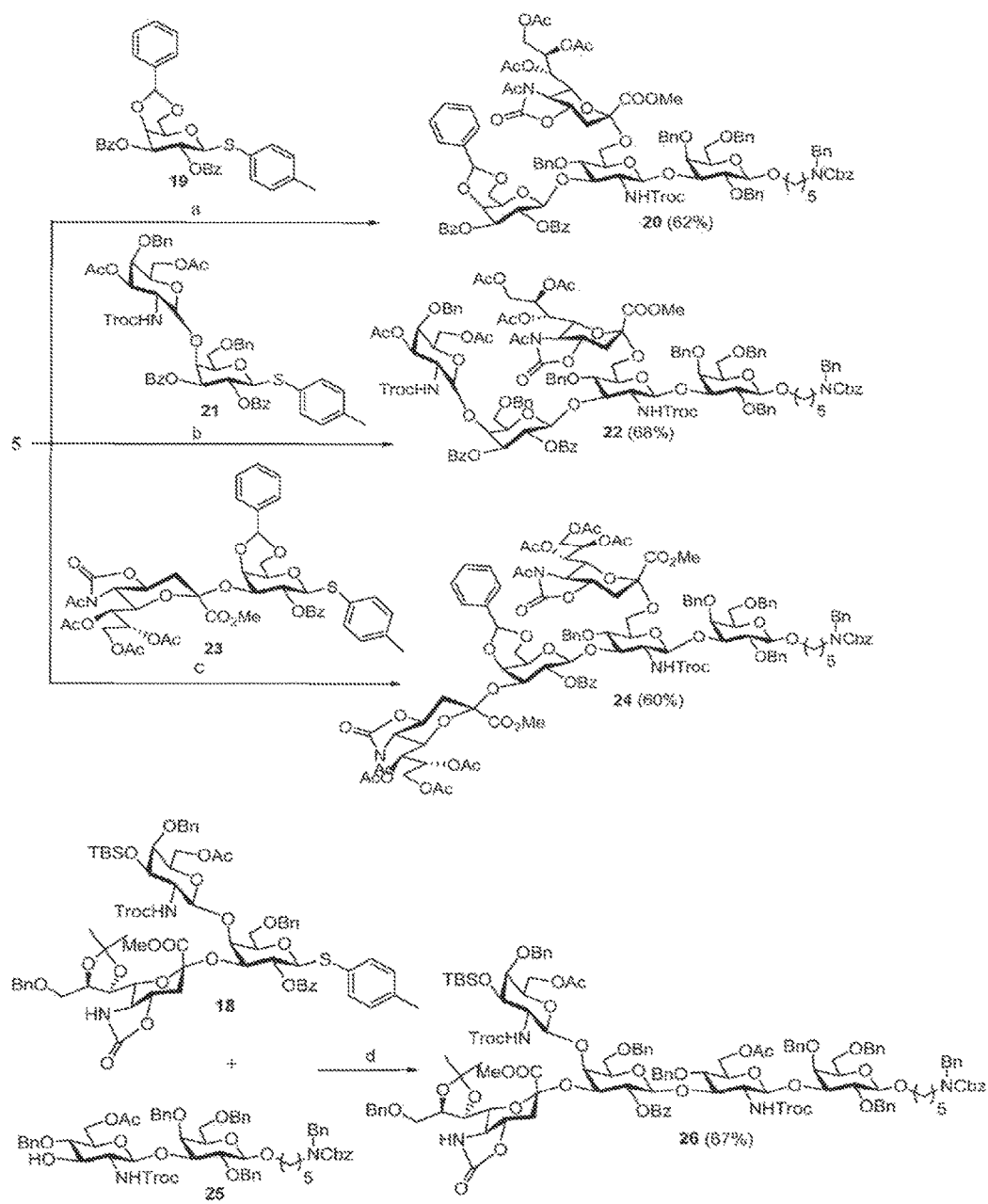
FIG. 9 shows synthesis of 20, 22, 24, and 26.
Figure 10:
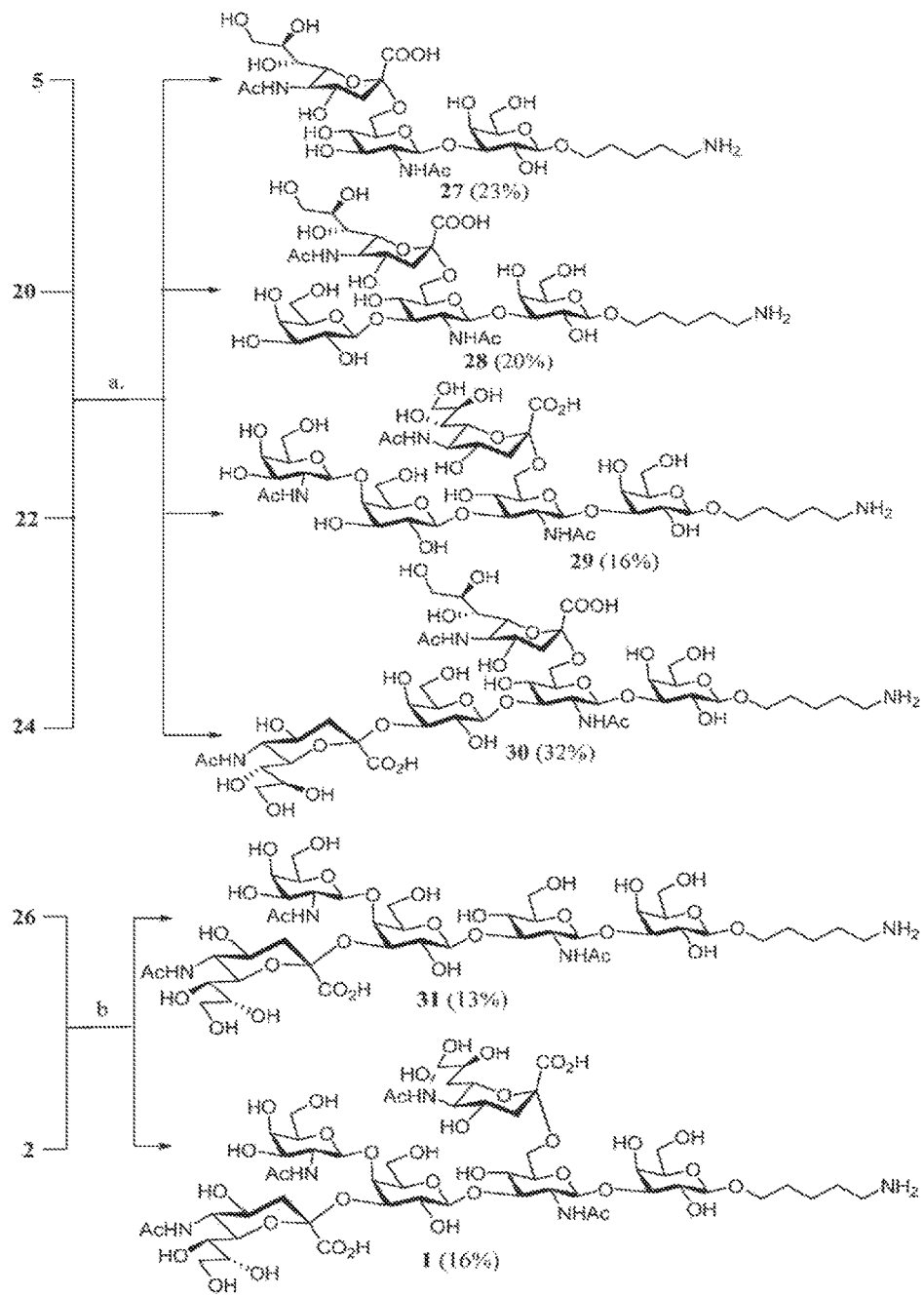
FIG. 10 shows global deprotection of 2, 5, 20, 22, 24, and 26.

Synthesis of compounds 20, 22, 24, and 26 follows the above method (FIG. 9). Donors 19, 21, or 23 were coupled to acceptor 5 to give tetrasaccharide 20, pentasaccharide 22, or pentasaccharide 24, respectively (Lu et al., *J. Chem.* 2009, 27, 2217; Hsu et al., *Chem-Eur. J.* 2010, 16, 1754). In addition, treatment of the trisaccharide donor 18 and disaccharide acceptor 25 with NIS and a catalytic amount of TBDMSOTf at 0° C. gave the protected pentasaccharide 26 in 67% yield.

Global deprotection of the protected hexasaccharide 2 and pentasaccharide 26 was achieved using a four-step procedure: (i) hydrolysis of acyl protecting groups; (ii) acetylation of the amine groups; (iii) removal of the isopropyl groups; and (iv) hydrogenolysis of the resulting benzyl ethers to provide the fully deprotected hexasaccharide 1 and pentasaccharide 31. In addition, using a similar strategy, deprotection of 5, 20, 22, and 24 gave the corresponding deprotected oligosaccharides 27-30, respectively, in good yields.

Synthetic Procedures

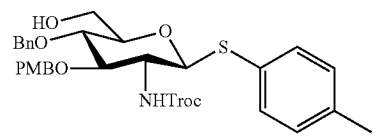

7

2,2,2-trichloroethyl(2S,3R,4R,5S,6R)-5-(benzyloxy)-6-(hydroxymethyl)-4-(4-methoxybenzyloxy)-2-(p-tolylthio)tetrahydro-2H-pyran-3-ylcarbamate (7)

Compound 6 (2.66 g, 5.286 mmole) was dissolved in dry DMF under argon, followed by addition of p-methoxybenzyl chloride (1.5 mL, 10.8 mmole). The resulting mixture was treated with NaH (60%, 0.46 g, 10.75 mmole) at 0° C. and slowly warmed to room temperature. After one hour, the reaction mixture was quenched with methanol, extracted with ethyl acetate (50 mL), and then washed with brine. The resulting organic phase was evaporated at low pressure to give a crude product, which was used without purification. This residue was dissolved in CH₂Cl₂ (30 mL), and BH₃THF in THF (1.0 M) (28 mL, 28 mmole) was added. The reaction mixture was stirred for 10 min, followed by dropwise addition of Bu₂BOTf (5.4 mL, 5.4 mmole) at 0° C. TLC indicated that the starting material had disappeared after 2 h. The resulting mixture was neutralized with triethylamine, and excess borane was quenched with methanol. The solution was concentrated and the residue was purified by chromatography (1:4 to 1:2 ethyl acetate/hexane). Then, the material residue and ethylenediamine (20 mL, 298 mmole) were dissolved in dry ethanol (50 mL). The mixture was heated at reflux for 16 h. The reaction was evaporated at low pressure, and the residue was dissolved in a mixture of THF and saturated NaHCO₃ (35 mL), followed by addition of TrocCl (0.9 mL, 6.53 mmole). The mixture was stirred for 16 h and, then, extracted with EtOAc (60 mL) and saturated aqueous NaHCO₃ (40 mL). The organic layer was dried over Na₂SO₄ and purified by chromatography (1:5 to 1:3 ethyl acetate/hexane) to give 7 as the white solid (0.85 g, 1.268 mmole). 7: $R_f$=0.68 (Hexane:EtOAc=3:1); ¹H NMR (600 MHz, CDCl₃) δ 7.36 (m, 7H), 7.20 (d, J=8.4 Hz, 2H), 7.10 (d, J=8.0 Hz, 2H), 6.84 (d, J=8.6 Hz, 2H), 5.08 (d, J=8.3 Hz, 1H), 4.88 (d, J=10.2 Hz, 1H), 4.83 (d, J=11.0 Hz, 1H), 4.78-4.72 (m, 3H), 4.65-4.62 (m, 2H), 3.88-3.82 (m, 2H), 3.78 (s, 3H), 3.72-3.66 (m, 1H), 3.53 (t, J=9.3 Hz, 1H), 3.42-3.34 (m, 2H), 2.32 (s, 3H), 1.96 (t, J=6.6 Hz, 1H); ¹³C NMR (150 MHz, CDCl₃) δ 159.6, 154.0, 138.6, 137.9, 133.3, 130.0, 128.7, 128.2, 128.1, 114.1, 95.6, 86.2, 81.6, 79.6, 78.5, 75.1, 75.0, 74.6, 62.2, 56.8, 55.4, 21.3; HRMS (ESI-TOF, MNa⁺) calculated for C₃₁H₃₄Cl₃NO₇SNa 694.0990, found 694.1135.

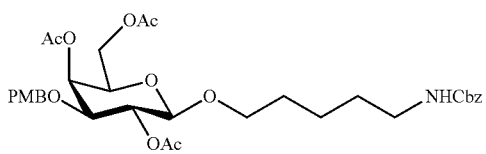

(2R,3S,4S,5R,6R)-2-(acetoxymethyl)-6-(5-(benzyloxycarbonylamino)pentyloxy)-4-(4-methoxybenzyloxy)tetrahydro-2H-pyran-3,5-diyl diacetate (9)

Acetic anhydride (15 mL) was added to a solution of compound 8 (4.0 g, 9.96 mmol) in pyridine (15 mL) at 0° C. The mixture was stirred for 12 h at 40° C., and methanol (5 mL) was added. The solution was concentrated into syrup and extracted with dichloromethane. The extract was successively washed with 2 N HCl, water, $NaHCO_{3(aq)}$, and water, then dried with $Na_2SO_4$, and concentrated. Column chromatography (1:2 ethyl acetate/hexane) of the residue on silica gel gave the per-acetylated thioglycoside as a white solid (5.17 g, 99%). To a solution of purified thioglycoside (5.17 g, 9.95 mmol) and benzyl 5-hydroxy pentylcarbamate (3.52 g, 15.92 mmol) in dichloromethane (30 mL), molecular sieves 4 Å (10.0 g) were added, and the mixture was stirred for 1 h at room temperature and then cooled to −30° C. To the stirred mixture, NIS (3.58 g, 15.92 mmol) and TlOH (0.42 mL, 4.78 mmol) were added, and the solution was stirred continuously for 3 h at −30° C. The precipitates were filtered off and washed with dichloromethane. The filtrates were combined, and the solution was successively washed with saturated $NaHCO_{3(aq)}$ and saturated $Na_2S_2O_{3(aq)}$, then dried with $Na_2SO_4$, and concentrated. Purification by flash silica-gel column chromatography (1:2 to 1:1 ethyl acetate/hexane) to give 9 as colorless oil. (3.86 g, 60%). 9: $R_f$=0.65 (Hexane:EtOAc=1:1); $^1$H NMR (600 MHz, $CDCl_3$) δ 7.34-7.29 (m, 5H), 7.18 (d, J=8.5 Hz, 2H), 6.85 (d, J=8.4 Hz, 2H), 5.47 (d, J=3.2 Hz, 1H), 5.09-5.05 (m, 3H), 4.61 (d, J=11.9 Hz, 1H), 4.33 (m, 2H), 4.16 (d, J=6.6 Hz, 2H), 3.87-3.82 (m, 1H), 3.79-3.75 (m, 4H), 3.50 (dd, J=10.0, 3.4 Hz, 1H), 3.44-3.39 (m, 1H), 3.16 (m, 2H), 2.13 (s, 3H), 2.06 (s, 3H), 2.00 (s, 3H), 1.61-1.45 (m, 4H), 1.37-1.30 (m, 2H); $^{13}$C NMR (150 MHz, $CDCl_3$) δ 170.3, 170.3, 169.2, 159.2, 156.3, 136.6, 129.4, 129.3, 128.3, 127.9, 113.6, 101.1, 76.0, 70.8, 70.7, 70.4, 69.4, 66.2, 65.9, 61.8, 55.1, 40.7, 29.4, 28.8, 22.9, 20.7, 20.6, 20.6; HRMS (ESI-TOF, MNa$^+$) calculated for $C_{33}H_{43}NO_{12}Na$ 668.2677, found 668.2674.

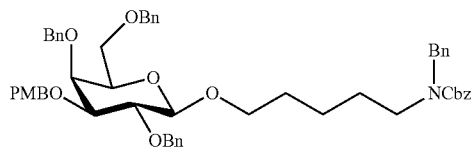

Benzylbenzyl(5-((2R,3R,4S,5S,6R)-3,5-bis(benzyloxy)-6-(benzyloxymethyl)-4-(4-methoxybenzyloxy)tetrahydro-2H-pyran-2-yloxy)pentyl)carbamate (10)

NaOMe (0.65 g, 12 mmol) was added to a solution of compound 9 (3.86 g, 5.98 mmol) in MeOH (120 mL), and the mixture was stirred at room temperature under $N_2$ atmosphere. After stirring for 10 h, the reaction mixture was neutralized with Amberlite IR-120 resin. The resin was removed by filtration, and the filtrate was concentrated and dried under reduced pressure. The residue was dried under high vacuum for 5 h. Then, NaH (60% in mineral oil; 1.12 g, 28.0 mmol) was added to a solution of residue in DMF (100 mL) at 0° C., and the resulting mixture was stirred for 10 min. Benzylbromide (3.0 mL, 25.08 mmol) was added, and the resulting mixture was warmed to 25° C. and stirred for 2 h. MeOH (4.0 mL) was then added to remove any remaining benzyl bromide. After further 30 min of stirring, the mixture was poured into iced water. The aqueous phase was extracted with EtOAc, and the combined organic layers was washed with brine, dried over $Na_2SO_4$, filtered, and concentrated. Purification by flash silica-gel column chromatography (1:4 to 1:3 ethyl acetate/hexane) to give 10 as colorless oil (4.47 g, 85%). 10: $R_f$=0.28 (Hexane:EtOAc=3:1); $^1$H NMR (600 MHz, $CDCl_3$) δ 7.33-7.24 (m, 27H), 6.84 (d, J=8.6 Hz, 2H), 5.15 (d, J=13.8 Hz, 2H), 4.92 (d, J=11.6 Hz, 1H), 4.88-4.84 (m, 1H), 4.73 (d, J=10.9 Hz, 1H), 4.68-4.59 (m, 3H), 4.46-4.38 (m, 4H), 4.29 (m, 1H), 3.91-3.84 (m, 2H), 3.79 (s, 3H), 3.77-3.74 (m, 1H), 3.56 (m, 2H), 3.49-3.46 (m, 3H), 3.18 (m, 2H), 1.60-1.47 (m, 4H), 1.29-1.24 (m, 2H); $^{13}$C NMR (150 MHz, $CDCl_3$) δ 159.1, 156.7, 156.1, 138.9, 138.7, 138.0, 136.8, 130.7, 129.2, 128.5, 128.4, 128.3, 128.2, 128.1, 128.0, 127.9, 127.8, 127.8, 127.5, 127.5, 127.2, 113.7, 103.9, 81.9, 79.6, 75.1, 74.5, 73.5, 73.4, 72.7, 69.7, 69.6, 68.9, 67.1, 55.2, 50.5, 50.2, 47.2, 46.2, 29.4, 28.0; 27.5, 23.4; HRMS (ESI-TOF, MNa$^+$) calculated for $C_{55}H_{61}NO_9Na$ 902.4239, found 902.4223.

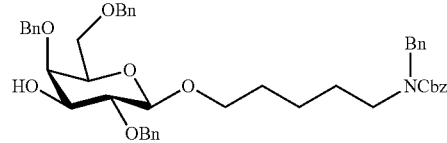

Benzylbenzyl(5-((2R,3R,4S,5R,6R)-3,5-bis(benzyloxy)-6-(benzyloxymethyl)-4-hydroxytetrahydro-2H-pyran-2-yloxy)pentyl)carbamate (11)

DDQ (1.16 g, 5.1 mmol) was added to a solution of compound 10 (4.47 g, 5.08 mmol) in $CH_2Cl_2/H_2O$ (10:1, 33 mL) at 0° C., and the resulting mixture was warmed to 25° C. and stirred for 2 h. The reaction mixture was diluted with $CH_2Cl_2$ (250 mL) and washed with saturated aqueous $NaHCO_3$ (50 mL) and brine (20 mL). The organic layer was dried with $Na_2SO_4$, and the solvents were removed under reduced pressure. The residue was purified by flash silica-gel column chromatography (1:3 to 1:2.5 ethylacetate/hexane) to give 11 as colorless oil (3.47 g, 90%). 11: $R_f$=0.58 (Hexane:EtOAc=2:1); $^1$H NMR (600 MHz, $CDCl_3$) δ 7.39-7.21 (m, 25H), 5.2 (d, J=17.0 Hz, 2H), 4.99 (m, 1H), 4.85 (d, J=11.7 Hz, 1H), 4.7 (dd, J=12.2, 12.2 Hz, 2H), 4.53 (m, 4H), 4.36 (m, 1H), 3.96-3.91 (m, 2H), 3.70-3.68 (m, 4H), 3.62 (dd, J=7.9, 7.9 Hz, 1H), 3.49 (m, 1H), 3.30-3.22 (m, 2H), 2.40 (s, 1H), 1.69-1.55 (m, 4H), 1.41-1.33 (m, 2H); $^{13}$C NMR (150 MHz, $CDCl_3$) δ 156.7, 156.2, 138.5, 137.9, 136.9, 136.8, 128.6, 128.5, 128.5, 128.3, 128.2, 128.1, 127.9, 127.8, 127.7, 127.3, 127.3, 127.2, 103.8, 79.6, 75.6, 75.0. 74.6, 74.1, 73.6, 73.5, 69.7, 69.6, 68.8, 67.2, 50.5, 50.2, 47.2, 46.2, 29.7, 29.4, 28.0, 27.5, 23.4; HRMS (ESI-TOF, MNa+) calculated for $C_{47}H_{53}NO_8Na$ 782.3663, found 782.3664.

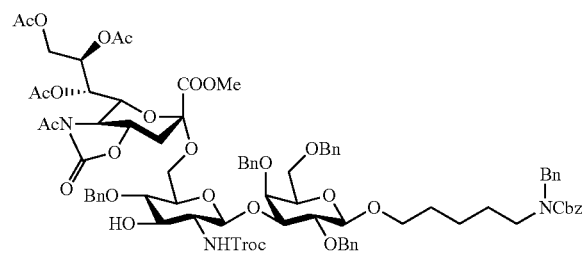

(1S,2R)-1-((3aR,4R,6R,7aS)-3-acetyl-6-(((2R,3S,4R,5R,6S)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-4-hydroxy-5-((2,2,2-trichloroethoxy)carbonylamino)tetrahydro-2H-pyran-2-yl)methoxy)-6-(methoxycarbonyl)-2-oxohexahydro-2H-pyrano[3,4-d]oxazol-4-yl) propane-1,2,3-triyl triacetate (5)

A solution of dibutyl sialyl phosphate 12 (0.1775 g, 0.27 mmole), acceptor 7 (0.1364 g, 0.20 mmole), pulverized activated 4 Å MS (0.4 g) in dry $CH_2Cl_2$ (3.5 mL), and acetonitrile (7 mL) was stirred under argon at room temperature for 3 h. The mixture was then cooled to −60° C., followed by addition of TMSOTf (50 μL, 0.28 mmole) via micro-syring and stirring for 30 min. Then, a solution of the acceptor 11 (0.0842 g, 0.11 mmole) in dry $CH_2Cl_2$ (1.0 mL) was slowly added to the reaction mixture. The mixture was warmed to −20° C. and stirred for 30 min, followed by addition of NIS (0.324 mmole). After 2 h, when TLC indicated that acceptor 11 was fully consumed, the reaction was neutralized by triethylamine, diluted with dichloromethane, and filtered with a pad of celite. The filtrate was poured into a mixture of saturated aq. $NaHCO_3$ and saturated aq. $Na_2S_2O_3$. The aqueous layer was extracted with two portions of ethyl acetate. The combined extracts were washed with brine, dried over $MgSO_4$, filtered, and concentrated in vacuo. The residue was purified by silica gel column chromatography (1:3 to 1:1.5 ethylacetate/hexane) to give 13 as white solid.

DDQ (0.0187 g, 0.082 mmol) was added to a solution of 13 in $CH_2Cl_2/H_2O$ (10:1, 5.5 mL) at room temperature and stirred overnight. The reaction mixture was diluted with $CH_2Cl_2$ (10 mL) and washed with saturated aqueous $NaHCO_3$ and brine. The organic layer was dried with $Na_2SO_4$, and the solvents were removed under reduced pressure. The residue was purified by flash silica-gel column chromatography (1:3 to 1:1.5 ethylacetate/hexane) to give 5 as a white solid (0.077 g, 42%). 5: $R_f$=0.23 (Hexane:EtOAc=2:1); $^1$H NMR (600 MHz, $CDCl_3$) δ 7.38-7.11 (m, 30H), 5.58-5.57 (m, 1H), 5.48-5.45 (m, 1H), 5.13 (d, J=13.6 Hz, 2H), 5.00-4.93 (m, 2H), 4.82-4.74 (m, 3H), 4.69 (d, J=12.0 Hz, 1H), 4.64 (d, J=10.5 Hz, 2H), 4.59-4.55 (m, 2H), 4.50-4.31 (m, 7H), 4.19 (dd, J=11.0, 4.1 Hz, 1H), 3.99-3.93 (m, 2H), 3.85-3.81 (m, 2H), 3.76-3.74 (m, 2H), 3.66 (dd, J=10.6, 9.8 Hz, 1H), 3.62-3.42 (m, 9H), 3.38-3.35 (m, 2H), 3.18-3.10 (m, 3H), 2.87 (dd, J=11.8, 2.9 Hz, 1H), 2.45 (s, 3H), 2.12-2.07 (m, 4H), 2.00 (s, 3H), 1.74 (s, 3H), 1.56-1.43 (m, 4H), 1.28-1.19 (m, 2H); $^{13}$C NMR (150 MHz, $CDCl_3$) δ 171.9, 170.6, 169.9, 169.9, 168.3, 156.6, 156.0, 155.1, 153.5, 138.8, 138.8, 138.1, 137.8, 137.7, 136.7, 136.6, 128.6, 128.9, 128.5, 128.4, 128.3, 128.3, 128.1, 128.0, 127.8, 127.7, 127.6, 127.3, 127.1, 103.8, 101.8, 99.2, 95.3, 80.2, 79.8, 77.4, 75.7, 75.2, 75.2, 74.8, 74.5, 74.3, 73.7, 73.5, 73.4, 71.4, 69.6, 68.5, 68.7, 68.3, 67.0, 67.0, 64.5, 63.0, 58.9, 58.1, 52.7, 50.4, 50.1, 47.0, 46.0, 36.4, 29.5, 29.2, 27.8, 27.4, 24.6, 23.2, 23.2, 21.1, 20.7, 20.4; HRMS (ESI-TOF, MNa+) calculated for $C_{82}H_{94}Cl_3N_3O_{26}Na$ 1666.5085, found 1666.5017.

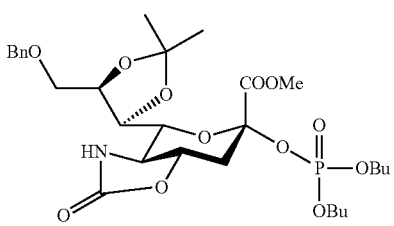

(3aR,4R,6S,7aS)-methyl 4-((4S,5R)-5-(benzyloxymethyl)-2,2-dimethyl-1,3-dioxolan-4-yl)-6-(dibutoxyphosphoryloxy)-2-oxohexahydro-2H-pyrano[3,4-d]oxazole-6-carboxylate (15)

A solution of thiosialoside donor 14 (6.2 g, 11.71 mmole), dibutyl phosphate (6.8 mL, 35.23 mmole), and pulverized activated 4 Å MS (8 g) in dry $CH_2Cl_2$ (140 mL) was stirred under argon at room temperature for 3 h. The reaction mixture was then cooled to 0° C., followed by the addition of NIS (5.55 g, 24.67 mmole) and 0.5M TfOH solution in dry $Et_2O$ (6.8 mL, 3.4 mmole). After stirring for 10 h, the reaction mixture was diluted with dichloromethane and filtered through a pad of celite. The filtrate was then poured into a mixture of saturated aq. $Na_2S_2O_3$ and $NaHCO_3$. The aqueous layer was extracted with two portions of dichloromethane. The collected organic phases were then washed with brine, dried over $Mg_2SO_4$, filtered, and concentrated in vacuo. The residue was purified by silica gel column chromatography (1:2 to 1:1.25 ethylacetate/hexane) to give 15 as oil (5.36 g, 72%). 15: $R_f$=0.40 (Hexane:EtOAc=1:1); $^1$H NMR (600 MHz, $CDCl_3$) δ 7.31-7.25 (m, 4H), 7.22-7.19 (m, 1H), 5.56 (s, 1H), 4.54 (t, J=12.3 Hz, 2H), 4.43 (q, J=6.3 Hz, 1H), 4.27 (dd, J=9.7, 1.5 Hz, 1H), 4.08-3.94 (m, 7H), 3.75 (s, 3H), 3.59 (t, J=10.5 Hz, 1H), 2.90 (dd, J=11.8, 3.4 Hz, 1H), 2.26 (t, J=12.3 Hz, 1H), 1.61-1.55 (m, 4H), 1.42 (s, 3H), 1.37-1.29 (m, 4H), 1.27 (s, 3H), 0.88-0.83 (m, 6H); $^{13}$C NMR (150 MHz, $CDCl_3$) δ 167.8, 167.8, 159.7, 159.6, 138.0, 128.2, 128.0, 127.5, 109.3, 99.2, 99.2, 76.1, 76.0, 76.0, 75.2, 73.2, 68.4, 68.2, 68.1, 67.7, 67.7, 57.6, 53.1, 38.1, 38.0, 32.0, 31.9, 31.9, 31.9, 26.2, 18.5, 13.4, 13.4; HRMS (ESI-TOF, MNa+) calculated for C29H44N1O12P1Na 652.2493, found 652.2495.

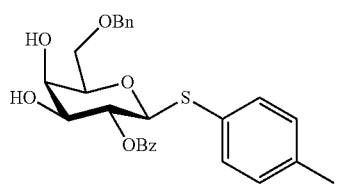

(2S,3R,4S,5R,6R)-6-(benzyloxymethyl)-4,5-dihydroxy-2-(p-tolylthio)tetrahydro-2H-pyran-3-yl benzoate (17)

A solution of compound 16 (0.7 g, 1.464 mmole) and pulverized activated 4 Å MS (1.7 g) in $CH_2Cl_2$ was stirred at room temperature. After stirring for 1 h, the mixture was cooled to −78° C. Then, to the stirred solution, $Et_3SiH$ (0.71 mL, 4.39 mmole) and TfOH (0.4 mL, 4.5 mmole) were added successively. After stirring for 1 h at −78° C., $Et_3N$ (5 mL) and MeOH (5 mL) were added successively, and the mixture was diluted with $CHCl_3$, washed with aqueous $NaHCO_3$, dried over $MgSO_4$, filtered, and concentrated. The crude product was purified by flash silica-gel column chromatography (1:2 to 1:1 ethylacetate/hexane) to give 17 as white solid (0.6 g, 85%). 17: $R_f$=0.38 (Hexane:EtOAc=1:1); $^1$H NMR (600 MHz, $CDCl_3$) δ 8.06 (dd, J=8.0, 0.95 Hz, 2H), 7.58-7.55 (m, 1H), 7.43 (dd, J=7.7, 7.7 Hz, 2H), 7.37-7.28 (m, 7H), 7.02 (d, J=7.9 Hz, 1H), 5.20 (t, J=9.6 Hz, 1H), 4.72 (d, J=9.75 Hz, 1H), 4.59-4.55 (m, 2H), 4.06 (t, J=3.5 Hz, 1H), 3.82 (d, J=5.3 Hz, 2H), 3.78-3.74 (m, 1H), 3.70-3.68 (m, 1H), 3.41 (d, J=7.8 Hz, 1H), 3.17 (d, J=4.0 Hz, 1H), 2.28 (s, 3H); $^{13}$C NMR (150 MHz, $CDCl_3$) δ 166.8, 138.1, 137.7, 133.3, 133.1, 130.0, 129.6, 129.6, 128.7, 128.4, 128.4, 127.8, 127.8, 86.3, 77.3, 73.9, 73.7, 72.1, 69.7, 69.7, 21.1; HRMS (ESI-TOF, MNa$^+$) calculated for $C_{27}H_{28}O_6SNa$ 503.1499, found 503.1494.

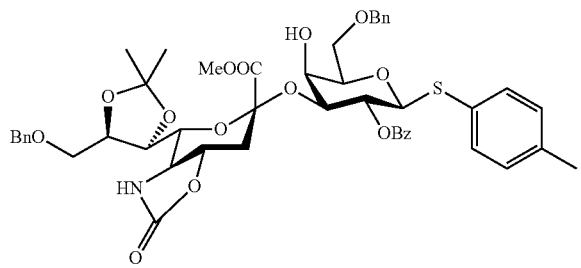

4

(3aR,4R,6S,7aS)-methyl 6-((2S,3R,4S,5S,6R)-3-(benzoyloxy)-6-(benzyloxymethyl)-5-hydroxy-2-(p-tolylthio)tetrahydro-2H-pyran-4-yloxy)-4-((4S,5R)-5-(benzyloxymethyl)-2,2-dimethyl-1,3-dioxolan-4-yl)-2-oxohexahydro-2H-pyrano[3,4-d]oxazole-6-carboxylate (4)

A solution of sialyl phosphate donor 15 (3.93 g, 6.25 mmole), acceptor 17 (2 g, 4.17 mmole), and pulverized activated 4 Å MS (6.2 g) in $CH_2Cl_2$ was stirred under argon at room temperature for 2 h. The reaction mixture was then cooled to −78° C., followed by addition of TMSOTf (1.51 mL, 8.32 mmole) via syringe. After stirring at the same temperature for 2 h, the reaction mixture was neutralized with triethylamine (3 mL), diluted with dichloromethane, and filtered through a pad of celite. The filtrate was washed with brine, dried over $MgSO_4$, filtered, and concentrated in vacuo. The residue was purified by flash silica-gel column chromatography (1:2 to 1:1.25 ethylacetate/hexane) to give 4 as white solid (3.75 g, 87%). 4: $R_f$=0.34 (Hexane:EtOAc=1:1); $^1$H NMR (600 MHz, $CDCl_3$) δ 8.01 (dd, J=8.5, 1.2 Hz, 2H), 7.59-7.56 (m, 1H), 7.44 (dd, J=7.7, 7.7 Hz, 2H), 7.34 (d, J=8.1 Hz, 2H), 7.31-7.24 (m, 10H), 7.00 (d, J=8.0 Hz, 2H), 5.48 (s, 1H), 5.42 (t, J=9.8 Hz, 1H), 4.70 (d, J=10.0 Hz, 1H), 4.54 (dd, J=9.5, 6.4 Hz, 2H), 4.51 (dd, J=10.3, 7.2 Hz, 2H), 4.45-4.42 (m, 1H), 4.30 (dd, J=9.6, 3.0 Hz, 1H), 4.13 (s, 1H), 4.04 (dd, J=7.0, 1.7 Hz, 1H), 3.93-3.85 (m, 3H), 3.81-3.74 (m, 3H), 3.68-3.66 (m, 4H), 3.42 (t, J=10.6 Hz, 1H), 2.61-2.58 (m, 2H), 2.27 (s, 3H), 1.94 (t, J=12.5 Hz, 1H), 1.73 (s, 1H), 1.41 (s, 3H), 1.30 (s, 3H); $^{13}$C NMR (150 MHz, $CDCl_3$) δ 168.7, 165.3, 159.8, 138.2, 137.9, 133.6, 133.1, 129.9, 129.7, 129.2, 128.7, 128.6, 128.5, 128.0, 127.9, 127.8, 127.8, 109.1, 99.9, 87.2, 77.5, 76.9, 76.2, 75.6, 75.3, 75.1, 73.7, 73.6, 69.6, 68.9, 68.7, 68.5, 58.2, 53.4, 36.5, 27.1, 24.7, 21.3; HRMS (ESI-TOF, M$^+$) calculated for $C_{48}H_{53}NO_{14}S$ 900.3260, found 900.3283.

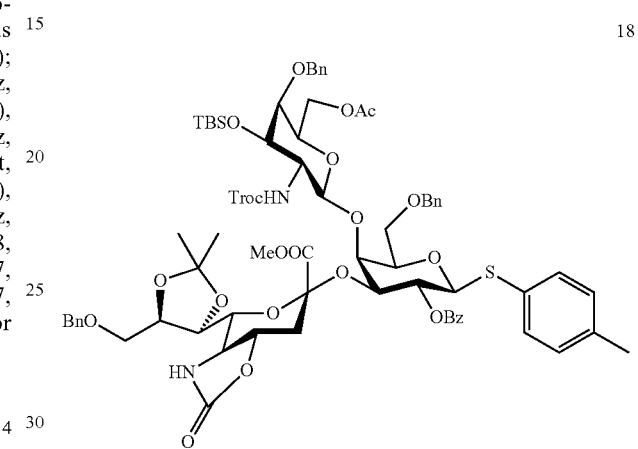

18

(3aR,4R,6S,7aS)-methyl 6-((2R,3S,4S,5R,6S)-3-((2S,3R,4R,5S,6R)-6-(acetoxy methyl)-5-(benzyloxy)-4-(tert-butyldimethylsilyloxy)-3-(((2,2,2-trichloroethoxy)carbonylamino)tetrahydro-2H-pyran-2-yloxy)-5-(benzoyloxy)-2-(benzyloxymethyl)-6-(p-tolylthio)tetrahydro-2H-pyran-4-yloxy)-4-((4S,5R)-5-(benzyloxymethyl)-2,2-dimethyl-1,3-dioxolan-4-yl)-2-oxohexahydro-2H-pyrano[3,4-d]oxazole-6-carboxylate (18)

A solution of donor 3 (2.34 g, 2.95 mmole), acceptor 4 (1.85 g, 2.06 mmole), and pulverized activated 4 Å MS (6.2 g) in $CH_2Cl_2$ was stirred under argon at room temperature for 2 h. The reaction mixture was then cooled to −50° C., followed by the addition of TMSOTf (0.6 mL, 3.307 mmole) via micro-syringe. After stirring at the same temperature for 2 h, the reaction mixture was neutralized with triethylamine (3 mL), diluted with dichloromethane, and filtered through a pad of celite. The filtrate was washed with brine, dried over $MgSO_4$, filtered, and concentrated in vacuo. The residue was purified by silica gel column chromatography (1:2.5 to 1:1.25 ethylacetate/hexane) to give 18 as white solid (2.23 g, 73%). 18: $R_f$=0.37 (Hexane:EtOAc=1:1); $^1$H NMR (600 MHz, $CDCl_3$) δ 8.00 (d, J=7.3 Hz, 3H), 7.59 (t, J=7.4 Hz, 1H), 7.47 (t, J=7.8 Hz, 2H), 7.38-7.36 (m, 4H), 7.32-7.25 (m, 13H), 6.99 (d, J=8.0 Hz, 2H), 5.50 (s, 1H), 5.36 (s, 1H), 5.07 (dd, J=50.6, 10.6 Hz, 2H), 4.90 (d, J=11.5 Hz, 1H), 4.72-4.54 (m, 6H), 4.49-4.46 (m, 2H), 4.43 (dd, J=13.0, 7.2 Hz, 1H), 4.10-4.02 (m, 7H), 3.98 (td, J=12.0, 3.6 Hz, 1H), 3.86-3.78 (m, 2H), 3.75-3.72 (m, 5H), 3.66-3.56 (m, 4H), 3.49 (t, J=10.6 Hz, 1H), 2.34 (dd, J=12.2, 3.6 Hz, 1H), 2.29-2.22 (m, 4H), 1.89 (s, 1H), 1.33 (s, 3H), 1.28 (s, 3H), 0.92 (s, 9H), 0.17 (s, 3H), 0.16 (s, 3H); $^{13}$C NMR (150 MHz, $CDCl_3$) δ 170.6, 168.9, 159.6, 154.2, 138.5, 138.5, 137.7, 133.5, 132.6, 129.8, 129.6, 129.2, 128.6, 128.5, 128.3, 128.3, 128.2, 127.9, 127.9, 127.8, 127.7, 127.6, 127.5, 127.3, 108.8, 101.8, 96.1, 78.5, 76.4, 75.4, 75.1, 75.0, 74.7, 74.6, 74.4, 73.6, 73.0, 72.2, 70.5, 68.1, 63.6, 58.1, 54.6, 54.0, 34.4, 27.0, 25.8, 25.8, 24.3, 21.1, 20.7, 18.0, −4.1, −4.7; HRMS (ESI-TOF, MNa+) calculated for $C_{72}H_{87}Cl_3N_2O_{21}SSiNa$ 1505.4244, found 1505.4245.

Then, a solution of the acceptor 5 (0.382 g, 0.232 mmole) in dry $CH_2Cl_2$ (1.0 mL) was slowly added to the reaction mixture. The mixture was warmed to 0° C. and stirred for 30 min, followed by addition of NIS (0.085 g, 0.377 mmole). After 24 h, when TLC indicated that acceptor 5 was fully consumed, the reaction was neutralized by triethylamine, diluted with dichloromethane, and filtered with a pad of

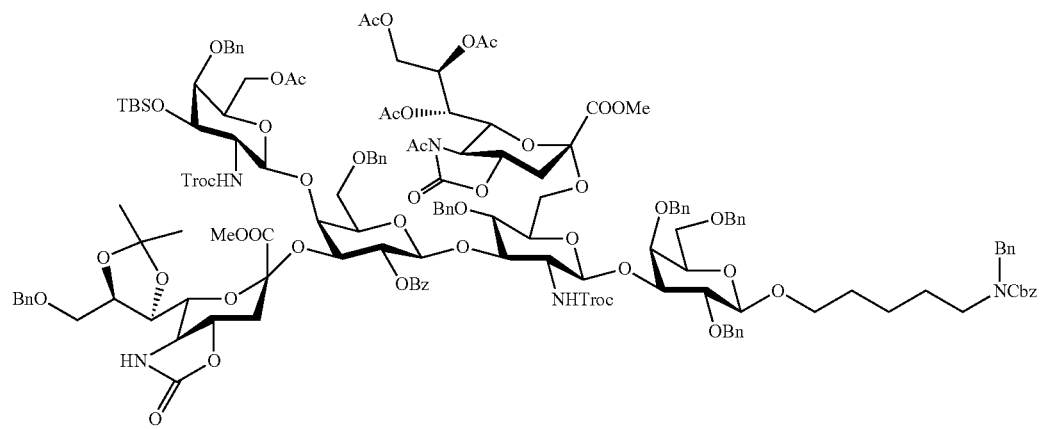

2

(1S,2R)-1-((3aR,4R,6R,7aS)-6-(((2R,3R,4R,5S,6S)-4-((2R,3R,4S,5S,6R)-5-((2S,3R,4S,6R)-6-(acetoxymethyl)-5-(benzyloxy)-4-(tert-butyldimethylsilyloxy)-3-((2,2,2-trichloroethoxy)carbonylamino)tetrahydro-2H-pyran-2-yloxy)-3-(benzoyloxy)-6-(benzyloxymethyl)-4-((3aR,4R,6S,7aS)-4-((4S,5R)-5-(benzyloxymethyl)-2,2-dimethyl-1,3-dioxolan-4-yl)-6-(methoxycarbonyl)-2-oxohexahydro-2H-pyrano[3,4-d]oxazol-6-yloxy)tetrahydro-2H-pyran-2-yloxy)-6-((2R,3S,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-5-((2,2,2-trichloroethoxy)carbonylamino)tetrahydro-2H-pyran-2-yl)methoxy)-3-acetyl-6-(methoxycarbonyl)-2-oxohexahydro-2H-pyrano[3,4-d]oxazol-4-yl)propane-1,2,3-triyl triacetate (2)

A solution of donor 18 (0.47 g, 0.317 mmole), acceptor 5 (0.26 g, 0.158 mmole), and pulverized activated 4 Å MS (1.3 g) in $CH_2Cl_2$ was stirred under argon at room temperature for 2 h. The reaction mixture was then cooled to −30° C., followed by addition of NIS (0.107 g, 0.476 mmole) and 0.5 M TfOH solution in dry $Et_2O$ (0.3 mL, 0.15 mmole). After stirring for 23 h at −10° C., the reaction mixture was diluted with dichloromethane and filtered through a pad of celite. The filtrate was then poured into a mixture of saturated aq. $Na_2S_2O_3$ and $NaHCO_3$. The aqueous layer was extracted with two portions of dichloromethane. The collected organic phases were then washed with brine, dried over $Mg_2SO_4$, filtered, and concentrated in vacuo. The residue was purified by silica gel column chromatography (1:2.5 to 1:1.25 ethylacetate/hexane) to give 2 as white solid (0.296 g, 62%).

One pot: A solution of GlaNAc donor 3 (0.302 g, 0.38 mmole), acceptor 4 (0.262 g, 0.291 mmole) and pulverized activated 4 Å MS (0.9 g) in dry $CH_2Cl_2$ (3.5 mL) was stirred under argon at room temperature for 3 h. The mixture was then cooled to −50° C., followed by addition of TBDMSOTf (88 µL, 0.382 mmole) via micro-syringe and stirring for 2 h.

celite. The filtrate was poured into a mixture of saturated aq. $NaHCO_3$ and saturated aq. $Na_2S_2O_3$. The aqueous layer was extracted with two portions of ethyl acetate. The combined extracts were washed with brine, dried over $MgSO_4$, filtered, and concentrated in vacuo. The residue was purified by silica gel column chromatography (1:2.5 to 1:1.25 ethylacetate/hexane) to give 2 as white solid (0.223 g, 32%). 2: $R_f$=0.32 (Hexane:EtOAc=1:1); $^1$H NMR (600 MHz, $CDCl_3$) δ 8.08 (d, J=7.4 Hz, 1H), 7.62 (t, J=7.4 Hz, 1H), 7.49 (t, J=7.9 Hz, 3H), 7.40 (d, J=7.2 Hz, 2H), 7.35-7.10 (m, 42H), 6.71 (t, J=7.4 Hz, 1H), 5.57 (dd, J=9.1, 1.3 Hz, 1H), 5.46 (ddd, J=9.0, 6.3, 2.6 Hz, 1H), 5.32 (s, 1H), 5.17-5.09 (m, 5H), 4.95-4.80 (m, 2H), 4.75-4.68 (m, 3H), 4.63 (dd, J=14.1, 6.4 Hz, 2H), 4.57 (d, J=10.9 Hz, 1H), 4.52-4.22 (m, 17H), 4.13 (t, J=8.6 Hz, 1H), 4.09-4.03 (m, 5H), 3.96-3.88 (m, 3H), 3.83-3.71 (m, 10H), 3.64-3.50 (m, 11H), 3.44-3.27 (m, 9H), 3.12-2.93 (m, 3H), 2.82 (dd, J=11.9, 3.2 Hz, 1H), 2.48 (s, 2H), 2.32-2.25 (m, 2H), 2.15-2.10 (m, 4H), 2.03 (s, 3H), 1.90 (s, 3H), 1.69 (s, 3H), 1.50-1.14 (m, 12H), 0.94 (s, 9H), 0.22-0.20 (m, 6H); $^{13}$C NMR (150 MHz, $CDCl_3$) δ 171.8, 170.7, 170.6, 170.4, 169.8, 169.3, 168.5, 164.3, 159.4, 156.6, 156.1, 154.3, 153.7, 153.2, 139.3, 139.1, 139.0, 138.3, 138.2, 137.8, 137.7, 136.8, 136.7, 133.6, 129.9, 129.7, 129.3, 129.2, 128.8, 128.7, 128.5, 128.4, 128.4, 128.3, 128.3, 128.1, 128.0, 127.9, 127.8, 127.8, 127.6, 127.3, 127.2, 127.1, 127.0, 126.6, 109.0, 103.8, 101.8, 101.0, 100.9, 99.1, 96.3, 96.0, 81.1, 79.3, 78.5, 78.0, 76.2, 75.7, 75.3, 75.3, 75.1, 75.1, 75.0, 74.8, 74.7, 74.6, 74.4, 74.1, 73.5, 73.4, 73.1, 72.9, 72.2, 71.1, 69.7, 69.7, 69.2, 69.0, 68.3, 67.9, 67.1, 64.3, 63.6, 62.9, 59.1, 58.3, 58.1, 54.5, 54.0, 53.7, 52.6, 50.4, 50.1, 47.1, 46.1, 36.6, 34.6, 31.7, 29.2, 27.8, 27.4, 27.1, 25.8, 25.7, 24.7, 24.2, 23.3, 21.1, 20.8, 20.6, 20.5, 18.0, −4.1, −4.8; HRMS (ESI-TOF, MNa+) calculated for $C_{147}H_{173}Cl_6N_5O_{47}SiNa$ 3024.9106, found 3024.9080.

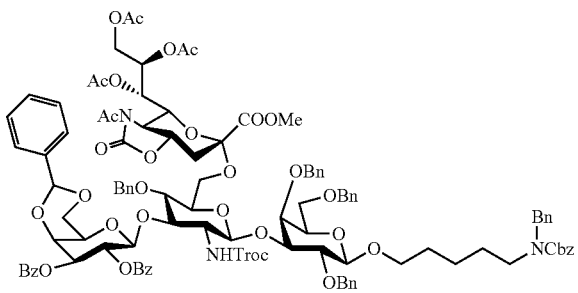

(1S,2R)-1-((3aR,4R,6R,7aS)-3-acetyl-6-(((2R,3S, 4R,5R,6S)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-4-((4aR,6R,7R,8S)-7,8-bis(benzoyloxy)-2-phenylhexahydropyrano[3,2-d][1,3]dioxin-6-yloxy)-5-((2,2,2-trichloroethoxy)carbonylamino)tetrahydro-2H-pyran-2-yl)methoxy)-6-(methoxycarbonyl)-2-oxohexahydro-2H-pyrano[3,4-d]oxazol-4-yl)propane-1,2,3-triyl triacetate (20)

A solution of donor 19 (0.239 g, 0.410 mmole), acceptor 5 (0.151 g, 0.092 mmole), and pulverized activated 4 Å MS (0.8 g) in $CH_2Cl_2$ was stirred under argon at room temperature for 2 h. The reaction mixture was then cooled to −30° C., followed by addition of NIS (0.104 g, 0.462 mmole) and TfOH (9 μL, 0.1 mmole). After stirring for 9 h at 0° C., the reaction mixture was diluted with dichloromethane and filtered through a pad of celite. The filtrate was then poured into a mixture of saturated aq. $Na_2S_2O_3$ and $NaHCO_3$. The aqueous layer was extracted with two portions of dichloromethane. The collected organic phases were then washed with brine, dried over $Mg_2SO_4$, filtered, and concentrated in vacuo. The residue was purified by silica gel column chromatography (1:3 to 1:1.25 ethylacetate/hexane) to give 20 as oil (0.12 g, 62%). 20: $R_f$=0.23 (Hexane:EtOAc=2:1); $^1$H NMR (600 MHz, $CDCl_3$) δ 8.02 (d, J=7.3 Hz, 2H), 7.95 (d, J=7.3 Hz, 2H), 7.50-7.44 (m, 6H), 7.36-7.12 (m, 35H), 5.84 (dd, J=10.3, 8.1 Hz, 1H), 5.58 (d, J=7.7 Hz, 1H), 5.53 (s, 1H), 5.41-5.38 (m, 1H), 5.23 (dd, J=10.3, 3.5 Hz, 1H), 5.13 (d, J=9.7 Hz, 3H), 4.87-4.77 (m, 4H), 4.63 (dd, J=26.0, 9.1 Hz, 2H), 4.57-4.33 (m, 9H), 4.26-4.24 (m, 2H), 4.18-4.16 (m, 2H), 4.03-4.01 (m, 2H), 3.92-3.80 (m, 5H), 3.67-3.33 (m, 14H), 3.13-3.06 (m, 3H), 2.83 (dd, J=11.8, 2.9 Hz, 1H), 2.47 (s, 3H), 2.15-2.05 (m, 4H), 2.01 (s, 3H), 1.82 (s, 3H), 1.57-1.34 (m, J=38.8, 32.6 Hz, 4H), 1.28-1.09 (m, 2H); $^{13}$C NMR (150 MHz, $CDCl_3$) δ 172.2, 171.8, 170.7, 170.0, 169.9, 168.4, 166.0, 165.3, 156.7, 156.1, 153.6, 139.4, 139.0, 138.2, 137.9, 137.7, 136.9, 136.7, 133.3, 133.2, 129.9, 129.8, 129.6, 129.1, 128.8, 128.5, 128.4, 128.4, 128.2, 128.2, 128.0, 127.9, 127.9, 127.8, 127.6, 127.3, 127.2, 127.1, 126.9, 126.2, 103.8, 101.3, 100.7, 99.4, 95.7, 80.5, 79.8, 79.6, 76.2, 75.7, 75.2, 75.0, 74.9, 74.6, 74.1, 73.9, 73.6, 73.5, 73.5, 72.7, 71.4, 69.7, 68.9, 68.5, 67.1, 66.6, 64.7, 63.5, 62.8, 59.1, 58.4, 52.8, 50.5, 50.2, 47.1, 46.1, 36.4, 29.3, 27.9, 27.4, 24.7, 23.3, 23.2, 21.1, 20.8, 20.7; HRMS (ESI-TOF, MNa$^+$) calculated for $C_{109}H_{116}Cl_3N_3O_{33}Na$ 2124.6462, found 2124.6302.

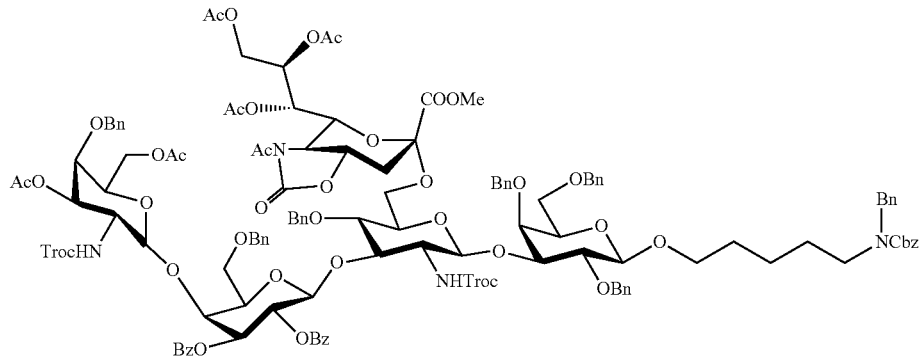

22

(1S,2R)-1-((3aR,4R,6R,7aS)-6-(((2R,3S,5R,6S)-4-((2R,3S,5S,6R)-5-((3R,4S,5S,6R)-4-acetoxy-6-(acetoxymethyl)-5-(benzyloxy)-3-((2,2,2-trichloroethoxy)carbonylamino)tetrahydro-2H-pyran-2-yloxy)-3,4-bis(benzoyloxy)-6-(benzyloxymethyl)tetrahydro-2H-pyran-2-yloxy)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-5-((2,2,2-trichloroethoxy)carbonylamino)tetrahydro-2H-pyran-2-yl)methoxy)-3-acetyl-6-(methoxycarbonyl)-2-oxohexahydro-2H-pyrano[3,4-d]oxazol-4-yl) propane-1,2,3-triyl triacetate (22)

A solution of donor 21 (0.365 g, 0.333 mmole), acceptor 5 (0.2 g, 0.122 mmole), and pulverized activated 4 Å MS (0.54 g) in CH$_2$Cl$_2$ was stirred under argon at room temperature for 2 h. The reaction mixture was then cooled to −30° C., followed by addition of NIS (0.093 g, 0.413 mmole) and TfOH (0.012 mL, 0.135 mmole). After stirring for 11 h at 0° C., the reaction mixture was diluted with dichloromethane and filtered through a pad of celite. The filtrate was then poured into a mixture of saturated aq. Na$_2$S$_2$O$_3$ and NaHCO$_3$. The aqueous layer was extracted with two portions of dichloromethane. The collected organic phases were then washed with brine, dried over Mg$_2$SO$_4$, filtered, and concentrated in vacuo. The residue was purified by silica gel column chromatography (1:4 to 1:1.75 ethylacetate/hexane) to give 22 as oil (0.217 g, 68%). 22: R$_f$=0.23 (Hexane:EtOAc=2:1); $^1$H NMR (600 MHz, CDCl$_3$) δ 8.04 (d, J=7.5 Hz, 3H), 7.91 (d, J=7.5 Hz, 1H), 7.62 (d, J=7.2 Hz, 1H), 7.55 (t, J=7.4 Hz, 1H), 7.45 (dt, J=15.5, 7.5 Hz, 2H), 7.38-7.10 (m, 44H), 6.85 (t, J=7.2 Hz, 1H), 5.64-5.61 (m, 2H), 5.48-5.47 (m, 1H), 5.28 (d, J=12.3 Hz, 1H), 5.18-5.11 (m, 3H), 5.03-4.92 (m, 3H), 4.84 (d, J=11.1 Hz, 1H), 4.76-4.65 (m, 5H), 4.56-4.28 (m, 16H), 4.20-4.17 (m, 3H), 4.13-4.10 (m, 1H), 4.01-3.93 (m, 3H), 3.85-3.80 (m, 2H), 3.75-3.52 (m, 13H), 3.47-3.24 (m, 7H), 3.14 (d, J=46.8 Hz, 2H), 2.91-2.89 (m, 1H), 2.49 (s, 3H), 2.20-2.13 (m, 4H), 2.04-2.02 (m, 6H), 1.95 (s, 3H), 1.79 (s, 3H), 1.55-1.42 (m, 4H), 1.25-1.20 (m, 2H); $^{13}$C NMR (150 MHz, CDCl$_3$) δ 171.8, 171.0, 170.6, 170.3, 170.2, 169.9, 168.6, 166.1, 165.3, 156.6, 156.1, 154.2, 153.8, 153.7, 139.3, 138.8, 138.7, 138.4, 137.9, 137.4, 136.8, 136.8, 134.0, 133.0, 129.8, 129.7, 129.7, 129.5, 128.9, 128.7, 128.6, 128.6, 128.5, 128.4, 128.4, 128.4, 128.3, 128.2, 128.2, 127.9, 127.8, 127.8, 127.6, 127.6, 127.3, 127.3, 127.2, 127.1, 127.1, 103.8, 103.2, 101.1, 100.9, 99.3, 96.3, 95.6, 80.6, 79.7, 79.3, 75.6, 75.4, 75.1, 75.0, 75.0, 74.8, 74.7, 74.5, 74.5, 74.3, 74.0, 73.6, 73.5, 73.4, 73.3, 73.0, 71.9, 71.3, 70.3, 69.7, 69.6, 69.0, 68.8, 68.4, 64.5, 62.9, 62.3, 59.1, 57.5, 50.5, 50.2, 47.1, 46.1, 36.6, 29.3, 27.8, 27.4, 24.7, 23.3, 23.2, 21.2, 20.8, 20.8, 20.7; HRMS (ESI-TOF, MNa$^+$) calculated for C$_{129}$H$_{140}$Cl$_6$N$_4$O$_{41}$Na 2637.7021, found 2637.6947.

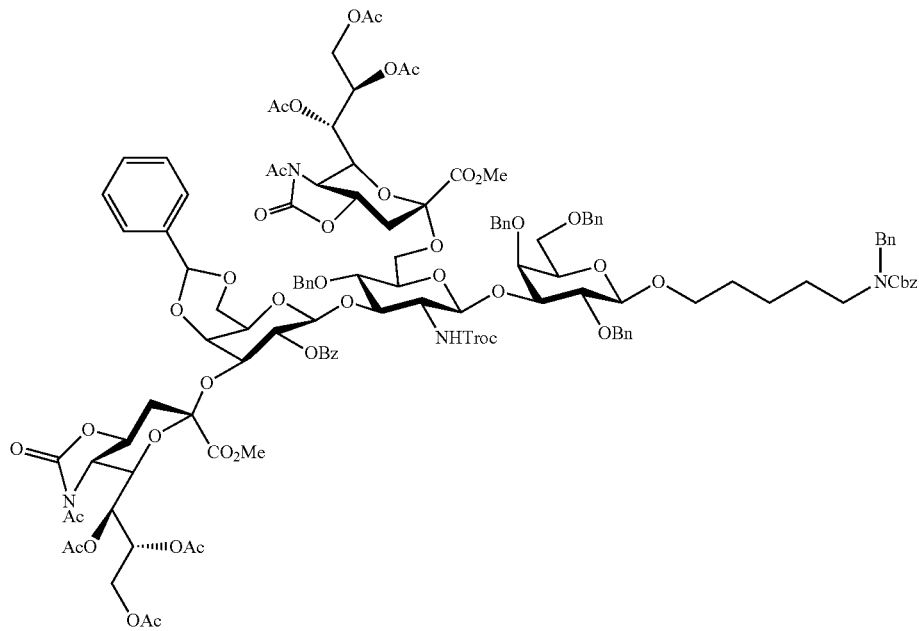

24

(1S,2R)-1-((3aR,4R,6R,7aS)-3-acetyl-6-(((2R,3S,4R,5R,6S)-4-((4aR,6R,7S,8S,8aS)-8-((3aS,4S,6R,7aR)-3-acetyl-6-(methoxycarbonyl)-2-oxo-4-((1S,2R)-1,2,3-triacetoxypropyl)hexahydro-2H-pyrano[3,4-d]oxazol-6-yloxy)-7-(benzoyloxy)-2-phenylhexahydropyrano[3,2-d][1,3]dioxin-6-yloxy)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-5-((2,2,2-trichloroethoxy)carbonylamino)tetrahydro-2H-pyran-2-yl)methoxy)-6-(methoxycarbonyl)-2-oxohexahydro-2H-pyrano[3,4-d]oxazol-4-yl) propane-1,2,3-triyltriacetate (24)

A solution of donor 23 (0.28 g, 0.299 mmole), acceptor 5 (0.32 g, 0.195 mmole), and pulverized activated 4 Å MS (0.6 g) in CH$_2$Cl$_2$ was stirred under argon at room temperature for 2 h. The reaction mixture was then cooled to −20° C., followed by addition of NIS (0.102 g, 0.455 mmole) and TfOH (0.009 mL, 0.101 mmole). After stirring for 3 h at −20° C., the reaction mixture was diluted with dichloromethane and filtered through a pad of celite. The filtrate was then poured into a mixture of saturated aq. Na$_2$S$_2$O$_3$ and NaHCO$_3$. The aqueous layer was extracted with two portions of dichloromethane. The collected organic phases were then washed with brine, dried over Mg$_2$SO$_4$, filtered, and concentrated in vacuo. The residue was purified by silica gel column chromatography (1:2.5 to 1:1 ethylacetate/hexane) to give 24 as oil (0.2884 g, 60%). 24: R$_f$=0.19 (Hexane: EtOAc=1:1); $^1$H NMR (600 MHz, CDCl$_3$) δ 8.15 (d, J=7.3 Hz, 2H), 7.58-7.52 (m, 3H), 7.45 (t, J=7.8 Hz, 2H), 7.39 (d, J=7.0 Hz, 2H), 7.32-7.19 (m, 27H), 7.14-7.08 (m, 4H), 5.62-5.55 (m, 3H), 5.47 (ddd, J=9.5, 7.3, 2.4 Hz, 1H), 5.43 (s, 1H), 5.35 (ddd, J=8.6, 5.9, 2.7 Hz, 1H), 5.18-5.09 (m, 3H), 4.87-4.74 (m, 4H), 4.65-4.35 (m, 13H), 4.27-4.26 (m, 3H), 4.20-4.04 (m, 6H), 3.91-3.74 (m, 5H), 3.66-3.43 (m, 16H), 3.28 (s, 3H), 3.09 (d, J=45.3 Hz, 2H), 2.81-2.77 (m, 2H), 2.47 (s, 3H), 2.47 (s, 3H), 2.19 (s, 3H), 2.15 (s, 3H), 2.09-2.06 (m, 5H), 2.00 (s, 1H), 2.00 (s, 3H), 1.79-1.77 (m, 6H), 1.50-1.38 (m, 4H), 1.25-1.09 (m, 2H); $^{13}$C NMR (150 MHz, CDCl$_3$) δ 172.0, 171.8, 170.8, 170.7, 170.1, 170.0, 169.9, 169.8, 168.3, 168.0, 165.1, 156.6, 156.1, 153.6, 153.4, 139.3, 139.0, 138.2, 138.1, 137.8, 136.8, 136.7, 133.3, 130.1, 129.7, 128.8, 128.7, 128.6, 128.4, 128.4, 128.4, 128.1, 128.1, 127.9, 127.9, 127.8, 127.7, 127.7, 127.4, 127.3, 127.2, 127.1, 126.8, 126.5, 103.8, 100.8, 100.6, 100.3, 99.3, 97.5, 96.2, 80.7, 79.4, 79.1, 76.3, 75.9, 75.1, 75.0, 74.9, 74.9, 74.8, 74.5, 74.1, 73.6, 73.5, 72.9, 72.8, 71.3, 70.8, 69.7, 69.7, 69.0, 68.5, 68.3, 68.0, 67.0, 66.2, 64.6, 63.5, 62.6, 59.0, 58.9, 58.5, 52.8, 52.7, 50.4, 50.1, 47.1, 46.1, 36.8, 36.3, 29.6, 29.3, 27.8, 27.4, 24.6, 23.3, 21.3, 21.1, 21.1, 20.8, 20.7, 20.6; HRMS (ESI-TOF, MNa$^+$) calculated for C$_{121}$H$_{135}$Cl$_3$N$_4$O$_{44}$Na 2477.7425, found 2477.7390.

((2R,3S,4R,5R,6S)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-4-hydroxy-5-((2,2,2-trichloroethoxy)carbonylamino)tetrahydro-2H-pyran-2-yl)methyl acetate (25)

Acetic anhydride (7 mL) was added to a solution of compound 7 (4.12 g, 6.14 mmol) in pyridine (7 mL) at room temperature. The mixture was stirred for 12 h at same temperature, and methanol (5 mL) was added. The solution was concentrated into syrup and extracted with dichloromethane. The extract was successively washed with 2 N HCl, water, NaHCO$_{3(aq)}$, and water, then dried with Na$_2$SO$_4$, and concentrated. Column chromatography (1:3 ethyl acetate/hexane) of the residue on silica gel gave the per-acetylated thioglycoside as white solid I (3.8 g, 87%). A solution of donor I (1.42 g, 1.99 mmole), acceptor 11 (1.00 g, 1.316 mmole), and pulverized activated 4 Å MS (2.0 g) in CH$_2$Cl$_2$ was stirred under argon at room temperature for 2 h. The reaction mixture was then cooled to −20° C., followed by addition of NIS (0.60 g, 2.67 mmole) and TfOH (0.016 mL, 0.18 mmole). After stirring for 2 h at the same temperature, the reaction mixture was diluted with dichloromethane and filtered through a pad of celite. The filtrate was then poured into a mixture of saturated aq. Na$_2$S$_2$O$_3$ and NaHCO$_3$. The aqueous layer was extracted with two portions of dichloromethane. The collected organic phases were then washed with brine, dried over Mg$_2$SO$_4$, filtered, and concentrated in vacuo. The residue was purified by silica gel column chromatography (1:3 to 1:2 ethylacetate/hexane) to give II as white solid (1.14 g, 64%). DDQ (0.40 g, 1.76 mmol) was added to a solution of compound II (1.14 g, 0.845 mmol) in CH$_2$Cl$_2$/H$_2$O (11:1, 36 mL) at rt, and the resulting mixture was stirred for 2 h. The reaction mixture was diluted with CH$_2$Cl$_2$ (250 mL) and washed with saturated aqueous NaHCO$_3$ (200 mL) and brine (35 mL). The organic layer was dried with Na$_2$SO$_4$, and the solvents were removed under reduced pressure. The residue was purified by flash silica-gel column chromatography (1:3 to 1:2 ethylacetate/hexane) to give 25 as colorless oil (0.635 g, 66%). 25: R$_f$=0.22 (Hexane:EtOAc=2:1); $^1$H NMR (600 MHz, CDCl$_3$) δ 7.35-7.11 (m, 30H), 5.13 (d, J=14.6 Hz, 2H), 5.01 (t, J=12.8 Hz, 1H), 4.89-4.84 (m, 3H), 4.67-4.64 (m, 3H), 4.58-4.53 (m, 3H), 4.44-4.27 (m, 6H), 4.22 (dd, J=11.4, 3.7 Hz, 1H), 3.86-3.81 (m, 2H), 3.76-3.68 (m, 2H), 3.55-3.46 (m, 5H), 3.45-3.33 (m, 4H), 3.14 (d, J=46.1 Hz, 2H), 1.96 (s, 3H), 1.55-1.42 (m, 4H), 1.27-1.18 (m, 2H); $^{13}$C NMR (150 MHz, CDCl$_3$) δ 170.6, 156.6, 156.0, 155.5, 138.7, 138.6, 137.7, 137.6, 136.7, 136.6, 128.5, 128.4, 128.4, 128.3, 128.3, 128.0, 127.7, 127.7, 127.4, 127.3, 127.2, 127.1, 127.0, 103.7, 101.7, 95.1, 80.7, 79.5, 77.4, 76.1, 75.5, 74.7, 74.6, 74.5, 74.3, 73.4, 72.7, 69.6, 69.5, 68.7, 67.0, 67.0, 62.9, 58.5, 50.4, 50.1, 47.0 46.0, 29.2, 27.8, 27.3, 23.2, 23.2, 20.7; HRMS (ESI-TOF, MNa$^+$) calculated for C$_{65}$H$_{73}$Cl$_3$N$_2$O$_{15}$Na 1251.3961, found 1251.3963.

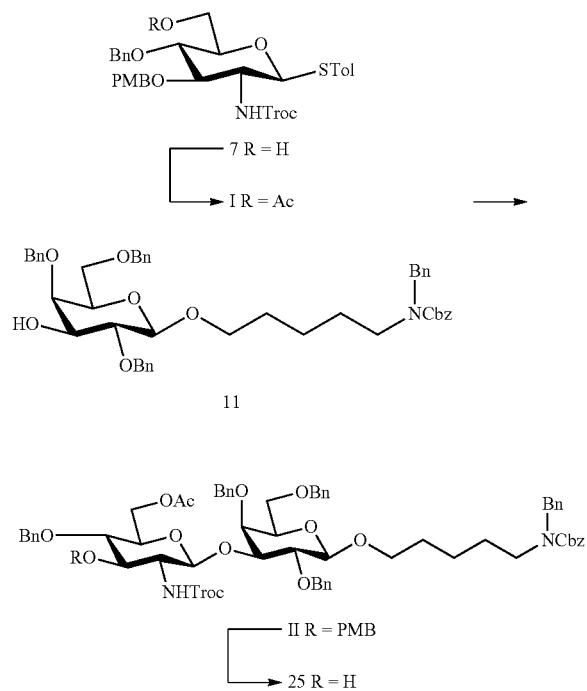

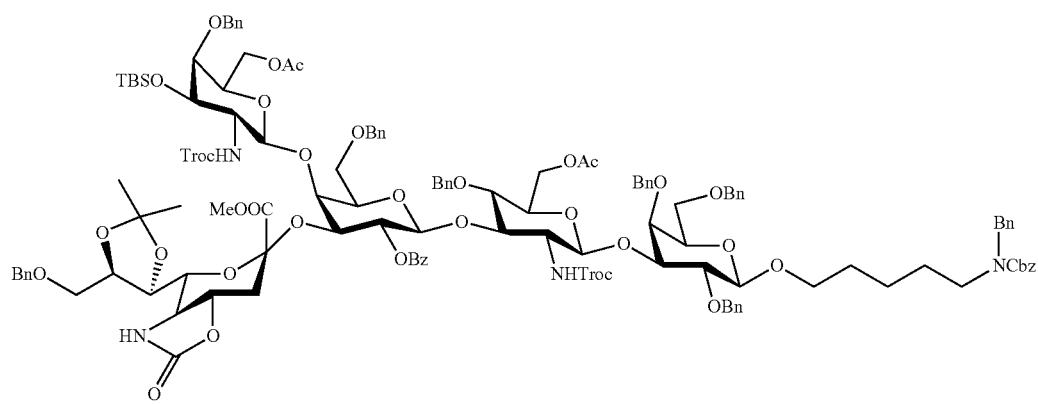

26

(3aR,4R,6S,7aS)-methyl 6-((2R,3S,4S,5R,6R)-3-((2S,3R,4R,5S,6R)-6-(acetoxy methyl)-5-(benzyloxy)-4-(tert-butyldimethylsilyloxy)-3-((2,2,2-trichloroethoxy)carbonylamino)tetrahydro-2H-pyran-2-yloxy)-6-((2R,3S,4R,5R,6S)-2-(acetoxymethyl)-6-((2R,3R,4S,5S,6R)-2-(5-(benzyl(benzyloxycarbonyl)amino)pentyloxy)-3,5-bis(benzyloxy)-6-(benzyloxymethyl)tetrahydro-2H-pyran-4-yloxy)-3-(benzyloxy)-5-((2,2,2-trichloroethoxy)carbonylamino)tetrahydro-2H-pyran-4-yloxy)-5-(benzoyloxy)-2-(benzyloxymethyl)tetrahydro-2H-pyran-4-yloxy)-4-((4S,5R)-5-(benzyloxymethyl)-2,2-dimethyl-1,3-dioxolan-4-yl)-2-oxohexahydro-2H-pyrano[3,4-d]oxazole-6-carboxylate (26)

A solution of donor 18 (0.209 g, 0.141 mmole), acceptor 25 (0.124 g, 0.101 mmole) and pulverized activated 4 Å MS (0.65 g) in dry $CH_2Cl_2$ (7 mL) was stirred under argon at room temperature for 2 h. The mixture was then cooled to −30° C., followed by addition of NIS (0.045 g, 0.2 mmole) and TBDMSOTf (23 μL, 0.10 mmole) via micro-syringe. After stirring for 8 h at 0° C., the reaction mixture was diluted with dichloromethane and filtered through a pad of celite. The filtrate was then poured into a mixture of saturated aq. $Na_2S_2O_3$ and $NaHCO_3$. The aqueous layer was extracted with two portions of dichloromethane. The collected organic phases were then washed with brine, dried over $Mg_2SO_4$, filtered, and concentrated in vacuo. The residue was purified by silica gel column chromatography (1:4 to 1:2 ethylacetate/hexane) to give 26 as oil (0.173 g, 67%). 26: $R_f$=0.41 (Hexane:EtOAc=1:1); $^1H$ NMR (600 MHz, $CDCl_3$) δ 8.17 (d, J=7.6 Hz, 1H), 7.66 (t, J=7.4 Hz, 1H), 7.53 (t, J=7.7 Hz, 2H), 7.41-7.10 (m, 45H), 6.00 (d, J=10.0 Hz, 1H), 5.67 (s, 1H), 5.50-5.47 (m, 1H), 5.18-5.17 (m, 3H), 5.03 (dd, J=58.0, 11.5 Hz, 2H), 4.87-4.84 (m, 3H), 4.77 (d, J=11.9 Hz, 1H), 4.69-4.35 (m, 19H), 4.29-4.20 (m, 5H), 4.15-4.06 (m, 4H), 4.00 (dd, J=15.5, 7.4 Hz, 2H), 3.90-3.80 (m, 3H), 3.70-3.47 (m, 14H), 3.43-3.37 (m, 3H), 3.12 (d, J=44.8 Hz, 2H), 2.89 (s, 1H), 2.46-2.44 (m, 1H), 2.20-2.16 (m, 1H), 2.01 (s, 3H), 1.80 (s, 3H), 1.53-1.18 (m, 12H), 0.90 (s, 9H), 0.04 (s, 3H), 0.02 (s, 3H); $^{13}C$ NMR (150 MHz, $CDCl_3$) δ 170.4, 170.4, 166.8, 164.4, 159.5, 156.6, 156.0, 154.2, 153.4, 139.3, 138.8, 138.6, 138.0, 137.8, 137.8, 137.0, 136.8, 136.7, 133.7, 129.7, 129.2, 128.9, 128.5, 128.5, 128.4, 128.3, 128.3, 128.2, 128.0, 127.9, 127.9, 127.8, 127.8, 127.7, 127.7, 127.6, 127.5, 127.3, 127.2, 127.1, 126.6, 108.4, 103.7, 101.3, 100.3, 96.1, 95.3, 81.2, 79.3, 79.2, 76.7, 76.0, 75.3, 75.0, 74.9, 74.7, 74.4, 74.3, 74.1, 73.7, 73.4, 73.3, 73.2, 72.9, 72.4, 72.3, 71.1, 70.2, 69.7, 69.6, 69.4, 68.7, 68.3, 67.0, 65.9, 62.7, 62.3, 58.5, 58.1, 53.3, 53.2, 50.4, 50.1, 47.0, 46.0, 35.2, 29.2, 27.7, 27.3, 25.6, 24.5, 23.2, 20.7, 20.6, 17.8, −4.1, −4.9; HRMS (ESI-TOF, $MNa^+$) calculated for $C_{130}H_{152}Cl_6N_4O_{36}SiNa$ 2609.7983, found 2609.8115.

General Procedures for Deprotection of Oligosaccharide 5, 20, 22, and 24 to Give 27, 28, 29, and 30, Respectively.

LiOH (5.0 mmole, 50.0 eq) was added to a stirred solution of protected oligosaccharide (0.1 mmole, 1.00 eq) in 1,4-dioxane (5.00 mL) and $H_2O$ (5.00 mL) at room temperature. After stirring at 80° C. for 36 h, the reaction mixture was evaporated in vacuo. The residue was purified by reverse-phase column chromatography (Bond Elut-C18) to give the product residue. $NaHCO_3$ (5.0 mmole, 50.0 eq) and acetic anhydride (5.0 mmole, 50.0 eq) were added to a stirred solution of the above residue in $H_2O$ (3.00 mL) at room temperature. After stirring at the same temperature for 1 h, $NaHCO_3$ (5.0 mmole, 50.0 eq) and acetic anhydride (5.0 mmole, 50.0 eq) were added into the reaction mixture at room temperature. After stirring at the same temperature for 1 h, LiOH (5.0 mmole, 50.0 eq) was added into the reaction mixture. After stirring at the same temperature for 12 h, the reaction mixture was evaporated in vacuo. The residue was purified by reverse-phase column chromatography (Bond Elut-C18). $Pd(OH)_2$ (1 mmole) was added to a stirred solution of the above residue in methanol (2.00 mL) and $H_2O$ (2.00 mL). The reaction mixture was hydrogenolyzed for 12 h under $H_2$ gas atmosphere. The reaction mixture was filtered, and the filtrate was evaporated in vacuo. The residue was purified by reverse-phase column chromatography (Bond Elut-C18) to give deprotected oligosaccharide.

27

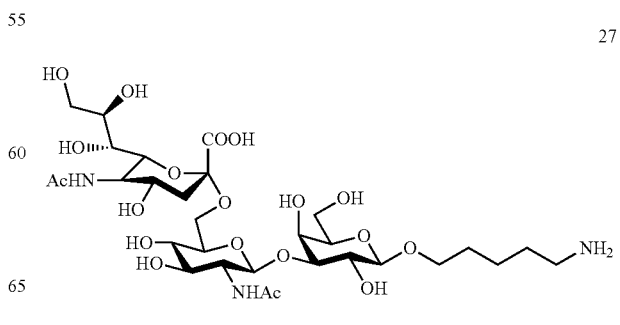

(2R,4S,5R,6R)-5-acetamido-2-(((2R,3S,4R,5R,6S)-
5-acetamido-6-((2R,3R,4S,5S,6R)-2-(5-aminopenty-
loxy)-3,5-dihydroxy-6-(hydroxymethyl)tetrahydro-
2H-pyran-4-yloxy)-3,4-dihydroxytetrahydro-2H-
pyran-2-yl)methoxy)-4-hydroxy-6-((1R,2R)-1,2,3-
trihydroxypropyl)tetrahydro-2H-pyran-2-carboxylic
acid (27)

Compound 27 (19 mg, 0.025 mmole, 23%) was prepared according to the general procedure for the deprotection of oligosaccharide from trisaccharide 5 (0.18 g, 0.109 mmole). $^1$H NMR (600 MHz, D$_2$O) δ 4.55 (d, J=8.4 Hz, 1H), 4.26 (d, J=7.9 Hz, 1H), 4.04 (d, J=3.2 Hz, 1H), 3.86-3.39 (m, 20H), 2.64-2.59 (m, 3H), 1.92 (s, 3H), 1.91 (s, 3H), 1.59 (t, J=12.2 Hz, 1H), 1.55-1.50 (m, 2H), 1.43-1.38 (m, 2H), 1.31-1.26 (m, 2H); $^{13}$C NMR (150 MHz, D$_2$O) δ 175.0, 174.9, 173.3, 102.7, 102.7, 100.0, 82.5, 74.7, 74.0, 73.4, 72.4, 71.6, 70.2, 69.6, 69.5, 68.2, 68.1, 68.1, 62.7, 62.5, 60.9, 55.5, 51.8, 40.0, 29.8, 28.3, 22.2, 22.1, 21.9; HRMS (ESI-TOF, MH$^+$) calculated for C$_{30}$H$_{53}$N$_3$O$_{19}$H 760.3346, found 760.3363.

28

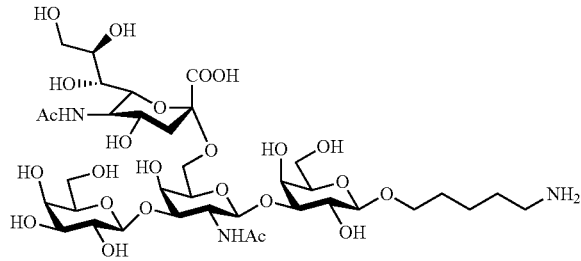

(2R,4S,5R,6R)-5-acetamido-2-(((2R,3S,4R,5R,6S)-
5-acetamido-6-((2R,3R,4S,5S,6R)-2-(5-aminopenty-
loxy)-3,5-dihydroxy-6-(hydroxymethyl)tetrahydro-
2H-pyran-4-yloxy)-3-hydroxy-4-((2R,3R,4S,5R,6R)-
3,4,5-trihydroxy-6-(hydroxymethyl)tetrahydro-2H-
pyran-2-yloxy)tetrahydro-2H-pyran-2-yl)methoxy)-
4-hydroxy-6-((1R,2R)-1,2,3-trihydroxypropyl)
tetrahydro-2H-pyran-2-carboxylic acid (28)

Compound 28 (46 mg, 0.050 mmole, 20%) was prepared according to the general procedure for the deprotection of oligosaccharide from tetrasaccharide 20 (0.46 g, 0.249 mmole). $^1$H NMR (600 MHz, D$_2$O) δ 4.70 (d, J=8.4 Hz, 1H), 4.43 (d, J=7.5 Hz, 1H), 4.37 (d, J=8.3 Hz, 1H), 4.16 (d, J=3.3 Hz, 1H), 3.98-3.50 (m, 26H), 3.00 (t, J=7.5 Hz, 2H), 2.73 (dd, J=12.3, 4.5 Hz, 1H), 2.02 (s, 3H), 2.01 (s, 3H), 1.71-1.63 (m, 5H), 1.48-1.43 (m, 2H); $^{13}$C NMR (150 MHz, D$_2$O) δ 174.9, 174.8, 173.3, 103.3, 102.7, 102.4, 100.1, 82.5, 81.6, 75.2, 74.7, 73.6, 72.4, 71.6, 70.6, 69.8, 69.6, 68.5, 68.3, 68.2, 68.1, 68.0, 62.8, 62.5, 60.9, 54.7, 51.7, 40.0, 39.3, 28.1, 26.3, 22.1, 22.0, 21.9; HRMS (ESI-TOF, MH$^+$) calculated for C$_{36}$H$_{63}$N$_3$O$_{24}$H 922.3874, found 922.3988.

29

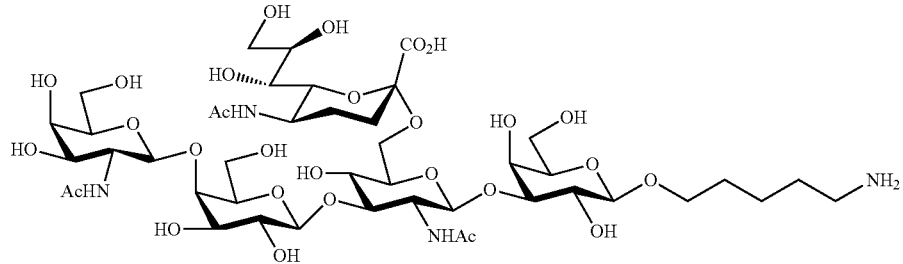

(2R,4S,5R,6R)-5-acetamido-2-(((2R,3S,4R,5R,6S)-
5-acetamido-4-((2R,3R,4R,5R,6R)-5-((2S,4R,5R,
6R)-3-acetamido-4,5-dihydroxy-6-(hydroxymethyl)
tetrahydro-2H-pyran-2-yloxy)-3,4-dihydroxy-6-
(hydroxymethyl)tetrahydro-2H-pyran-2-yloxy)-6-
((2R,3R,4S,5S,6R)-2-(5-aminopentyloxy)-3,5-
dihydroxy-6-(hydroxymethyl)tetrahydro-2H-pyran-
4-yloxy)-3-hydroxytetrahydro-2H-pyran-2-yl)
methoxy)-4-hydroxy-6-((1R,2R)-1,2,3-
trihydroxypropyl)tetrahydro-2H-pyran-2-carboxylic
acid (29)

Compound 29 (23 mg, 0.020 mmole, 16%) was prepared according to the general procedure for the deprotection of oligosaccharide from pentasaccharide 22 (0.33 g, 0.126 mmole). $^1$H NMR (600 MHz, D$_2$O) δ 4.69 (d, J=8.4 Hz, 1H), 4.62 (d, J=8.1 Hz, 1H), 4.43 (d, J=7.6 Hz, 1H), 4.37 (d, J=7.7 Hz, 1H), 4.16 (d, J=3.4 Hz, 1H), 4.07 (d, J=2.9 Hz, 1H), 3.97-3.52 (m, 30H), 3.40-3.37 (m, 1H), 2.99 (t, J=7.5 Hz, 2H), 2.73 (dd, J=12.4, 4.6 Hz, 1H), 2.04-2.00 (m, 9H), 1.71-1.63 (m, 5H), 1.48-1.43 (m, 2H); $^{13}$C NMR (151 MHz, D$_2$O) δ 174.9 174.8 173.3 103.0 102.7 102.5 102.4 100.1 82.5 81.1 75.9 74.7 74.7 74.2 73.6 72.4 72.3 71.6 70.8 70.6 69.8 69.6 68.2 68.1 68.1 68.0 67.7 62.8 62.5 61.0 60.5 54.7 52.6 51.7 40.0 39.3 28.1 26.3 22.3 22.2 22.0 21.9; HRMS (ESI-TOF, MH$^+$) calculated for C$_{44}$H$_{76}$N$_4$O$_{29}$H 1125.4668, found 1125.4872.

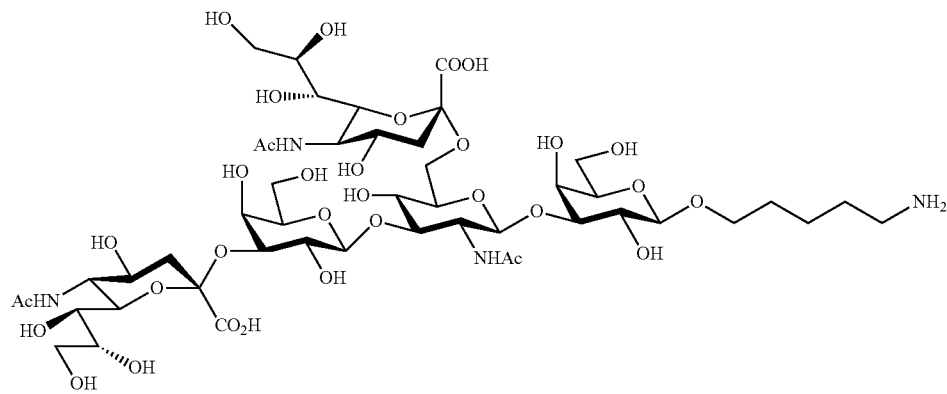

30

(2R,4S,5R,6R)-5-acetamido-2-(((2R,3S,4R,5R,6S)-5-acetamido-4-((2R,3R,4S,5S,6R)-4-((2S,4R,5R,6S)-5-acetamido-2-carboxy-4-hydroxy-6-((1S,2S)-1,2,3-trihydroxypropyl)tetrahydro-2H-pyran-2-yloxy)-3,5-dihydroxy-6-(hydroxymethyl)tetrahydro-2H-pyran-2-yloxy)-6-((2R,3R,4S,5S,6R)-2-(5-aminopentyloxy)-3,5-dihydroxy-6-(hydroxymethyptetrahydro-2H-pyran-4-yloxy)-3-hydroxytetrahydro-2H-pyran-2-yl)methoxy)-4-hydroxy-6-((1R,2R)-1,2,3-trihydroxypropyl)tetrahydro-2H-pyran-2-carboxylic acid (30)

Compound 30 (28 mg, 0.023 mmole, 32%) was prepared according to the general procedure for the deprotection of oligosaccharide from pentasaccharide 24 (0.18 g, 0.073 mmole). $^1$H NMR (600 MHz, D$_2$O) δ 4.70 (d, J=8.6 Hz, 1H), 4.48 (d, J=7.8 Hz, 1H), 4.37 (d, J=7.9 Hz, 1H), 4.15 (d, J=3.2 Hz, 1H), 4.06 (dd, J=9.8, 3.0 Hz, 1H), 3.96-3.50 (m, 32H), 2.99 (t, J=7.5 Hz, 2H), 2.75-2.71 (m, 2H), 2.01-2.00 (m, 9H), 1.76 (t, J=12.1 Hz, 1H), 1.70-1.63 (m, 5H), 1.47-1.42 (m, 2H); $^{13}$C NMR (150 MHz, D$_2$O) δ 174.9, 174.9, 174.8, 173.8, 173.3, 103.3, 102.6, 102.3, 100.1, 99.5, 82.4, 81.8, 75.5, 75.0, 74.7, 73.6, 72.7, 72.4, 71.7, 71.6, 69.8, 69.6, 69.0, 68.3, 68.2, 68.1, 68.0, 67.9, 67.1, 62.8, 62.5, 62.3, 60.9, 54.6, 51.7, 51.5, 40.0, 39.7, 37.2, 30.1, 28.0, 26.3, 22.2, 22.0, 21.9; HRMS (ESI-TOF, MNa$^+$) calculated for C$_{47}$H$_{80}$N$_4$O$_{32}$Na 1235.4648, found 1235.4697.

General Procedures for Deprotection of Oligosaccharide 26, and 2 to Give 31, and 1, Respectively.

LiOH (5.0 mmole, 50.0 eq) was added to a stirred solution of protected oligosaccharide (0.1 mmole, 1.00 eq) in 1,4-dioxane (5.0 mL) and H$_2$O (5.0 mL) at room temperature. After stirring at 95° C. for 36 h, the reaction mixture was evaporated in vacuo. The residue was purified by reverse-phase column chromatography (Bond Elut-C18) to give the product residue. A solution of the above residue in pyridine (10.0 mmole, 100.0 eq) and acetic anhydride (10.0 mmole, 100.0 eq) was stirred at room temperature for 14 h. The resulting solution was concentrated and co-evaporated with toluene twice. Purification of the residue by silica gel chromatography (1:11 to 1:2 MeOH:DCM) provided the product residue. A resulting residue was dissolved in Acetonitrile (1 mL), and BF$_3$—OEt$_2$ (2.5 mmole, 25.0 eq) and one drop of water were added at 0° C. After stirring for 4 h at same temperature, the reaction mixture was allowed to warm gradually to room temperature and stirred for 2 h continually at room temperature. The NaHCO$_3$(aq) was poured into the solution and the solution was extracted by DCM four times and concentrated under reduced vacuum. The residue was purified by flash column chromatography (1:9 to 1:2 MeOH:DCM) to give the product residue. A solution of resulting residue and LiOH (5.0 mmole, 50.0 eq) in 1,4-Dioxane (1.0 mL) and H$_2$O (1.0 mL) was stirred for 12 h at room temperature. The reaction mixture was evaporated in vacuo and the residue was purified by reverse-phase column chromatography (Bond Elut-C18). Pd(OH)$_2$ (1 mmole) was added to a stirred solution of the above residue in methanol (2.00 mL) and H$_2$O (2.0 mL). The reaction mixture was hydrogenolyzed for 18 h under H$_2$ gas atmosphere. The reaction mixture was filtered, and the filtrate was evaporated in vacuo. The residue was purified by reverse-phase column chromatography (Bond Elut-C18) to give deprotected oligosaccharide.

31

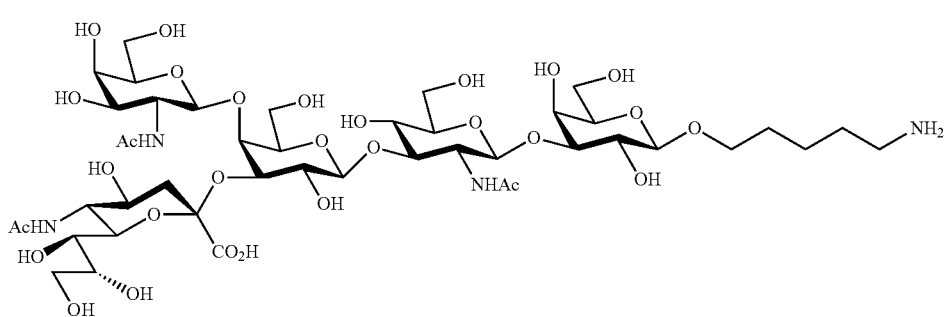

(2R,4R,5S,6S)-5-acetamido-2-((2R,3R,4R,5S,6R)-2-((2S,3R,4R,5S,6R)-3-acetamido-2-((2R,3R,4S,5S,6R)-2-(5-aminopentyloxy)-3,5-dihydroxy-6-(hydroxymethyl)tetrahydro-2H-pyran-4-yloxy)-5-hydroxy-6-(hydroxymethyl)tetrahydro-2H-pyran-4-yloxy)-5-((2S,4R,5R,6R)-3-acetamido-4,5-dihydroxy-6-(hydroxymethyl)tetrahydro-2H-pyran-2-yloxy)-3-hydroxy-6-(hydroxymethyl)tetrahydro-2H-pyran-4-yloxy)-4-hydroxy-6-((1R,2R)-1,2,3-trihydroxypropyl)tetrahydro-2H-pyran-2-carboxylic acid (31)

Compound 31 (12 mg, 0.011 mmole, 13%) was prepared according to the general procedure for the deprotection of oligosaccharide from pentasaccharide 26 (0.22 g, 0.085 mmole). $^1$H NMR (600 MHz, D$_2$O) δ 4.73-4.70 (m, 2H), 4.51 (d, J=8.0 Hz, 1H), 4.37 (d, J=8.0 Hz, 1H), 4.13-4.08 (m, 3H), 3.94-3.44 (m, 29H), 3.36-3.33 (m, 1H), 2.98 (t, J=7.4 Hz, 2H), 2.66 (dd, J=12.7, 4.7 Hz, 1H), 2.02-2.01 (m, 9H), 1.90 (t, J=12.0 Hz, 1H), 1.70-1.63 (m, 4H), 1.47-1.42 (m, 2H); $^{13}$C NMR (150 MHz, D$_2$O) δ 174.9, 174.8, 174.8, 174.0, 102.8, 102.7, 102.6, 102.3, 101.3, 82.2, 81.9, 76.7, 75.1, 74.6, 74.4, 73.9, 72.9, 72.2, 71.1, 69.9, 69.6, 69.5, 68.6, 68.3, 68.2, 67.9, 67.6, 62.7, 61.0, 60.8, 60.4, 54.5, 52.2, 51.5, 39.3, 37.1, 28.1, 26.4, 26.4, 26.4, 22.5, 22.2, 22.0, 21.9; HRMS (ESI-TOF, MH$^+$) calculated for C$_{44}$H$_{76}$N$_4$O$_{29}$H 1125.4668, found 1125.4471.

3.37 (t, J=9 Hz, 1H), 3.03 (t, J=7.5 Hz, 2H), 2.76 (dd, J=12.4, 4.5 Hz, 1H), 2.69 (dd, J=12.8, 4.5 Hz, 1H), 2.05-2.04 (m, 12H), 1.93 (t, J=12 Hz, 1H), 1.74-1.66 (m, 5H), 1.51-1.46 (m, 2H); $^{13}$C NMR (150 MHz, D$_2$O) δ 174.9, 174.8, 174.0, 173.4, 102.9, 102.6, 102.4, 101.3, 100.1, 82.5, 81.7, 76.7, 74.7, 74.6, 74.4, 74.0, 73.6, 72.9, 72.4, 72.2, 71.6, 71.1, 69.8, 69.6, 69.5, 68.6, 68.3, 68.3, 68.2, 68.1, 67.9, 67.7, 62.9, 62.7, 62.5, 61.1, 61.0, 60.4, 54.5, 52.3, 51.8, 51.5, 40.0, 39.3, 37.1, 28.1, 26.3, 22.5, 22.3, 22.0, 21.9; HRMS (ESI-TOF, MH$^+$) calculated for C$_{55}$H$_{94}$N$_5$O$_{37}$ 1416.5622, found 1416.6175.

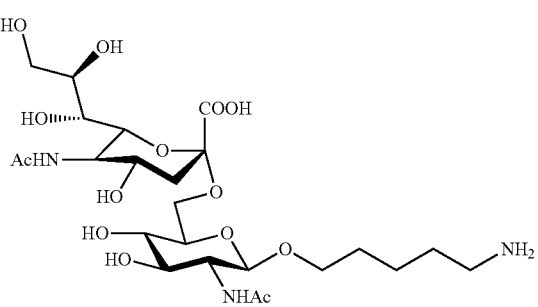

33

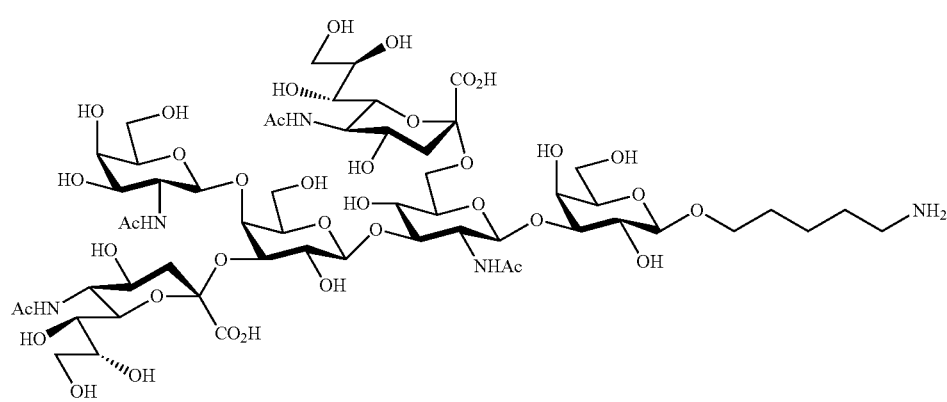

1

(2R,4R,5S,6S)-5-acetamido-2-((2R,3S,4R,5R,6R)-3-((2S,3R,4R,5R,6R)-3-acetamido-4,5-dihydroxy-6-(hydroxymethyl)tetrahydro-2H-pyran-2-yloxy)-6-((2S,3R,4R,5S,6R)-3-acetamido-6-(((2R,4S,5R,6R)-5-acetamido-2-carboxy-4-hydroxy-6-((1R,2R)-1,2,3-trihydroxypropyl)tetrahydro-2H-pyran-2-yloxy)methyl)-2-((2R,3R,4S,5S,6R)-2-(5-aminopentyloxy)-3,5-dihydroxy-6-(hydroxymethyl)tetrahydro-2H-pyran-4-yloxy)-5-hydroxytetrahydro-2H-pyran-4-yloxy)-5-hydroxy-2-(hydroxymethyl)tetrahydro-2H-pyran-4-yloxy)-4-hydroxy-6-((1R,2R)-1,2,3-trihydroxypropyl)tetrahydro-2H-pyran-2-carboxylic acid (1)

Compound 1 (53 mg, 0.037 mmole, 16%) was prepared according to the general procedure for the deprotection of oligosaccharide from hexasaccharide 2 (0.70 g, 0.234 mmole). $^1$H NMR (600 MHz, D$_2$O) δ 4.73 (d, J=8.4, 8.22 Hz, 2H), 4.54 (d, J=7.9 Hz, 1H), 4.40 (d, J=7.98 Hz, 1H), 4.18-4.11 (m, 3H), 3.99-3.55 (m, 37H), 3.52-3.50 (m, 1H),

(2R,4S,5R,6R)-5-acetamido-2-(((2R,3S,4R,5R,6R)-5-acetamido-6-(5-aminopentyloxy)-3,4-dihydroxytetrahydro-2H-pyran-2-yl)methoxy)-4-hydroxy-6-((1R,2R)-1,2,3-trihydroxypropyl)tetrahydro-2H-pyran-2-carboxylic acid (33)

$^1$H NMR (600 MHz, D$_2$O) δ 4.496 (d, J=8.5 Hz, 1H), 3.96 (dd, J=10.7, 5.3 Hz, 1H), 3.90-3.86 (m, 3H), 3.83 (t, J=10.1 Hz, 1H), 3.75 (d, J=9.7 Hz, 1H), 3.72-3.59 (m, 6H), 3.54-3.48 (m, 3H), 3.03-2.97 (t, J=7.6 Hz, 2H), 2.75 (dd, J=12.5, 4.7 Hz, 1H), 2.04 (s, 3H), 2.04 (s, 3H), 1.74-1.66 (m, 3H), 1.63-1.58 (m, 2H), 1.45-1.37 (m, 2H); $^{13}$C NMR (150 MHz, D$_2$O) δ 175.0, 174.4, 173.4, 101.3, 100.1, 74.2, 73.6, 72.5, 71.7, 70.2, 69.7, 68.2, 68.1, 62.8, 62.6, 55.5, 51.8, 40.1, 39.3, 28.1, 26.3, 22.1, 22.0; HRMS (ESI-TOF, MH$^+$) calculated for C$_{24}$H$_{43}$N$_3$O$_{14}$ 598.2818, found 598.2805.

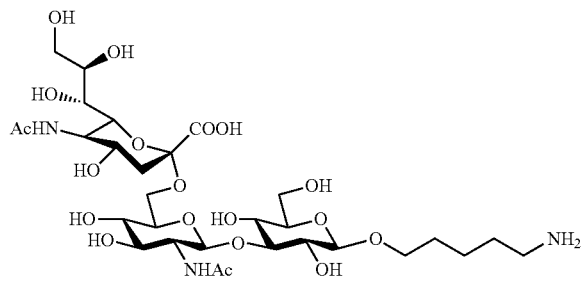

(2R,4S,5R,6R)-5-acetamido-2-(a2R,3S,4R,5R,6S)-5-acetamido-6-((2R,3R,4S,5R,6R)-2-(5-aminopentyloxy)-3,5-dihydroxy-6-(hydroxymethyl)tetrahydro-2H-pyran-4-yloxy)-3,4-dihydroxytetrahydro-2H-pyran-2-yl)methoxy)-4-hydroxy-6-((1R,2R)-1,2,3-trihydroxypropyl)tetrahydro-2H-pyran-2-carboxylic acid (34)

$^1$H NMR (600 MHz, D$_2$O) δ 4.66 (d, J=8.5 Hz, 1H), 4.43 (d, J=8.1 Hz, 1H), 3.96-3.85 (m, 5H), 3.83 (t, J=10.1 Hz, 1H), 3.77-3.72 (m, 3H), 3.71-3.62 (m, 4H), 3.60-3.54 (m, 4H), 3.50-3.44 (m, 3H), 3.31 (t, J=8.6 Hz, 1H), 3.00 (t, J=7.5 Hz, 2H), 2.72 (dd, J=12.4, 4.7 Hz, 1H), 2.04 (s, 3H), 2.03 (s, 3H), 1.75-1.64 (m, 5H), 1.49-1.42 (m, 2H); $^{13}$C NMR (150 MHz, D$_2$O) δ 174.9, 174.7, 173.4, 102.2, 102.1, 100.0, 86.1, 75.3, 74.2, 73.4, 72.4, 72.3, 71.7, 70.0, 69.9, 68.5, 68.2, 68.2, 63.1, 62.5, 60.8, 55.5, 51.8, 40.0, 39.3, 28.1, 28.4, 22.1, 22.0; HRMS (ESI-TOF, MNa$^+$) calculated for C$_{30}$H$_{53}$N$_3$O$_{19}$Na 7823165, found 782.3174.

(2R,4R,5S,6S)-5-acetamido-2-((2R,3S,4R,5R,6R)-3-((2S,4R,5R,6R)-3-acetamido-4,5-dihydroxy-6-(hydroxymethyl)tetrahydro-2H-pyran-2-yloxy)-6-((2S,3R,4R,5S,6R)-3-acetamido-6-(((2R,4S,5R,6R)-5-acetamido-2-carboxy-4-hydroxy-6-((1R,2R)-1,2,3-trihydroxypropyl)tetrahydro-2H-pyran-2-yloxy)methyl)-2-((2R,3S,4S,5R,6R)-3,5-dihydroxy-2-(hydroxymethyl)-6-(5-(3-mercaptopropanamido)pentyloxy)tetrahydro-2H-pyran-4-yloxy)-5-hydroxytetrahydro-2H-pyran-4-yloxy)-5-hydroxy-2-(hydroxymethyl)tetrahydro-2H-pyran-4-yloxy)-4-hydroxy-6-((1R,2R)-1,2,3-trihydroxypropyl)tetrahydro-2H-pyran-2-carboxylic acid (32)

DTSSP (8.6 mg, 0.0141 mmole) was added to a solution of free amine 1 (1.0 mg, 0.007 mmole) in 0.1 M phosphate buffer (3.0 mL), pH 7.4. Then the solution was stirred overnight. The reaction mixture was warmed to 40° C., followed by addition of DTT (9.5 mg, 0.0615 mmole). After stirring for 1.5 h at the same temperature, the reaction mixture was concentrated in vacuo, and the residue was purified by LH-20 column to afford a white solid 32 (8.2 mg, 78%). $^1$H NMR (600 MHz, D$_2$O) δ 4.75-4.73 (m, 2H), 4.55 (d, J=8.1 Hz, 1H), 4.40 (d, J=8.0 Hz, 1H), 4.17-4.11 (m, 3H), 4.01 (dd, J=10.9, 5.4 Hz, 1H), 3.95-3.52 (m, 36H), 3.38 (dd, J=9.6, 8.0 Hz, 1H), 3.24 (t, J=6.8 Hz, 2H), 2.80 (t, J=6.7 Hz, 2H), 2.76 (dd, J=12.5, 4.6 Hz, 1H), 2.70 (dd, J=12.6, 4.6 Hz, 1H), 2.56 (t, J=6.7 Hz, 3H), 2.06 (s, 3H), 2.06 (s, 3H), 2.05 (s, 3H), 2.04 (s, 3H), 1.95 (t, J=12.1 Hz, 1H), 1.77 (t, J=12.2 Hz, 1H), 1.68-1.64 (m, 2H), 1.59-1.55 (m, 2H), 1.47-1.36 (m, 3H); $^{13}$C NMR (150 MHz, D$_2$O) δ 174.9, 174.8, 174.1, 174.0, 173.4, 102.9, 102.7, 102.6, 102.5, 101.4, 100.2, 82.5, 81.7, 76.8, 74.7, 74.6, 74.4, 74.0, 73.7, 72.9, 72.4, 72.2, 71.6, 71.2, 70.2, 69.7, 69.6, 68.6, 68.3, 68.2, 68.1, 67.9, 67.7, 64.6, 62.9, 62.7, 62.5, 61.1, 61.0, 60.4, 54.6, 52.3, 51.8, 51.5, 40.0, 39.3, 39.2, 37.1, 28.3, 27.9, 22.5, 22.4, 22.3, 22.0, 19.9; HRMS (ESI-TOF, MNa$^+$) calculated for C$_{58}$H$_{97}$N$_5$O$_{38}$SNa 1526.5424, found 1526.5442.

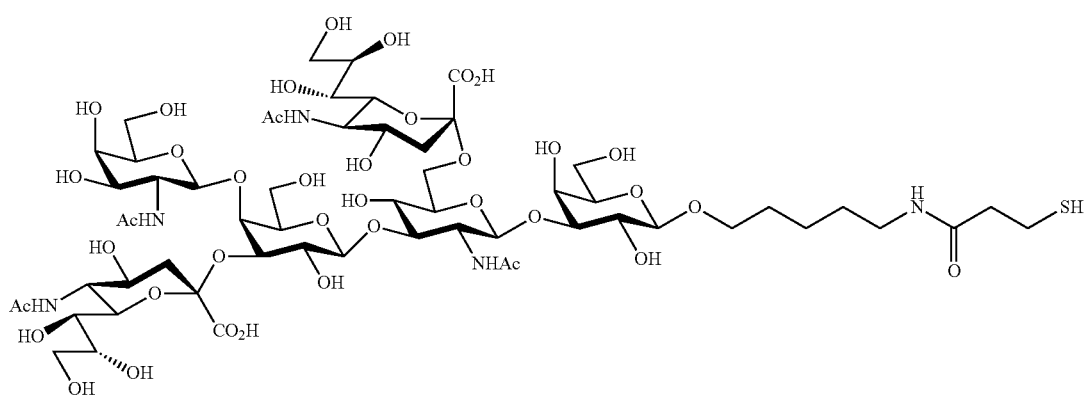

Biological Assays

Figure 11:
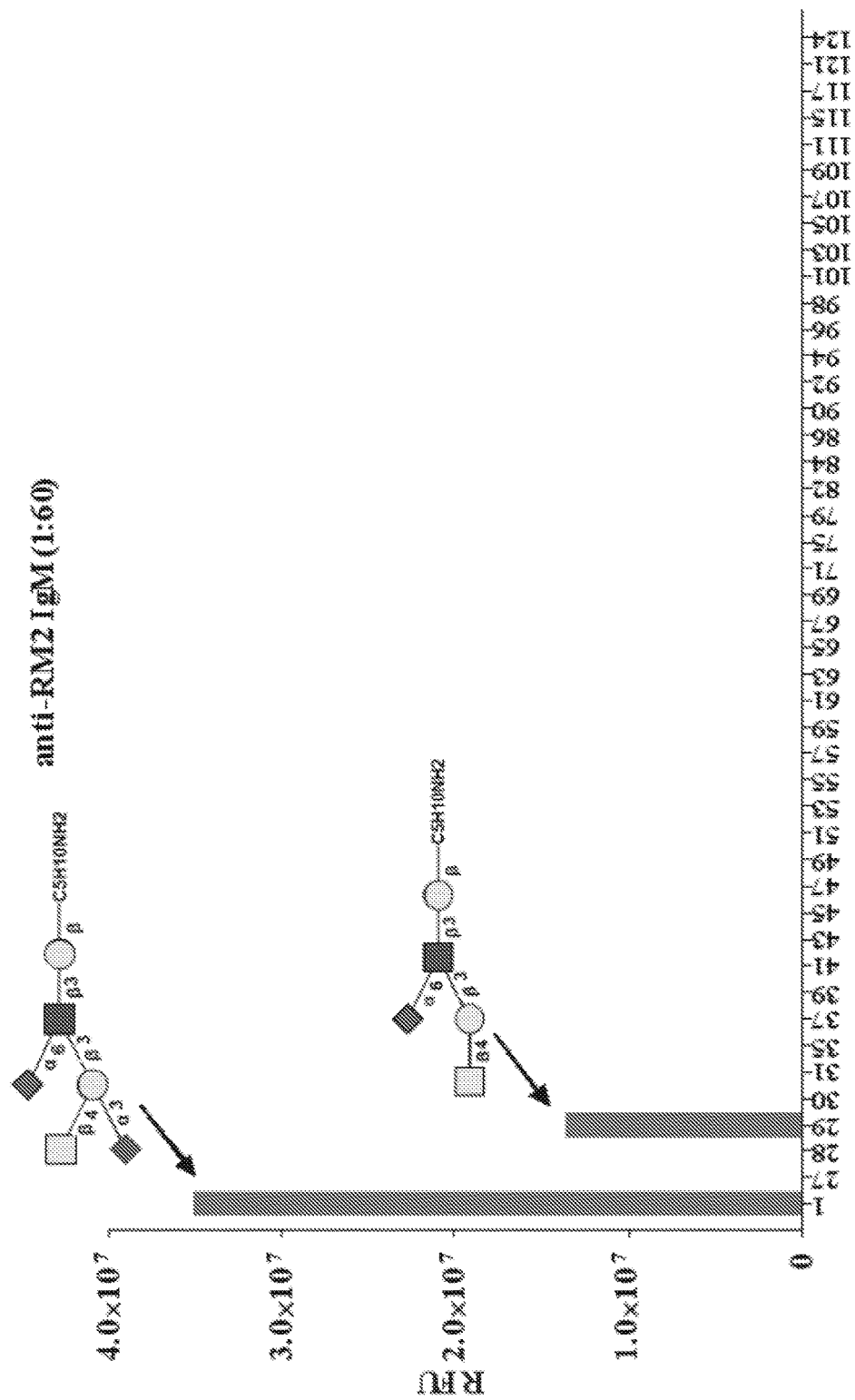
FIG. 11 shows binding specificity of monoclonal antibodies RM2 to RM2 antigen and its fragments.
Figure 20:
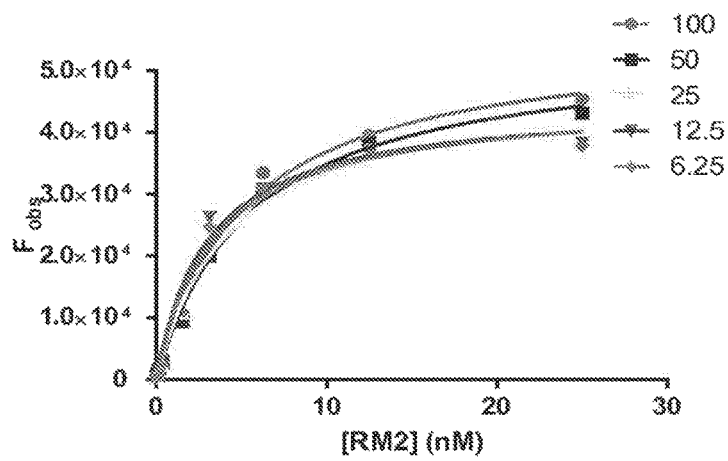
FIG. 20 shows binding curves for RM2 printed at different concentrations (100, 50, 25, 12.5, and 6.25 µM) are shown. The curves were obtained by using Cy3-labeled goat anti-mouse IgM secondary antibody.
Figure 21:
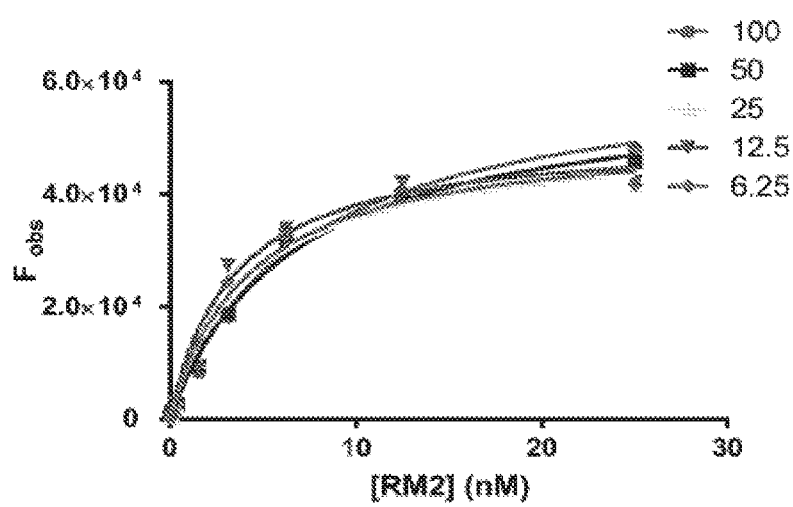
FIG. 21 shows binding curve for RM2 antibody for 29 printed at different concentrations.

An expanded glycan array containing the synthesized hexasaccharide 1 and its analogs along with the other ninety glycans are incorporated to a glycan array for testing (Figure S4). All glycans were directly immobilized onto NHS-coated glass slides by taking an aliquot from a stock solution of sugar at a fixed concentration (100 µM). The assay involved an initial treatment with RM2 (a mouse IgM anti-RM2 monoclonal antibody, a kind gift from Prof. Saito), followed by incubation with a fluorescein-tagged anti mouse IgM secondary antibody against its primary antibody. After one hour incubation, the slides were washed with ddH$_2$O twice and scanned to show the binding specificity of the antibody to printed oligosaccharides. The resulted images showed that monoclonal RM2 antibody recognize hexasaccharide 1 specifically, indicating that the synthetic hexasaccharide 1 contains the same antigenic epitope with which RM2 antibody reacts on prostate cancer cells (FIG. 11). It indicates that synthesized hexasaccharide 1 is the RM2 antigen. To determine the dissociation the dissociation constants of RM2 and truncated analogs on the surface interacting with the antibody in a multivalent manner, the direct measurement method was experimented (Liang, P. H.; Wang, S. K.; Wong, C. H. J. Am. Chem. Soc. 2007, 129, 11177), using different concentrations of antibodies and printed sugars. The results showed that when the printing concentration is below 6.25 µM, the average distance between printed sugars is too far to have enough multivalent effect with antibody RM2. At the printing concentrations from 100 µM to 6.25 µM, however, it was observed that the $K_{D,surf}$ values measured were narrowly distributed from the individual curves (FIG. 20 and Table 1). Using the same method, the $K_{D,surf}$ values were determined for the truncated RM2 analog 29 interacting with the antibody (FIG. 21 and Table S2). Overall, the relative binding specificity of RM2 for the epitopes was RM2>pentasaccharide 29 (Table 1).

TABLE 1

$K_{D,surf}$ (nM) values of different antibodies and different RM2 analogs.

| | $K_{D,surf}$ (nM) ± SD(nM) | |
|---|---|---|
| Antibody | RM2 (1) | Pentasaccharide 29 |
| RM2 | 4.545 ± 0.903 | 5.756 ± 1.140 |

Figure 12:
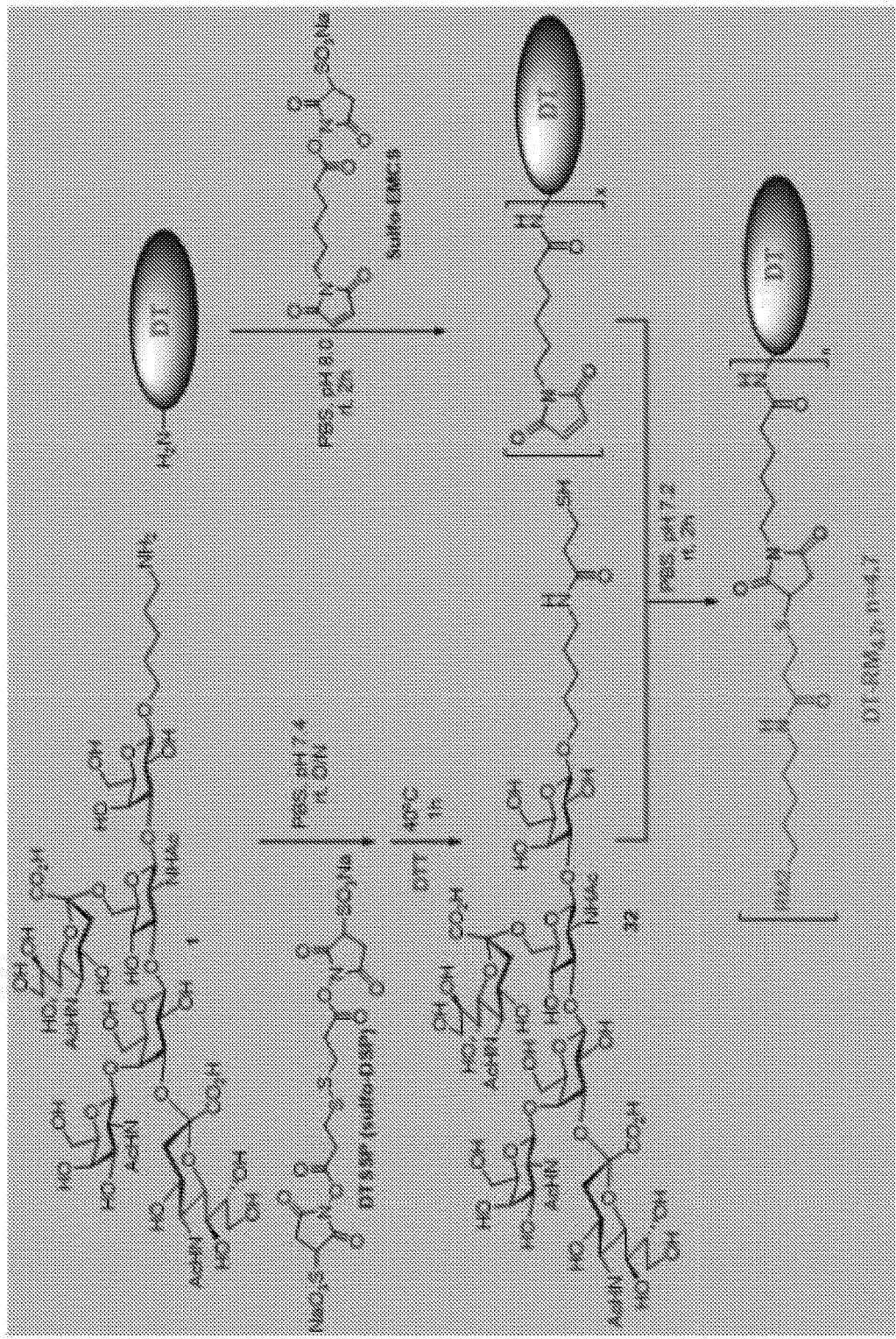
FIG. 12 shows the scheme for producing synthetic candidate carbohydrate-based vaccine.

Preparation of DT-RM$_{4.7}$ as a Vaccine Candidate with Glycolipid C34 as Adjuvant To develop a general protocol (Huang et al., Proc. Natl. Acad. Sci. U.S.A. 2013, 110, 2517) for carbohydrate-carrier protein conjugation (FIG. 12 and Table 4), the thiol-maleimide coupling method is adopted. The amine group of the hexasaccharide 1 was reacted with 2 equiv. of 3,3'-Dithiobis(sulfo-succinimidylpropionate) (DTSSP) and an amine-reactive N-hydroxysulfosuccinimide (sulfo-NHS) ester at each end of an 8-carbon spacer arm in pH 7.4 phosphate buffer at room temperature for 8 h to afford the corresponding half ester. Next, the disulfide bond was cleaved in the presence of dithiothreitol (DTT) at 40° C. for 2 h to obtain the free thio product 32 as Michael donors in 78% yield after purification on a size exclusion column LH-20. Furthermore, in order to generate the thio active maleimide group on the protein, CRM197 was reacted with an excess of N-(ε-Maleimidocaproyloxy)sulfosuccinimide ester (Sulfo-EMCS) in pH 7.0 phosphate buffer for 2 h. The number of maleimide-linker on the protein was determined by MALDI-TOF mass spectrometer. In average, 12.85 molecules of maleimide linkers were coupled on each molecule of diphtheria toxin mutant CRM197. Finally, for protein conjugation, the purified thiolated hexasaccharide 32 was incubated with the derivatized protein in pH 7.2 phosphate buffer for 2 h at room temperature to obtain the RM2 antigen-CRM197 glycoconjugate which was shown to contain 4.7 molecules of RM2 antigen per molecule of CRM197 (DT-RM$_{4.7}$) (Table 4. To study the effect of adjuvant on Ab response, groups of BALB/c mice were immunized intramuscularly with 2 µg of DT-RM$_{4.7}$ in combination with 2 µg of C1, C34, or Alu. Three vaccinations were given at two-week intervals. Two weeks after the third injection, sera were collected and subsequently tested with the previously mentioned glycan microarray (96 glycans) (FIGS. 24A thru 24I) to estimate the level and diversity of anti-RM2 related antibody. The results showed that mouse anti-RM2 IgG titers increased as vaccination proceeded and peaked after the third vaccination. Among the DT-RM$_{4.7}$ vaccinated groups, it was found that DT-RM$_{4.7}$/C34 induced higher levels of anti-RM2 IgG titers than DT-RM$_{4.7}$/C1 and DT-RM$_{4.7}$/Alu after dilution to 12,000-fold (FIG. 13).

Search for the Best Epitope Ratio of DT-RM Vaccine Adjuvanted with C34

Figure 13:
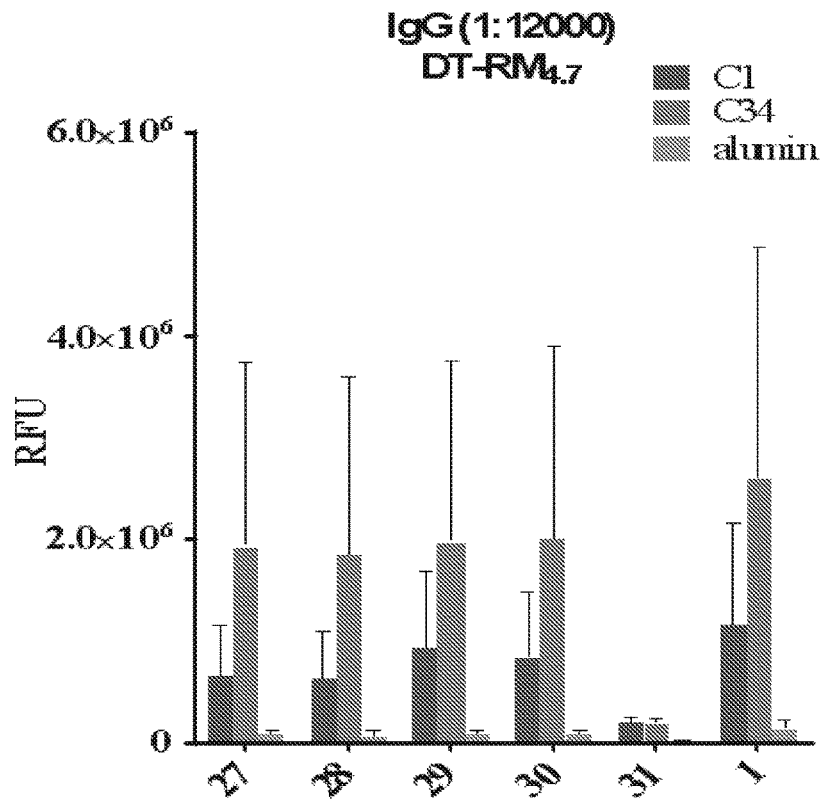
FIG. 13 shows female BALB/c mice were immunized with 2 µg of RM2 antigen of DT-RM4.7 in combination with 2 µg of C1, C34, or Alu. Mouse serum was collected two weeks after the final immunization, and the production of IgG against RM2 antigen and its truncated analogs after dilution to 12,000-fold. Data represent as total fluorescence intensity of five mice±the SEM.
Figure 13:
Figure 13:
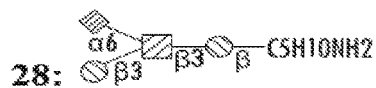
Figure 13:
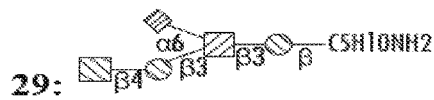
Figure 13:
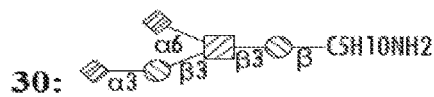
Figure 13:
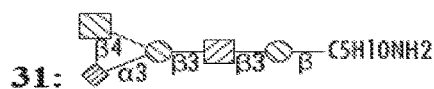
Figure 13:
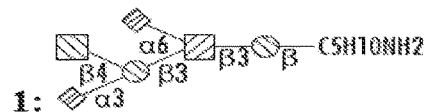
Figure 14:
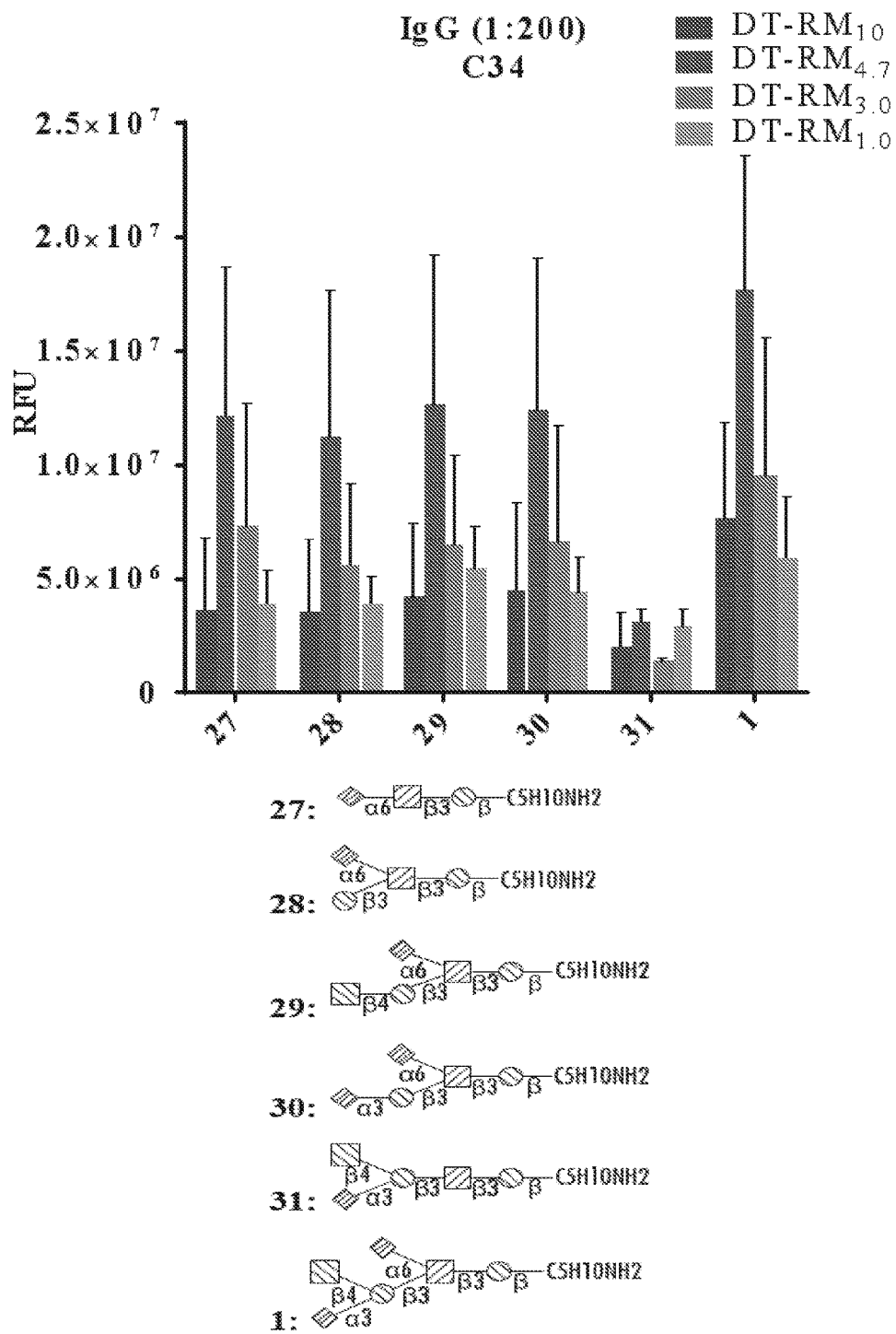
FIG. 14 shows the induced IgG titers against RM2 antigen and glycan binding profile of IgG collected from different epitope ratios of DT-RM/C34-immunized mice.
Figure 22A:
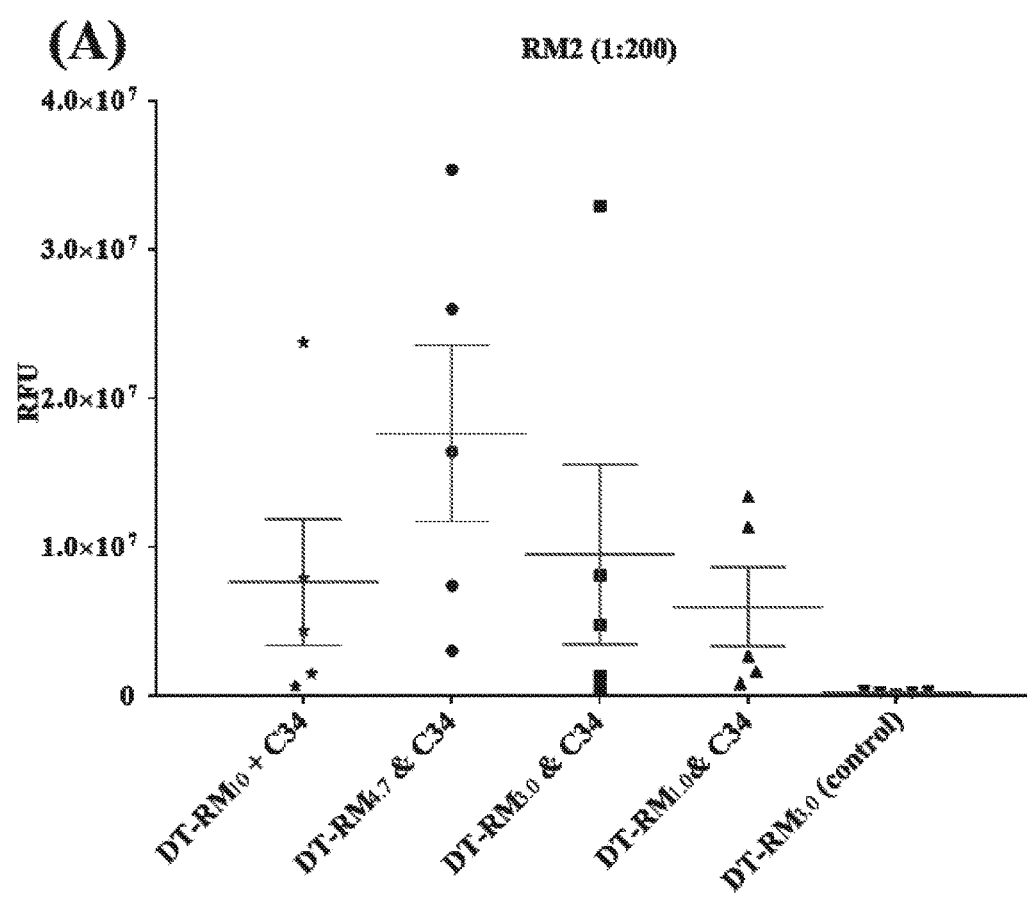
FIG. 22 shows serum IgG antibodies and IgM antibodies response against RM2 in immunized mice with different epitope ratio of DT-RM/C34. (A) 200-fold dilution of IgG antibodies. (B) 800-fold dilution of IgG antibodies. (C) 4,000-fold dilution of IgG antibodies. (D) 12000-fold dilution of IgG antibodies. (E) 60-fold dilution of IgM antibodies.
Figure 22B:
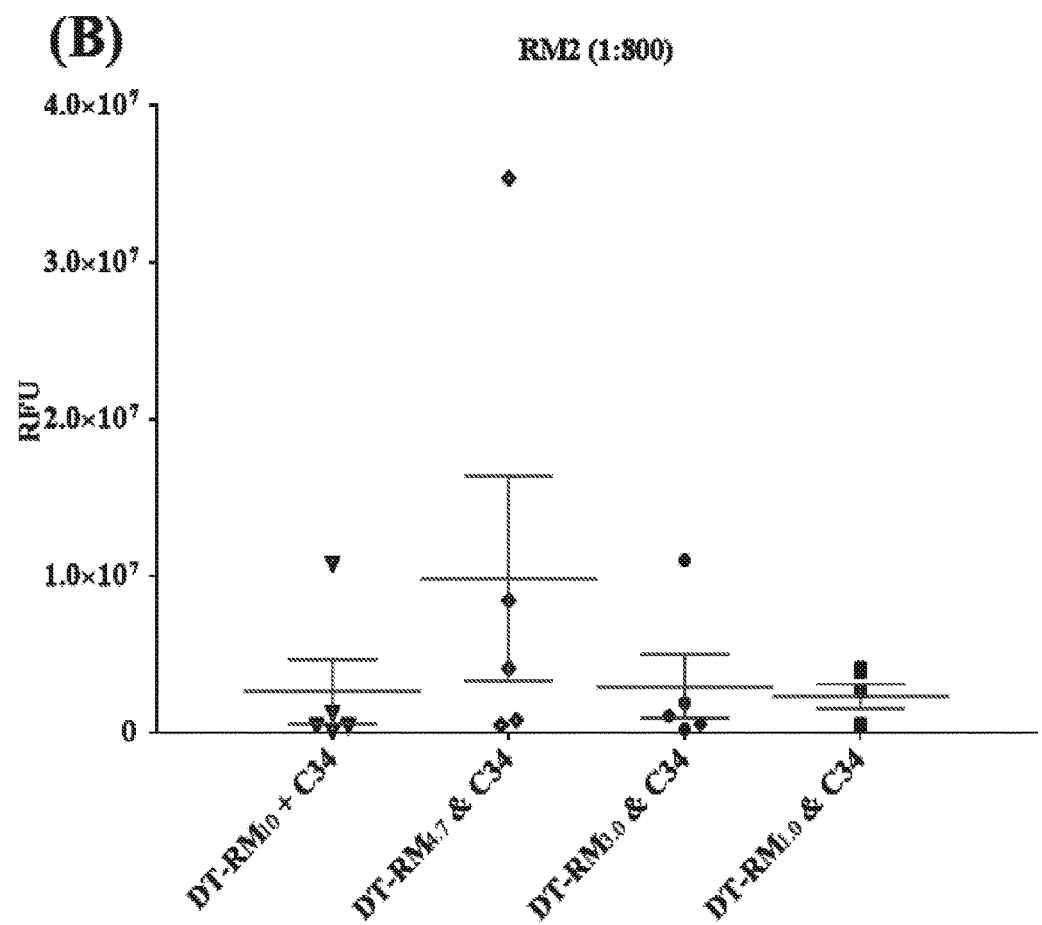
Figure 22C:
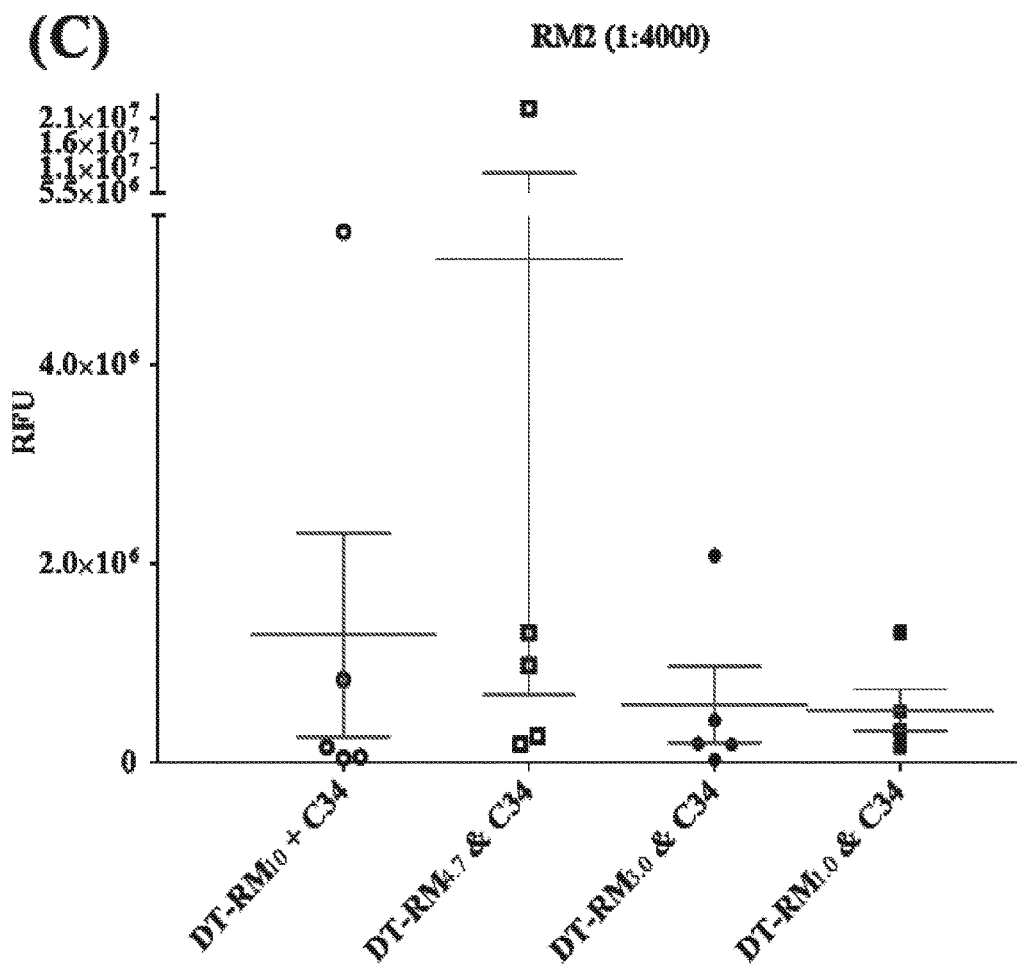
Figure 22D:
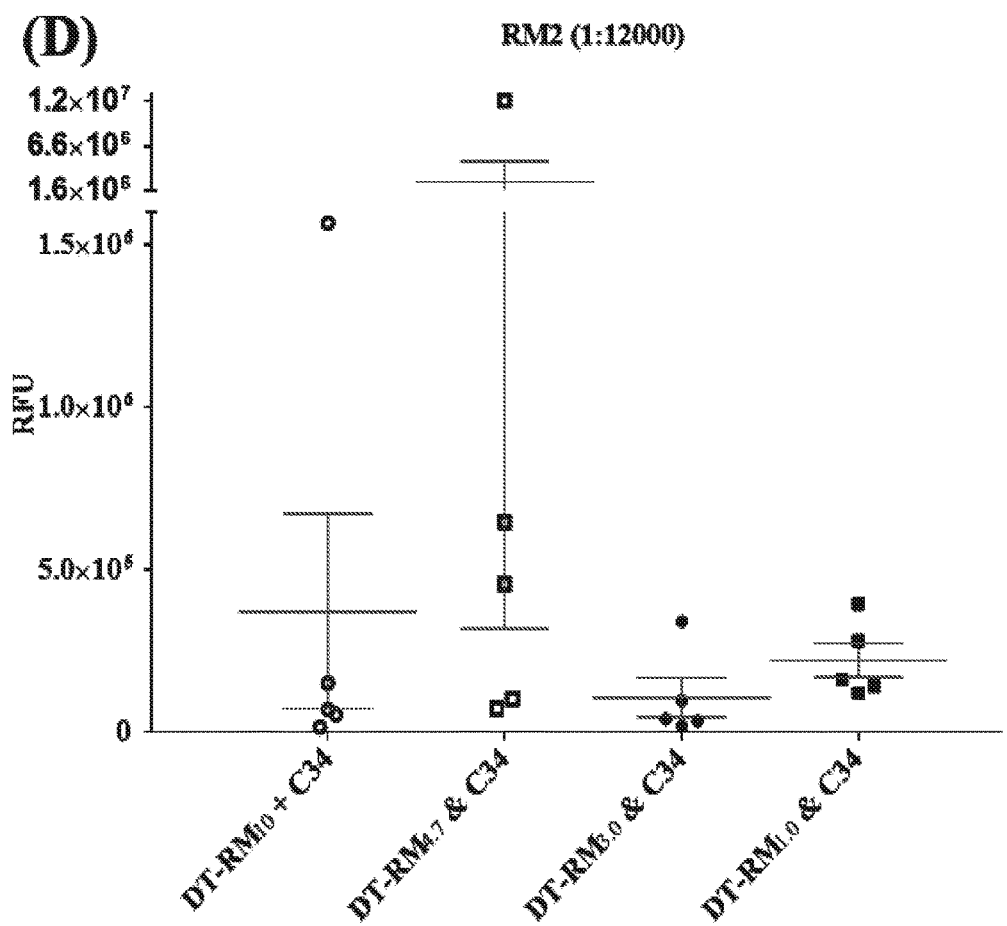
Figure 22E:
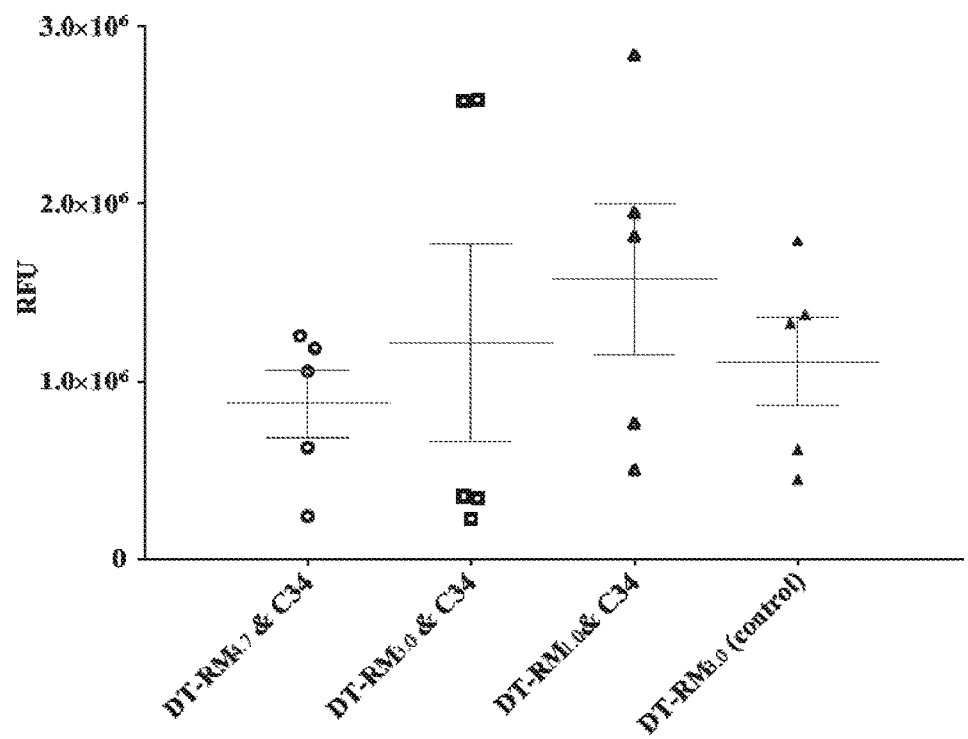
Figure 23:
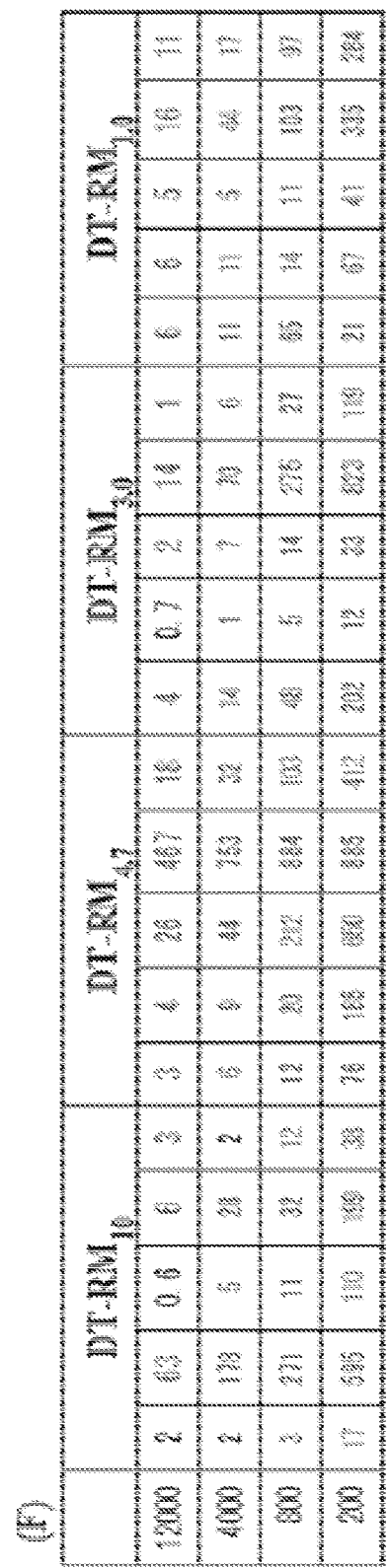
FIG. 23 shows Serum IgG antibodies and IgM antibodies response against RM2 in immunized mice with different epitope ratio of DT-RM/C34 wherein the signal to noise (S/N) ratio of serum IgG antibodies against RM2 in different immunized mice with various fold dilution.
Figure 24C:
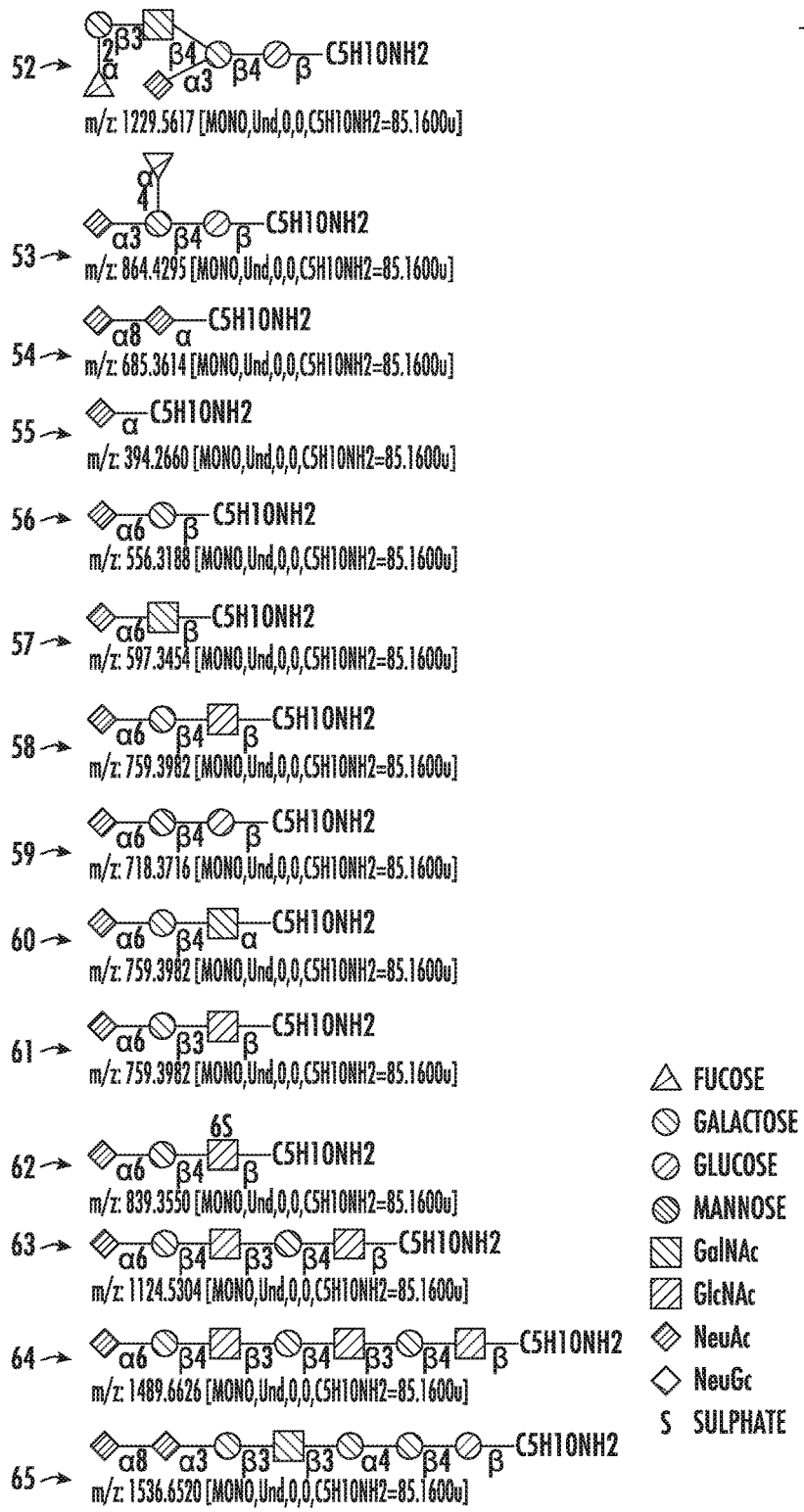
Figure 24D:
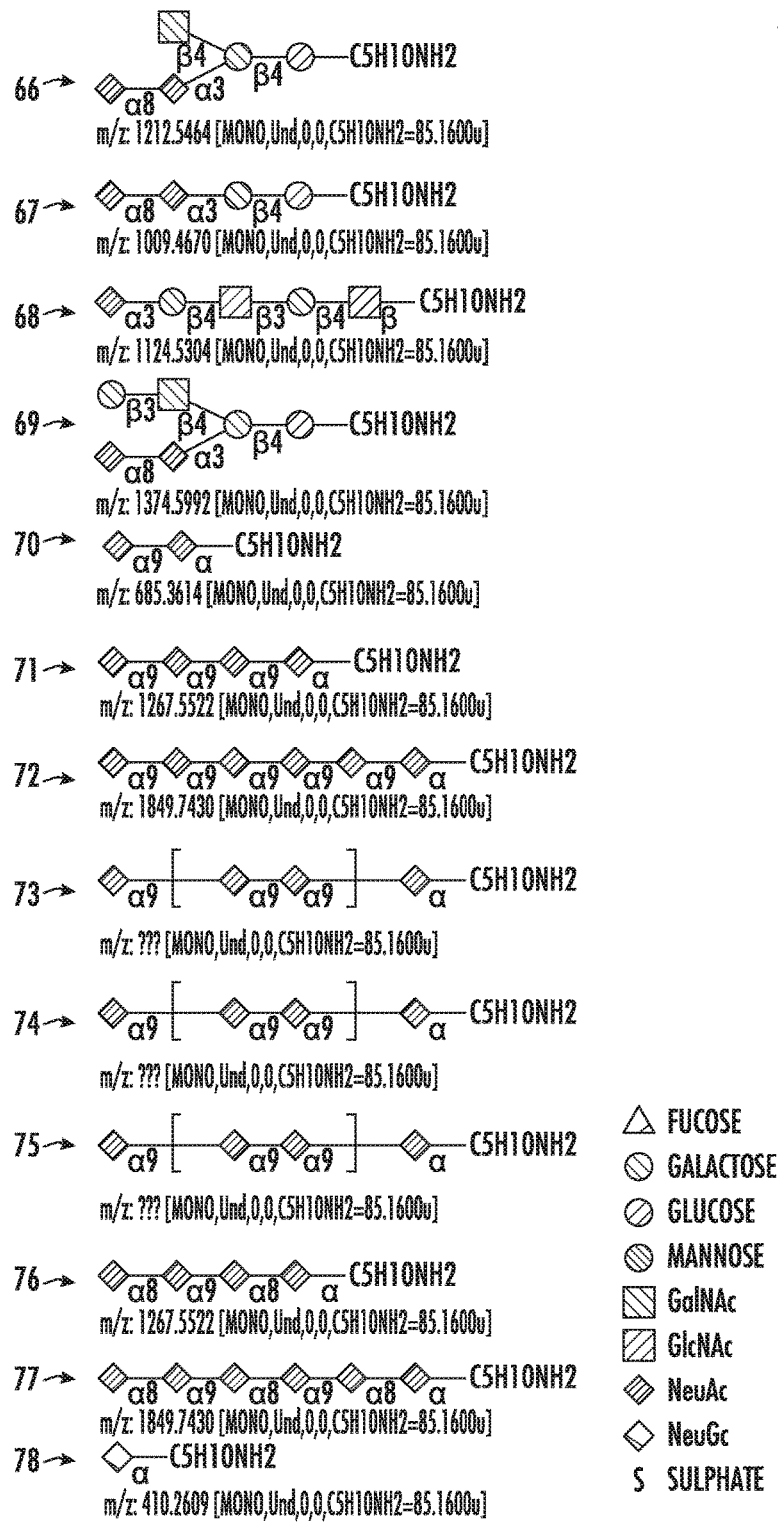
Figure 24F:
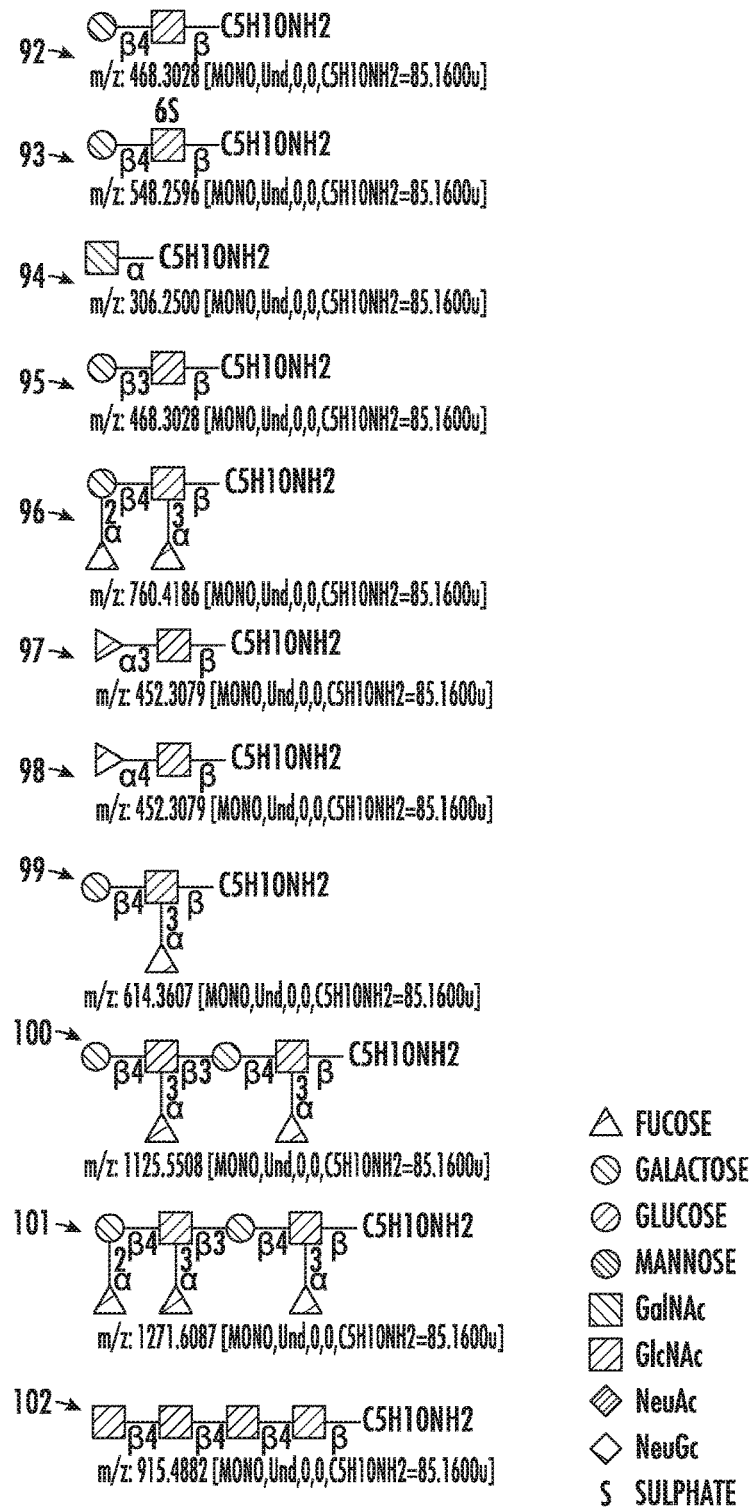
Figure 24G:
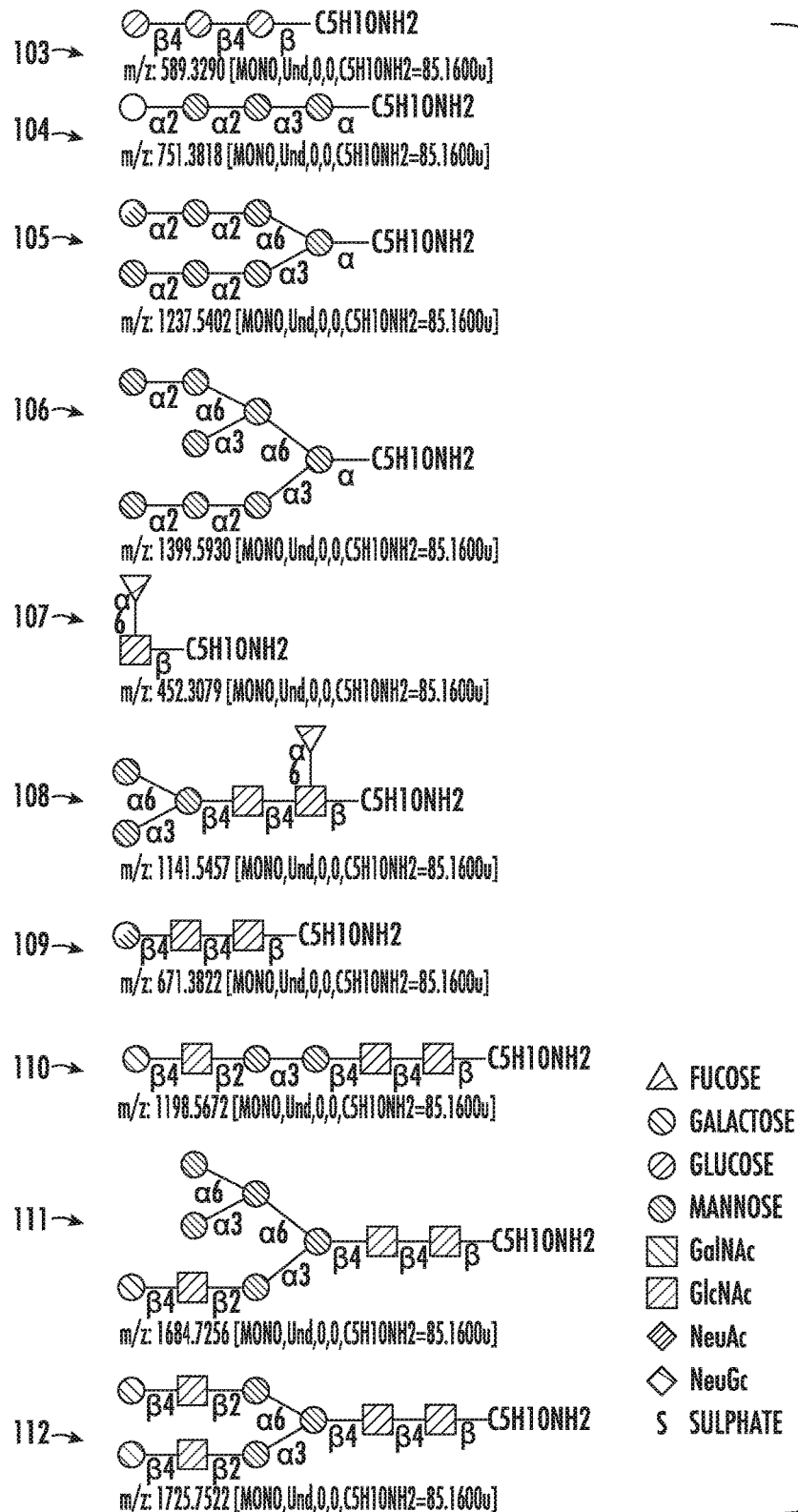
Figure 24I:
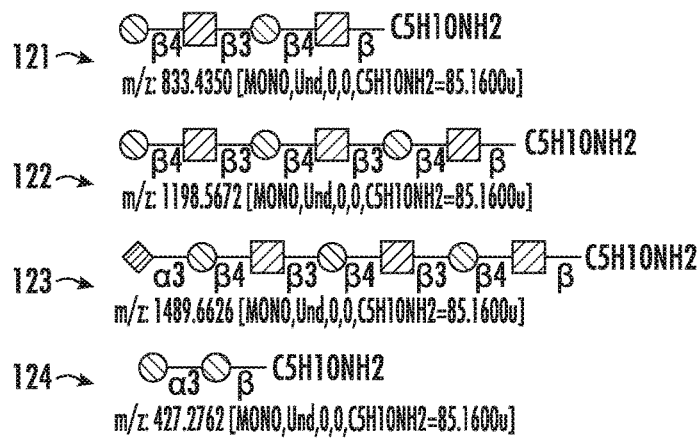

After indentifying C34 as an effective adjuvant for DT-RM$_{4.7}$, different epitope ratio of vaccine was explored by changing the amount of RM2 antigen attached to each carrier protein DT (FIG. 13). Various equivalents of thiolated hexasaccharide 32 and different protein concentrations generally would generate diverse carbohydrate-protein ratios. The number of RM2 antigens on the protein was determined by MALDI-TOF mass spectrometer. After dialysis and analysis, on average, 1.0, 3.0, 4.7, and 10 molecules of RM2 antigen to one molecule DT to give DT-RM$_{1.0}$, DT-RM$_{3.0}$, DT-RM$_{4.7}$, and DT-RM$_{10.0}$ (Table 4). Using the same vaccination protocol mentioned previously, sera were collected 2 weeks after the third vaccination, and the elicited Abs were subsequently profiled by a RM2-coated glycan microarray. In general, it was observed that when immunized with DT-RM$_{3.0}$ alone without adjuvant, mice generated only low titers of anti-RM2 IgG (FIG. 22A). The glycan microarray results showed that, on average, 4.7 RM2 antigens conjugated to one DT induced the most abundant IgG titers against RM2 (FIG. 14 and FIG. 22). Alternatively, when immunized with DT-RM$_{3.0}$ alone without adjuvant, mice generated only low titers of anti-RM2 IgG (FIG. 22A). When the signal to noise (S/N) ratio is fixed to >3, the induced IgG could be diluted to 12,000-fold before the signal disappeared (FIG. 23). However, the induced IgM titer could only be diluted to 60-fold (FIG. 22E), and the IgM signals reached to the background after dilution to 200-fold.

Figure 15:
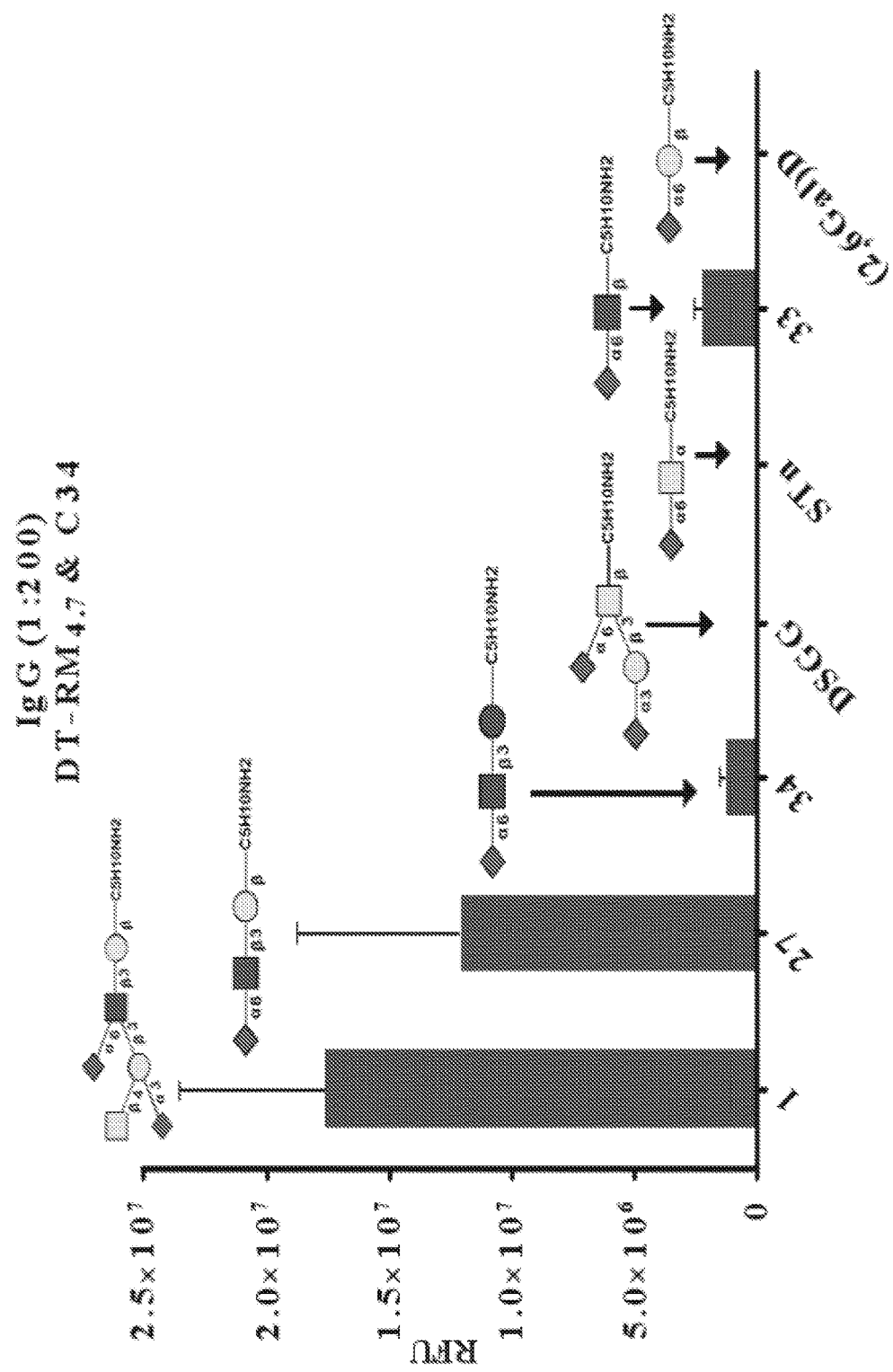
FIG. 15 shows specificity analysis of the induced antibodies by DT-RM4.7/C34 vaccine.

The specificity analysis of the induced IgG antibodies by DT-RM$_{4.7}$/C34 vaccine showed that the induced antibodies had a strong binding to the RM2 antigen and weaker binding to its trisaccharide 27, tetrasaccharide 28, pentasacharide 29, and pentasaccharide 30 (FIG. 14). It was observed that these oligosaccharides all contain the same epitope trisaccharide 27 (NeuAcα2→6GlcNAcβ1→3Galβ1→R). To further evaluate the vaccine specificity, a glycan microarray created by STn, DSGG, RM2 antigen, RM2 antigen analogs, and RM2 antigen fragments was constructed (FIG. 15). In general, specificity analysis of the induced antibodies by DT-RM$_{4.7}$/C34 vaccine showed that the induced antibodies mainly bound to the RM2 antigen and to its trisaccharide epitope 27, a lesser extent to disaccharide 32 (NeuAcα2→6GlcNAcβ1→R) and trisaccharide 33

(NeuAcα2→6GlcNAcβ1→3Gluβ1→R). Besides, there is no detectable signal of binding to NeuAcα2→6Gal, DSGG, or STn.

Figure 16:
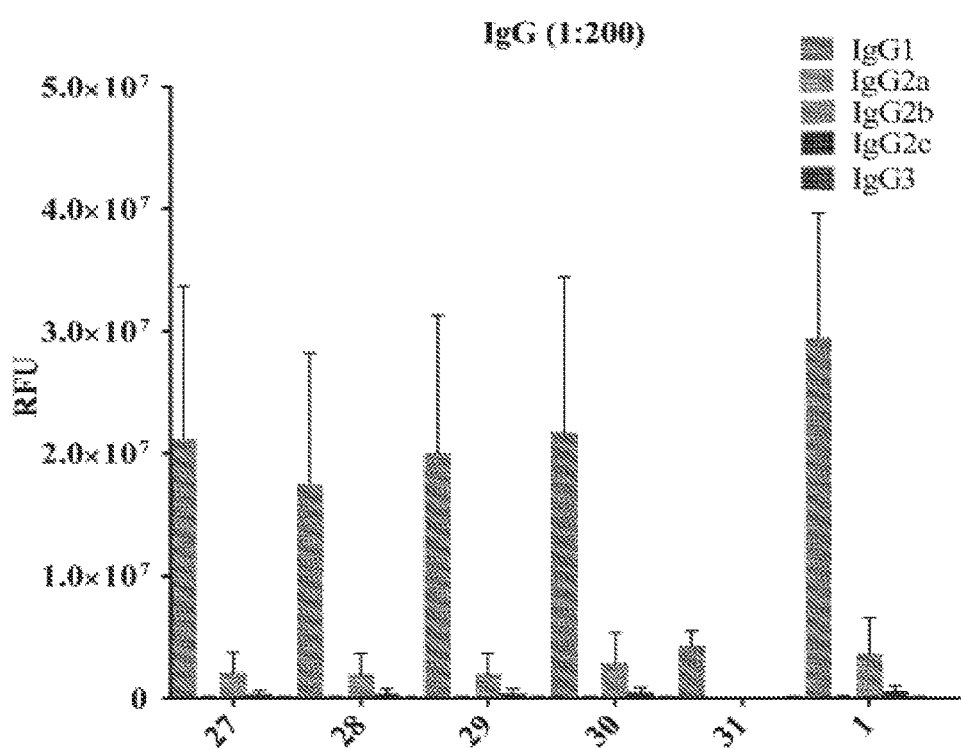
FIG. 16 shows the glycan binding profiles of induced IgG subtypes titers collected from DT-RM4.7/C34-immunized mice two weeks after the third injection.

It was reported that DT could induce antigen-specific T cell proliferation and elevate splenocytes production of IL-2, IFN-γ, and IL-6, suggesting their role in the Th1 driven pathway (Miyaji, E. N.; Mazzantini, R. P.; Dias, W. O.; Nascimento, A. L.; Marcovistz, R.; Matos, D. S.; Raw, I.; Winter, N.; Gicquel, B.; Rappuoli, R.; Leite, L. C. Infect. Immun. 2001, 69, 869; (b) Godefroy, S.; Peyre, A.; Garcia, N.; Muller, S.; Sesardic, D.; Partidos, C. D. Infect. Immun. 2005, 73, 4803; (c) Stickings, P.; Peyre, M.; Coombes, L.; Muller, S.; Rappuoli, R.; Del Giudice, G.; Partidos, C. D.; Sesardic, D. Infect. Immun. 2008, 76, 1766). Furthermore, the glycolipid C34 was able to induce higher production of IFN-γ and IL-4, indicating a more Th1-skewed antigen (Wu, T. N.; Lin, K. H.; Chang, Y. J.; Huang, J. R.; Cheng, J. Y.; Yu, A. L.; Wong, C. H. Proc. Natl. Acad. Sci. U.S.A. 2011, 108, 17275). But, the induced subtypes anti-DT-RM$_{4.7}$/C34 antibodies were mainly IgG1 antibodies with a trace amount of IgG2b and IgG2c antibodies and no detectable IgG2a (FIG. 16).

Figure 17:
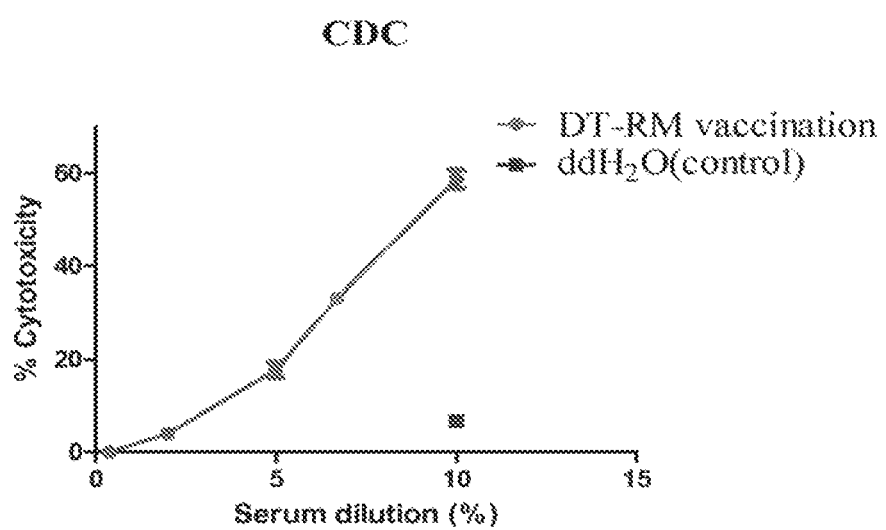
FIG. 17 shows CDC activity of the induced antibodies by serum from vaccination mice in the presence of rabbit complement. Lysis of human prostate cancer cell line LNCap at different concentrations.

Complement-dependent cytotoxicity (CDC) is one of the most potent cell killing mechanisms mediating the immune response in which IgG or IgM antibodies bind to antigens on the tumor or cancer cell surface. Complement activation, initiated through complement protein C1q binding to the Fc region of the IgM or IgG isotype antibodies, represents the important activity of antibodies against circulating tumor cells and micrometastases. To evaluate the therapeutic potential of anti-RM2 antibodies, we tested the complement-dependent cytotoxicity with prostate cancer cell line LNCap in the presence of new born rabbit complement. The ability of antibodies to induce complement activation is strongly dependent on the antibody isotype and epitope recognized. Thus, isotype IgG1 and IgG3 are able to activate the complement cascade particularly well through C1q, in contrast to IgG2 and IgG4[27]. As shown above, our vaccine formulation resulted in a higher titer of subclass IgG1 antibodies than other subclasses, and the immune serum showed a strong complement-mediated cytotoxicity activity on the RM2-positive human prostate cancer cell line LNCap (FIG. 17). These data suggested that our carbohydrate-based vaccine DT-RM, based on the chemically synthetic hexacharide 1 and a mutated diphtheria toxin (DT) with adjuvant C34 may create an efficient immune stimulation in human.

Biological Experimental Procedures

Determination of Surface Dissociation Constant.

The slides were spotted with solution of RM2 1 and 29 with concentrations 100, 50, 25, 12.5, and 6.25 μM 2 rows from top to bottom with 5 replicates horizontally placed in each grids. The glycan microarray was blocked with 50 mM ethanolamine for 1 h at 0° C. and washed three times with PBST buffer before use. The monoclonal RM2 antibody was diluted with 3% BSA/PBST buffer (PBST buffer: PBS and 0.05% Tween-20, pH 7.4). Next, Cy3-conjugated goat anti-mouse IgM antibody was added into the diluted solution to precomplex with primary antibody. The precomplexed solution was applied to each well and incubated at 0° C. for 1 h in the dark. Finally, the slides were washed by PBST washing buffer and ddH$_2$O in sequence. The slides were spin-dried for 5 minutes before scanned at 635 nm with a microarray fluorescence chip reader (GenePix 4300A; Molecular Devices Corporation). Scanned images were analyzed with GenePix Pro-6.0 analysis software (Axon Instruments, Union City, Calif., USA).

TABLE 2

Surface dissociation constants ($K_{D, surf}$) of antibody RM2 and RM2 on microarray

| Printing concentration RM2, μM | $F_{max}$ | $K_{D, surf}$, nM |
| --- | --- | --- |
| 100 | 55,756 | 5.104 |
| 50 | 53,982 | 5.479 |
| 25 | 47,714 | 4.277 |
| 12.5 | 45,028 | 3.140 |
| 6.25 | 45,483 | 4.724 |

$K_{D,surf}$ values (nM) for RM2 concentrations against the fluorescent intensity at different concentrations of printed sugar.

TABLE 3

Surface dissociation constants ($K_{D, surf}$) of antibody RM2 and 29 on microarray

| Printing concentration RM2, μM | $F_{max}$ | $K_{D, surf}$, nM |
| --- | --- | --- |
| 100 | 62,859 | 6.962 |
| 50 | 59,045 | 6.440 |
| 25 | 50,970 | 4.496 |
| 12.5 | 50,900 | 4.047 |
| 6.25 | 51,597 | 5.127 |

General Procedure for Generating Maleimide Activation DT:

DT (Diphtheria toxin) was dissolved in 0.1 M phosphate buffer pH 6.6 or 8.0 (~1 mg/ml), and Sulfo-EMCS (1.0 mg) was added to the solution. The solution was stirred gently for 2 h at room temperature. The mixture was then diluted with deionized water and centrifuge against 5 changes of deionized water by Amicon Ultra-0.5 (10 kDa, 2×). The solution was lyphophilized to white solid. The obtained maleimide DT can be characterized by MALDI-TOF (positive mode, matrix sinapinic acid, H$_2$O) analysis to determine the maleimide incorporation rate. MALDI-TOF found 60806 (60,806−58,326/193=12.85); MALDI-TOF found 63464 (63,464−58,326/193=26.6)

General Procedure for Generating Protein Carbohydrate Conjugates:

Modified DT was dissolved in 0.1 M phosphate buffer pH 7.2 (~1 mg/ml), and different ratio of thiolated hexasaccharide 32 was added to the solution. The mixture was stirred for 2 h at room temperature. The mixture was then diluted with deionized water and centrifuge against 5 changes of deionized water by Amicon Ultra-0.5 (10 kDa, 2×). The solution was lyphophilized to white solid. The obtained DT-RM series can be characterized by MALDI-TOF (positive mode, matrix sinapinic acid, H$_2$O) analysis to determine the carbohydrate incorporation rate.

TABLE 4

The preparation of RM2-DT conjugates

| Entry | DT (mg) | number of maleimide | RM2-SH (5 mg/mL) | Hapten Incorporation | product |
|---|---|---|---|---|---|
| 1 | 1 | 26.6 ($4.1 \times 10^{-7}$ mole) | 0.33 mL ($11.1 \times 10^{-7}$ mole) | 10 | DT-RM$_{10}$ |
| 2 | 1 | 12.85 ($2.14 \times 10^{-7}$ mole) | 0.19 mL ($6.42 \times 10^{-7}$ mole) | 4.7 | DT-RM$_{4.7}$ |
| 3 | 2 | 12.85 ($4.28 \times 10^{-7}$ mole) | 0.14 mL ($4.63 \times 10^{-7}$ mole) | 3.0 | DT-RM$_{3.0}$ |
| 4 | 6 | 12.85 ($12.84 \times 10^{-7}$ mole) | 0.15 mL ($4.96 \times 10^{-7}$ mole) | 1.0 | DT-RM$_{3.0}$ |

(1) MALDI-TOF found 78822 → DT-RM$_{10}$;
(2) MALDI-TOF found 67975 → DT-RM$_{4.7}$;
(3) MALDI-TOF found 65316 → DT-RM$_{3.0}$;
(4) MALDI-TOF found 62025 → DT-RM$_{3.0}$.

Mice Dosage and Immunization Schedule.

For comparing immunogenicity of DT-RM vaccine with different amount of RM2 attached to each carrier protein DT, groups of three five mice (8-week-old female Balb/c mice, BioLASCO, Taiwan) were immunized intramuscularly with DT-RM$_{1.0}$, DT-RM$_{3.0}$, DT-RM$_{4.7}$, or DT-RM$_{10.0}$ with or without adjuvant C1, C34, or AlPO$_3$, respectively. Each vaccination contained 2 µg of RM2 (DT-RM$_{1.0}$, DT-RM$_{3.0}$, DT-RM$_{4.7}$, or DT-RM$_{10.0}$) with or without 2 µg of C1, C34, or Alu, respectively. Control mice were injected with phosphate buffer saline (PBS). Three vaccinations were given at two weeks intervals. Two weeks after the third injection, sera were obtained and subsequent tested with a RM2-coated glycan microarray to estimate the level and diversity of anti-RM2 related antibody.

Glycan Microarray Fabrication.

Microarrays were printed (BioDot; CartesianTechnologies) by robotic pin (SMP3; TeleChem In-ternational Inc.) deposition of 0.7 nL 100 µM amine-containing glycans in printing buffer (300 mM phosphate buffer, pH 8.5, containing 0.01% TritonX-100) from a 14-well microtiter plate onto N-Hydroxysuccinimide (NHS)-coated glass slides. Subsequently, a 96-glycan microarray (Fig. S2) was used to determine the polyclonal Ab spectrum of DT-RM series-induced antiserum. Printed slides were allowed to react in an atmosphere of 80% humidity for 1 h followed by desiccation overnight. These slides were stored at room temperature in a desiccator prior to use.

Serologic Assay with Glycan Microarray.

Mouse sera were diluted with 1% BSA/PBST buffer (PBST buffer: PBS and 0.05% Tween-20, pH 7.4). The glycan microarray was blocked with 50 mM ethanolamine for 1 h at 0° C. and washed three times with PBST buffer before use. The serum dilutions were then introduced to the glycan microarray and incubated at 0° C. for 1 h. Next, Cy3-conjugated goat anti-mouse IgG (H+L), IgG1, IgG2a, IgG2b, IgG2c, IgG3, or anti-mouse IgM was added to the microarray slide and then sealed for 1 h incubation at 0° C. in the dark. Finally, the slides were washed three times with PBST, PBST washing buffer, and ddH$_2$O in sequence. The slides were spin-dried for 5 minutes before scanned at 635 nm with a microarray fluorescence chip reader (GenePix 4300A; Molecular Devices Corporation). Scanned images were analyzed with GenePix Pro-6.0 analysis software (Axon Instruments, Union City, Calif., USA).

Complement-Dependent Cytotoxicity (CDC) Test.

Complement-dependent cytotoxicity was tested by non-radioactive cytotoxicity assay. LNCap cells were added to wells of U-bottomed tissue culture microtiter plates at a concentration of $1.25 \times 10^4$ cells/25 µL and incubated with different dilutions of PBS or post-vaccination sera or with medium (RPMI-1640) alone. Next, 50 µL of rabbit complement diluted 1:25 in complete medium (RPMI-1640) was added to triplicate samples and incubated for 90 mins. at 37° C. Thus, the final complement dilution in the assay was 1:50. Following incubation, 150 µL medium (RPMI-1640) were added for every wells and supernatants (50.0 µL) were collected by centrifugation. Reconstituted LDH substrate mix (50 µL) was added to each well of the assay plate containing sample transferred from the cytotoxicity assay plate. Then, the plate was sealed for 30 min for incubation at room temperature in the dark. Finally, stop solution (50 µL) was added to each well, and the absorbance at 490 nm was recorded immediately. All assays were performed in triplicate, and the spontaneous release was evaluated in the presence of complement. The percentage specific lysis was calculated as follows: Cytotoxicity (%)=100×[experimental release−spontaneous release]/[maximum release−spontaneous release]

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A glycan conjugate having Formula (II-a) or Formula (II-b)

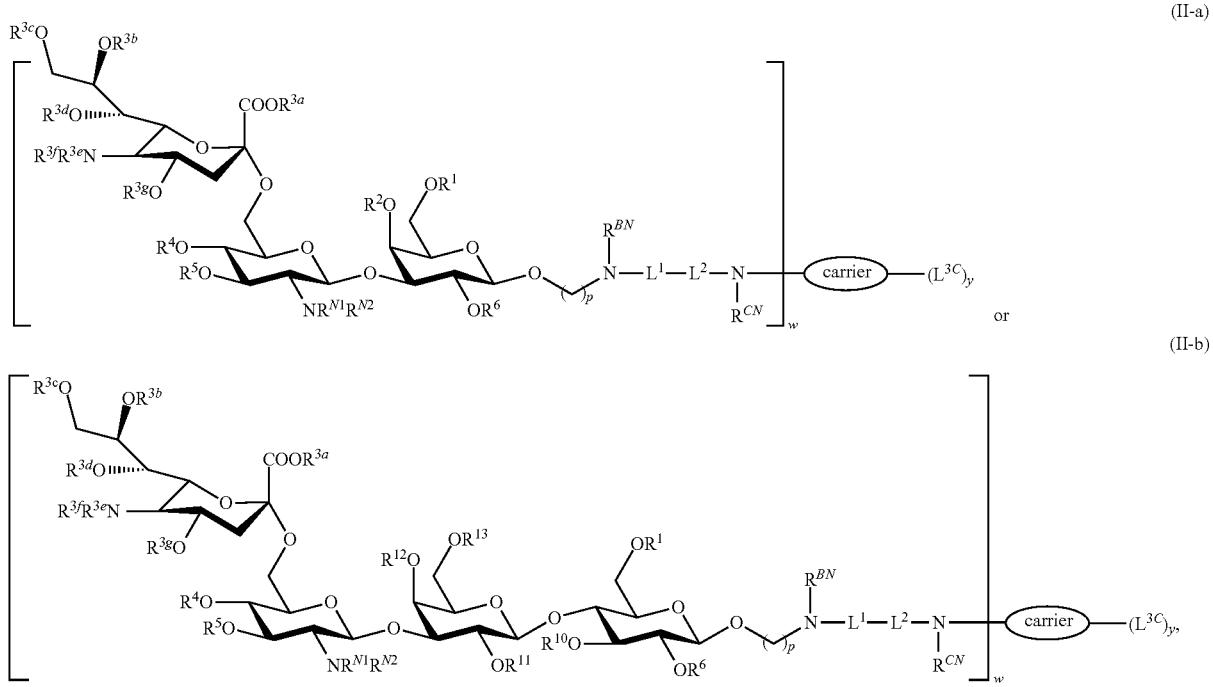

or a pharmaceutically acceptable salt thereof,
wherein
- each instance of $R^1$, $R^2$, $R^4$, $R^5$, $R^6$, $R^{10}$, $R^{11}$, $R^{12}$, and $R^{13}$ is independently hydrogen, optionally substituted $C_{1-6}$ alkyl, optionally substituted carbohydrate, or an oxygen protecting group; or optionally $R^1$ and $R^2$ are taken with the intervening atoms to form an optionally substituted heterocyclic ring; or optionally $R^4$ and $R^5$ are taken with the intervening atoms to form an optionally substituted heterocyclic ring;
- each instance of $R^{N1}$, $R^{N2}$, and $R^{BN}$ is independently hydrogen, optionally substituted $C_{1-6}$ alkyl, optionally substituted acyl, or a nitrogen protecting group;
- p is an integer of 1 to 10, inclusive;
- each instance of $L^1$ is independently a bond, —O—, —S—, —$NR^{L1a}$—, —C(=O)—, —$NR^{L1a}$C(=O)—, —$NR^{L1a}$C(=O)O—, —C(=O)$NR^{L1a}$—, —OC(=O)$NR^{L1a}$—, —SC(=O)—, —C(=O)S—, —OC(=O)—, —C(=O)O—, —$NR^{L1a}$C(=S)—, —C(=S)$NR^{L1a}$—, trans-$CR^{L1b}$=$CR^{L1b}$—, cis-$CR^{L1b}$=$CR^{L1b}$—, —C≡C—, —OC($R^{L1b}$)$_2$—, —C($R^{L1b}$)$_2$O—, —$NR^{L1a}$C($R^{L1b}$)$_2$—, —C($R^{L1b}$)$_2NR^{L1a}$—, —SC($R^{L1b}$)$_2$—, —C($R^{L1b}$)$_2$S—, —S(=O)$_2$O—, —OS(=O)$_2$—, —S(=O)$_2NR^{L1a}$—, —$NR^{L1a}$S(=O)$_2$—, or an optionally substituted $C_{1-20}$ hydrocarbon chain, optionally wherein one or more carbon units of the hydrocarbon chain is replaced with —O—, —S—, —$NR^{L1a}$—, —C(=O)—, $NR^{L1a}$C(=O)—, —$NR^{L1a}$C(=O)O—, —C(=O)$NR^{L1a}$—, —OC(=O)$NR^{L1a}$—, —SC(=O)—, —C(=O)S—, —OC(=O)—, —C(=O)O—, —$NR^{L1a}$C(=S)—, —C(=S)$NR^{L1a}$—, trans-$CR^{L1b}$=$CR^{L1b}$—, cis-$CR^{L1b}$=$CR^{L1b}$—, —C≡C—, —S(=O)$_2$O—, —OS(=O)$_2$—, —S(=O)$_2NR^{L1a}$—, or —$NR^{L1a}$S(=O)$_2$—, wherein $R^{L1a}$ is hydrogen, optionally substituted $C_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring;
- each instance of $L^2$ is independently a moiety derived from a crosslinking reagent capable of crosslinking the carrier and $L^1$-H;
- each instance of $L^{3C}$ is independently a crosslinking reagent or a moiety derived from a crosslinking reagent, wherein the crosslinking reagent is capable of crosslinking the carrier and $L^1$-H;
- each instance of $R^{CN}$ is independently hydrogen, optionally substituted $C_{1-6}$ alkyl, optionally substituted acyl, or a nitrogen protecting group;
- w is an integer of 1 to 100, inclusive;
- y is 0 or an integer of 1 to 100, inclusive;
- $R^5$ is independently hydrogen, optionally substituted $C_{1-6}$ alkyl, or an oxygen protecting group; or optionally $R^4$ and $R^5$ are taken with the intervening atoms to form an optionally substituted heterocyclic ring;
- each instance of $R^{3a}$, $R^{3b}$, $R^{3c}$, $R^{3d}$, and $R^{3g}$ is independently hydrogen, optionally substituted $C_{1-6}$ alkyl, optionally substituted carbohydrate, or an oxygen protecting group; or optionally $R^{3c}$ and $R^{3b}$ are taken with the intervening atoms to form an optionally substituted heterocyclic ring; or optionally $R^{3b}$ and $R^{3d}$ are taken with the intervening atoms to form an optionally substituted heterocyclic ring; or optionally $R^{3f}$ and $R^{3g}$ are taken with the intervening atoms to form an optionally substituted heterocyclic ring; and each instance of $R^{3f}$ and $R^{3e}$ is independently hydrogen, optionally substituted $C_{1-6}$ alkyl, or a nitrogen protecting group.

2. The glycan conjugate of claim 1 having Formula (III-a) or Formula (III-b)

$R^{3c}$ and $R^{3b}$ are taken with the intervening atoms to form an optionally substituted heterocyclic ring; or optionally $R^{3b}$ and $R^{3d}$ are taken with the intervening atoms to form an optionally substituted heterocyclic ring; or optionally $R^{3f}$ and $R^{3g}$ are taken with the intervening atoms to form an optionally substituted heterocyclic ring; or optionally $R^{5a}$ and $R^{5b}$ are taken with the intervening atoms to form an optionally substituted heterocyclic ring; or optionally $R^{5b}$ and $R^{5c}$ are taken with the intervening atoms to form an optionally substituted heterocyclic ring; and

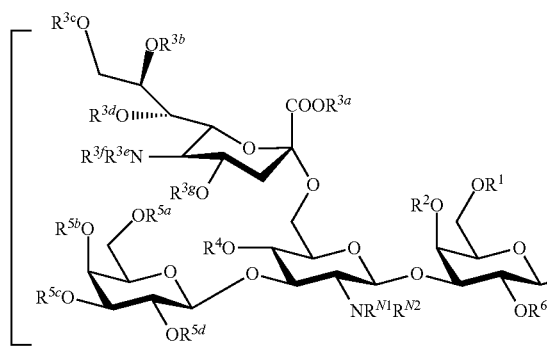

(III-a)

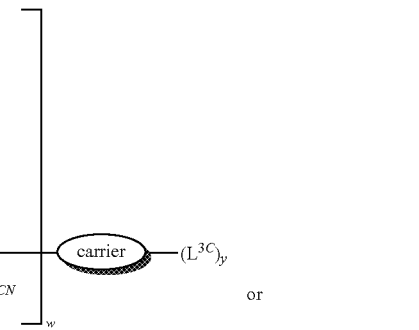

or

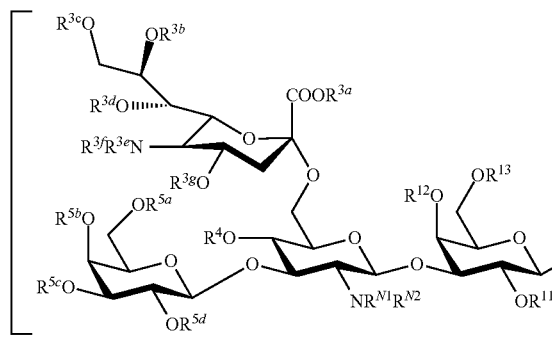

(III-b)

or a pharmaceutically acceptable salt thereof, wherein each instance of $R^{3a}$, $R^{3b}$, $R^{3c}$, $R^{3d}$, $R^{3g}$, $R^{5a}$, $R^{5b}$, $R^{5c}$, and $R^{5d}$ is independently hydrogen, optionally substituted $C_{1-6}$ alkyl, optionally substituted carbohydrate, or an oxygen protecting group; or optionally each instance of $R^{3f}$ and $R^{3e}$ is independently hydrogen, optionally substituted $C_{1-6}$ alkyl, or a nitrogen protecting group.

3. The glycan conjugate of claim 1 having Formula (IV-a) or (IV-b)

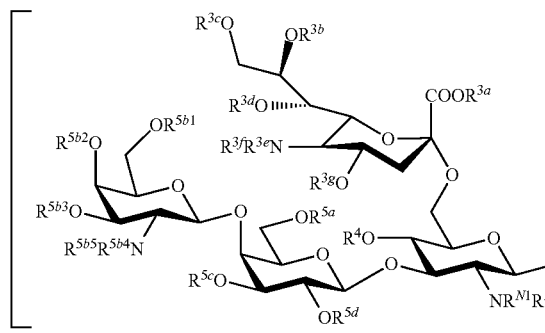

(IV-a)

or (IV-b)

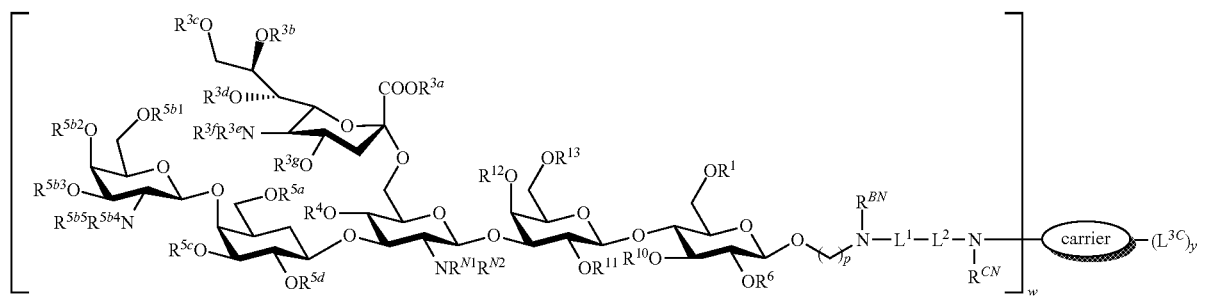

or a pharmaceutically acceptable salt thereof, each instance of $R^{3a}$, $R^{3b}$, $R^{3c}$, $R^{3d}$, $R^{3g}$, $R^{5a}$, $R^{5c}$, $R^{5d}$, $R^{5b1}$, $R^{5b2}$, and $R^{5b3}$ is independently hydrogen, optionally substituted $C_{1-6}$ alkyl, optionally substituted carbohydrate, or an oxygen protecting group; or optionally $R^{3c}$ and $R^{3b}$ are taken with the intervening atoms to form an optionally substituted heterocyclic ring; or optionally $R^{3b}$ and $R^{3d}$ are taken with the intervening atoms to form an optionally substituted heterocyclic ring; or optionally $R^{3f}$ and $R^{3g}$ are taken with the intervening atoms to form an optionally substituted heterocyclic ring; or optionally $R^{5c}$ and $R^{5d}$ are taken with the intervening atoms to form an optionally substituted heterocyclic ring; or optionally $R^{5b1}$ and $R^{5b2}$ are taken with the intervening atoms to form an optionally substituted heterocyclic ring; or optionally $R^{5b2}$ and $R^{5b3}$ are taken with the intervening atoms to form an optionally substituted heterocyclic ring; or optionally $R^{5b3}$ and $R^{5b4}$ are taken with the intervening atoms to form an optionally substituted heterocyclic ring; and each instance of $R^{3f}$, $R^{3e}$, $R^{5b4}$, and $R^{5b5}$ is independently hydrogen, optionally substituted $C_{1-6}$ alkyl, or a nitrogen protecting group.

4. The glycan conjugate of claim 1 having Formula (V-a) or (V-b)

(V-a)

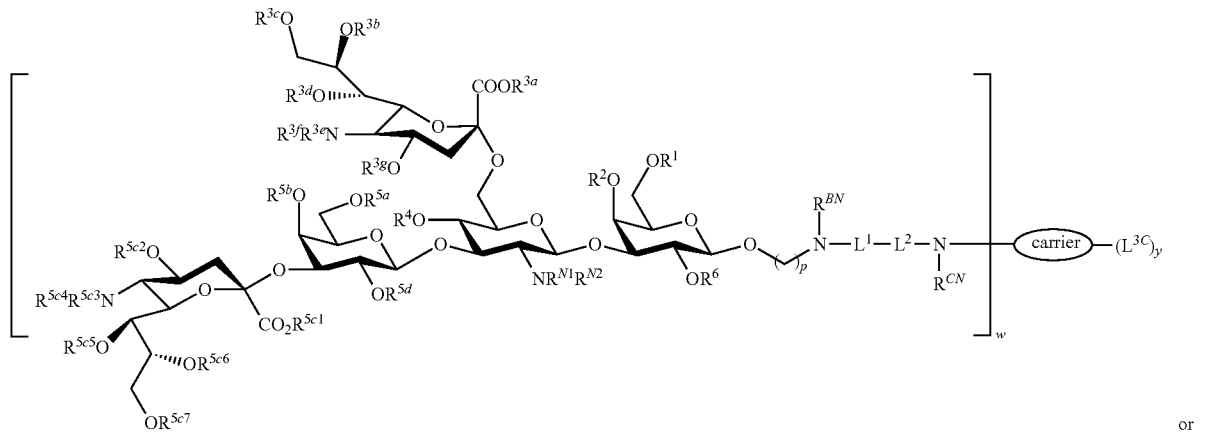

or
(V-b)

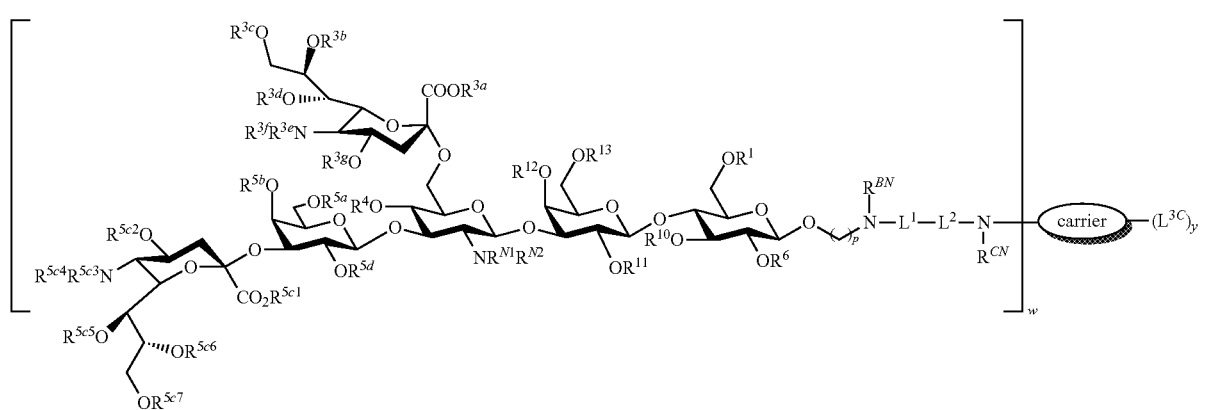

or a pharmaceutically acceptable salt thereof, each instance of $R^{3a}$, $R^{3b}$, $R^{3c}$, $R^{3d}$, $R^{3g}$, $R^{5a}$, $R^{5b}$, $R^{5d}$, $R^{5c1}$, $R^{5c2}$, $R^{5c5}$, $R^{5c6}$, and $R^{5c7}$ is independently hydrogen, optionally substituted $C_{1-6}$ alkyl, optionally substituted carbohydrate, or an oxygen protecting group; or optionally $R^{3c}$ and $R^{3b}$ are taken with the intervening atoms to form an optionally substituted heterocyclic ring; or optionally $R^{3b}$ and $R^{3d}$ are taken with the intervening atoms to form an optionally substituted heterocyclic ring; or optionally $R^{3f}$ and $R^{3g}$ are taken with the intervening atoms to form an optionally substituted heterocyclic ring; or optionally $R^{5a}$ and $R^{5b}$ are taken with the intervening atoms to form an optionally substituted heterocyclic ring; or optionally $R^{5c2}$ and $R^{5c4}$ are taken with the intervening atoms to form an optionally substituted heterocyclic ring; or optionally $R^{5c5}$ and $R^{5c6}$ are taken with the intervening atoms to form an optionally substituted heterocyclic ring; or optionally $R^{5c6}$ and $R^{5c7}$ are taken with the intervening atoms to form an optionally substituted heterocyclic ring; and each instance of $R^{3f}$, $R^{3e}$, $R^{5c3}$, and $R^{5c4}$ is independently hydrogen, optionally substituted $C_{1-6}$ alkyl, or a nitrogen protecting group.

5. The glycan conjugate of claim 1 having Formula (VI-a) or Formula (VI-b)

each instance of $R^{5a}$, $R^{5d}$, $R^{5b1}$, $R^{5b2}$, $R^{5b3}$, $R^{5c1}$, $R^{5c2}$, $R^{5c5}$, $R^{5c6}$, and $R^{5c7}$ is independently hydrogen, optionally substituted $C_{1-6}$ alkyl, optionally substituted carbohydrate, or an oxygen protecting group; or optionally $R^{5b1}$ and $R^{5b2}$ are taken with the intervening atoms to form an optionally substituted heterocyclic ring; or optionally $R^{5b2}$ and $R^{5b3}$ are taken with the intervening atoms to form an optionally substituted heterocyclic ring; or optionally $R^{5b3}$ and $R^{5b4}$ are taken with the intervening atoms to form an optionally substituted heterocyclic ring; or optionally $R^{5c2}$ and $R^{5c4}$ are taken with the intervening atoms to form an optionally substituted heterocyclic ring; or optionally $R^{5c5}$ and $R^{5c6}$ are taken with the intervening atoms to form an optionally substituted heterocyclic ring; or optionally $R^{5c6}$ and $R^{5c7}$ are taken with the intervening atoms to form an optionally substituted heterocyclic ring; and each instance of $R^{5b4}$, $R^{5b5}$, $R^{5c3}$, and $R^{5c4}$ is independently hydrogen, optionally substituted $C_{1-6}$ alkyl, or a nitrogen protecting group.

6. The glycan conjugate of claim 1 having Formula (VII-a) or (VII-b)

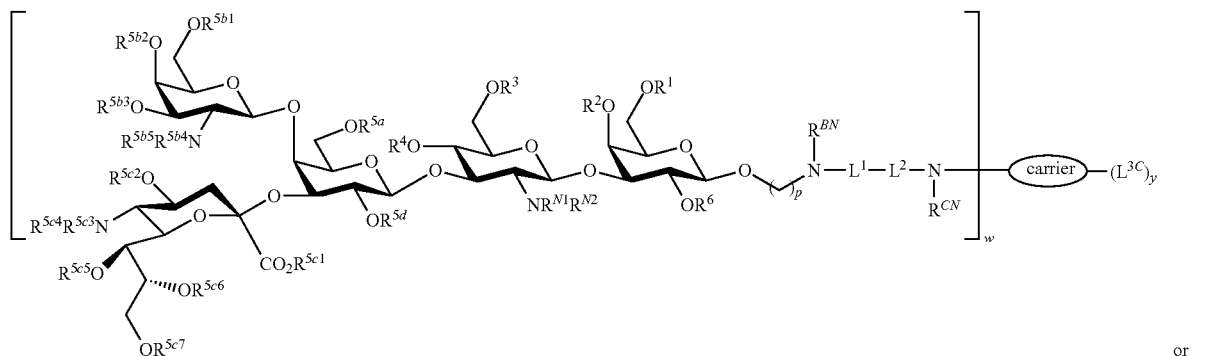

(VI-a)

or

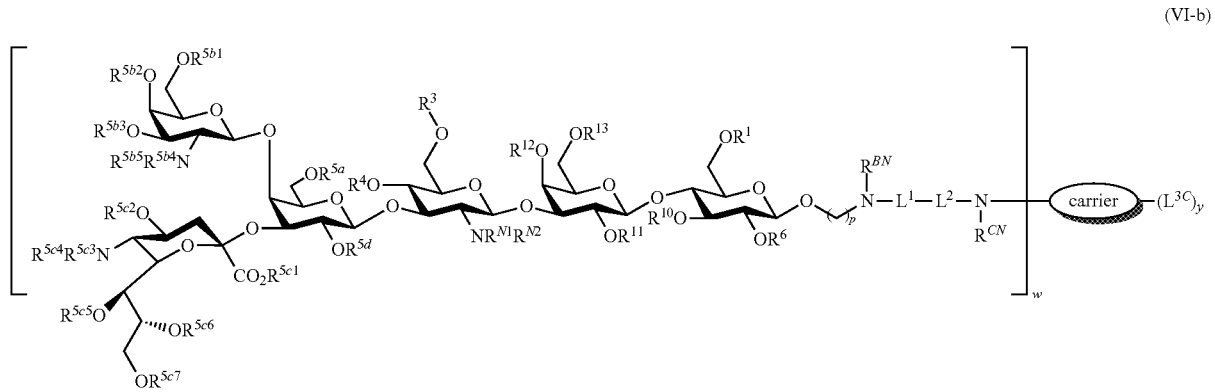

(VI-b)

or a pharmaceutically acceptable salt thereof,

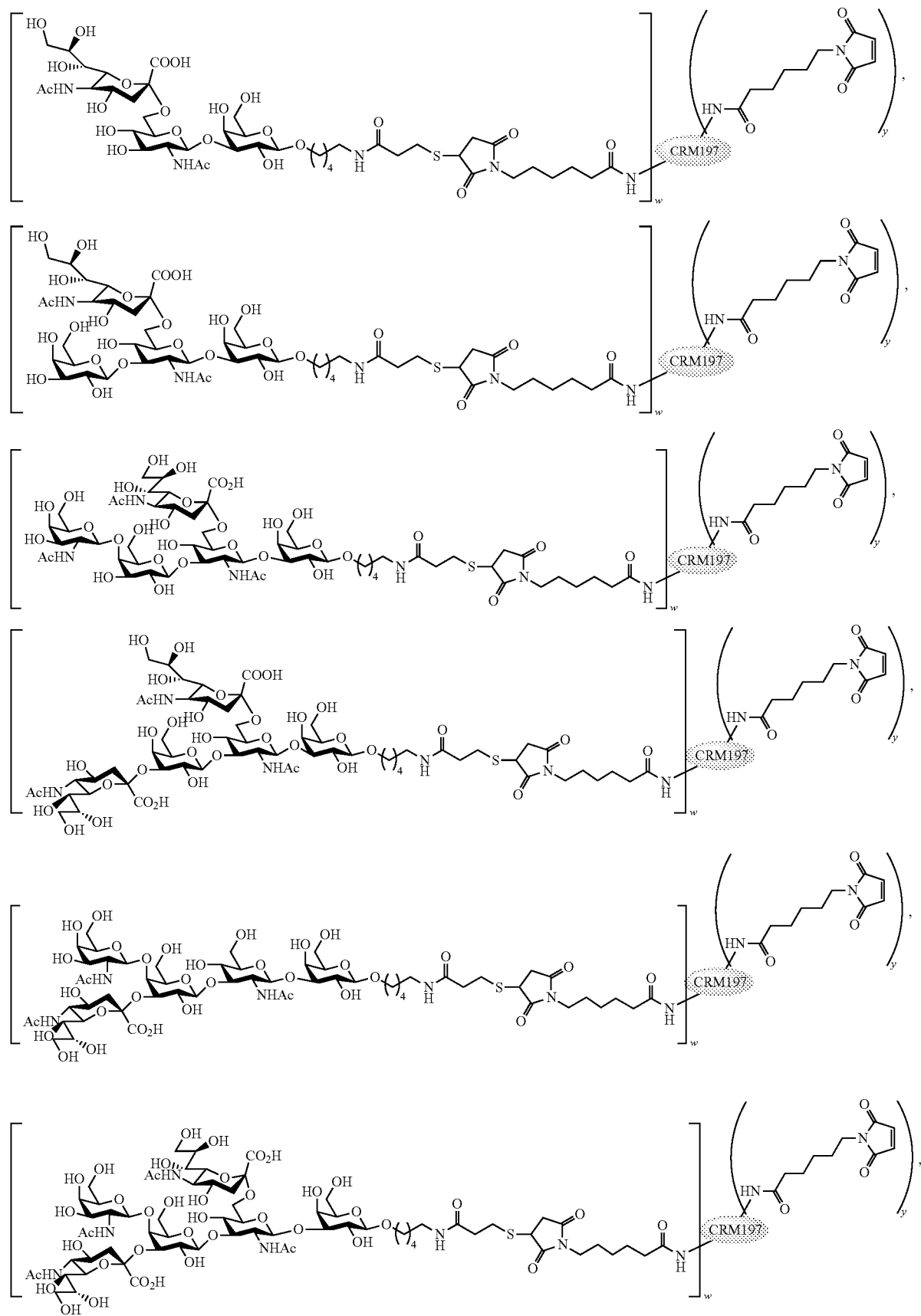

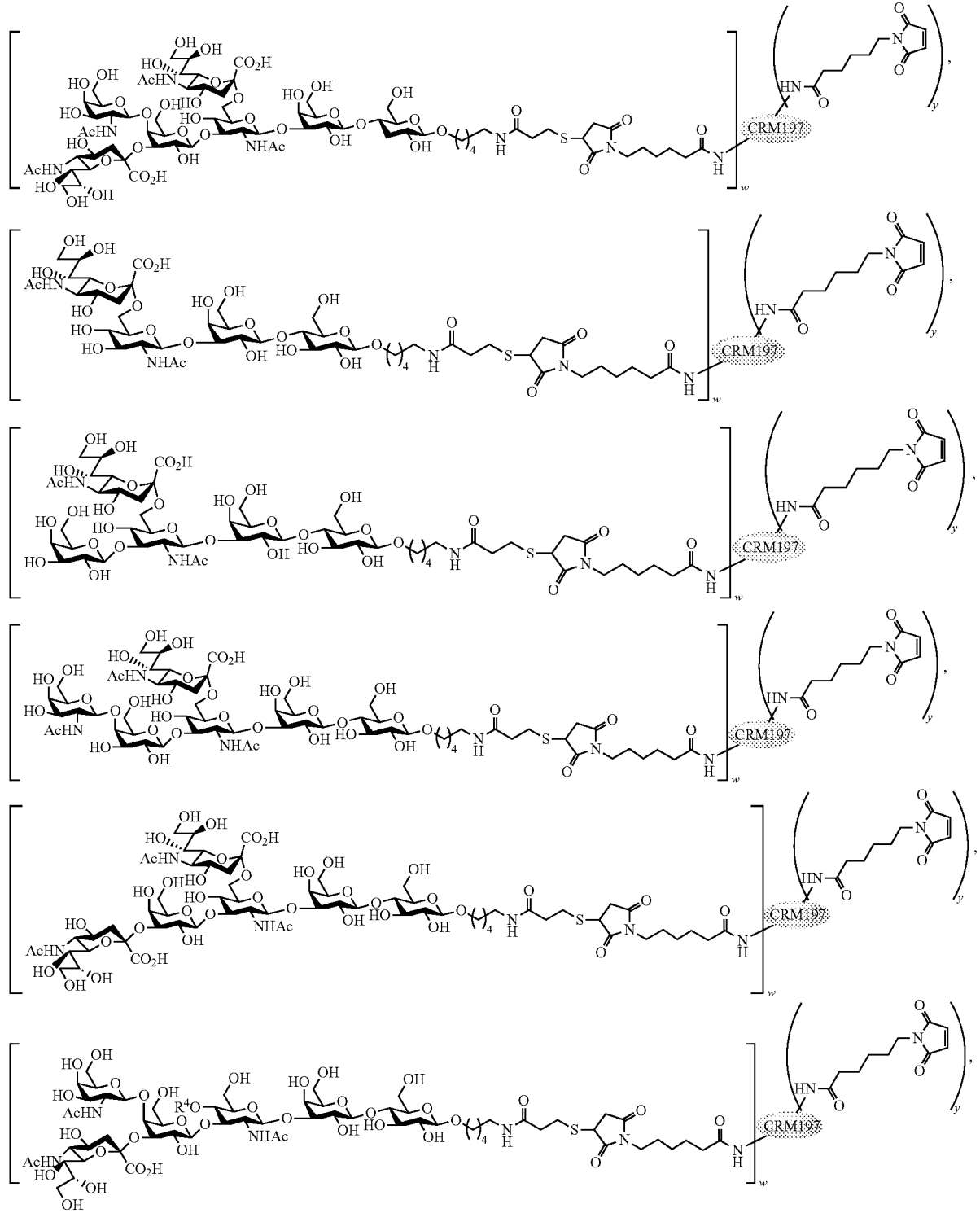

or a pharmaceutically acceptable salt thereof, each instance of $R^{3a}$, $R^{3b}$, $R^{3c}$, $R^{3d}$, $R^{3g}$, $R^{5a}$, $R^{5d}$, $R^{5b1}$, $R^{5b2}$, $R^{5b3}$, $R^{5c1}$, $R^{5c2}$, $R^{5c5}$, $R^{5c6}$, and $R^{5c7}$ is independently hydrogen, optionally substituted $C_{1-6}$ alkyl, optionally substituted carbohydrate, or an oxygen protecting group; or optionally $R^{5b1}$ and $R^{5b2}$ are taken with the intervening atoms to form an optionally substituted heterocyclic ring; or optionally $R^{5b2}$ and $R^{5b3}$ are taken with the intervening atoms to form an optionally substituted heterocyclic ring; or optionally $R^{5b3}$ and $R^{5b4}$ are taken with the intervening atoms to form an optionally substituted heterocyclic ring; or optionally $R^{5c2}$ and $R^{5c4}$ are taken with the intervening atoms to form an optionally substituted heterocyclic ring; or optionally $R^{5c5}$ and $R^{5c6}$ are taken with the intervening atoms to form an optionally substituted heterocyclic ring; or optionally $R^{5c6}$ and $R^{5c7}$ are taken with the intervening atoms to form an optionally substituted heterocyclic ring; and each instance of $R^{3f}$, $R^{3e}$, $R^{5b4}$, $R^{5b5}$, $R^{5c3}$, and $R^{5c4}$ is independently hydrogen, optionally substituted $C_{1-6}$ alkyl, or a nitrogen protecting group.

7. The glycan conjugate of any one of claims 1-6, wherein w is an integer of 1 to 20, inclusive.

8. The glycan conjugate of any one of claims 1-6, wherein y is 0 or an integer of 1 to 20, inclusive.

9. The glycan conjugate of any one of claims 1-6, wherein p is 5.

10. The glycan conjugate of any one of claims 1-6, wherein $R^{11}$, $R^{12}$, and $R^{13}$ are hydrogen.

11. The glycan conjugate of any one of claims 1-6, wherein $R^{10}$, $R^{11}$, $R^{12}$, and $R^{13}$ are hydrogen.

12. The glycan conjugate of any one of claims 1-6, wherein $R^1$, $R^2$, $R^4$, and $R^6$ are hydrogen.

13. The glycan conjugate of any one of claims 1-6, wherein $R^{N1}$ is acetyl.

14. The glycan conjugate of any one of claims 1-6, wherein $R^{N2}$ is hydrogen.

15. The glycan conjugate of any one of claims 1-6, wherein $R^{BN}$ is hydrogen.

16. The glycan conjugate of any one of claims 1-6, wherein $R^{CN}$ is hydrogen.

17. The glycan conjugate of any one of claims 1-6, wherein the carrier is a protein, a lipid, a lipolized protein, a virus, a peptide comprising a T cell epitope, or a dendrimer of glycopeptides.

18. The glycan conjugate of claim 17, wherein the carrier is a toxin protein selected from the group consisting of diphtheria toxin cross-reacting material 197 (DT-CRM197), diphtheria toxoid, tetanus toxoid, and outer-membrane protein (OMP).

19. The glycan conjugate of claim 18, wherein the toxin protein is DT-CRM197.

20. The glycan conjugate of claim 19, wherein the glycan conjugate is of the formula

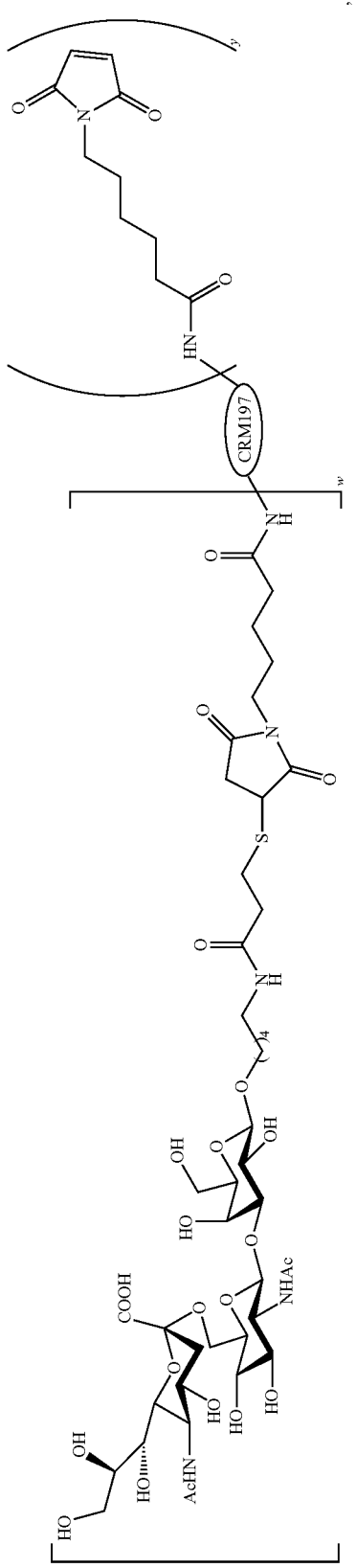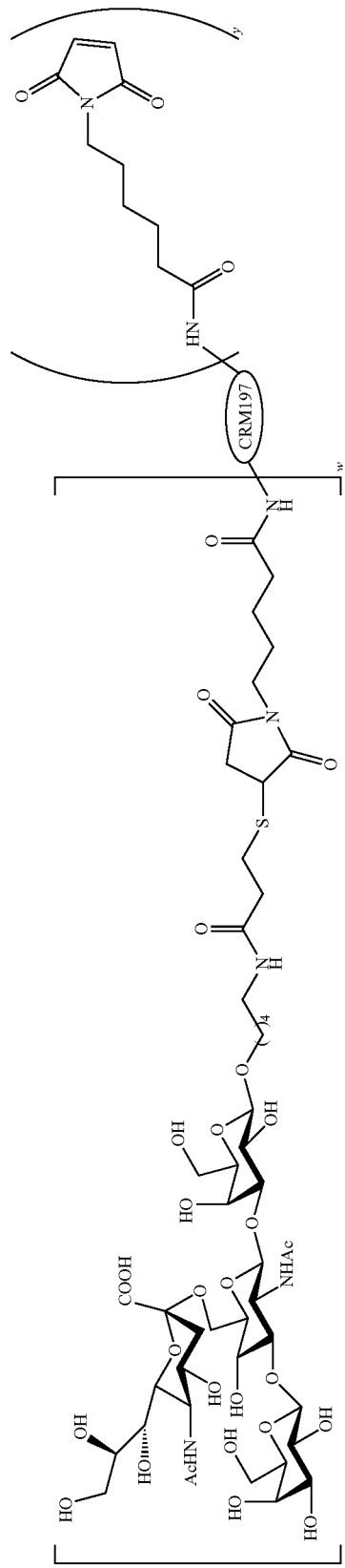

-continued
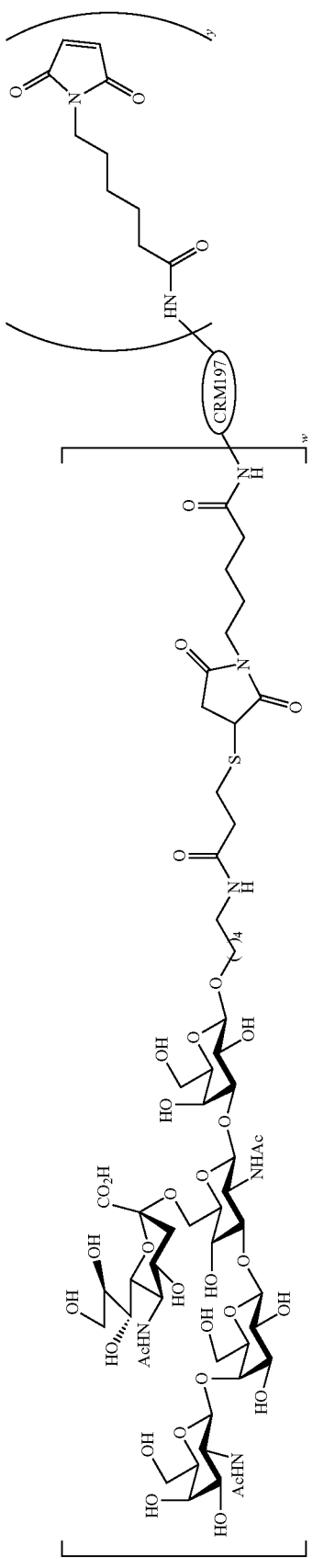 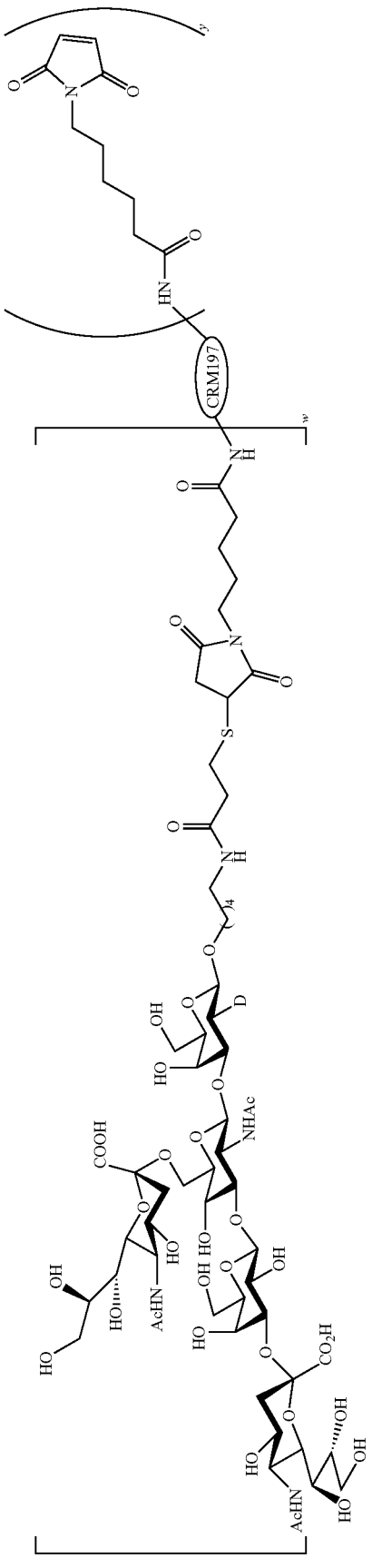

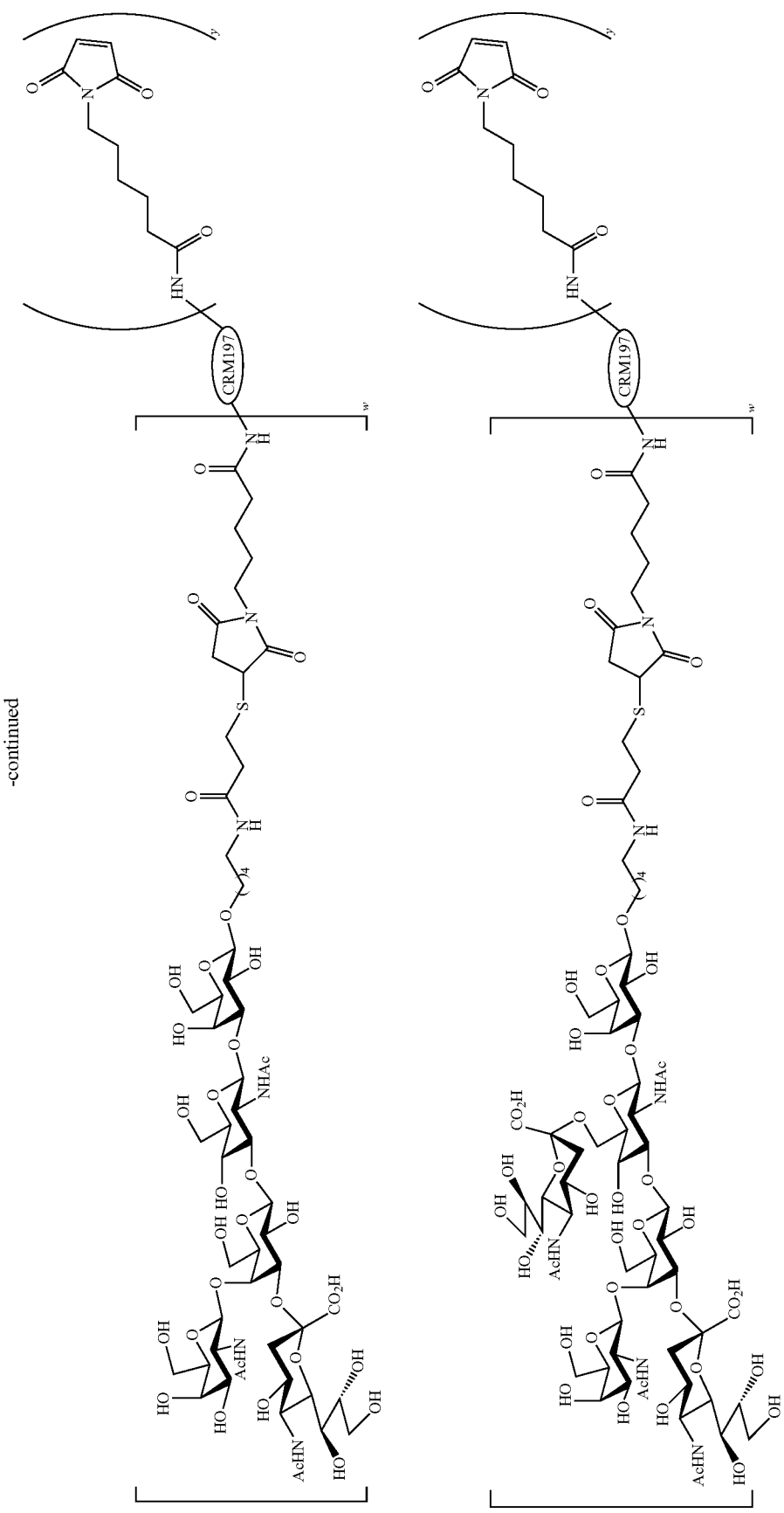

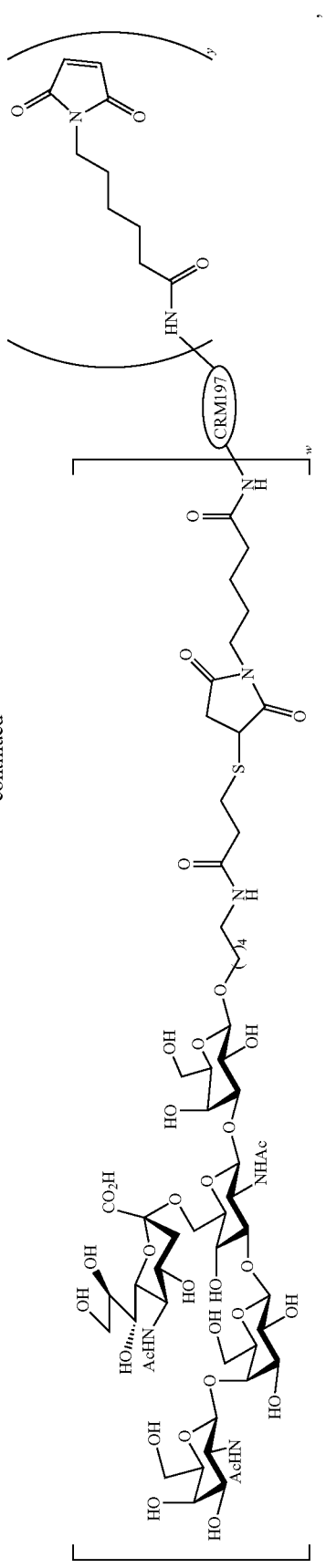
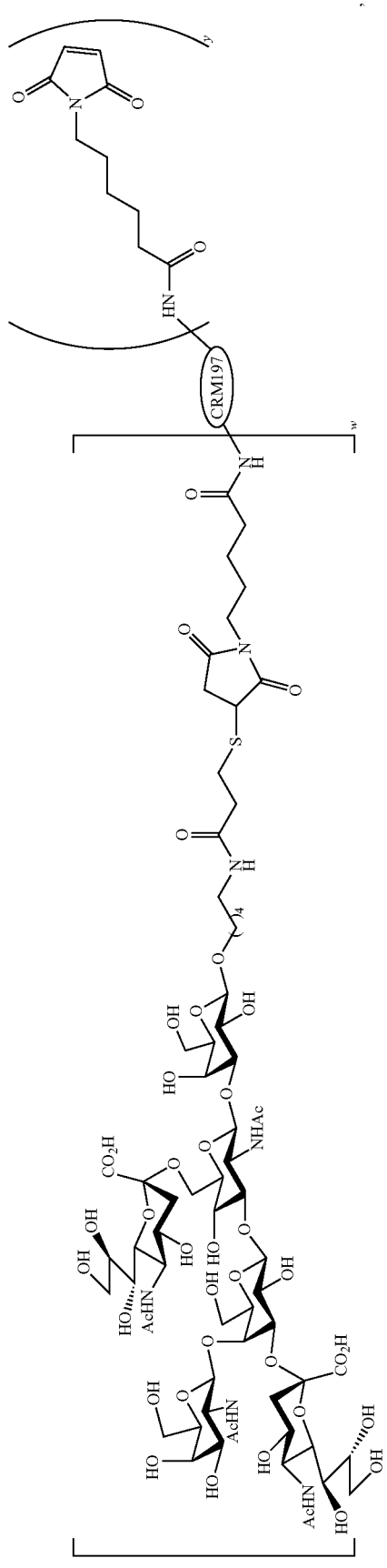

-continued
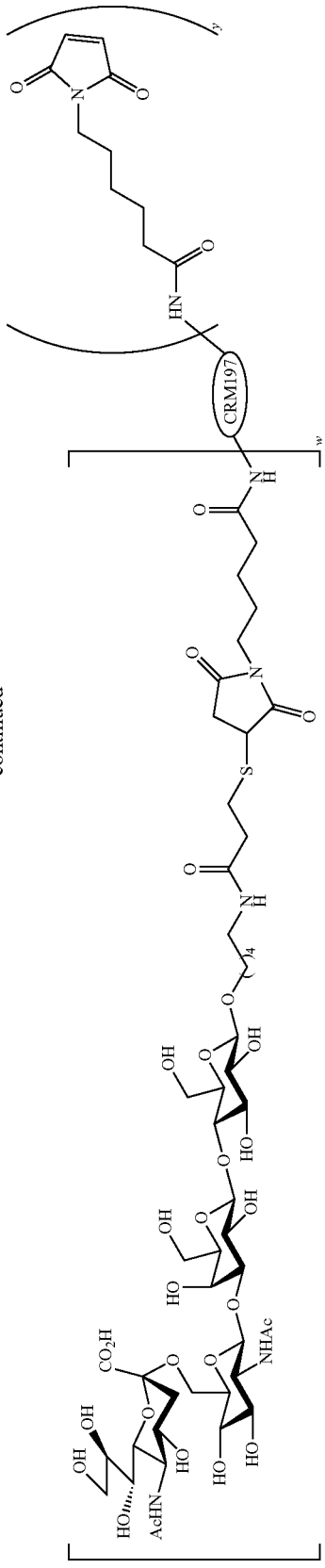
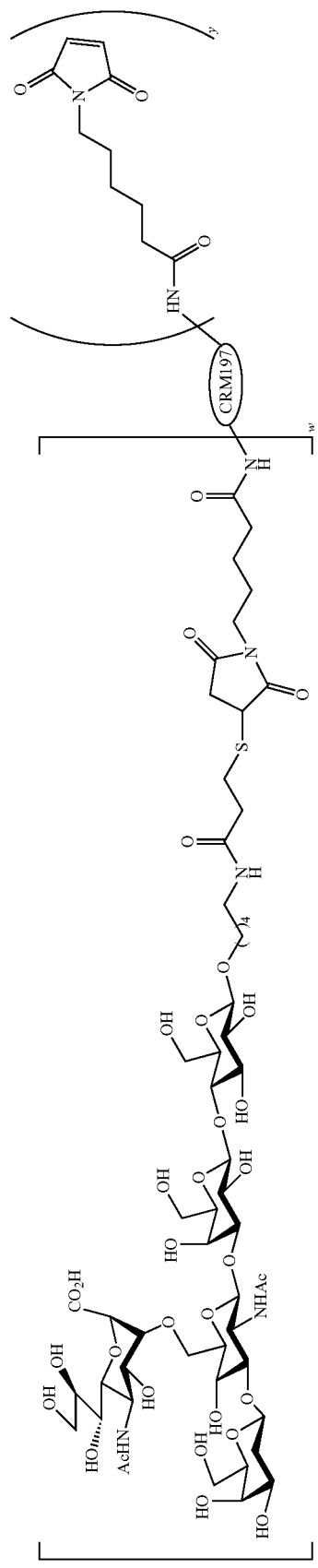

-continued
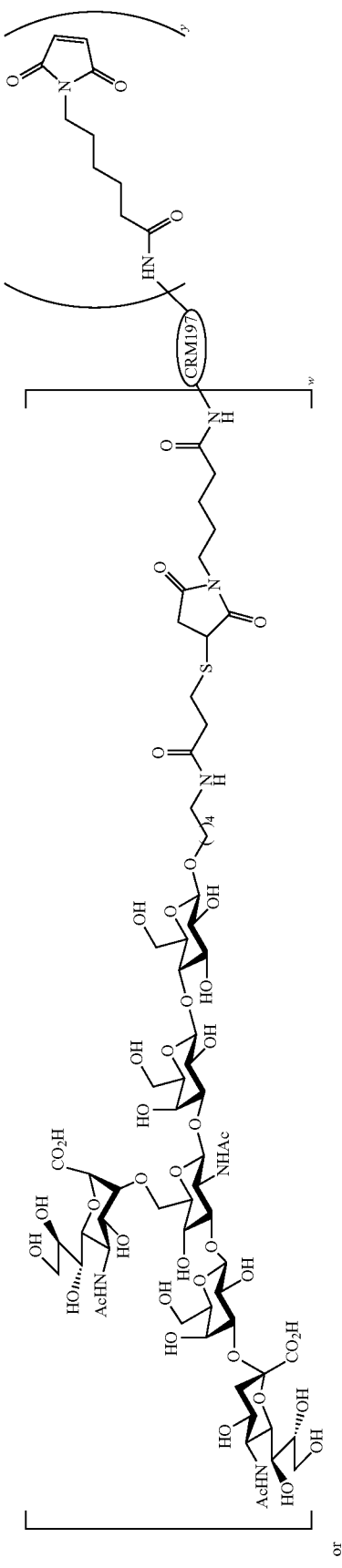
or
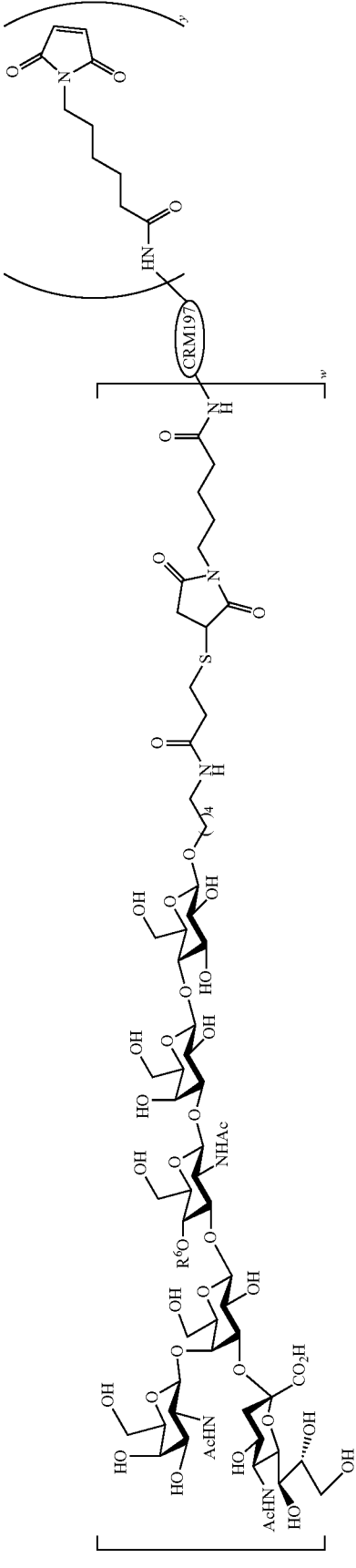

21. A glycan conjugate mixture comprising at least two of the glycan conjugates of any one of claims 1-6.

22. A glycan conjugate mixture comprising at least two of the glycan conjugates of any one of claims 1-6 wherein the average value of w is from about 1.0 to about 100.0.

23. The glycan conjugate mixture of claim 22, wherein the average value of w is about 1.0 to about 20.0.

24. The glycan conjugate mixture of claim 22, wherein the average value of w is about 1.0.

25. The glycan conjugate mixture of claim 22, wherein the average value of w is about 3.0.

26. The glycan conjugate mixture of claim 22, wherein the average value of w is about 4.7.

27. The glycan conjugate mixture of claim 22, wherein the average value of w is about 10.0.

28. The glycan conjugate mixture of claim 22, wherein the average value of w is about 12.7.

29. An immunogenic composition, comprising
(i) a glycan conjugate of any one of claims 1-6; and
(ii) a pharmaceutically acceptable excipient.

30. The immunogenic composition of claim 29 further comprising an adjuvant.

31. The immunogenic composition of claim 30, wherein the adjuvant is C34, 7DW8-5, C17, C23, C30, α-galactoceramide, Aluminum salt, Squalene, MF59, or QS-21.

32. A method of treating a proliferative disease in a subject comprising administering to the subject an effective amount of a glycan conjugate according to any one of claims 1-6.

33. A method of diagnosing a proliferative disease in a subject comprising administering to the subject an effective amount of a glycan conjugate according to any one of claims 1-6.

34. The method of claim 32, wherein the proliferative disease is cancer.

35. The method of claim 34, wherein the cancer is selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

36. The method of claim 35, wherein the cancer is prostate cancer.

37. A kit comprising a glycan conjugate according to any one of claims 1-6 and instructions for use thereof.

38. A method of preparing the glycan conjugate of claim 1, comprising coupling a compound of the following formulae:

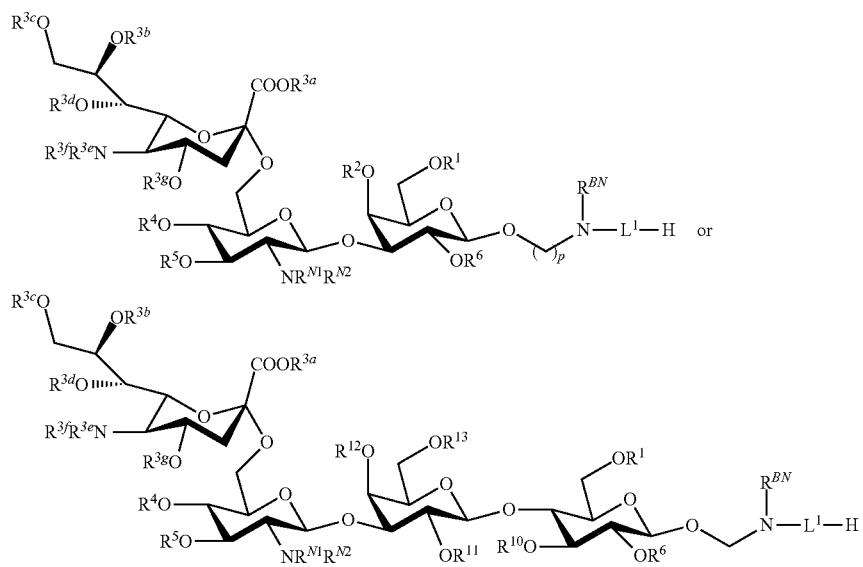

or a salt thereof, with a compound of Formula (C-2)

(C-2)

or a salt thereof, wherein
$L^{2C}$ is a crosslinking reagent capable of crosslinking the carrier and $L^1$-H.

39. The method of claim 38, wherein $L^{2C}$ is a crosslinking reagent capable of crosslinking an amine group and —SH.

40. The method of claim 39, wherein $L^{2C}$ is of one of the following formulae:

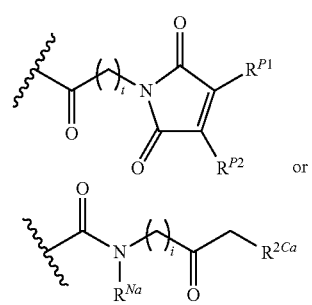

or a salt thereof, wherein
each instance of $R^{P1}$ and $R^{P2}$ are each independently hydrogen, halogen, or optionally substituted C1-6 alkyl;

each instance of $R^{2Ca}$ is a leaving group selected from —Br, —Cl, —I, —OS(=O)$_2$R$^{2CO}$, or —OS(=O)R$^{2CO}$, wherein R$^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and each of t and i is independently an integer of 1 to 8, inclusive.

41. The method of any one of claim 38-40, wherein the molar ratio of the compound of Formula (C-1) to the compound of Formula (C-2) is from about 1 to about 100.

42. The method of claim 41, wherein the coupling is carried out in the presence of phosphate buffered saline (PBS).

43. The method of any one of claims 38-40, further comprising deprotecting a compound of the following formulae:

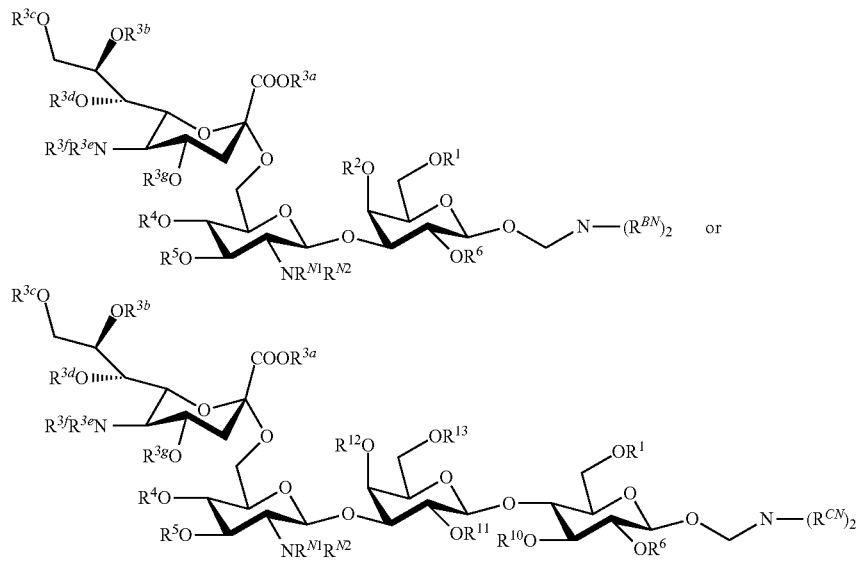

to give a compound of the following corresponding formulae

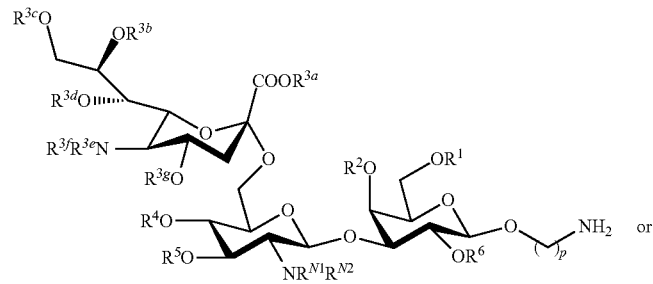

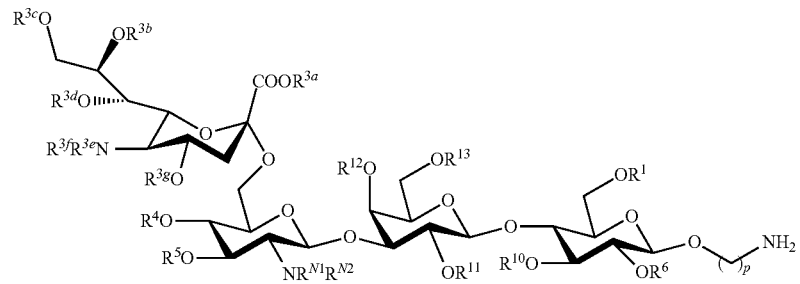

wherein each instance of $RC^N$ is optionally substituted alkyl, or a nitrogen protecting group.

44. The method of claim 43, wherein the deprotection is carried out in the presence of LiOH.

45. The method of claim 43, wherein the deprotection is carried out in the presence of LiOH, then $Ac_2O$ and $NaHCO_3$, then LiOH.

46. The method of claim 43, further comprising
(a) activating a compound of Formula (C-4a) or Formula (C-4b) to give a compound of Formula (C-1a) or Formula (C-1b); and
(b) activating the carrier to give a compound of Formula (C-2).

47. An immunogenic composition, comprising
(i) a glycan conjugate of claim 7; and
(ii) a pharmaceutically acceptable excipient.

48. The immunogenic composition of claim 47 further comprising an adjuvant.

49. The immunogenic composition of claim 48, wherein the adjuvant is C34, 7DW8-5, C17, C23, C30, α-galactoceramide, Aluminum salt, Squalene, MF59, or QS-21.

50. An immunogenic composition, comprising
(i) a glycan conjugate of claim 8; and
(ii) a pharmaceutically acceptable excipient.

51. The immunogenic composition of claim 50 further comprising an adjuvant.

52. The immunogenic composition of claim 51, wherein the adjuvant is C34, 7DW8-5, C17, C23, C30, α-galactoceramide, Aluminum salt, Squalene, MF59, or QS-21.

53. An immunogenic composition, comprising
(i) a glycan conjugate of claim 9; and
(ii) a pharmaceutically acceptable excipient.

54. The immunogenic composition of claim 53 further comprising an adjuvant.

55. The immunogenic composition of claim 54, wherein the adjuvant is C34, 7DW8-5, C17, C23, C30, α-galactoceramide, Aluminum salt, Squalene, MF59, or QS-21.

56. An immunogenic composition, comprising
(i) a glycan conjugate of claim 9; and
(ii) a pharmaceutically acceptable excipient.

57. The immunogenic composition of claim 56 further comprising an adjuvant.

58. The immunogenic composition of claim 57, wherein the adjuvant is C34, 7DW8-5, C17, C23, C30, α-galactoceramide, Aluminum salt, Squalene, MF59, or QS-21.

59. An immunogenic composition, comprising
(i) a glycan conjugate of claim 10; and
(ii) a pharmaceutically acceptable excipient.

60. The immunogenic composition of claim 59 further comprising an adjuvant.

61. The immunogenic composition of claim 60, wherein the adjuvant is C34, 7DW8-5, C17, C23, C30, α-galactoceramide, Aluminum salt, Squalene, MF59, or QS-21.

62. An immunogenic composition, comprising
(i) a glycan conjugate of claim 11; and
(ii) a pharmaceutically acceptable excipient.

63. The immunogenic composition of claim 62 further comprising an adjuvant.

64. The immunogenic composition of claim 63, wherein the adjuvant is C34, 7DW8-5, C17, C23, C30, α-galactoceramide, Aluminum salt, Squalene, MF59, or QS-21.

65. An immunogenic composition, comprising
(i) a glycan conjugate of claim 12; and
(ii) a pharmaceutically acceptable excipient.

66. The immunogenic composition of claim 65 further comprising an adjuvant.

67. The immunogenic composition of claim 66, wherein the adjuvant is C34, 7DW8-5, C17, C23, C30, α-galactoceramide, Aluminum salt, Squalene, MF59, or QS-21.

68. An immunogenic composition, comprising
(i) a glycan conjugate of claim 13; and
(ii) a pharmaceutically acceptable excipient.

69. The immunogenic composition of claim 68 further comprising an adjuvant.

70. The immunogenic composition of claim 69, wherein the adjuvant is C34, 7DW8-5, C17, C23, C30, α-galactoceramide, Aluminum salt, Squalene, MF59, or QS-21.

71. An immunogenic composition, comprising
(i) a glycan conjugate of claim 14; and
(ii) a pharmaceutically acceptable excipient.

72. The immunogenic composition of claim 71 further comprising an adjuvant.

73. The immunogenic composition of claim 72, wherein the adjuvant is C34, 7DW8-5, C17, C23, C30, α-galactoceramide, Aluminum salt, Squalene, MF59, or QS-21.

74. An immunogenic composition, comprising
(i) a glycan conjugate of claim 15; and
(ii) a pharmaceutically acceptable excipient.

75. The immunogenic composition of claim 74 further comprising an adjuvant.

76. The immunogenic composition of claim 75, wherein the adjuvant is C34, 7DW8-5, C17, C23, C30, α-galactoceramide, Aluminum salt, Squalene, MF59, or QS-21.

77. An immunogenic composition, comprising
(i) a glycan conjugate of claim 16; and
(ii) a pharmaceutically acceptable excipient.

78. The immunogenic composition of claim 77 further comprising an adjuvant.

79. The immunogenic composition of claim 78, wherein the adjuvant is C34, 7DW8-5, C17, C23, C30, α-galactoceramide, Aluminum salt, Squalene, MF59, or QS-21.

80. An immunogenic composition, comprising
(i) a glycan conjugate of claim 17; and
(ii) a pharmaceutically acceptable excipient.

81. The immunogenic composition of claim 80 further comprising an adjuvant.

82. The immunogenic composition of claim 81, wherein the adjuvant is C34, 7DW8-5, C17, C23, C30, α-galactoceramide, Aluminum salt, Squalene, MF59, or QS-21.

83. An immunogenic composition, comprising
(i) a glycan conjugate of claim 18; and
(ii) a pharmaceutically acceptable excipient.

84. The immunogenic composition of claim 83 further comprising an adjuvant.

85. The immunogenic composition of claim 84, wherein the adjuvant is C34, 7DW8-5, C17, C23, C30, α-galactoceramide, Aluminum salt, Squalene, MF59, or QS-21.

86. An immunogenic composition, comprising
(i) a glycan conjugate of claim 19; and
(ii) a pharmaceutically acceptable excipient.

87. The immunogenic composition of claim 86 further comprising an adjuvant.

88. The immunogenic composition of claim 87, wherein the adjuvant is C34, 7DW8-5, C17, C23, C30, α-galactoceramide, Aluminum salt, Squalene, MF59, or QS-21.

89. An immunogenic composition, comprising
(i) a glycan conjugate of claim 20; and
(ii) a pharmaceutically acceptable excipient.

90. The immunogenic composition of claim 89 further comprising an adjuvant.

91. The immunogenic composition of claim 90, wherein the adjuvant is C34, 7DW8-5, C17, C23, C30, α-galactoceramide, Aluminum salt, Squalene, MF59, or QS-21.

92. An immunogenic composition, comprising
(i) a glycan conjugate mixture of claim 21 and
(ii) a pharmaceutically acceptable excipient.

93. The immunogenic composition of claim 92 further comprising an adjuvant.

94. The immunogenic composition of claim 93, wherein the adjuvant is C34, 7DW8-5, C17, C23, C30, α-galactoceramide, Aluminum salt, Squalene, MF59, or QS-21.

95. An immunogenic composition, comprising
(i) a glycan conjugate mixture of claim 22 and
(ii) a pharmaceutically acceptable excipient.

96. The immunogenic composition of claim 95 further comprising an adjuvant.

97. The immunogenic composition of claim 96, wherein the adjuvant is C34, 7DW8-5, C17, C23, C30, α-galactoceramide, Aluminum salt, Squalene, MF59, or QS-21.

98. An immunogenic composition, comprising
(i) a glycan conjugate mixture of claim 23, and
(ii) a pharmaceutically acceptable excipient.

99. The immunogenic composition of claim 98 further comprising an adjuvant.

100. The immunogenic composition of claim 99, wherein the adjuvant is C34, 7DW8-5, C17, C23, C30, α-galactoceramide, Aluminum salt, Squalene, MF59, or QS-21.

101. A kit comprising a glycan conjugate according to claim 21, and instructions for use thereof.

102. A kit comprising a glycan conjugate according to claim 22, and instructions for use thereof.

103. A kit comprising an immunogenic composition of claim 29, and instructions for use thereof.

104. A kit comprising an immunogenic composition of claim 30, and instructions for use thereof.

105. A kit comprising an immunogenic composition of claim 31, and instructions for use thereof.

106. A method of treating a proliferative disease in a subject comprising administering to the subject an effective amount of a glycan conjugate according to claim 17.

107. A method of treating a proliferative disease in a subject comprising administering to the subject an effective amount of a glycan conjugate according to claim 18.

108. A method of treating a proliferative disease in a subject comprising administering to the subject an effective amount of a glycan conjugate according to claim 19.

109. A method of treating a proliferative disease in a subject comprising administering to the subject an effective amount of a glycan conjugate according to claim 20, wherein w is an integer of 1 to 20 and y is an integer of 1 to 20.

110. A method of treating a proliferative disease in a subject comprising administering to the subject an effective amount of a glycan conjugate mixture according to claim 21.

111. A method of treating a proliferative disease in a subject comprising administering to the subject an effective amount of a glycan conjugate mixture according to claim 22.

112. A method of treating a proliferative disease in a subject comprising administering to the subject an effective amount of a glycan conjugate mixture according to claim 23.

113. A method of treating a proliferative disease in a subject comprising administering to the subject an effective amount of an immunogenic composition according to claim 29.

114. A method of treating a proliferative disease in a subject comprising administering to the subject an effective amount of an immunogenic composition according to claim 30.

115. A method of treating a proliferative disease in a subject comprising administering to the subject an effective amount of an immunogenic composition according to claim 31.

116. The method of claim 106, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

117. The method of claim 116, wherein the cancer is prostate cancer.

118. The method of claim 107, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

119. The method of claim 118, wherein the cancer is prostate cancer.

120. The method of claim 108, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

121. The method of claim 120, wherein the cancer is prostate cancer.

122. The method of claim 109, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

123. The method of claim 122, wherein the cancer is prostate cancer.

124. The method of claim 110, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

125. The method of claim 124, wherein the cancer is prostate cancer.

126. The method of claim 111, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

127. The method of claim 126, wherein the cancer is prostate cancer.

128. The method of claim 112, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

129. The method of claim 128, wherein the cancer is prostate cancer.

130. The method of claim 113, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

131. The method of claim 130, wherein the cancer is prostate cancer.

132. The method of claim 114, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

133. The method of claim 132, wherein the cancer is prostate cancer.

134. The method of claim 115, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

135. The method of claim 134, wherein the cancer is prostate cancer.

136. A method of diagnosing a proliferative disease in a subject comprising administering to the subject an effective amount of a glycan conjugate according to claim 17.

137. A method of diagnosing a proliferative disease in a subject comprising administering to the subject an effective amount of a glycan conjugate according to claim 18.

138. A method of diagnosing a proliferative disease in a subject comprising administering to the subject an effective amount of a glycan conjugate according to claim 19.

139. A method of diagnosing a proliferative disease in a subject comprising administering to the subject an effective amount of a glycan conjugate according to claim 20, wherein w is an integer of 1 to 20, and y is an integer of 1 to 20.

140. A method of diagnosing a proliferative disease in a subject comprising administering to the subject an effective amount of a glycan conjugate mixture according to claim 21.

141. A method of diagnosing a proliferative disease in a subject comprising administering to the subject an effective amount of a glycan conjugate mixture according to claim 22.

142. A method of diagnosing a proliferative disease in a subject comprising administering to the subject an effective amount of a glycan conjugate mixture according to claim 23.

143. A method of diagnosing a proliferative disease in a subject comprising administering to the subject an effective amount of an immunogenic composition according to claim 29.

144. A method of diagnosing a proliferative disease in a subject comprising administering to the subject an effective amount of an immunogenic composition according to claim 30.

145. A method of diagnosing a proliferative disease in a subject comprising administering to the subject an effective amount of an immunogenic composition according to claim 31.

146. The method of claim 33, wherein the proliferative disease is cancer selected from the group consisting of breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

147. The method of claim 146, wherein the cancer is prostate cancer.

* * * * *